US010006862B2

(12) United States Patent
Lair et al.

(10) Patent No.: US 10,006,862 B2
(45) Date of Patent: Jun. 26, 2018

(54) CONTINUOUS PROCESS FOR PERFORMING MULTIPLE NUCLEIC ACID AMPLIFICATION ASSAYS

(71) Applicant: GEN-PROBE INCORPORATED, San Diego, CA (US)

(72) Inventors: Gary D. Lair, San Diego, CA (US); Thanh N. Nguyen, Laguna Niguel, CA (US); Haitao Li, San Diego, CA (US); Florence Li, San Diego, CA (US); Byron J. Knight, San Diego, CA (US); Robert E. Heinz, San Diego, CA (US); Jerzy A. Macioszek, Chevy Chase, MD (US); Christopher B. Davis, San Diego, CA (US); Robert F. Scalese, Carlsbad, CA (US)

(73) Assignee: GEN-PROBE INCORPORATED, San Diego, CA (US)

(*) Notice: Subject to any disclaimer, the term of this patent is extended or adjusted under 35 U.S.C. 154(b) by 0 days. days.

(21) Appl. No.: 15/600,245

(22) Filed: May 19, 2017

(65) Prior Publication Data
US 2017/0261431 A1    Sep. 14, 2017

Related U.S. Application Data

(60) Continuation of application No. 14/195,793, filed on Mar. 3, 2014, now Pat. No. 9,726,607, which is a
(Continued)

(51) Int. Cl.
*B01L 3/00* (2006.01)
*G01N 21/00* (2006.01)
(Continued)

(52) U.S. Cl.
CPC ....... *G01N 21/6428* (2013.01); *C12Q 1/6851* (2013.01); *G01N 21/76* (2013.01);
(Continued)

(58) Field of Classification Search
CPC . B01L 7/00; B01L 7/52; C12M 41/12; C12M 41/14
See application file for complete search history.

(56) References Cited

U.S. PATENT DOCUMENTS

| 749,104 A | 1/1904 | Schoenefeldt |
| 1,010,016 A | 11/1911 | Campau |

(Continued)

FOREIGN PATENT DOCUMENTS

| DE | 4128698 A1 | 3/1993 |
| DE | 9405224.7 | 5/1994 |

(Continued)

OTHER PUBLICATIONS

US 5,998,201, 12/1999, Maes et al. (withdrawn)
(Continued)

*Primary Examiner* — Nathan A Bowers
(74) *Attorney, Agent, or Firm* — Charles B. Cappellari; Richard Wydeven

(57) ABSTRACT

A continuous process for performing multiple nucleic acid amplification assays, where at least a portion of a second subset of reaction mixtures are transferred to a heater while a first subset of reaction mixtures are being subjected to conditions for performing a nucleic acid amplification assay. During the process, a plurality of reaction mixtures from the first and second subsets of reaction mixtures are simultaneously subjected to conditions sufficient to perform multiple nucleic acid amplification assays in the reaction mixtures.
(Continued)

The presence or absence of a target nucleic acid in the first subset of reaction mixtures is determined while the reaction mixtures are in the heater.

25 Claims, 71 Drawing Sheets

Related U.S. Application Data division of application No. 12/791,390, filed on Jun. 1, 2010, now Pat. No. 8,663,922, which is a continuation of application No. 11/372,221, filed on Mar. 10, 2006, now Pat. No. 8,008,066.

(60) Provisional application No. 60/659,874, filed on Mar. 10, 2005.

(51) Int. Cl.
| | |
|---|---|
| *G01N 21/64* | (2006.01) |
| *G01N 35/00* | (2006.01) |
| *G01N 35/02* | (2006.01) |
| *G01N 35/04* | (2006.01) |
| *G01N 35/10* | (2006.01) |
| *G01N 21/76* | (2006.01) |
| *C12Q 1/6851* | (2018.01) |

(52) U.S. Cl.
CPC ..... *G01N 35/0092* (2013.01); *G01N 35/0098* (2013.01); *G01N 35/0099* (2013.01); *G01N 35/025* (2013.01); *G01N 35/026* (2013.01); *G01N 35/04* (2013.01); *G01N 35/1002* (2013.01); *G01N 2021/6419* (2013.01); *G01N 2021/6421* (2013.01); *G01N 2021/6432* (2013.01); *G01N 2021/6439* (2013.01); *G01N 2035/0097* (2013.01); *G01N 2035/00356* (2013.01); *G01N 2035/00524* (2013.01); *G01N 2035/0441* (2013.01); *G01N 2035/0443* (2013.01); *G01N 2035/0444* (2013.01); *G01N 2035/0455* (2013.01); *G01N 2035/0491* (2013.01)

(56) References Cited

U.S. PATENT DOCUMENTS

| | | |
|---|---|---|
| 2,313,045 A | 3/1943 | Brown |
| 3,504,376 A | 3/1970 | Bendnar et al. |
| 3,562,962 A | 2/1971 | Ohno |
| 3,565,582 A | 2/1971 | Young |
| 3,626,190 A | 12/1971 | Cannon |
| 3,644,095 A | 2/1972 | Netheler et al. |
| 3,663,816 A | 5/1972 | Scherzer et al. |
| 3,676,076 A | 7/1972 | Grady |
| 3,754,444 A | 8/1973 | Ure et al. |
| 3,883,305 A | 5/1975 | Hoskins et al. |
| 3,985,649 A | 10/1976 | Eddleman |
| 4,039,288 A | 8/1977 | Moran |
| 4,054,415 A | 10/1977 | Seligson et al. |
| 4,169,125 A | 9/1979 | Rodriquez et al. |
| 4,170,625 A | 10/1979 | Welch |
| 4,234,539 A | 11/1980 | Ginsberg et al. |
| 4,235,840 A | 11/1980 | Mendoza et al. |
| 4,268,477 A | 5/1981 | Herzstark |
| 4,276,051 A | 6/1981 | Ginsbert et al. |
| 4,291,230 A | 9/1981 | Heiss |
| 4,298,571 A | 11/1981 | Difulvio et al. |
| 4,305,668 A | 12/1981 | Bilbrey |
| 4,313,735 A | 2/1982 | Yamashita et al. |
| 4,315,891 A | 2/1982 | Sakurada |
| 4,344,768 A | 8/1982 | Parker et al. |
| 4,346,056 A | 8/1982 | Sakurada |
| RE31,108 E | 12/1982 | Ginsberg et al. |
| 4,366,119 A | 12/1982 | Takeuchi |
| RE31,150 E | 2/1983 | Ginsberg et al. |
| 4,451,433 A | 5/1984 | Yamashita et al. |
| 4,459,265 A | 7/1984 | Berglund |
| 4,478,095 A | 10/1984 | Bradley et al. |
| 4,479,720 A | 10/1984 | Mochida et al. |
| 4,483,823 A | 11/1984 | Umetsu et al. |
| 4,483,927 A | 11/1984 | Takekawa |
| 4,497,774 A | 2/1985 | Scordato |
| 4,501,164 A | 2/1985 | Stockdale et al. |
| 4,528,159 A | 7/1985 | Liston |
| 4,595,562 A | 6/1986 | Liston et al. |
| 4,612,289 A | 9/1986 | Furuta et al. |
| 4,647,199 A | 3/1987 | Ferber et al. |
| 4,647,432 A | 3/1987 | Wakatake |
| 4,678,752 A | 7/1987 | Thorne et al. |
| 4,683,195 A | 7/1987 | Mullis et al. |
| 4,683,202 A | 7/1987 | Mullis |
| 4,695,430 A | 9/1987 | Coville et al. |
| 4,699,766 A | 10/1987 | Yamashita |
| 4,699,767 A | 10/1987 | Aihara |
| 4,731,225 A | 3/1988 | Wakatake |
| 4,747,693 A | 5/1988 | Kahl |
| 4,755,055 A | 7/1988 | Johnson et al. |
| 4,761,268 A | 8/1988 | Anderson et al. |
| 4,764,342 A | 8/1988 | Kelln et al. |
| 4,774,055 A | 9/1988 | Wakatake et al. |
| 4,781,891 A | 11/1988 | Galle et al. |
| 4,826,660 A | 5/1989 | Smith et al. |
| 4,834,944 A | 5/1989 | Wakatake |
| 4,844,868 A | 7/1989 | Rokugawa |
| 4,848,917 A | 7/1989 | Benin et al. |
| 4,849,176 A | 7/1989 | Sakagami |
| 4,855,110 A | 8/1989 | Marker et al. |
| 4,863,690 A | 9/1989 | Berthold et al. |
| 4,865,986 A | 9/1989 | Coy et al. |
| 4,871,676 A | 10/1989 | Yamada |
| 4,883,644 A | 11/1989 | Perlman |
| 4,895,650 A | 1/1990 | Wang |
| 4,906,433 A | 3/1990 | Minekane |
| 4,908,186 A | 3/1990 | Sakamaki |
| 4,908,320 A | 3/1990 | Zakowski et al. |
| 4,919,887 A | 4/1990 | Wakatake |
| 4,961,906 A | 10/1990 | Anderson et al. |
| 4,965,049 A | 10/1990 | Lillig et al. |
| 4,981,801 A | 1/1991 | Suzuki et al. |
| 5,043,141 A | 8/1991 | Wilson et al. |
| 5,051,238 A | 9/1991 | Umetsu et al. |
| 5,075,079 A | 12/1991 | Kerr et al. |
| 5,082,628 A | 1/1992 | Andreotti et al. |
| 5,084,242 A | 1/1992 | Sakuma et al. |
| 5,086,233 A | 2/1992 | Stafford et al. |
| 5,089,233 A | 2/1992 | Devaney et al. |
| 5,104,231 A | 4/1992 | Collier et al. |
| 5,104,621 A | 4/1992 | Pfost et al. |
| 5,104,807 A | 4/1992 | Mitsumaki et al. |
| 5,104,808 A | 4/1992 | Laska et al. |
| 5,122,343 A | 6/1992 | Ishizaka et al. |
| 5,128,103 A | 7/1992 | Wang et al. |
| 5,139,743 A | 8/1992 | Ishizaka et al. |
| 5,139,745 A | 8/1992 | Barr et al. |
| 5,141,871 A | 8/1992 | Kureshy et al. |
| 5,147,610 A | 9/1992 | Watanabe et al. |
| 5,154,888 A | 10/1992 | Zander et al. |
| 5,154,889 A | 10/1992 | Muraishi |
| 5,167,448 A | 12/1992 | Herold et al. |
| 5,183,638 A | 2/1993 | Wakatake |
| 5,186,827 A | 2/1993 | Liberti et al. |
| 5,192,505 A | 3/1993 | Sakagami |
| 5,192,506 A | 3/1993 | Kuresy et al. |
| 5,207,987 A | 5/1993 | Kuresy et al. |
| 5,213,761 A | 5/1993 | Sakagami |
| 5,215,714 A | 6/1993 | Okada et al. |
| 5,219,727 A | 6/1993 | Wang et al. |
| 5,223,218 A | 6/1993 | Fukuoka et al. |
| 5,229,297 A | 7/1993 | Schnipelsky et al. |
| 5,232,665 A | 8/1993 | Burkovich et al. |
| 5,232,669 A | 8/1993 | Pardinas |
| 5,234,665 A | 8/1993 | Ohta et al. |

(56) References Cited

U.S. PATENT DOCUMENTS

| | | |
|---|---|---|
| 5,240,678 A | 8/1993 | Litsche |
| 5,240,679 A | 8/1993 | Stettler |
| 5,246,665 A | 9/1993 | Tyranski et al. |
| 5,250,261 A | 10/1993 | Porte |
| 5,254,315 A | 10/1993 | Nurse et al. |
| 5,260,028 A | 11/1993 | Astle |
| 5,270,210 A | 12/1993 | Weyrauch et al. |
| 5,277,871 A | 1/1994 | Fuji et al. |
| 5,288,463 A | 2/1994 | Chemelli |
| 5,290,513 A | 3/1994 | Berthold et al. |
| 5,294,404 A | 3/1994 | Grandone et al. |
| 5,306,510 A | 4/1994 | Meltzer |
| 5,314,663 A | 5/1994 | Mimura |
| 5,314,825 A | 5/1994 | Weyrauch et al. |
| 5,316,726 A | 5/1994 | Babson et al. |
| 5,318,914 A | 6/1994 | Matte et al. |
| 5,320,809 A | 6/1994 | Dunn et al. |
| 5,320,966 A | 6/1994 | Mitsumaki et al. |
| 5,324,481 A | 6/1994 | Dunn et al. |
| 5,330,916 A | 7/1994 | Williams et al. |
| 5,332,549 A | 7/1994 | MacIndoe, Jr. |
| 5,340,747 A | 8/1994 | Eden |
| 5,346,303 A | 9/1994 | Heinonen et al. |
| 5,358,691 A | 10/1994 | Clark et al. |
| 5,360,741 A | 11/1994 | Hunnell |
| 5,374,395 A | 12/1994 | Robinson et al. |
| 5,380,666 A | 1/1995 | Wuerschum |
| 5,384,094 A | 1/1995 | Schacher |
| 5,389,339 A | 2/1995 | Petschek et al. |
| 5,397,709 A | 3/1995 | Berndt |
| 5,401,465 A | 3/1995 | Smethers et al. |
| 5,403,711 A | 4/1995 | Walder et al. |
| 5,413,686 A | 5/1995 | Klein |
| 5,415,839 A | 5/1995 | Zaun et al. |
| 5,415,840 A | 5/1995 | Sano et al. |
| 5,419,871 A | 5/1995 | Musak et al. |
| 5,422,271 A | 6/1995 | Chen et al. |
| 5,424,212 A | 6/1995 | Pinsl-Ober et al. |
| 5,434,083 A | 7/1995 | Mitsumaki et al. |
| 5,439,646 A | 8/1995 | Tanimizu et al. |
| 5,443,791 A | 8/1995 | Cathcart et al. |
| 5,445,794 A | 8/1995 | Wihlborg |
| 5,447,687 A | 9/1995 | Lewis et al. |
| 5,451,528 A | 9/1995 | Raymoure et al. |
| 5,457,027 A | 10/1995 | Nadeau et al. |
| 5,460,780 A | 10/1995 | Devaney, Jr. et al. |
| 5,466,574 A | 11/1995 | Liberti et al. |
| 5,470,744 A | 11/1995 | Astle |
| 5,476,774 A | 12/1995 | Wang et al. |
| 5,476,796 A | 12/1995 | Takahashi et al. |
| 5,482,834 A | 1/1996 | Gillespie |
| 5,482,839 A | 1/1996 | Ashihara et al. |
| 5,482,861 A | 1/1996 | Clark et al. |
| 5,507,410 A | 4/1996 | Clark et al. |
| 5,525,300 A | 6/1996 | Danssaert et al. |
| 5,527,673 A | 6/1996 | Reinhartz et al. |
| 5,536,471 A | 7/1996 | Clark et al. |
| 5,536,475 A | 7/1996 | Moubayed et al. |
| 5,538,848 A | 7/1996 | Livak et al. |
| 5,538,849 A | 7/1996 | Uematsu et al. |
| 5,548,826 A | 8/1996 | Sayers |
| 5,558,839 A | 9/1996 | Matte et al. |
| 5,567,595 A | 10/1996 | Kok |
| 5,571,325 A | 11/1996 | Ueyama et al. |
| 5,571,481 A | 11/1996 | Powell et al. |
| 5,575,976 A | 11/1996 | Choperena et al. |
| 5,576,215 A | 11/1996 | Burns et al. |
| 5,578,269 A | 11/1996 | Yaremko et al. |
| 5,578,270 A | 11/1996 | Reichler et al. |
| 5,580,524 A | 12/1996 | Forrest et al. |
| 5,582,796 A | 12/1996 | Carey et al. |
| 5,585,068 A | 12/1996 | Panetz et al. |
| 5,587,129 A | 12/1996 | Kurosaki et al. |
| 5,595,707 A | 1/1997 | Copeland et al. |
| 5,599,501 A | 2/1997 | Carey et al. |
| 5,605,665 A | 2/1997 | Clark et al. |
| 5,610,069 A | 3/1997 | Clark et al. |
| 5,620,898 A | 4/1997 | Yaremko et al. |
| 5,635,364 A | 6/1997 | Clark et al. |
| 5,637,275 A | 6/1997 | Carey et al. |
| 5,639,425 A | 6/1997 | Komiyama et al. |
| 5,639,668 A | 6/1997 | Neel et al. |
| 5,646,049 A | 7/1997 | Tayi |
| 5,653,940 A | 8/1997 | Carey et al. |
| 5,656,493 A | 8/1997 | Mullis et al. |
| 5,658,532 A | 8/1997 | Kurosaki et al. |
| 5,658,799 A | 8/1997 | Choperena et al. |
| 5,670,114 A | 9/1997 | Sakazume et al. |
| 5,670,120 A | 9/1997 | Degenhardt et al. |
| 5,670,375 A | 9/1997 | Seaton et al. |
| 5,677,188 A | 10/1997 | Mitsumaki et al. |
| 5,679,309 A | 10/1997 | Bell |
| 5,681,530 A | 10/1997 | Kuster et al. |
| 5,686,046 A | 11/1997 | Malek et al. |
| 5,691,146 A | 11/1997 | Mayrand |
| 5,693,292 A | 12/1997 | Choperena et al. |
| 5,698,450 A | 12/1997 | Ringrose et al. |
| 5,702,950 A | 12/1997 | Tajima |
| 5,705,062 A | 1/1998 | Knobel |
| 5,714,380 A | 2/1998 | Neri et al. |
| 5,716,583 A | 2/1998 | Smethers et al. |
| 5,720,377 A | 2/1998 | Lapeus et al. |
| 5,720,923 A | 2/1998 | Haff et al. |
| 5,723,591 A | 3/1998 | Livak et al. |
| 5,730,938 A | 3/1998 | Carbonari et al. |
| 5,730,939 A | 3/1998 | Kurumada et al. |
| 5,736,105 A | 4/1998 | Astle |
| 5,736,333 A | 4/1998 | Livak et al. |
| 5,738,827 A | 4/1998 | Marquiss |
| 5,741,461 A | 4/1998 | Takahashi et al. |
| 5,746,977 A | 5/1998 | Imai et al. |
| 5,746,978 A | 5/1998 | Beinhaus et al. |
| 5,748,978 A | 5/1998 | Beinhaus et al. |
| 5,750,338 A | 5/1998 | Collins et al. |
| 5,762,872 A | 6/1998 | Buler et al. |
| 5,762,873 A | 6/1998 | Fanning et al. |
| 5,773,268 A | 6/1998 | Korenberg et al. |
| 5,773,662 A | 6/1998 | Imai et al. |
| 5,779,981 A | 7/1998 | Danssaert et al. |
| 5,786,182 A | 7/1998 | Catanzariti et al. |
| 5,789,153 A | 8/1998 | Falkner et al. |
| 5,789,252 A | 8/1998 | Fujita et al. |
| 5,795,547 A | 8/1998 | Moser et al. |
| 5,795,784 A | 8/1998 | Arnquist et al. |
| 5,800,989 A | 9/1998 | Linn et al. |
| 5,807,523 A | 9/1998 | Watts et al. |
| 5,814,277 A | 9/1998 | Bell et al. |
| 5,826,129 A | 10/1998 | Hasebe et al. |
| 5,827,478 A | 10/1998 | Carey et al. |
| 5,827,479 A | 10/1998 | Yamazaki et al. |
| 5,827,653 A | 10/1998 | Sammes et al. |
| 5,834,255 A | 11/1998 | van Gemen et al. |
| 5,837,195 A | 11/1998 | Malek et al. |
| 5,840,487 A | 11/1998 | Nadeau et al. |
| 5,843,376 A | 12/1998 | Ishihara et al. |
| 5,846,491 A | 12/1998 | Choperena et al. |
| 5,849,247 A | 12/1998 | Uzan et al. |
| 5,855,847 A | 1/1999 | Oonuma et al. |
| 5,863,506 A | 1/1999 | Farren |
| 5,876,668 A | 3/1999 | Kawashima et al. |
| 5,876,930 A | 3/1999 | Livak et al. |
| 5,882,594 A | 3/1999 | Kawaguchi et al. |
| 5,882,596 A | 3/1999 | Breeser et al. |
| 5,882,918 A | 3/1999 | Goffe |
| 5,885,353 A | 3/1999 | Strodtbeck et al. |
| 5,885,529 A | 3/1999 | Babson et al. |
| 5,885,530 A | 3/1999 | Babson et al. |
| 5,888,454 A | 3/1999 | Leistner et al. |
| 5,897,783 A | 4/1999 | Howe et al. |
| 5,912,145 A | 6/1999 | Stanley |
| 5,919,622 A | 7/1999 | Macho et al. |
| 5,928,869 A | 7/1999 | Nadeau et al. |
| 5,935,791 A | 8/1999 | Nadeau et al. |
| 5,948,691 A | 9/1999 | Ekiriwang et al. |

(56) References Cited

U.S. PATENT DOCUMENTS

| | | |
|---|---|---|
| 5,952,202 A | 9/1999 | Aoyagi et al. |
| 5,958,763 A | 9/1999 | Goffe |
| 5,985,670 A | 11/1999 | Markin |
| 5,985,671 A | 11/1999 | Leistner et al. |
| 5,985,672 A | 11/1999 | Kegelman et al. |
| 5,988,869 A | 11/1999 | Davidson et al. |
| 5,994,056 A | 11/1999 | Higuchi |
| 6,027,691 A | 2/2000 | Watts et al. |
| 6,033,574 A | 3/2000 | Siddiqi |
| 6,033,880 A | 3/2000 | Haff et al. |
| 6,042,786 A | 3/2000 | Oonuma et al. |
| 6,043,880 A | 3/2000 | Andrews et al. |
| 6,051,101 A | 4/2000 | Ohtani et al. |
| 6,056,923 A | 5/2000 | Diamond et al. |
| 6,066,455 A | 5/2000 | Kruse-Mueller et al. |
| 6,066,458 A | 5/2000 | Haaland et al. |
| 6,068,978 A | 5/2000 | Zaun et al. |
| 6,071,395 A | 6/2000 | Lange |
| 6,086,827 A | 7/2000 | Horner et al. |
| 6,096,272 A | 8/2000 | Clark et al. |
| 6,103,193 A | 8/2000 | Iwahashi et al. |
| 6,110,676 A | 8/2000 | Coull et al. |
| 6,110,678 A | 8/2000 | Weisburg et al. |
| 6,117,392 A | 9/2000 | Hanawa et al. |
| 6,117,398 A | 9/2000 | Bienhaus et al. |
| 6,117,683 A | 9/2000 | Kodama et al. |
| 6,124,138 A | 9/2000 | Woudenberg et al. |
| 6,129,428 A | 10/2000 | Helwig et al. |
| 6,140,054 A | 10/2000 | Wittwer et al. |
| 6,143,578 A | 11/2000 | Bendele et al. |
| 6,146,592 A | 11/2000 | Kawashima |
| 6,156,565 A | 12/2000 | Maes et al. |
| 6,165,778 A | 12/2000 | Kedar |
| 6,180,408 B1 | 1/2001 | Kwok et al. |
| 6,193,892 B1 | 2/2001 | Krueger et al. |
| 6,214,293 B1 | 4/2001 | Pantoliano et al. |
| 6,232,079 B1 | 5/2001 | Wittwer et al. |
| 6,235,479 B1 | 5/2001 | Rogers |
| 6,274,321 B1 | 8/2001 | Blumberg |
| 6,277,332 B1 | 8/2001 | Sucholeiki |
| 6,300,068 B1 | 10/2001 | Berg et al. |
| 6,303,305 B1 | 10/2001 | Wittwer et al. |
| 6,312,929 B1 | 11/2001 | McMillan |
| 6,335,166 B1 | 1/2002 | Ammann et al. |
| 6,346,384 B1 | 2/2002 | Pollner |
| 6,355,934 B1 | 3/2002 | Osgood et al. |
| 6,377,342 B1 | 4/2002 | Coeurveille |
| 6,379,888 B1 | 4/2002 | Nadeau et al. |
| 6,337,621 B1 | 5/2002 | Wittwer |
| 6,387,621 B1 | 5/2002 | Wittwer |
| 6,396,581 B1 | 5/2002 | Hayashi et al. |
| 6,399,952 B1 | 6/2002 | Maher et al. |
| 6,403,035 B1 | 6/2002 | Caratsch |
| 6,409,925 B1 | 6/2002 | Gombinsky et al. |
| 6,410,235 B1 | 6/2002 | Weindel et al. |
| 6,413,780 B1 | 7/2002 | Bach et al. |
| 6,436,349 B1 | 8/2002 | Carey et al. |
| 6,456,944 B1 | 9/2002 | Burkhardt et al. |
| 6,472,156 B1 | 10/2002 | Wittwer et al. |
| 6,503,751 B2 | 1/2003 | Hugh |
| 6,506,563 B1 | 1/2003 | Ward et al. |
| 6,517,777 B2 | 2/2003 | Liljestrand et al. |
| 6,517,782 B1 | 2/2003 | Horner et al. |
| 6,517,783 B2 | 2/2003 | Horner et al. |
| 6,577,580 B2 | 6/2003 | Haga |
| 6,586,234 B1 | 7/2003 | Burg et al. |
| 6,597,450 B1 | 7/2003 | Andrews et al. |
| 6,605,213 B1 | 8/2003 | Ammann et al. |
| 6,617,138 B1 | 9/2003 | Rudi et al. |
| 6,691,041 B2 | 2/2004 | Sagner et al. |
| 6,699,661 B1 | 3/2004 | Kurane et al. |
| 6,713,297 B2 | 3/2004 | McMillan et al. |
| 6,730,501 B2 | 5/2004 | Eyre et al. |
| 6,764,649 B2 | 7/2004 | Ammann |
| 6,783,934 B1 | 8/2004 | McMillan et al. |
| 6,790,623 B2 | 9/2004 | Weindel et al. |
| 6,815,164 B2 | 11/2004 | Kurn |
| 6,818,437 B1 | 11/2004 | Gambini et al. |
| 6,825,921 B1 | 11/2004 | Modlin et al. |
| 6,890,742 B2 | 5/2005 | Ammann et al. |
| 6,902,900 B2 | 6/2005 | Davies et al. |
| 6,911,323 B2 | 6/2005 | Persson et al. |
| 6,919,058 B2 | 7/2005 | Andersson et al. |
| 6,919,175 B1 | 7/2005 | Beinhaus et al. |
| 6,942,971 B2 | 9/2005 | McMillan et al. |
| 6,943,029 B2 | 9/2005 | Copeland et al. |
| 6,961,948 B2 | 11/2005 | Seki et al. |
| 7,081,226 B1 | 7/2006 | Wittwer et al. |
| 7,081,339 B2 | 7/2006 | Siepnev |
| 7,087,414 B2 | 8/2006 | Gerdes et al. |
| 7,094,540 B2 | 8/2006 | Kurane et al. |
| 7,115,384 B2 | 10/2006 | Clark et al. |
| 7,118,982 B2 | 10/2006 | Govyadinov et al. |
| 7,125,691 B2 | 10/2006 | Sagner et al. |
| 7,183,084 B2 | 2/2007 | Jaeger |
| 7,188,030 B2 | 3/2007 | Ward et al. |
| 7,220,385 B2 | 5/2007 | Blecka et al. |
| 7,252,937 B2 | 8/2007 | Kaltenboeck |
| 7,262,008 B2 | 8/2007 | Catanzariti et al. |
| 7,267,945 B2 | 9/2007 | Baskin et al. |
| 7,273,749 B1 | 9/2007 | Wittwer et al. |
| 7,354,707 B2 | 4/2008 | Kurane et al. |
| 7,373,253 B2 | 5/2008 | Eyre |
| 7,390,458 B2 | 6/2008 | Burow et al. |
| 7,390,459 B2 | 6/2008 | Lebl et al. |
| 7,498,164 B2 | 3/2009 | Oldham et al. |
| 7,635,588 B2 | 12/2009 | King et al. |
| 7,745,205 B2 | 6/2010 | Wittwer et al. |
| 7,794,659 B2 | 9/2010 | Lair et al. |
| 7,897,337 B2 | 3/2011 | Macioszek et al. |
| 7,932,081 B2 | 4/2011 | Lair et al. |
| 7,964,413 B2 | 6/2011 | Macioszek et al. |
| 8,008,066 B2 | 8/2011 | Lair et al. |
| 8,349,564 B2 | 1/2013 | Macioszek et al. |
| 2002/0009394 A1 | 1/2002 | Koster et al. |
| 2002/0014443 A1 | 2/2002 | Hansen et al. |
| 2002/0028489 A1 | 3/2002 | Ammann et al. |
| 2002/0031446 A1 | 3/2002 | Friedlander et al. |
| 2002/0031768 A1 | 3/2002 | McMillan et al. |
| 2002/0034746 A1 | 3/2002 | McMillan et al. |
| 2002/0058262 A1 | 5/2002 | Sagner et al. |
| 2002/0064867 A1 | 5/2002 | Clark et al. |
| 2002/0086417 A1 | 7/2002 | Chen et al. |
| 2002/0090320 A1 | 7/2002 | Burow et al. |
| 2002/0098117 A1 | 7/2002 | Ammann et al. |
| 2002/0108857 A1 | 8/2002 | Paschetto et al. |
| 2002/0119464 A1 | 8/2002 | McMillan |
| 2002/0123156 A1 | 9/2002 | Tajima |
| 2002/0131895 A1 | 9/2002 | Gjerdingen et al. |
| 2002/0137039 A1 | 9/2002 | Gessner |
| 2002/0137194 A1 | 9/2002 | Ammann et al. |
| 2002/0137197 A1 | 9/2002 | Ammann et al. |
| 2002/0150450 A1 | 10/2002 | Bevirt et al. |
| 2002/0155619 A1 | 10/2002 | Kurihara et al. |
| 2002/0197611 A1 | 12/2002 | Chagovetz |
| 2003/0003463 A1 | 1/2003 | Rothberg et al. |
| 2003/0027206 A1 | 2/2003 | Ammann et al. |
| 2003/0032172 A1 | 2/2003 | Colston, Jr. et al. |
| 2003/0044826 A1 | 3/2003 | Ward et al. |
| 2003/0054542 A1 | 3/2003 | Burns et al. |
| 2003/0064507 A1 | 4/2003 | Gallagher et al. |
| 2003/0087240 A1 | 5/2003 | Whitcombe et al. |
| 2003/0087397 A1 | 5/2003 | Klein et al. |
| 2003/0104438 A1 | 6/2003 | Eyre et al. |
| 2003/0129614 A1 | 7/2003 | Parameswaran et al. |
| 2003/0148302 A1 | 8/2003 | Woo et al. |
| 2003/0148332 A1 | 8/2003 | Taylor et al. |
| 2003/0165832 A1 | 9/2003 | Sagner et al. |
| 2003/0219754 A1 | 11/2003 | Oleksy et al. |
| 2004/0014202 A1 | 1/2004 | King et al. |
| 2004/0029260 A1 | 2/2004 | Hansen et al. |
| 2004/0033518 A1 | 2/2004 | Wittwer et al. |
| 2004/0076983 A1 | 4/2004 | Karisen |
| 2004/0096881 A1 | 5/2004 | Blasko et al. |

(56) References Cited

U.S. PATENT DOCUMENTS

| | | |
|---|---|---|
| 2004/0115796 A1 | 6/2004 | Burns |
| 2005/0064582 A1 | 3/2005 | Wittwer et al. |
| 2005/0118620 A1 | 6/2005 | Vess |
| 2005/0130198 A1 | 6/2005 | Ammann et al. |
| 2005/0220669 A1 | 10/2005 | Malyarov et al. |
| 2005/0220670 A1 | 10/2005 | Palmieri et al. |
| 2006/0024330 A1 | 2/2006 | Wai et al. |
| 2006/0204972 A1 | 9/2006 | Kurnik |
| 2006/0211130 A1 | 9/2006 | Macioszek et al. |
| 2006/0292571 A1 | 12/2006 | Babiel et al. |
| 2006/0292619 A1 | 12/2006 | Carrick et al. |
| 2007/0004028 A1 | 1/2007 | Lair et al. |
| 2007/0143070 A1 | 6/2007 | Kurnik et al. |
| 2007/0243600 A1 | 10/2007 | Lair et al. |
| 2010/0075336 A1 | 3/2010 | Knight et al. |
| 2011/0147610 A1 | 6/2011 | Macioszek et al. |

FOREIGN PATENT DOCUMENTS

| | | |
|---|---|---|
| EP | 0171140 A2 | 2/1986 |
| EP | 0272055 A2 | 6/1988 |
| EP | 0293782 A1 | 12/1988 |
| EP | 0336309 A2 | 10/1989 |
| EP | 0 410 645 A2 | 1/1991 |
| EP | 0409126 A2 | 1/1991 |
| EP | 0411620 A2 | 2/1991 |
| EP | 0435481 A2 | 7/1991 |
| EP | 0458138 A2 | 11/1991 |
| EP | 0502638 A2 | 9/1992 |
| EP | 0513618 A2 | 11/1992 |
| EP | 0525577 A2 | 2/1993 |
| EP | 0 542 422 A1 | 5/1993 |
| EP | 0542422 A1 | 5/1993 |
| EP | 0569214 A2 | 11/1993 |
| EP | 0571033 A1 | 11/1993 |
| EP | 0 410 645 A2 | 1/1994 |
| EP | 0628824 A1 | 12/1994 |
| EP | 0 640 828 B1 | 1/1995 |
| EP | 0640828 B1 | 3/1995 |
| EP | 0136126 A2 | 4/1995 |
| EP | 0885958 A1 | 12/1998 |
| EP | 1024355 A1 | 8/2000 |
| EP | 1138784 A2 | 10/2001 |
| EP | 1 701 275 A2 | 9/2006 |
| GB | 2081118 A | 2/1982 |
| GB | 2131168 A | 6/1984 |
| JP | 56-29466 | 8/1954 |
| JP | 56-31358 | 8/1954 |
| JP | 57171266 | 4/1981 |
| JP | 60-241884 A | 11/1985 |
| JP | 61-274697 A | 12/1986 |
| JP | 62-000863 | 1/1987 |
| JP | 62-44663 | 2/1987 |
| JP | 63003265 | 1/1988 |
| JP | 02-66461 | 3/1990 |
| JP | 03-007571 A | 1/1991 |
| JP | 03-105251 A2 | 5/1991 |
| JP | 3-502167 A | 5/1991 |
| JP | 04-328467 A | 11/1992 |
| JP | 4-359154 | 12/1992 |
| JP | 05-10957 | 1/1993 |
| JP | 5-317030 A | 12/1993 |
| JP | 6-197797 | 7/1994 |
| JP | 6-509647 A | 10/1994 |
| JP | 07-75544 A | 3/1995 |
| JP | 7-501933 A | 3/1995 |
| JP | 7/107975 A2 | 4/1995 |
| JP | 7/107999 A2 | 4/1995 |
| JP | 07-163397 A | 6/1995 |
| JP | 7-191042 A | 7/1995 |
| JP | 7-506184 A | 7/1995 |
| JP | 8-9957 A | 1/1996 |
| JP | 8/320274 A | 12/1996 |
| JP | 9-224644 | 2/1997 |
| JP | 9-503660 A | 4/1997 |
| JP | 9-121899 A | 5/1997 |
| JP | 9-504428 A | 5/1997 |
| JP | 9-504610 A | 5/1997 |
| JP | 10-201464 A | 8/1998 |
| JP | 11-503315 A | 3/1999 |
| JP | 2000-500331 A | 1/2000 |
| JP | 2000-214090 A | 8/2000 |
| JP | 2001-503730 A | 3/2001 |
| JP | 2001-314194 A | 11/2001 |
| JP | 2001-314195 A | 11/2001 |
| JP | 2002-513936 A | 5/2002 |
| JP | 2004-520574 A | 7/2004 |
| WO | WO 90/008840 A1 | 8/1990 |
| WO | WO 9115768 A1 | 10/1991 |
| WO | WO 93/03383 A1 | 2/1993 |
| WO | WO 93/07292 A1 | 4/1993 |
| WO | WO 93/20450 A1 | 10/1993 |
| WO | WO 93/25912 A2 | 12/1993 |
| WO | WO 95/11454 A1 | 4/1995 |
| WO | WO 96/31781 A1 | 10/1996 |
| WO | WO 97/16561 A1 | 5/1997 |
| WO | WO 9731105 A1 | 8/1997 |
| WO | WO 97/34908 A1 | 9/1997 |
| WO | 97/46707 A2 | 11/1997 |
| WO | WO 9746707 A2 | 12/1997 |
| WO | WO 98/00697 A1 | 1/1998 |
| WO | 99/57561 A2 | 11/1999 |
| WO | 01/04608 A1 | 1/2001 |
| WO | WO 01/04608 A | 1/2001 |
| WO | 01/066799 A2 | 9/2001 |
| WO | 01/75153 A2 | 10/2001 |
| WO | 03/029924 A2 | 4/2003 |
| WO | 2003067215 A2 | 8/2003 |
| WO | 03097808 A2 | 11/2003 |
| WO | 04/087950 A2 | 10/2004 |
| WO | 2004/087950 A2 | 10/2004 |
| WO | 05/030990 A1 | 4/2005 |

OTHER PUBLICATIONS

EPO Search Report., European Patent Application No. 11001533.6, dated May 9, 2014.
USPTO Notice of Allowance, U.S. Appl. No. 12/630,302, dated Apr. 17, 2013.
USPTO Supplemental Notice of Allowance, U.S. Appl. No. 12/630,302, dated May 28, 2013.
USPTO Notice of Allowance, U.S. Appl. No. 11/372,468, dated Aug. 2, 2013.
USPTO Notice of Allowance, U.S. Appl. No. 12/791,390, dated Oct. 16, 2013.
USPTO Final Office Action, U.S. Appl. No. 12/791,390, dated Nov. 8, 2012.
USPTO Non-final Office Action, U.S. Appl. No. 12/630,302, dated Nov. 13, 2012.
USPTO Notice of Allowance U.S. Appl. No. 12/939,420, dated Sep. 10, 2012.
JPO Notice of Reasons for Rejection, Japanese Application No. 2008-501021, dated Sep. 7, 2011.
USPTO Office Action, U.S. Appl. No. 12/939,420, dated Dec. 1, 2011.
USPTO Office Action, U.S. Appl. No. 13/031,889, dated Dec. 6, 2011.
USPTO Final Office Action in U.S. Appl. No. 11/372,221, dated Apr. 27, 2010.
USPTO Non-Final Office Action in U.S. Appl. No. 11/372,220, dated Dec. 21, 2009.
USPTO Final Office Action in U.S. Appl. No. 11/372,223, dated Mar. 22, 2010.
USPTO Final Office Action in U.S. Appl. No. 11/372,222, dated Dec. 7, 2009.
USPTO Office Action, U.S. Appl. No. 11/372,221, dated Jul. 14, 2009.
USPTO Office Action, U.S. Appl. No. 11/372,220, dated Jul. 1, 2009.

(56) References Cited

OTHER PUBLICATIONS

USPTO Office Action, U.S. Appl. No. 11/372,222, dated Nov. 18, 2009.
PCT Search Report, International Application No. PCT/US06/08823, dated Sep. 20, 2006.
PCT Written Opinion, International Application No. PCT/US06/08823, dated Sep. 20, 2006.
PCT International Preliminary Examination Report, International Application No. PCT/US06/08823, dated Sep. 20, 2007.
EPO Search Report, European Patent Application No. 05019226.9, dated Feb. 12, 2007.
USPTO Final Office Action, U.S. Appl. No. 11/372,220, dated Jul. 9, 2010.
USPTO Office Action, U.S. Appl. No. 12/143,593, dated Sep. 2, 2010.
USPTO Final Office Action, U.S. Appl. No. 11/372,217, dated Aug. 28, 2009.
EPO Office Action, European Patent Application No. 08003851.6, dated Mar. 13, 2009.
USPTO Notice of Allowance, U.S. Appl. No. 11/372,220, dated Apr. 14, 2011.
USPTO Office Action, U.S. Appl. No. 11/372,221, dated Sep. 3, 2010.
USPTO Final Office Action, U.S. Appl. No. 11/372,217, dated Aug. 19, 2010.
USPTO Final Office Action, U.S. Appl. No. 13/031,889, dated Apr. 25, 2012.
USPTO Office Action, U.S. Appl. No. 13/031,889, dated Aug. 12, 2013.
USPTO Office Action, U.S. Appl. No. 13/031,889, dated Jan. 22, 2014.
USPTO Office Action, U.S. Appl. No. 13/031,889, dated Apr. 9, 2015.
USPTO Office Action, U.S. Appl. No. 13/031,889, dated Aug. 25, 2015.
USPTO Notice of Allowance, U.S. Appl. No. 13/031,889, dated Feb. 12, 2016.
USPTO Advisory Action, U.S. Appl. No. 11/372,222, dated Mar. 18, 2010.
USPTO Office Action, U.S. Appl. No. 11/372,222, dated Jul. 28, 2010.
CIPO Notice of Allowance, Canadian Patent Application No. 2,842,404, dated Aug. 4, 2015.
CIPO Examination Report, Canadian Patent Application No. 2,842,402, dated Jan. 23, 2015.
CIPO Examination Report, Canadian Patent Application No. 2,842,402, dated May 11, 2015.
CIPO Notice of Allwance, Canadian Patent Application No. 2,842,402, dated Aug. 24, 2015.
EPO Extended Search Report, European Patent Application No. 08001232.1, dated Apr. 14, 2014.
EPO Extended Search Report, European Patent Application No. 08003069.5, dated Apr. 28, 2014.
EPO Communication pursuant to Article 94(3) EPC, European Patent Application No. 08003069.5, dated Oct. 1, 2015.
JPO Office Action, Japanese Patent Application No. 2011-268074, dated Sep. 9, 2013.
JPO Office Action, Japanese Patent Application No. 2011-268074, dated Sep. 19, 2014.
JPO Office Action, Japanese Patent Application No. 2012-138987, dated Jan. 30, 2015.
JPO Office Action, Japanese Patent Application No. 2012-138987, dated Jan. 30, 2014.
JPO Notice of Allowance, Japanese Patent Application No. 2012-138987, dated Apr. 26, 2015.
JPO Office Action, Japanese Patent Application No. 2015-008239, dated Mar. 11, 2015.
EPO Search Report, European Patent Application No. 08003851.6, dated Aug. 19, 2008.
USPTO Office Action, U.S. Appl. No. 11/372,217, dated Dec. 16, 2008.
USPTO Office Action, U.S. Appl. No. 11/372,220, dated Jan. 2, 2009.
USPTO Office Action, U.S. Appl. No. 11/372,222, dated Apr. 16, 2009.
USPTO Office Action, U.S. Appl. No. 11/372,223, dated May 18, 2009.
USPTO Office Action, U.S. Appl. No. 11/372,217, dated Feb. 5, 2010.
USPTO Final Office Action, U.S. Appl. No. 11/372,223, dated Mar. 22, 2010.
USPTO Advisory Action, U.S. Appl. No. 11/372,217, dated Nov. 2, 2010.
USPTO Notice of Allowance, U.S. Appl. No. 11/372,217, dated Dec. 10, 2010.
USPTO Notice of Allowance, U.S. Appl. No. 11/372,222, dated Dec. 27, 2010.
USPTO Final Office Action, U.S. Appl. No. 12/939,420, dated Jun. 13, 2012.
ABI PRISM 7700 Sequence Detection System, User Bulletin #2, "Relative Quantitation of Gene Expression," Dec. 11, 1997, pp. 1-36, PE Applied Biosystems, U.S.A.
Chiche et al. Protein model structure evaluation using the solvation free energy of folding. PNAS, vol. 87, 1990, pp. 3240-3243.
Definition of Inflection. The Hutchinson Unabridged Encyclopedia with Atlas and Weather Guide, 2009, 1 page. Retrieved online on Jan. 12, 2010 <<http://www.credoreference.com/entry/heliconhe/inflection/1 >>.
Deniz et al. Single-molecule protein foiling: Diffusion fluorescence resonance energy transfer studies of the denaturation of chymotrypsin inhibitor 2. PNAS, 2000, vol. 97, pp. 5179-5184.
Dodge et al. A microfluidic platform using molecular beacon-based temperature calibration for thermal dehybridization of surface-bound DNA. Analytical Chemistry, available online Feb. 10, 2004, vol. 76, pp. 1778-1787.
EPO Search Report, European Patent Application No. 1 001 0799.4, dated Apr. 13, 2011.
Gruber et al., "Quantitation of Viral DNA by Real-Time PCR Applying Duplex Amplification, Internal Standardization, and Two-Color Fluorescence Detection," Appl. and Environ. Microbiol., 2001, 67(6):2837-2839, American Society for Microbiology, Washington, D.C.
Ishihama et al. Nano-scale monitoring of the thermally-induced unfolding of proteins using capillary electrophoresis with in-column incubation. Analytical Sciences. 1997, vol. 13, pp. 931-938.
Ke et al. Influence of nearest neighbor sequence on the stability of base pair mismatches in long DNA: determination by temperature-gradient gel electrophoresis. Nucleic Acids Research, 1993, vol. 21, pp. 5137-5143.
Notice of Final Rejection, Japanese Application No. 2003-501021, dated Feb. 27, 2012.
Roche Applied Sciences Technical Note No. LC 13/2000, LightCycler, "Relative Quantification," Roche Diagnostics, Germany.
Roche Molecular Biochemicals Technical Note No. LC 12/2000, LightCycler, "Absolute Quantification with External Standards and an Internal Control," Roche Diagnostics, Germany.
Weusten et al., "Prionciples of Quantitation of viral loads using nucleic acid sequence-based amplification in combination with homogeneous detection using molecular beacons," Nucleic Acids Res., 2002, 30(6):e26 (pp. 1-7), Oxford University Press, England.
Zhao et al., "Comprehensive Algorithm for Quantitative Real-Time Polymerase Chain Reaction," J. Comput. Biol., 2005, 12(8)1047-1064, Mary Ann Liebert, Inc., N.Y.
European Examination Report, European Application No. 10010799.4-1222, dated Jun. 18, 2012.
USPTO Office Action, U.S. Appl. No. 12/791,390, dated Jun. 27, 2012.

(56) References Cited

OTHER PUBLICATIONS

Anonymous, "Cup and Tip Supply Ring," Research Disclosure, Mason Publications, Emsworth GB, No. 318, 3 pages (Oct. 1990).

Bowie et al., "α-Thalassemia Subtyping the Detection of Silent Mutations by High-Resolution Fragment Analysis and DNA Sequencing", Mol. Diagn., 3: 43-53 (Mar. 1998).

Kristensen et al., "High-Throughput Screening for Known Mutations by Automated Analysis of Single Sequencing Reactions", BioTechniques, 24: 832-835 (May 1998).

Leonard et al., "Preparation of PCR Products for DNA Sequencing", BioTechniques, 24: 314-317 (Feb. 1998).

Schmitz et al., "Recent Advances in Molecular Genetics of Cardiovascular Disorders—Implications for Atherosclerosis and Diseases of Cellular Lipid Metabolism", Pathol. Oncol. Res. 4: 153-161 (1998).

Van Gemen et al., "The One-tube Quantitative HIV-1 RNA NASBA: Precision, Accuracy, and Application", PCR Methods and Applications, 4:S177-S184, Cold Spring Harbor Laboratory (1995).

Wu et al., "Strategies for Unambiguous Detection of Allelic Heterozygosity via Direct DNA Sequencing of PCR Products: Application to the HLA DRB1 Locus", Mol. Diagn., 1: 89-98 (Jun. 1996).

JPO Notice of Allowance, Japanese Patent Application No. 2015-008239, dated Aug. 20, 2015.

DiDomenico et al., COBAS AMPLICOR™: fully automated RNA and DNA amplification and detection system for routine diagnostic PCR, Clin. Chem., 1996, 42(12):1915-1923, American Association for Clinical Chemistry, USA.

EPO Examination Report, European Patent Application No. 08001232.1, dated Jul. 13, 2016.

CIPO Examination Report, Canadian Patent Application No. 2,929,501, dated Jul. 7, 2016.

CIPO Notice of Allowance, Canadian Patent Application No. 2,929,501, dated Nov. 15, 2016.

EPO Examination Report, European Patent Application No. 08001232.1, dated Jan. 31, 2017.

EPO Examination Report, European Patent Application No. 08003069.5, dated Nov. 23, 2016.

EPO Communication pursuant to Article 94(3) EPC, European application No. 08001232.1, dated Sep. 9, 2017.

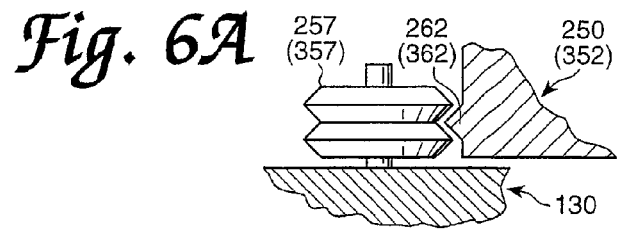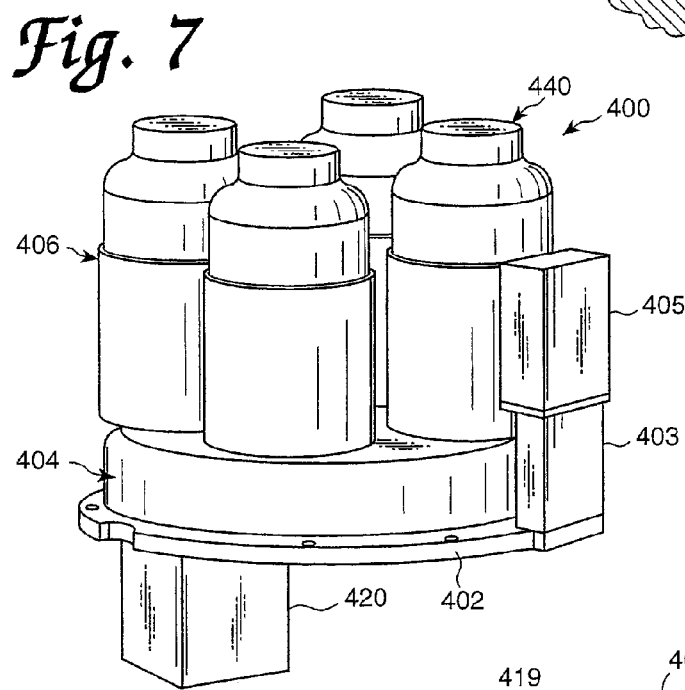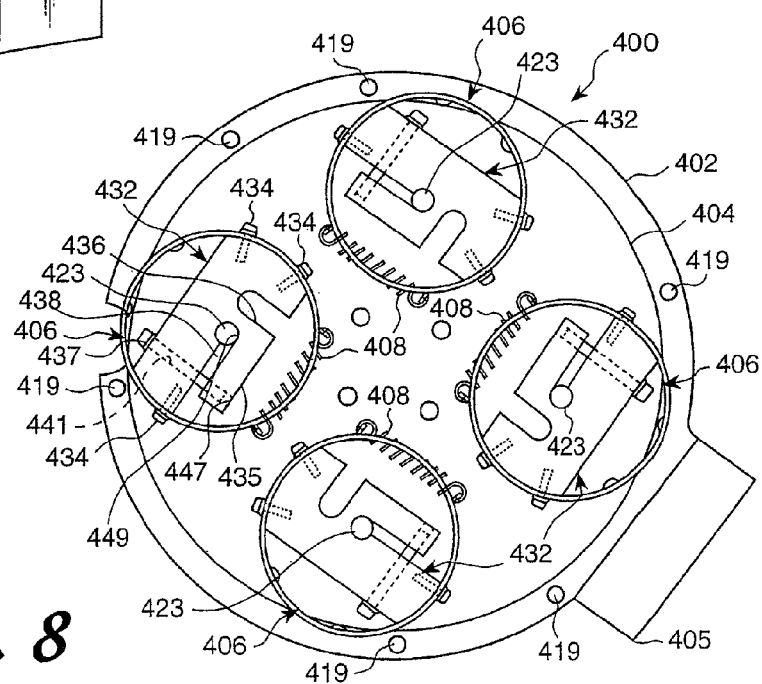

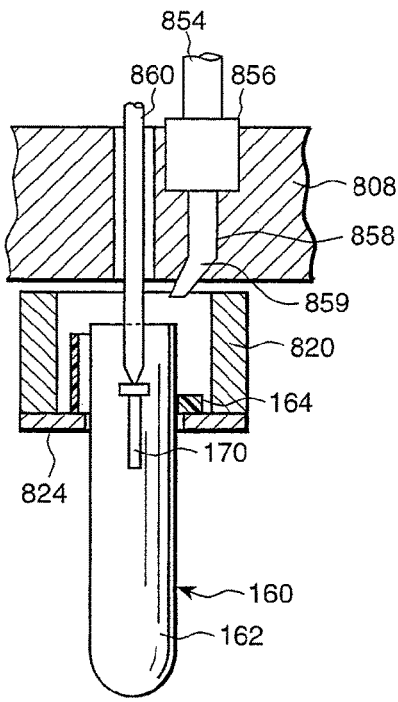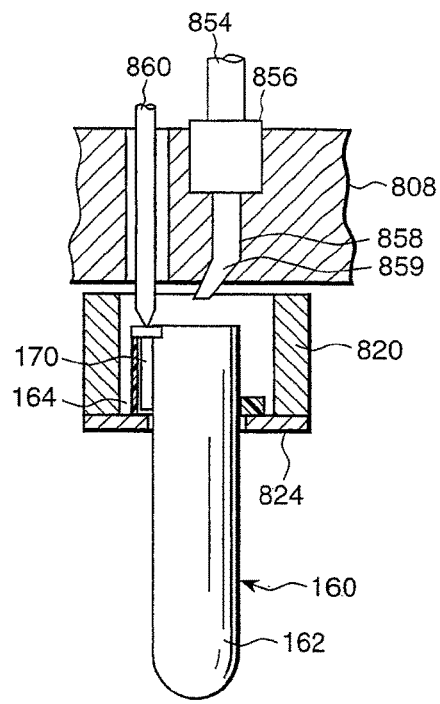

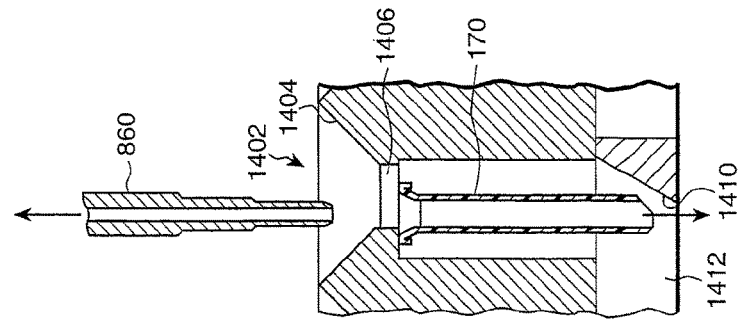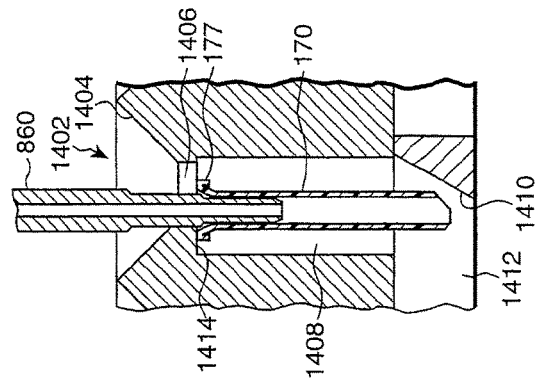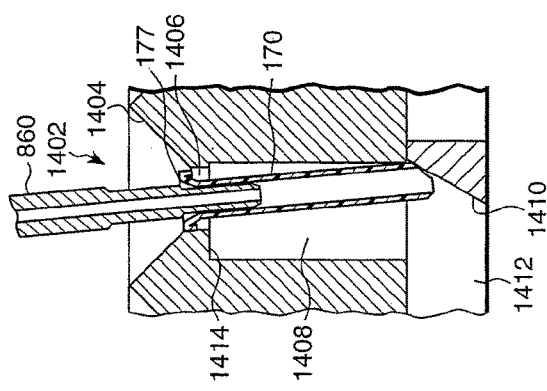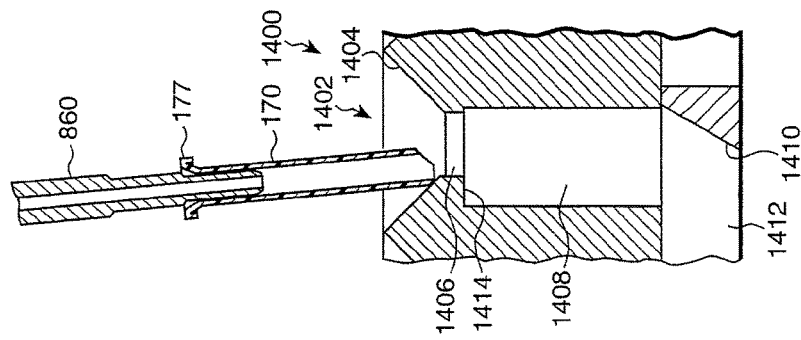

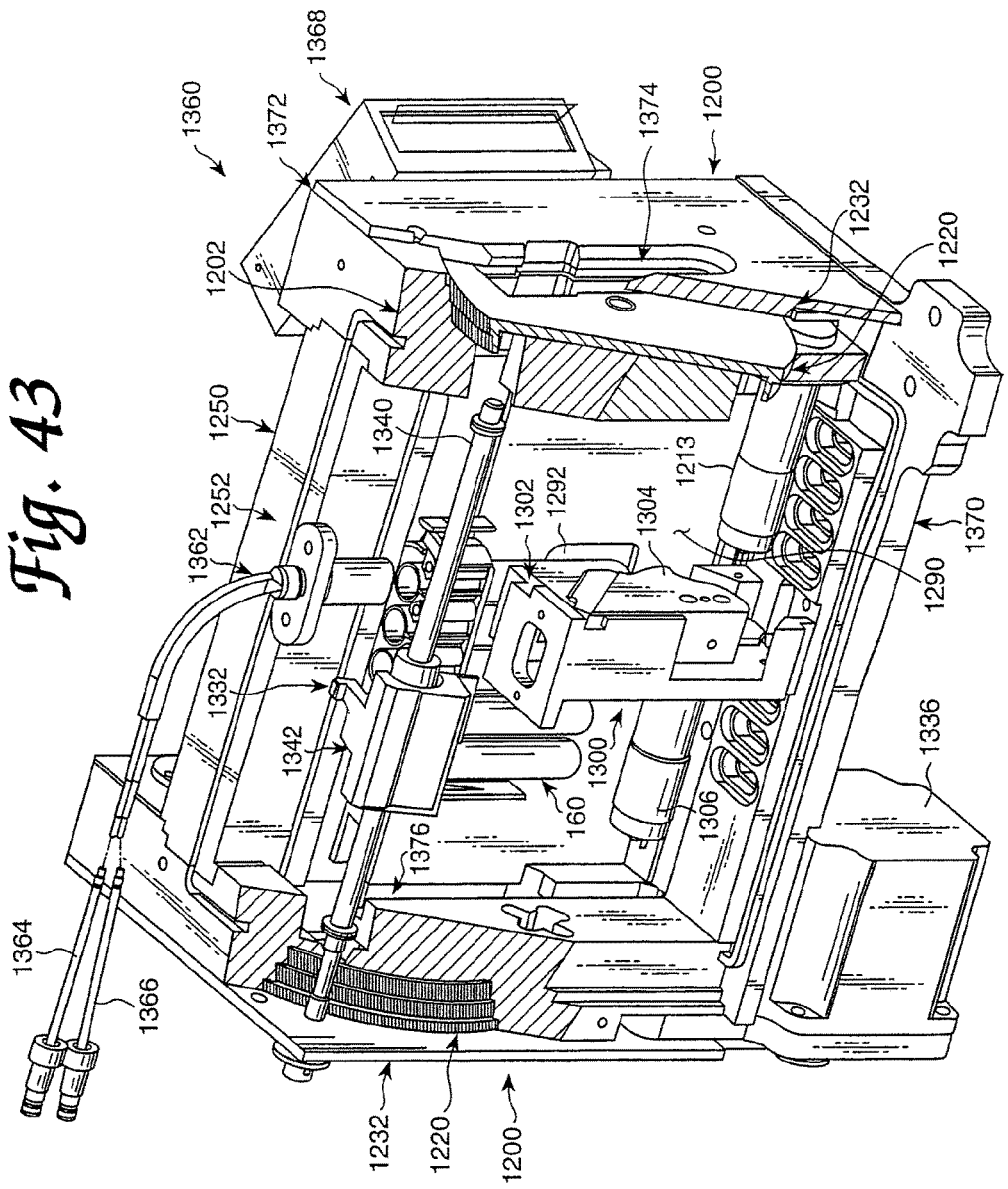

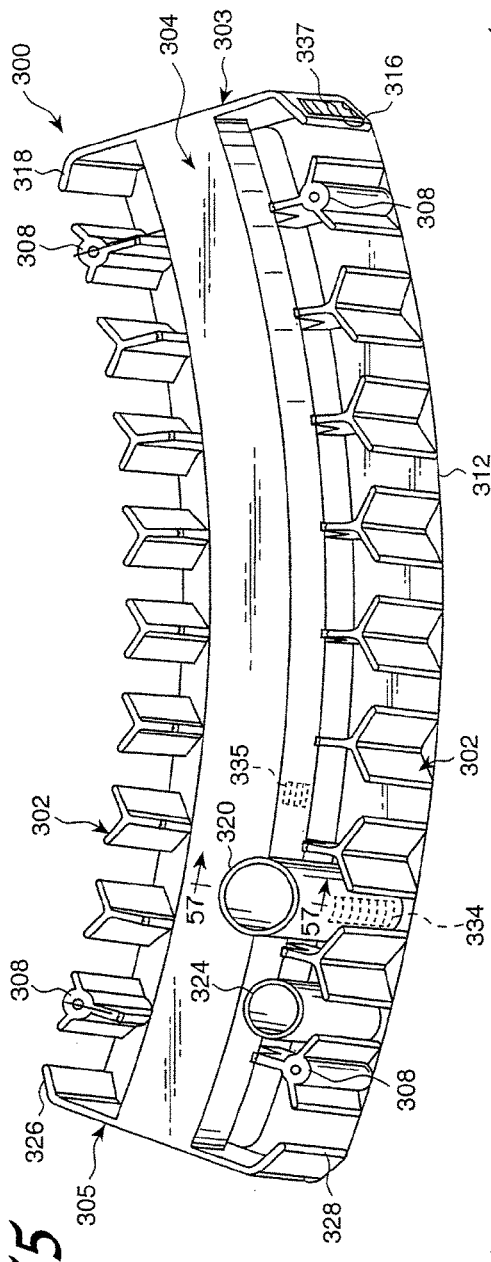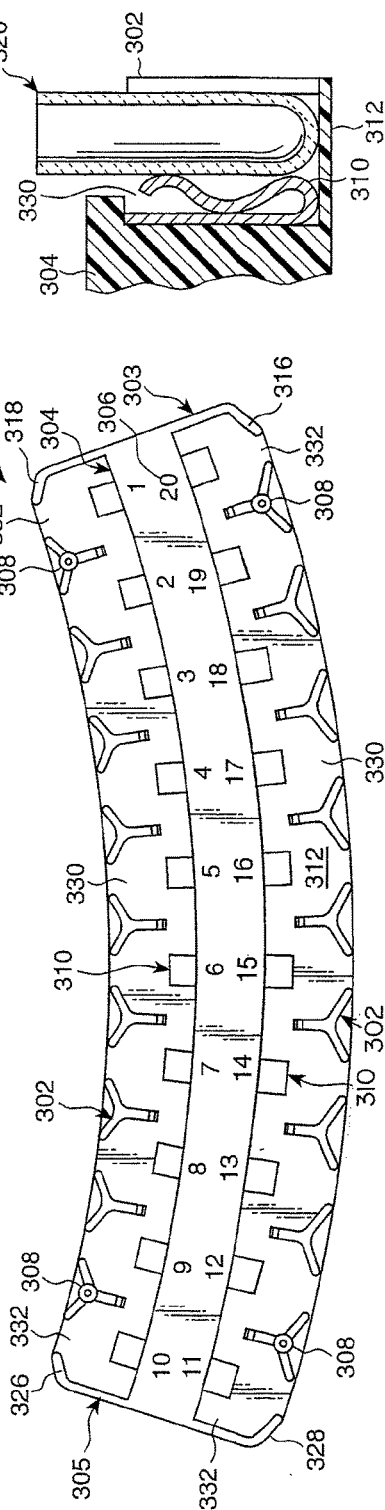

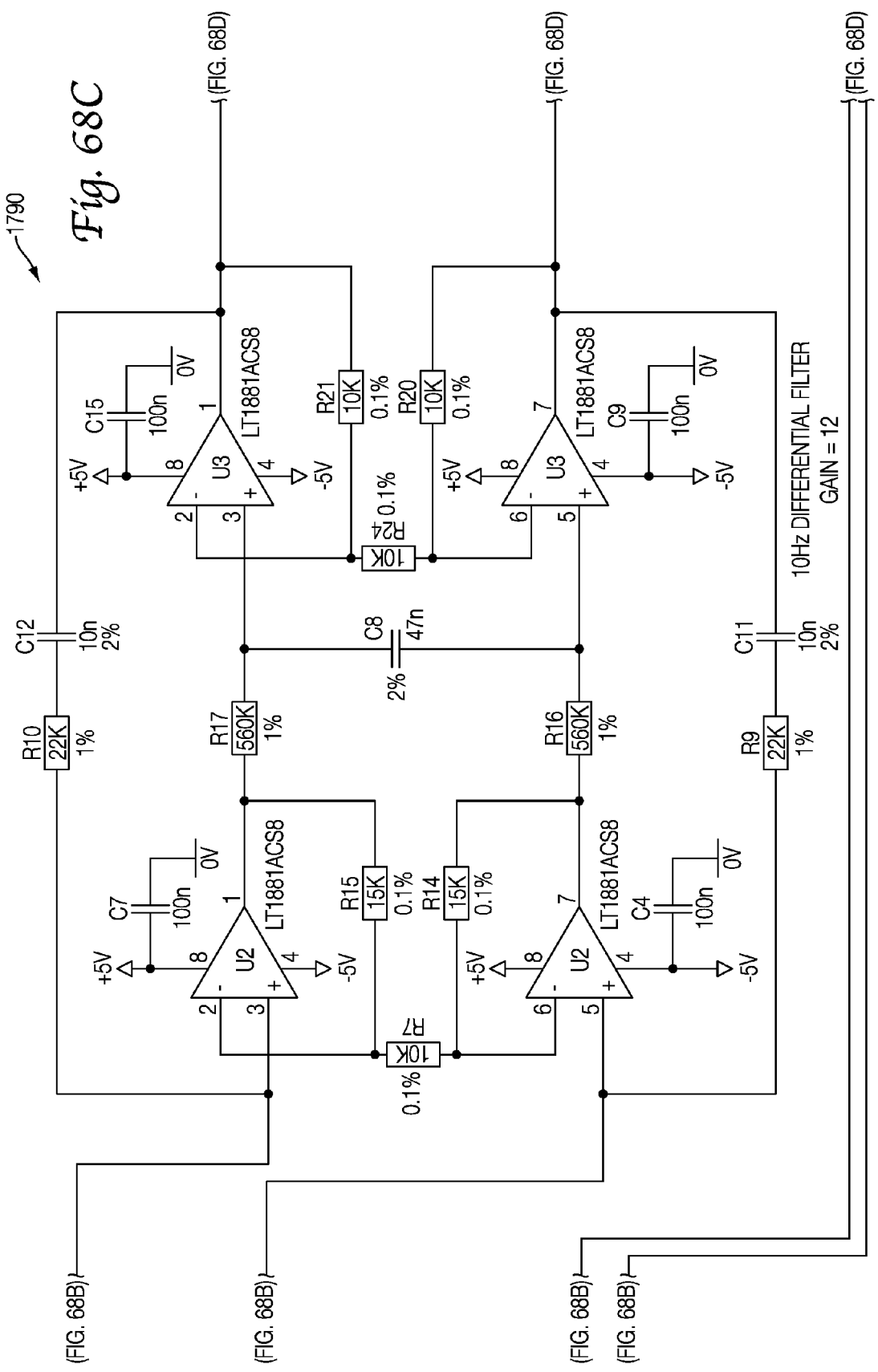

ial analyzer for simultaneously performing multiple nucleic acid-based assays, and more specifically to a system and method for performing multiple nucleic acid amplification assays, including both real-time and end-point amplifications assays. The present invention also relates to an apparatus and method for continuously processing the contents of a plurality of reaction receptacles following a real-time amplification procedure. The present invention further relates to a method for reducing the presence of amplification inhibitors in reaction receptacles prior to performing nucleic acid amplification reactions.

CONTINUOUS PROCESS FOR PERFORMING MULTIPLE NUCLEIC ACID AMPLIFICATION ASSAYS

RELATED APPLICATIONS

This application is a continuation of U.S. application Ser. No. 14/195,793, filed Mar. 3, 2014, now pending, which is a divisional of U.S. application Ser. No. 12/791,390, filed Jun. 1, 2010, now U.S. Pat. No. 8,663,922, which is a continuation of U.S. application Ser. No. 11/372,221, filed Mar. 10, 2006, now U.S. Pat. No. 8,008,066, which claims the benefit of U.S. Provisional Application No. 60/659,874 filed Mar. 10, 2005, the contents of each of which application is hereby incorporated by reference herein.

FIELD

The present invention relates generally to an automated analyzer for simultaneously performing multiple nucleic acid-based assays, and more specifically to a system and method for performing multiple nucleic acid amplification assays, including both real-time and end-point amplifications assays. The present invention also relates to an apparatus and method for continuously processing the contents of a plurality of reaction receptacles following a real-time amplification procedure. The present invention further relates to a method for reducing the presence of amplification inhibitors in reaction receptacles prior to performing nucleic acid amplification reactions.

BACKGROUND

Nucleic acid-based assays can enable highly specific and sensitive detection of nucleic acid analytes from a variety of sources, including clinical, industrial, environmental, and food sources. These assays can be used to determine or monitor for the presence or amount of biological antigens (e.g., prions), cell abnormalities, disease states, and disease-associated pathogens, including parasites, fungi, bacteria and viruses present in a host organism or sample. Nucleic acid-based assays may be qualitative or quantitative, with the quantitative assays providing useful information to practitioners for evaluating the extent of infection or disease or to determine the state of a disease over time. Quantitative assays can also be used, for example, to assess the effectiveness of a therapeutic treatment program or, alternatively, to determine the extent of an infection or contamination by a particular organism or virus.

All nucleic acid-based assay formats involve a number of process steps leading to the identification, detection or quantification of one or multiple target nucleic acids in a sample. When necessary, the specifically targeted nucleic acid sequences of a nucleic acid-based assay may be unique to an identifiable group of organisms (as used herein, the term "organisms" is inclusive of viruses), where the group is defined by at least one shared nucleic acid sequence that is common to all members of the group and that is specific to that group. (A "group" of organisms is generally a phylogenetic grouping of organisms, such as a strain, species or genus of organisms and may be limited to a single organism.) Generally, the uniqueness of the targeted nucleic acid sequence or sequences need only be limited to the particular sample type being assayed (e.g., a human sample versus an industrial or environmental sample). Nucleic acid-based methods and means for detecting individual and groups of organisms are disclosed by Kohne, "Method for Detection, Identification and Quantitation of Non-Viral Organisms," U.S. Pat. No. 4,851,330, and Hogan et al., "Nucleic Acid Probes for Detection and/or Quantitation of Non-Viral Organisms," U.S. Pat. No. 5,541,308.

After determining what organisms are to be targeted by an assay, the first step is to select or design a probe which exhibits specificity for a nucleic acid sequence belonging to those organisms which define the group. Nucleic acid-based assays can be designed to detect either deoxyribonucleic acid (DNA) or ribonucleic acid (RNA), including ribosomal RNA (rRNA), transfer RNA (tRNA) or messenger RNA (mRNA). For prokaryotic and eukaryotic organisms, rRNA or the encoding DNA (rDNA) is generally a preferred target for detection. Ribosomal RNA sequences are particularly preferred targets for non-amplified, nucleic acid-based assays because of their relative abundance in cells, and because rRNA contains regions of sequence variability that can be exploited to design probes capable of distinguishing between even closely related organisms. Viruses, which do not contain ribosomal nucleic acid, and cellular changes are often best detected by targeting DNA, RNA, or a messenger RNA (mRNA) sequence. See, e.g., McDonough et al., "Detection of Human Immunodeficiency Virus Type 1, U.S. Pat. No. 6,649,749; and Fradet et al., "Methods to Detect Prostate Cancer in a Sample," U.S. Patent Application Publication No. US 2005-0282170 A1. Such viruses may include positive-strand RNA viruses (e.g., hepatitis C virus), where the RNA genome is mRNA, negative-strand RNA viruses (e.g., influenza viruses), retroviruses (e.g., human immunodeficiency virus), single-stranded DNA viruses (e.g., parvoviruses), and double-stranded DNA viruses (e.g., adenoviruses), which would require a melting step to render the double-stranded target region sufficiently single-stranded for amplification or detection. When the focus of a nucleic acid-based assay is the detection of a genetic abnormality, then the probes are usually designed to detect identifiable changes in the genetic code, an example of which is the abnormal Philadelphia chromosome associated with chronic myelocytic leukemia. See, e.g., Stephenson et al., "Deoxynucleic Acid Molecules Useful as Probes for Detecting Oncogenes Incorporated Into Chromosomal DNA," U.S. Pat. No. 4,681,840.

When performing a nucleic acid-based assay, preparation of the sample is necessary to release and stabilize target nucleic acids which may be present in the sample. Sample preparation can also serve to eliminate nuclease activity and remove or inactivate potential inhibitors of nucleic acid amplification (discussed below) or detection of the target nucleic acids. See, e.g., Ryder et al., "Amplification of Nucleic Acids From Mononuclear Cells Using Iron Complexing and Other Agents," U.S. Pat. No. 5,639,599, which discloses methods for preparing nucleic acid for amplification, including the use of complexing agents able to complex with ferric ions released by lysed red blood cells. The method of sample preparation can vary and will depend in part on the nature of the sample being processed (e.g., blood, urine, stool, pus or sputum). When target nucleic acids are being extracted from a white blood cell population present in a diluted or undiluted whole blood sample, a differential lysis procedure is generally followed. See, e.g., Ryder et al., "Preparation of Nucleic Acid From Blood," European Patent Application No. 0 547 267 A2. Differential lysis procedures are well known in the art and are designed to specifically isolate nucleic acids from white blood cells, while limiting or eliminating the presence or activity of red blood cell products, such as heme, which can interfere with nucleic acid amplification or detection. Other lytic methods are disclosed by, for example, Cummins et al., "Methods of Extracting Nucleic Acids and PCR Amplification Without Using a Proteolytic Enzyme," U.S. Pat. No. 5,231,015, and Clark et al., "Methods for Extracting Nucleic Acids From a Wide Range of Organisms by Nonlytic Permeabilization," U.S. Pat. No. 5,837,452; and Cunningham et al., "Compositions, Methods and Kits for Determining the Presence of *Cryptosporidium* Organisms in a Test Sample," U.S. Patent Application Publication No. US 2002-0055116 A1.

To purify the sample and remove nucleases and other materials capable of interfering with amplification or detection, the targeted nucleic acid can be isolated by target-capture means using a "capture probe" which binds the target nucleic acid and is or becomes either directly or indirectly bound to a solid substrate, such as a magnetic or silica particle. See, e.g., Ranki et al., "Detection of Microbial Nucleic Acids by a One-Step Sandwich Hybridization Test," U.S. Pat. No. 4,486,539; Stabinsky, "Methods and Kits for Performing Nucleic Acid Hybridization Assays," U.S. Pat. No. 4,751,177; Boom et al., "Process for Isolating Nucleic Acid," U.S. Pat. No. 5,234,809; Englehardt et al., "Capture Sandwich Hybridization Method and Composition," U.S. Pat. No. 5,288,609; Collins, "Target and Background Capture Methods and Apparatus for Affinity Assays," U.S. Pat. No. 5,780,224; and Weisburg et al., "Two-Step Hybridization and Capture of a Polynucleotide," U.S. Pat. No. 6,534,273. When the solid support is a magnetic particle, magnets in close proximity to the reaction receptacle are used to draw and hold the magnetic particles to the side of the receptacle, thereby isolating any bound nucleic acid within the reaction receptacle. Other methods for isolating bound nucleic acid in a reaction receptacle include centrifugation and immobilizing the capture probe on the reaction receptacle. See, e.g., Boom et al., supra, and Urdea, "Polynucleotide Capture Assay Employing in Vitro Amplification," U.S. Pat. No. 5,200,314. Once the bound nucleic acid is thus isolated, the bound nucleic acid can be separated from unbound nucleic acid and other cellular and sample material by aspirating the fluid contents of the reaction receptacle and optionally performing one or more wash steps with a wash solution.

In most cases, it is desirable to amplify the target sequence. Nucleic acid amplification involves the use of nucleic acid polymerases to enzymatically synthesize nucleic acid amplification products (copies) containing a sequence that is either complementary or homologous to the template nucleic acid sequence being amplified. The amplification products may be either extension products or transcripts generated in a transcription-based amplification procedure. Examples of nucleic acid amplification procedures practiced in the art include the polymerase chain reaction (PCR), strand displacement amplification (SDA), loop-mediated isothermal amplification (LAMP) ligase chain reaction (LCR), immuno-amplification, and a variety of transcription-based amplification procedures, including transcription-mediated amplification (TMA), nucleic acid sequence based amplification (NASBA), and self-sustained sequence replication (3SR). See, e.g., Mullis, "Process for Amplifying, Detecting, and/or Cloning Nucleic Acid Sequences," U.S. Pat. No. 4,683,195; Walker, "Strand Displacement Amplification," U.S. Pat. No. 5,455,166; Notomi et al., "Process for Synthesizing Nucleic Acid," U.S. Pat. No. 6,410,278; Birkenmeyer, "Amplification of Target Nucleic Acids Using Gap Filling Ligase Chain Reaction," U.S. Pat. No. 5,427,930; Cashman, "Blocked-Polymerase Polynucleotide Immunoassay Method and Kit," U.S. Pat. No. 5,849,478; Kacian et al., "Nucleic Acid Sequence Amplification Methods," U.S. Pat. No. 5,399,491; Malek et al., "Enhanced Nucleic Acid Amplification Process," U.S. Pat. No. 5,130,238; and Lizardi et al., *BioTechnology*, 6:1197 (1988). Nucleic acid amplification is especially beneficial when the amount of target sequence present in a sample is very low. By amplifying the target sequences and detecting the synthesized amplification product, the sensitivity of an assay can be vastly improved, since fewer target sequences are needed at the beginning of the assay to ensure detection of the targeted nucleic acid sequences.

Detection of a target nucleic acid requires the use of a probe having a nucleotide base sequence which binds to a target sequence contained within the target nucleic acid or, alternatively, amplification product containing the target sequence or its complement. Probes useful for distinguishing between sources of nucleic acid are selected or designed such that they do not detectably bind to nucleic acid from non-target organisms which may be present in the sample under the selected assay conditions. While probes may include non-nucleotide components, the target binding portion of a probe will include DNA, RNA and/or analogs thereof in order to effect hybridization to the target sequence or its complement. See, e.g., Becker et al., "Modified Oligonucleotides for Determining the Presence of a Nucleic Acid Analyte in a Sample," U.S. Patent Application No. US 2003-0036058 A1 (discloses the use of 2'-O-methyl modified probes); and Nielsen et al., "Peptide Nucleic Acids," U.S. Pat. No. 5,539,082 (discloses the use of probes having a 2-aminoethylglycine backbone which couples the nucleobase subunits by means of a carboxylmethyl linker to the central secondary amine). For detection purposes, probes may include a detectable label, such as a radiolabel, fluorescent dye, biotin, enzyme or chemiluminescent compound, where the label may be provided either before, during or after hybridization to the probe to the target sequence or its complement. See, e.g., Higuchi, "Homogenous Methods for Nucleic Amplifications and Detection," U.S. Pat. No. 5,994,056 (discloses the use of intercalating agents such as eithidium bromide); and Urdea et al., "Solution Phase Nucleic Acid Sandwich Assays Having Reduced Background Noise," U.S. Pat. No. 5,635,352 (discloses use of label probes for binding to cruciform structures containing a target nucleic acid).

Nucleic acid-based assays may be based on a homogenous or a heterogenous format. One form of a heterogenous assay involves preferentially binding a probe:target complex to a solid support, such as glass, minerals or polymeric materials, and removing any unbound probe prior to detection. In an alternative approach, it is the unbound probe which is associated with the solid support while probe complexed with the target sequence remains free in solution and can be separated for detection. Homogenous assays generally take place in solution without a solid phase separation step and commonly exploit chemical differences between a probe free in solution and a probe which has formed part of a target:probe complex. An example of a homogenous assay is the Hybridization Protection Assay (HPA), the particulars of which are disclosed by Arnold et al., "Homogenous Protection Assay," U.S. Pat. No. 5,639,604. Detection in HPA is based on differential hydrolysis which permits specific detection of an acridinium ester-labeled probe hybridized to the target sequence or its complement. See, e.g., Arnold et al., "Protected Chemiluminescent Labels," U.S. Pat. No. 4,950,613; Campbell et al., "Chemilunescent Acridium Labelling Compounds," U.S. Pat. No. 4,946,958; Arnold et al., "Acridinium Ester Labelling and Purification of Nucleotide Probes," U.S. Pat. No. 5,185,439; and Arnold et al, "Linking Reagents for Nucleotide Probes," U.S. Pat. No. 5,585,481. This detection format includes both a hybridization step and a selection step. In the hybridization step, an excess of acridinium ester-labeled probe is added to the reaction receptacle and permitted to anneal to the target sequence or its complement. Following the hybridization step, label associated with unhybridized probe is rendered non-chemiluminescent in the selection step by the addition of an alkaline reagent. The alkaline reagent specifically hydrolyzes only that acridinium ester label associated with unhybridized probe, leaving the acridinium ester of the probe:target hybrid intact and detectable. Chemiluminescence from the acridinium ester of the hybridized probe can then be measured using a luminometer and signal is expressed in relative light units or RLU.

Other homogenous assays include those disclosed by the following: Gelfand et al., "Reaction Mixtures for Detection of Target Nucleic Acids," U.S. Pat. No. 5,804,375; Nadeau et al., "Detection of Nucleic Acids by Fluorescence Quenching," U.S. Pat. No. 5,958,700; Tyagi et al., "Detectably Labeled Dual Conformation Oligonucleotide Probes, Assays and Kits," U.S. Pat. No. 5,925,517; Morrison, "Competitive Homogenous Assay," U.S. Pat. No. 5,928,862; and Becker et al., "Molecular Torches," U.S. Pat. No. 6,849,412. These patents each describe unimolecular or bimolecular probes which may be used to determine the amount of a target nucleic acid in an amplification procedure in real-time, where signal changes associated with the formation of probe:target complexes are detected during amplification and used to calculate an estimated amount of a target nucleic acid present in a sample. Algorithms for calculating the quantity of target nucleic acid originally present in a sample based on signal information collected during an amplification procedure include that disclosed by Wittwer et al., "PCR Method for Nucleic Acid Quantification Utilizing Second or Third Order Rate Constants," U.S. Pat. No. 6,232,079; Sagner et al., "Method for the Efficiency-Corrected Real-Time Quantification of Nucleic Acids," U.S. Pat. No. 6,691,041; McMillan et al., "Methods for Quantitative Analysis of a Nucleic Acid Amplification Reaction," U.S. Pat. No. 6,911,327; and Chismar et al., "Method and Algorithm for Quantifying Polynucleotides," U.S. Provisional Application No. 60/693,455, which enjoys common ownership herewith.

After the nucleic acid-based assay is run, and to avoid possible contamination of subsequent amplification reactions, the reaction mixture can be treated with a deactivating reagent which destroys nucleic acids and related amplification products in the reaction receptacle. Such reagents can include oxidants, reductants and reactive chemicals which modify the primary chemical structure of a nucleic acid. These reagents operate by rendering nucleic acids inert towards an amplification reaction, whether the nucleic acid is RNA or DNA. Examples of such chemical agents include solutions of sodium hypochlorite (bleach), solutions of potassium permanganate, formic acid, hydrazine, dimethyl sulfate and similar compounds. More details of deactivation protocols can be found in Dattagupta et al., "Method and Kit for Destroying the Ability of Nucleic Acid to Be Amplified," U.S. Pat. No. 5,612,200, and Nelson et al., "Reagents, Methods and Kits for Use in Deactivating Nucleic Acids," U.S. Patent Application Publication No. US 2005-0202491 A1.

Given the large number of complex steps associated with nucleic acid-based amplification assays, and the different processing and equipment requirements of each type of amplification assay, a need exists for an automated system capable of processing the contents of a plurality of reaction receptacles according to different amplification assay protocols, and most especially for performing both real-time and end-point amplification assays on the same platform and/or within a self-contained housing. Real-time amplification assays involve periodically determining the amount of targeted amplification products as the amplification reaction is taking place, thereby making it easier to provide quantitative information about target nucleic acids present in a sample, whereas end-point amplifications determine the amount of targeted amplification products after the amplification reaction has occurred, generally making them more useful for providing qualitative information about target nucleic acids. To improve flow through and, thereby, to reduce the amount of time needed to process large volumes of samples, there is also a need for a system capable of continuously processing the contents of multiple reaction receptacles according to a real-time amplification protocol without having to interrupt the system to manually or automatically load a new batch of reaction receptacles for processing. Additionally, there is a need for a reagent and method for reducing the amount of amplification inhibitors in reaction receptacles that could affect qualitative or quantitative determinations.

SUMMARY

The above-described needs are addressed by an automated analyzer constructed and operated in accordance with aspects of the present invention. In general, the automated analyzer integrates and coordinates the operation of various automated stations, or modules, involved in performing one or more assays on a plurality of reaction mixtures contained in reaction receptacles. The analyzer is preferably a self-contained, stand-alone unit. Assay sample materials and reaction receptacles, as well as the various solutions, reagents, and other materials used in performing the assays are preferably stored within the analyzer, as are the waste products generated when assays are performed. The analyzer is an integrated nucleic acid testing system that fully automates all assay steps from sample processing through amplification and multi-format detection. In a preferred embodiment, the instrument is capable of running both real-time and end-point amplification assays. After daily set up is completed, the operator may choose to run an end-point amplification assay, a real-time amplification assay, or both. For real-time amplification assays, the analyzer of the present invention is capable of processing the contents of multiple reaction receptacles in a continuous as opposed to a batch mode, thereby greatly increasing the speed at which results can be calculated and reported. In operation, the analyzer can also be used to reduce the presence of amplification inhibitors by providing a surface treating agent that is used to coat the inner surfaces of reaction receptacles prior to or during an isolation and purification step to remove sample material and/or reagents from reaction receptacles.

The analyzer includes a computer controller which runs analyzer-controlling and assay-scheduling software to coordinate operation of the stations of the analyzer and movement of each reaction receptacle through the analyzer.

Reaction receptacles can be loaded in an input queue which sequentially presents each receptacle at a pick-up position to be retrieved by a transport mechanism, which automatically transports the reaction receptacles between the stations of the analyzer.

Sample containers are carried on a first ring assembly, and disposable pipette tips are carried on a second ring assembly. Containers of target capture reagent, including a suspension of solid support material, are carried on an inner rotatable assembly constructed and arranged to selectively agitate the containers or present the containers for access by the probe of an automatic robotic pipette system. Reaction mixtures, including fluid sample material and target capture reagent, are prepared by the pipette system within each reaction receptacle.

The analyzer further includes receptacle mixers for mixing the contents of a receptacle placed therein. The mixer may be in fluid communication with fluid containers and may include dispensers for dispensing one or more fluids into the receptacle. One or more incubators carry multiple receptacles in a temperature-controlled chamber and permit individual receptacles to be automatically placed into and removed from the chamber. Magnetic separation stations automatically perform a magnetic separation and wash procedure on the contents of a receptacle placed in the station.

In the preferred method of operation, assay results may be ascertained by the amount of light emitted from a receptacle at the conclusion of the appropriate preparation steps. Accordingly, the analyzer includes a luminometer (a type of signal detecting device) for detecting and/or quantifying the amount of light emitted by the contents of the reaction receptacle. A deactivation queue may be provided to deactivate the contents of a reaction receptacle placed therein at the conclusion of the assay.

Reaction receptacles can be independently transported between stations by the transport mechanism, and the stations can be operated in parallel to perform different assay procedures simultaneously on different reaction receptacles, thereby facilitating efficient, high through-put operation of the analyzer. Moreover, the present invention facilitates arranging the various stations associated with a nucleic acid-based assay onto a single, contained platform, thereby achieving efficient space utilization.

Other objects, features, and characteristics of the present invention, including the methods of operation and the function and interrelation of the elements of structure, will become more apparent upon consideration of the following description and the appended claims, with reference to the accompanying drawings, all of which form a part of this disclosure, wherein like reference numerals designate corresponding parts in the various figures.

DESCRIPTION OF THE DRAWINGS

FIG. 6A is a partial cross-sectional view along the line 6A-6A in FIG. 5;

FIG. 7 is a perspective view of a multi-axis mixer of the processing deck of the analyzer of the present invention;

FIG. 8 is a plan view of the multi-axis mixer;

FIG. 27 is a partial cross-sectional view of a wash solution dispenser nozzle, an aspirator tube with a contamination-limiting tiplet engaged with an end thereof, and a receptacle carrier unit of the particles, showing a multi-tube unit reaction receptacle employed in a preferred mode of operation of the analyzer carried in the receptacle carrier unit and the aspirator tube and contamination-limiting tiplet inserted into a reaction tube of the multi-tube unit;

FIG. 28 is a partial cross-sectional view of the wash solution dispenser nozzle, the aspirator tube, and the receptacle carrier unit of the particles, showing the multi-tube unit carried in the receptacle carrier unit and the aspirator tube engaging the contamination-limiting tiplet held in a contamination-limiting element holding structure of the multi-tube unit;

FIGS. 30A-30D show a partial cross-section of a second embodiment of a tiplet stripping hole and a tiplet stripping operation using the tiplet stripping hole;

FIG. 43 is a break away perspective view of a second embodiment of the luminometer of the present invention;

FIG. 45A is a perspective view of an aperture plate of the shutter assembly of the luminometer of the second embodiment;

FIG. 55 is a perspective view of a sample tube tray employed in a preferred mode of operation of the analyzer of the present invention;

FIG. 56 is a top plan view of the sample tube tray;

FIG. 57 is a partial cross-section of the sample tube tray through line "57-57" in FIG. 55;

FIGS. 68A-68F show a diagram of a circuit for the optical detection module;

DETAILED DESCRIPTION OF THE PREFERRED EMBODIMENT

While the present invention may be embodied in a variety of forms, the following descriptions and accompanying drawings are merely intended to disclose some of those forms as specific examples of the present invention. Accordingly, the present invention is not intended to be limited to the forms or embodiments so described and illustrated. Instead, the full scope of the present invention is set forth in the appended claims.

Analyzer Overview

Figure 1:
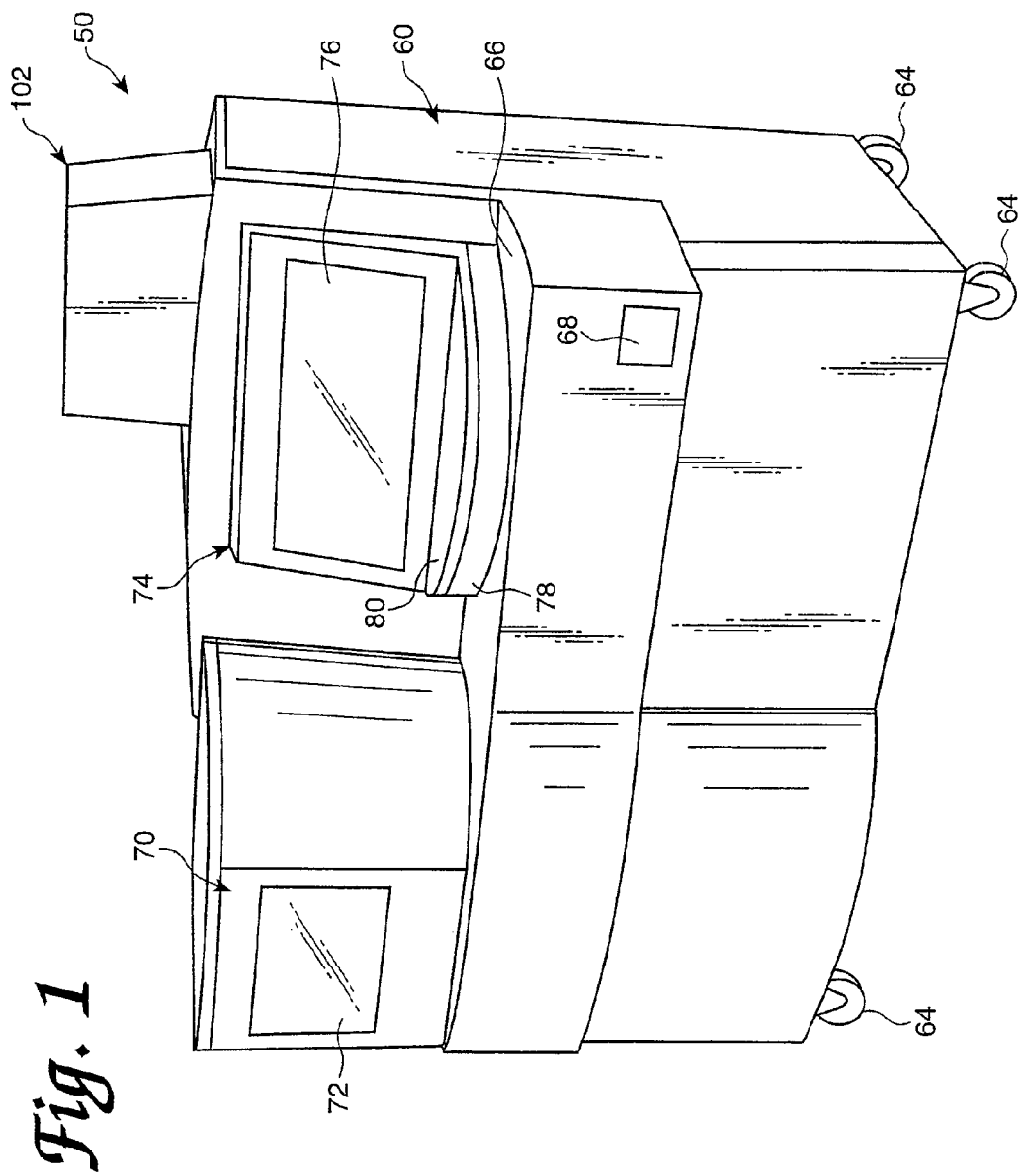
FIG. 1 is a perspective view of an automated nucleic acid-based diagnostic analyzer according to the present invention.
Figure 2:
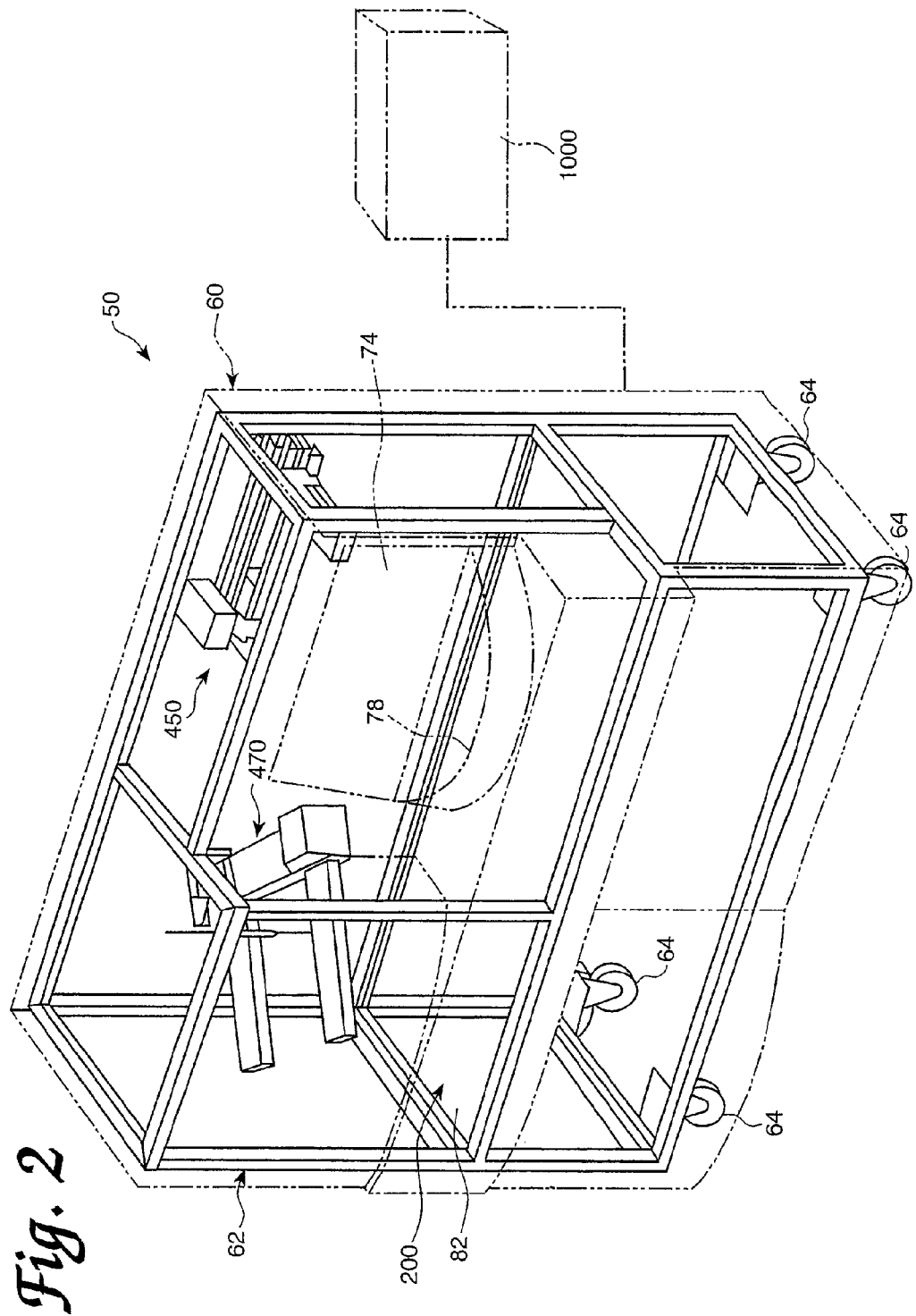
FIG. 2 is a perspective view of the structural frame of the analyzer of the present invention.

An automated diagnostic analyzer according to the present invention is designated generally by reference number 50 in FIGS. 1 and 2. Analyzer 50 includes a housing 60 built over an internal frame structure 62, preferably made of steel. The analyzer 50 is preferably supported on caster wheels 64 structurally mounted to the frame structure 62 so as to make the analyzer movable.

The various stations involved in performing an automated assay and the assay samples are housed within housing 60. In addition, the various solutions, reagents, and other materials used in performing the assays are preferably stored within the housing 60, as are the waste products generated when assays are performed with the analyzer 50.

Housing 60 includes a test receptacle loading opening 68, which is shown in FIG. 1 to be disposed in a forwardly facing panel of the housing 60, but could as well be located in other panels of the housing 60. A pipette door 70 having a view window 72 and a carousel door 74 having a view window 76 are disposed above a generally horizontal work surface 66. A forwardly protruding arcuate panel 78 accommodates a sample carousel, which will be described below. A flip-up arcuate sample door 80 is pivotally attached to the housing so as to be vertically pivotal with respect to arcuate panel 78 so as to provide access to a forward portion of the sample carousel behind the panel 78. Sensors indicate when the doors are closed, and the sample door 80, the carousel door 74, and the pipette door 70 are locked during analyzer operation. The locking mechanism for each door preferably consists of a hook attached to a DC rotary solenoid (rated for continuous duty) with a spring return. Preferred rotary solenoids are available from Lucas Control Systems, of Vandalia, Ohio, Model Nos. L-2670-034 and L-1094-034.

An extension portion 102, preferably made of a transparent or translucent material, extends above the top portion of housing 60 so as to provide vertical clearance for moving components within the housing 60.

The assays are performed primarily on a processing deck 200, which is the general location of the various assay stations of the analyzer 50 described below. For simplicity of the illustration, the processing deck 200 is shown in FIG. 2 without any of the assay stations mounted thereon. The processing deck 200 comprises a datum plate 82 to which the various stations are directly or indirectly mounted. Datum plate 82 preferably comprises a machined aluminum plate. The processing deck 200, also known as the chemistry deck, separates the interior of the housing into the chemistry area, or upper chassis, above the datum plate 82 and the storage areas, or lower chassis 1100, located below the datum plate 82.

A number of fans and louvers are preferably provided in the upper chassis portion of the housing 60 to create air circulation throughout the upper chassis to avoid excessive temperatures in the upper chassis.

As the analyzer 50 of the present invention is computer controlled, the analyzer 50 includes a computer controller, schematically represented as box 1000 in FIG. 2, which runs high-level analyzer-controlling software known as the "assay manager program". The assay manager program includes a scheduler routine which monitors and controls test sample movement through the chemistry deck 200.

The computer controller 1000 which controls the analyzer 50 may include a stand-alone computer system including a CPU, keyboard, monitor, and may optionally include a printer device. A portable cart may also be provided for storing and supporting the various computer components. Alternately, the computer hardware for running the analyzer-controlling software may be integrally housed within the housing 60 of the analyzer 50.

Low level analyzer control, such as control of electric motors and heaters used throughout the analyzer 50 and monitoring of fluid levels within bulk fluid and waste fluid containers, is performed by an embedded controller, preferably comprising a Motorola 68332 microprocessor. Stepper motors used throughout the analyzer are also preferably controlled by preprogrammed, off-the-shelf, microprocessor chips available from E-M Technologies, Bala Cynwyd, Pa.

Figure 3:
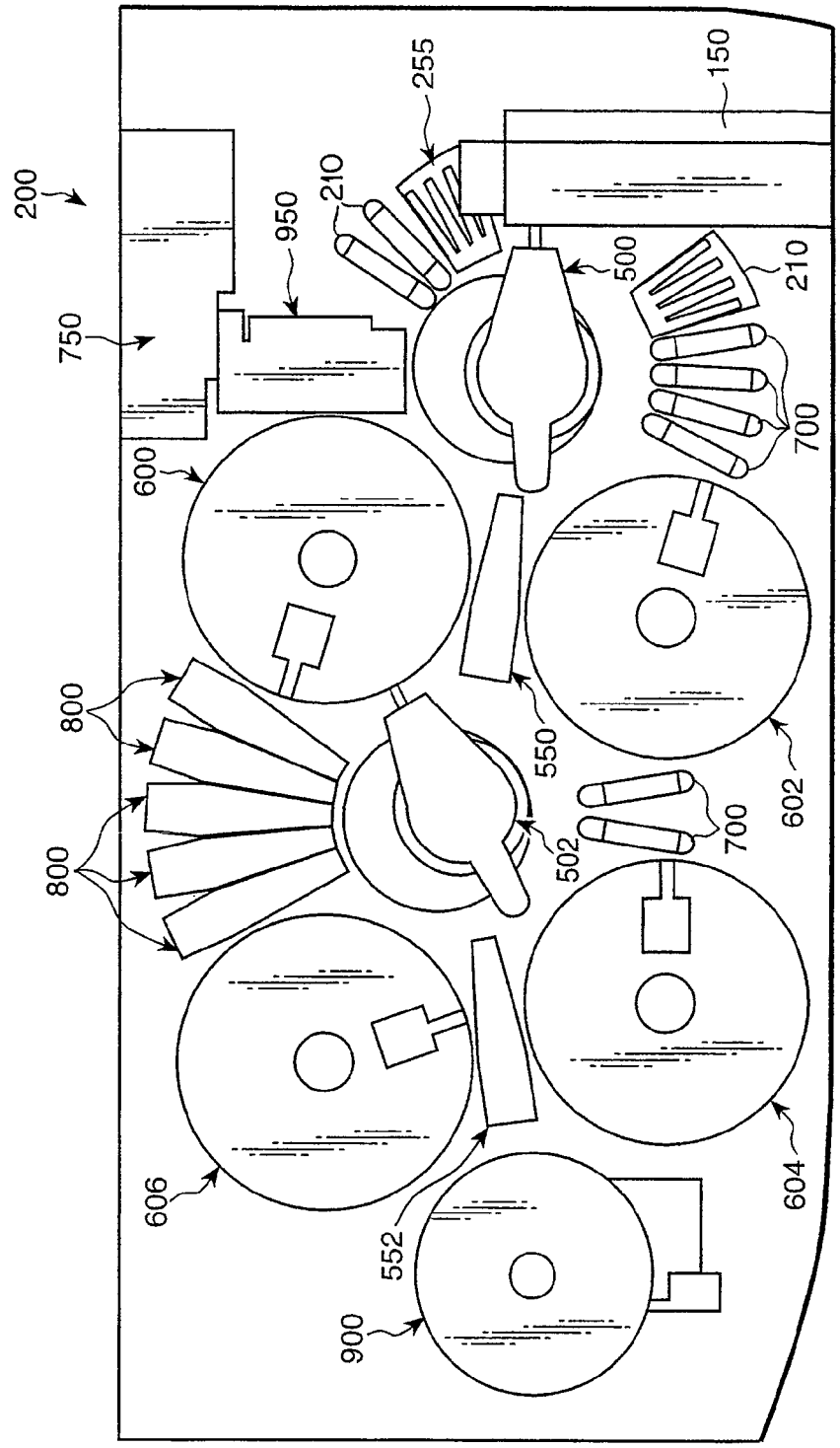
FIG. 3 is a plan view of a portion of the assay processing deck of the analyzer of the present invention.
Figure 4:
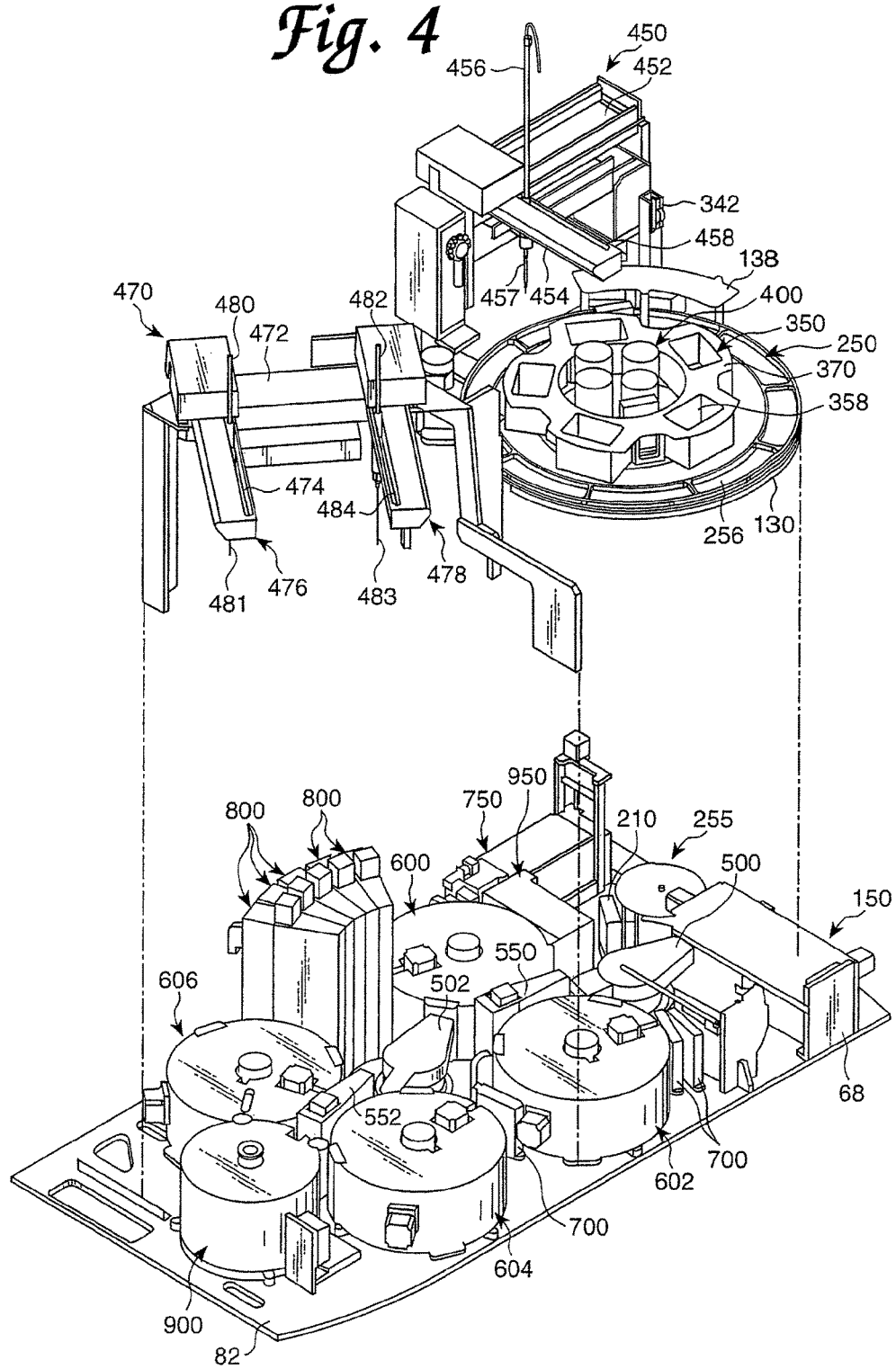
FIG. 4 is an exploded perspective view of the assay processing deck.

The processing deck 200 is shown schematically in FIGS. 3 and 4. FIG. 3 represents a schematic plan view of a portion of the processing deck 200, and FIG. 4 represents a schematic perspective view of the processing deck. The datum plate 82 forms the foundation of the processing deck 200 on which all stations are directly or indirectly attached.

Processing deck 200 includes a reaction receptacle input queue 150 which extends from opening 68 in front of housing 60. A plurality of reaction receptacles are loaded in a stacked fashion in the input queue 150. The purpose of the input queue is to hold a prescribed number of reaction receptacles and to sequentially present them at a pick-up position to be retrieved by a transport mechanism (described below). A reflective sensor at the pick-up position verifies the presence of a receptacle at that position. The input queue also includes a device for counting the number of receptacles resident therein at any given time.

A reaction receptacle shuttle assembly (not shown) within the queue moves the receptacles along a receptacle advance path toward the pick-up position. Optical sensors indicate when the shuttle assembly is in its home and fully extended positions. The queue includes a drawer which may be pulled out for loading the receptacles therein. Before the drawer is opened, however, it must be unlocked and the shuttle must disengage from the receptacle advance path. When the drawer is again closed, it is locked and the shuttle engages the receptacles and moves them toward the pick-up position. Optical sensors indicate when the drawer is closed and when the shuttle has engaged a receptacle. As each receptacle is removed from the pick-up position by the transport mechanism, the receptacle shuttle advances the receptacles one receptacle-width, so that the next receptacle is in the pick-up position.

While the analyzer 50 may be adapted for use with reaction receptacles consisting of single reaction receptacles or integrally formed units containing a plurality of reaction receptacles having any of a number of different shapes, sizes and configurations, the reaction receptacles of the present invention are preferably integrally formed linear arrays of reaction tubes known as multi-tube units or MTUs. These preferred reaction receptacles will be described in more detail below.

A first ring assembly, which in the preferred embodiment comprises a sample ring 250, is mounted on a pivoting jig plate 130 at a distance above the datum plate 82. Sample ring 250 is generally circular and preferably holds up to nine sample trays 300 in an annular fluid container carrier portion thereof, and each of the sample trays preferably holds 20 sample-containing containers, or test tubes 320. The sample ring 250 is constructed and arranged to be rotatable about a first generally vertical axis of rotation and delivers the sample tubes 320 to a sample pipette assembly 450, preferably an automated robotic pipette system. The forward portion of sample ring 250 is accessible through the flip-up carousel door 80 provided in housing 60 so that trays 300 of test tubes 320 can be easily loaded onto the sample ring 250 and unloaded from the sample ring. Sample ring 250 is driven by a motor, as will be described in more detail below.

A second ring assembly, which in the preferred embodiment comprises a pipette tip wheel 350, is located in an interior portion of the sample ring 250, so that at least a portion of the outer perimeter of the pipette tip wheel 350 is disposed radially inwardly of the inner periphery of the ring 250. Pipette tip wheel 350 carries thereon a plurality of commercially available packages of pipette tips. Pipette tip wheel 350 is motor driven to rotate independently of sample ring 250 about a second axis of rotation that is generally parallel to the first axis of rotation of the sample ring 250.

An inner rotatable assembly constructed and arranged to carry a plurality of fluid containers is provided at an interior portion of the pipette tip wheel 350. In the preferred embodiment, the inner rotatable assembly comprises a multi-axis mixer 400 located radially inside the pipette tip wheel 350 (i.e., the second ring assembly) and sample ring 250 (i.e., the first ring assembly). The multi-axis mixer 400 includes a rotating turntable 414 that is rotatable about a third axis of rotation that is generally parallel to the first and second axes of rotation and on which are mounted four independently and eccentrically rotating container holders 406. Each of the container holders 406 receives a container, preferably in the form of a plastic bottle, containing a fluid suspension of magnetic particles with immobilized polynucleotides and polynucleotide capture probes. Each container holder 406 is generally cylindrical in shape and includes an axis of symmetry, or axis of rotation. The multi-axis mixer 400 rotates each of the containers eccentrically with respect to the center of the holder 406, while simultaneously rotating the turntable 414 about its center so as to provide substantially constant agitation of the containers to maintain the magnetic particles in suspension within the fluid.

The sample pipette assembly, or robot, 450 is mounted to the frame structure 62 (see FIG. 2) in a position above the sample ring 250 and pipette tip wheel 350. The sample pipette assembly 450 includes a pipette unit 456 having a tubular probe 457 mounted on a gantry assembly to provide X, Y, Z motion. Specifically, the pipette unit 456 is linearly movable in the Y-direction along a track 458 formed in a lateral rail 454, and the lateral rail 454 is longitudinally movable in the X-direction along a longitudinal track 452. The pipette unit 456 provides vertical, or Z-axis motion of the probe 457. Drive mechanisms within the sample pipette assembly 450 position the pipette unit 456 to the correct X, Y, Z coordinates within the analyzer 50 to pipette fluids, to wash the probe 457 of the pipette unit 456, to discard a protective tip from an end of the probe 457 of the pipette unit 456, or to stow the pipette unit 456 during periods of nonuse, e.g., in a "home" position. Each axis of the sample pipette assembly 450 is driven by a stepper motor in a known and conventional manner.

The pipette assembly is preferably an off-the-shelf product. Presently preferred is the Robotic Sample Processor, Model No. RSP9000, available from Cavro Inc. of Sunnyvale, Calif. This model includes a single gantry arm.

The sample pipette assembly 450 is preferably coupled to a syringe pump (not shown) (the Cavro XP 3000 has been used) and a DC driven diaphragm system fluid wash pump (not shown). The syringe pump of the sample pipette assembly 450 is preferably mounted to the internal frame structure 62 within the housing 60 of the analyzer 50 at a position above the left-hand side of the chemistry deck 200 and is connected to pipette unit 456 by suitable tubing (not shown) or other conduit structures.

A sample preparation opening 252 is provided in the jig plate 130, so that the sample pipette assembly 450 can access a reaction receptacle 160 in the input queue 150 located below the jig plate 130.

The sample pipette assembly 450 of the analyzer 50 engages sample tubes 320 carried on the sample ring 250 through openings 140, 142 of an elevated cover plate 138 and engages pipette tips carried on the pipette tip wheel 350 near the back portions of the sample ring 250 and pipette tip wheel 350, respectively. Accordingly, an operator can have access to the forward portions of sample ring 250 and pipette tip wheel 350 through the carousel door opening 80 during operation of the analyzer without interfering with pipetting procedures.

A tip wash/disposal station 340 is disposed adjacent to the sample ring 250 on the jig plate 130. Station 340 includes a tip disposal tube 342 and a wash station basin 346. During sample preparation, the pipette unit 456 of the sample pipette assembly 450 can move into position above the wash station basin 346 where the tubular probe 457 can be washed by pumping distilled water through the probe 457, the basin of the wash station 346 being connected, preferably by a flexible hose (not shown), to a liquid waste container in the lower chassis 1100.

The tip disposal tube 342 comprises an upstanding tubular member. During sample transfer from a sample tube 320 to a reaction receptacle 160, an elongated pipette tip is frictionally secured onto the end of the tubular probe 457 of the pipette unit 456, so that sample material does not come into contact with the tubular probe 457 of the pipette unit 456 when material is drawn from a sample tube 320 and into the elongated pipette tip. After a sample has been transferred from a sample tube 320, it is critical that the pipette tip used in transferring that sample not be used again for another unrelated sample. Therefore, after sample transfer, the pipette unit 456 moves to a position above the tip disposal tube 342 and ejects the used, disposable pipette tip into the tip disposal tube 342 which is connected to one of the solid waste containers carried in the lower chassis 1100.

An elongated pipette tip is preferably also frictionally secured to the probe 457 for transferring target capture reagent from containers carried on the multi-axis mixer 400 to a reaction receptacle 160. Following reagent transfer, the pipette tip is discarded.

As noted, the sample ring 250, the pipette tip wheel 350, and the multi-axis mixer 400 are preferably mounted on a hinged jig plate 130 (see FIGS. 5 and 6) supported above the datum plate 82. The jig plate 130 is hinged at a back end 132 thereof (see FIG. 6) so that the plate, and the ring 250, the wheel 350, and the mixer 400 mounted thereon, can be pivoted upwardly to permit access to the area of the chemistry deck below the jig plate.

A first, or right-side, transport mechanism 500 is mounted on the datum plate 82 below the jig plate 130 and sample ring 250 on generally the same plane as the input queue 150. Transport mechanism 500 includes a rotating main body portion 504 defining a receptacle carrier assembly and an extendible manipulating hook 506 mounted within the main body 504 and extendible and retractable with respect thereto by means of a powered hook member drive assembly. Each of the reaction receptacles 160 preferably includes manipulating structure that can be engaged by the extendible manipulating hook 506, so that the transport mechanism 500 can engage and manipulate a reaction receptacle 160 and move it from one location on the processing deck 200 to another as the reaction receptacle is sequentially moved from one station to another during the performance of an assay within the reaction receptacle 160.

A second, or left-side, transport mechanism 502, of substantially identical construction as first transport mechanism 500, is also included on the processing deck 200.

A plurality of receptacle parking stations 210 are also located below the jig plate 130. The parking stations 210, as their name implies, are structures for holding sample-containing reaction receptacles until the assay performing stations of the processing deck 200 of the analyzer 50 are ready to accept the reaction receptacles. The reaction receptacles are retrieved from and inserted into the parking stations 210 as necessary by the transport mechanism 500.

A right-side orbital mixer 550 is attached to the datum plate 82 and receives reaction receptacles 160 inserted therein by the right-side transport mechanism 500. The orbital mixer is provided to mix the contents of the reaction receptacle 160. After mixing is complete, the right-side transport mechanism 500 removes the reaction receptacle from the right-side orbital mixer 550 and moves it to another location in the processing deck.

A number of incubators 600, 602, 604, 606, of substantially identical construction are provided. Incubators 600, 602, 604, and 606 are preferably rotary incubators. Although the particular assay to be performed and the desired throughput will determine the desired number of necessary incubators, four incubators are preferably provided in the analyzer 50.

As will be described in more detail below, each incubator (600, 602, 604, 606) has a first, and may also have a second, receptacle access opening through which a transport mechanism 500 or 502 can insert a reaction receptacle 160 into the incubator or retrieve a reaction receptacle 160 from the incubator. Within each incubator (600, 602, 604, 606) is a rotating receptacle carrier carousel which holds a plurality of reaction receptacles 160 within individual receptacle stations while the receptacles are being incubated. For the nucleic acid-based diagnostic assay preferably performed on the analyzer 50 of the present invention, first rotary incubator TC is a TC incubator (also known as the "TC incubator"), second rotary incubator 602 is an active temperature and pre-read cool-down incubator (also known as the "AT incubator"), third rotary incubator 604 is an amplification incubator (also known as the "AMP incubator"), and fourth rotary incubator 606 is a hybridization incubator (also known as the "HYB incubator"). (The names assigned to the incubators are for convenience only, signifying their uses in one preferred end-point amplification assay, and are not to be viewed as limiting other possible uses of these incubators). The construction, function, and role of the incubators in the overall performance of the assay will be described in more detail below.

The processing deck 200 preferably also includes a plurality of temperature ramping stations 700. Two such stations 700 are shown attached to the datum plate 82 between incubators 602 and 604 in FIG. 3. Additional ramping stations may be disposed at other locations on the processing deck 200 where they will be accessible by one of the transport mechanisms 500, 502.

A reaction receptacle 160 may be placed into or removed from a temperature ramping station 700 by either transport mechanism 500 or 502. Each ramping station 700 either raises or lowers the temperature of the reaction receptacle and its contents to a desired temperature before the receptacle is placed into an incubator or another temperature sensitive station. By bringing the reaction receptacle and its contents to a desired temperature before inserting it into one of the incubators (600, 602, 604, 606), temperature fluctuations within the incubator are minimized.

The processing deck 200 also includes magnetic separation stations 800 for performing a magnetic separation wash procedure. Each magnetic separation station 800 can accommodate and perform a wash procedure on one reaction receptacle 160 at a time. Therefore, to achieve the desired throughput, five magnetic separation stations 800 working in parallel are preferred. Receptacles 160 are inserted into and removed from the magnetic separation stations 800 by the left-side transport mechanism 502.

A reagent cooling bay 900 is attached to the datum plate 82 roughly between the incubators 604 and 606. Reagent cooling bay 900 comprises a carousel structure having a plurality of container receptacles for holding bottles of temperature sensitive reagents. The carousel resides within a cooled housing structure having a lid with pipette-access holes formed therein.

A second, or left-side, orbital mixer 552, substantially identical to right-side orbital mixer 550, is disposed between incubators 606 and 604. The left-side orbital mixer 552 includes dispenser nozzles and lines for dispensing fluids into the reaction receptacle resident within the left-side orbital mixer 552.

A reagent pipette assembly, or robot, 470 includes a double gantry structure attached to the frame structure 62 (see FIG. 2) and is disposed generally above the incubators 604 and 606 on the left-hand side of the processing deck 200. Specifically, reagent pipette assembly 470 includes pipette units 480 and 482. Pipette unit 480 includes a tubular probe 481 and is mounted for linear movement, generally in the X-direction, along track 474 of lateral rail 476, and pipette unit 482, including a tubular probe 483, is also mounted for linear motion, generally in the X-direction, along track 484 of lateral rail 478. Lateral rails 476 and 478 can translate, generally in a Y-direction, along the longitudinal track 472. Each pipette unit 480, 482 provides independent vertical, or Z-axis, motion of the respective probe 481, 483. Drive mechanisms within the assembly 470 position the pipette units 480, 482 to the correct X, Y, Z coordinates within the analyzer 50 to pipette fluids, to wash the tubular probes 481, 483 of the respective pipette units 480, 482, or to stow the pipette units 480, 482 during periods of nonuse, e.g., in "home" positions. Each axis of the pipette assembly 470 is driven by a stepper motor.

The reagent pipette assembly 470 is preferably an off-the-shelf product. The presently preferred unit is the Cavro Robotic Sample Processor, Model No. RSP9000, with two gantry arms.

The pipette units 480, 482 of the reagent pipette assembly 470 are each preferably coupled to a respective syringe pump (not shown) (the Cavro XP 3000 has been used) and a DC driven diaphragm system fluid wash pump. The syringe pumps of the reagent pipette assembly 470 are preferably mounted to the internal frame structure 62 within the housing 60 of the analyzer 50 at a position above the left-hand side of the chemistry deck 200 and are connected to the respective pipette units 480, 482 by suitable tubing (not shown) or other conduit structures.

Each pipette unit 480, 482 preferably includes capacitive level sensing capability. Capacitive level sensing, which is generally known in the medical instrumentation arts, employs capacitance changes when the dielectric of a capacitor, formed by the pipette unit as one plate of the capacitor and the structure and hardware surrounding a container engaged by the pipette unit as the opposite plate, changes from air to fluid to sense when the probe of the pipette unit has penetrated fluid within a container. By ascertaining the vertical position of the probe of the pipette unit, which may be known by monitoring the stepper motor which drives vertical movement of the pipette unit, the level of the fluid within the container engaged by the pipette unit may be determined.

Pipette unit 480 transfers reagents from the reagent cooling bay 900 into reaction receptacles disposed within the HYB incubator 606 or the orbital mixer 552, and pipette unit 482 transfers reagent materials from the reagent cooling bay 900 into reaction receptacles disposed within the AMP incubator 604 or the orbital mixer 552.

The pipette units 480, 482 use capacitive level sensing to ascertain fluid level within a container and submerge only a small portion of the end of the probe of the pipette unit to pipette fluid from the container. Pipette units 480, 482 preferably descend as fluid is pipetted into the respective tubular probes 481, 483 to keep the end of the probes submerged to a constant depth. After drawing reagent into the tubular probe of the pipette unit 480 or 482, the pipette units create a minimum travel air gap of 10 µL in the end of the respective probe 481 or 483 to ensure no drips from the end of the probe as the pipette unit is moved to another location above the chemistry deck 200.

The results of the assay preferably performed in the analyzer 50 of the present invention are ascertained by the amount of chemiluminescence, or light, emitted from a reaction tube 162 at the conclusion of the appropriate preparation steps. Specifically, the results of the assay are determined from the amount of light emitted by label associated with hybridized polynucleotide probe at the conclusion of the assay. Accordingly, the processing deck 200 includes a luminometer 950 for detecting and/or quantifying the amount of light emitted by the contents of the reaction receptacle. Briefly, the luminometer 950 comprises a housing through which a reaction receptacle travels under the influence of a transport mechanism, a photomultiplier tube, and associated electronics. Various luminometer embodiments will be described in detail below.

The processing deck 200 also preferably includes a deactivation queue 750. The assay performed in the analyzer 50 involves the isolation and amplification of nucleic acids belonging to at least one organism or cell of interest. Therefore, it is desirable to deactivate the contents of the reaction receptacle 160, typically by dispensing a bleach-based reagent into the reaction receptacle 160 at the conclusion of the assay. This deactivation occurs within the deactivation queue 750.

Following deactivation, the deactivated contents of the reaction receptacle 160 are stored in one of the liquid waste containers of the lower chassis 1100 and the used reaction receptacle is discarded into a dedicated solid waste container within the lower chassis 1100. The reaction receptacle is preferably not reused.

Analyzer Operation

The operation of the analyzer 50, and the construction, cooperation, and interaction of the stations, components, and modules described above will be explained by describing the operation of the analyzer 50 on a single test sample in the performance of one type of assay which may be performed with analyzer 50. Other diagnostic assays, which require the use of one or more of the stations, components, and modules described herein, may also be performed with the analyzer 50. The description herein of a particular assay procedure is merely for the purpose of illustrating the operation and interaction of the various stations, components, and modules of the analyzer 50 and is not intended to be limiting. Those skilled in the art of diagnostic testing will appreciate that a variety of chemical and biological assays can be performed in an automated fashion with the analyzer 50 of the present invention.

The analyzer 50 is initially configured for an assay run by loading bulk fluids into the bulk fluid storage bay of the lower chassis 1100 and connecting the bulk fluid containers to the appropriate hoses (not shown).

The analyzer is preferably powered up in a sequential process, initially powering the stations, or modules, that will be needed early in the process, and subsequently powering the stations that will not be needed until later in the process. This serves to conserve energy and also avoids large power surges that would accompany full analyzer power-up and which could trip circuit breakers. The analyzer also employs a "sleep" mode during periods of nonuse. During sleep mode, a minimal amount of power is supplied to the analyzer, again to avoid large surges necessary to power-up an analyzer from complete shut-down.

A number of reaction receptacles 160, preferably in the form of plastic, integrally formed multiple-tube units (MTUs), which are described in more detail below, are loaded through opening 68 into the input queue 150. Henceforth, the reaction receptacles 160 will be referred to as MTUs, consistent with the preferred manner of using the analyzer 50.

The reaction receptacle shuttle assembly (not shown) within the input queue 150 moves the MTUs 160 from the loading opening 68 to the pick-up position at the end of the queue 150. The right-side transport mechanism 500 takes an MTU 160 from the end of the queue 150 and moves to a bar code reader (not shown) to read the unique bar code label on that MTU which identifies that MTU. From the bar code reader, the MTU is moved to an available sample transfer station 255 below opening 252.

Multiple Tube Units

Figure 58:
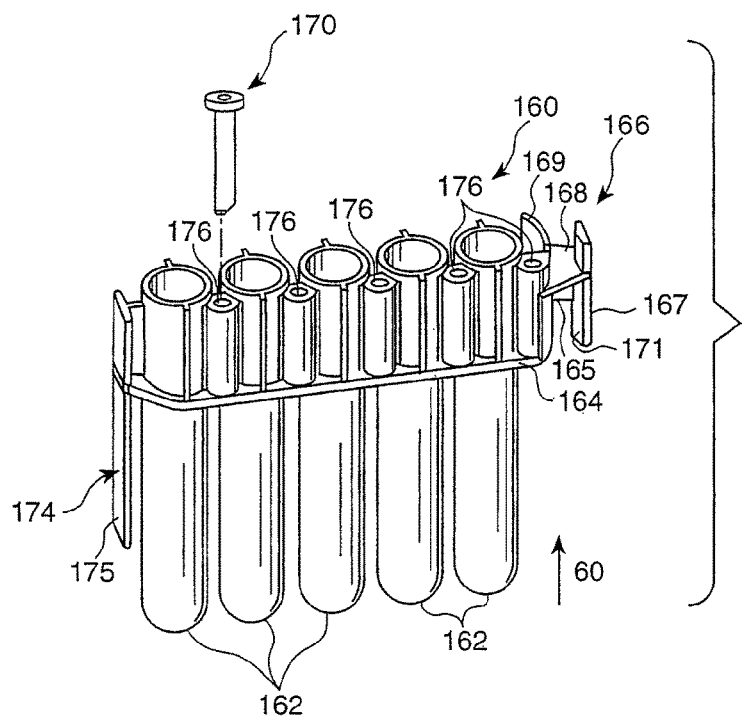
FIG. 58 is a perspective view of a multi-tube unit employed in a preferred mode of operation of the analyzer of the present invention.

The preferred MTU is an embodiment of a multi-vessel reaction receptacle disclosed by Homer et al., "Reaction Receptacle Apparatus," U.S. Pat. No. 6,086,827. As shown in FIG. 58, an MTU 160 comprises a plurality of individual reaction tubes 162, preferably five. The reaction tubes 162, preferably in the form of cylindrical tubes with open top ends and closed bottom ends, are connected to one another by a connecting rib structure 164 which defines a downwardly facing shoulder extending longitudinally along either side of the MTU 160. In one embodiment, the dimensions of each reaction tube 162 of the MTU 160 are 12×75 mm, although the analyzer 50 could be readily adapted to accommodate differently dimensioned reaction receptacles which are provided individually or as part of a multi-vessel reaction receptacle.

The MTU 160 is preferably formed from injection molded polypropylene. The most preferred polypropylene is sold by Montell Polyolefins, of Wilmington, Del., product number PD701NW. The Montell material is used because it is readily moldable, chemically compatible with the preferred mode of operation of the analyzer 50, and has a limited number of static discharge events which can interfere with accurate detection or quantification of chemiluminescence.

An arcuate shield structure 169 is provided at one end of the MTU 160. An MTU manipulating structure 166 to be engaged by one of the transport mechanisms 500, 502 extends from the shield structure 169. MTU manipulating structure 166 comprises a laterally extending plate 168 extending from shield structure 169 with a vertically extending piece 167 on the opposite end of the plate 168. A gusset wall 165 extends downwardly from lateral plate 168 between shield structure 169 and vertical piece 167.

Figure 60:
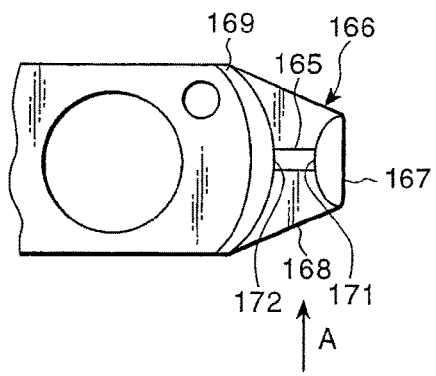
FIG. 60 is an enlarged bottom view of a portion of the multi-tube unit, viewed in the direction of arrow "60" in FIG. 58.

As shown in FIG. 60 the shield structure 169 and vertical piece 167 have mutually facing convex surfaces. The MTU 160 is engaged by the transport mechanisms 500, 502 and other components, as will be described below, by moving an engaging member laterally (in the direction "A") into the space between the shield structure 169 and the vertical piece 167. The convex surfaces of the shield structure 169 and vertical piece 167 provide for wider points of entry for an engaging member undergoing a lateral relative motion into the space. The convex surfaces of the vertical piece 167 and shield structure 169 include raised portions 171, 172, respectively, formed at central portions thereof. The purpose of portions 171, 172 will be described below.

A label-receiving structure 174 having a flat label-receiving surface 175 is provided on an end of the MTU 160 opposite the shield structure 169 and MTU manipulating structure 166. Labels, such as scannable bar codes, can be placed on the surface 175 to provide identifying and instructional information on the MTU 160.

The MTU 160 preferably includes tiplet holding structures 176 adjacent the open mouth of each respective reaction tube 162. Each tiplet holding structure 176 provides a cylindrical orifice within which is received a contact-limiting tiplet 170. The construction and function of the tiplet 170 will be described below. Each holding structure 176 is constructed and arranged to frictionally receive a tiplet 170 in a manner that prevents the tiplet 170 from falling out of the holding structure 176 when the MTU 160 is inverted, but permits the tiplet 170 to be removed from the holding structure 176 when engaged by a pipette.

Figure 59:
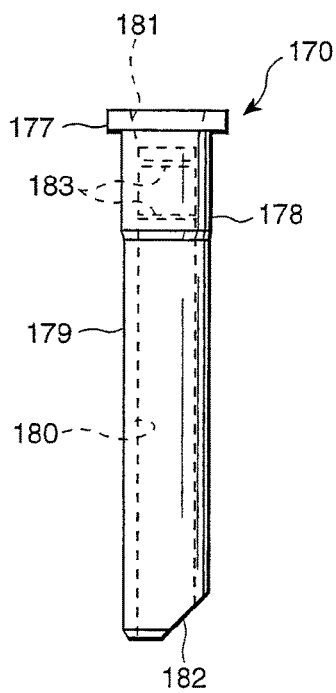
FIG. 59 is a side elevation of a contact-limiting pipette tiplet employed in a preferred mode of operation of the analyzer of the present invention and carried on the multi-tube unit shown in FIG. 58.

As shown in FIG. 59, the tiplet 170 comprises a generally cylindrical structure having a peripheral rim flange 177 and an upper collar 178 of generally larger diameter than a lower portion 179 of the tiplet 170. The tiplet 170 is preferably formed from conductive polypropylene. When the tiplet 170 is inserted into an orifice of a holding structure 176, the flange 177 contacts the top of structure 176 and the collar 178 provides a snug but releasable interference fit between the tiplet 170 and the holding structure 176.

An axially extending through-hole 180 passes through the tiplet. Hole 180 includes an outwardly flared end 181 at the top of the tiplet 170 which facilitates insertion of a pipette tubular probe (not shown) into the tiplet 170. Two annular ridges 183 line the inner wall of hole 180. Ridges 183 provide an interference friction fit between the tiplet 170 and a tubular probe inserted into the tiplet 170.

The bottom end of the tiplet 170 preferably includes a beveled portion 182. When tiplet 170 is used on the end of an aspirator that is inserted to the bottom of a reaction receptacle, such as a reaction tube 162 of an MTU 160, the beveled portion 182 prevents a vacuum from forming between the end of the tiplet 170 and the bottom of the reaction reaction tube.

Lower Chassis

Figure 52:
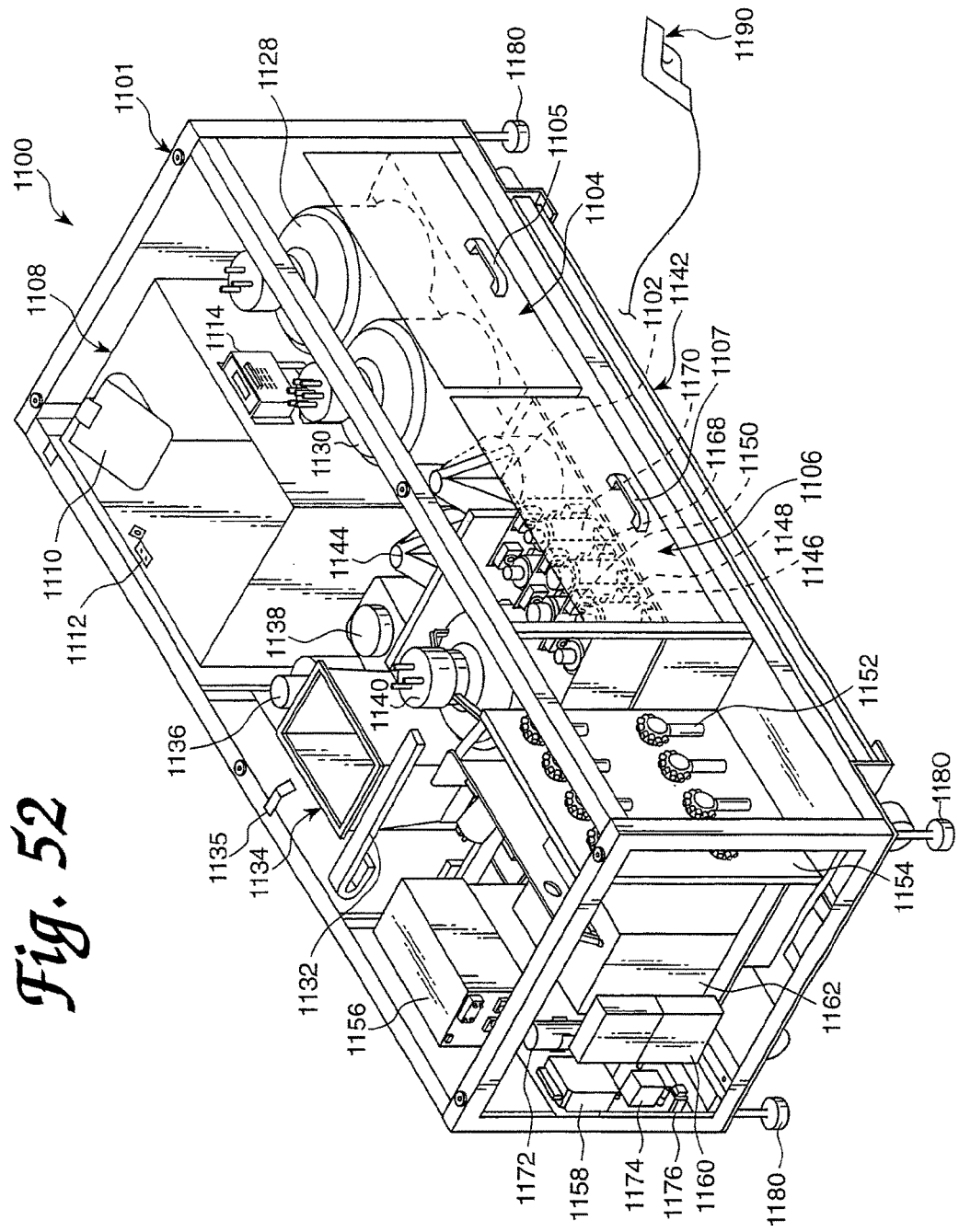
FIG. 52 is a perspective view of a lower chassis of the analyzer of the present invention.
Figure 53:
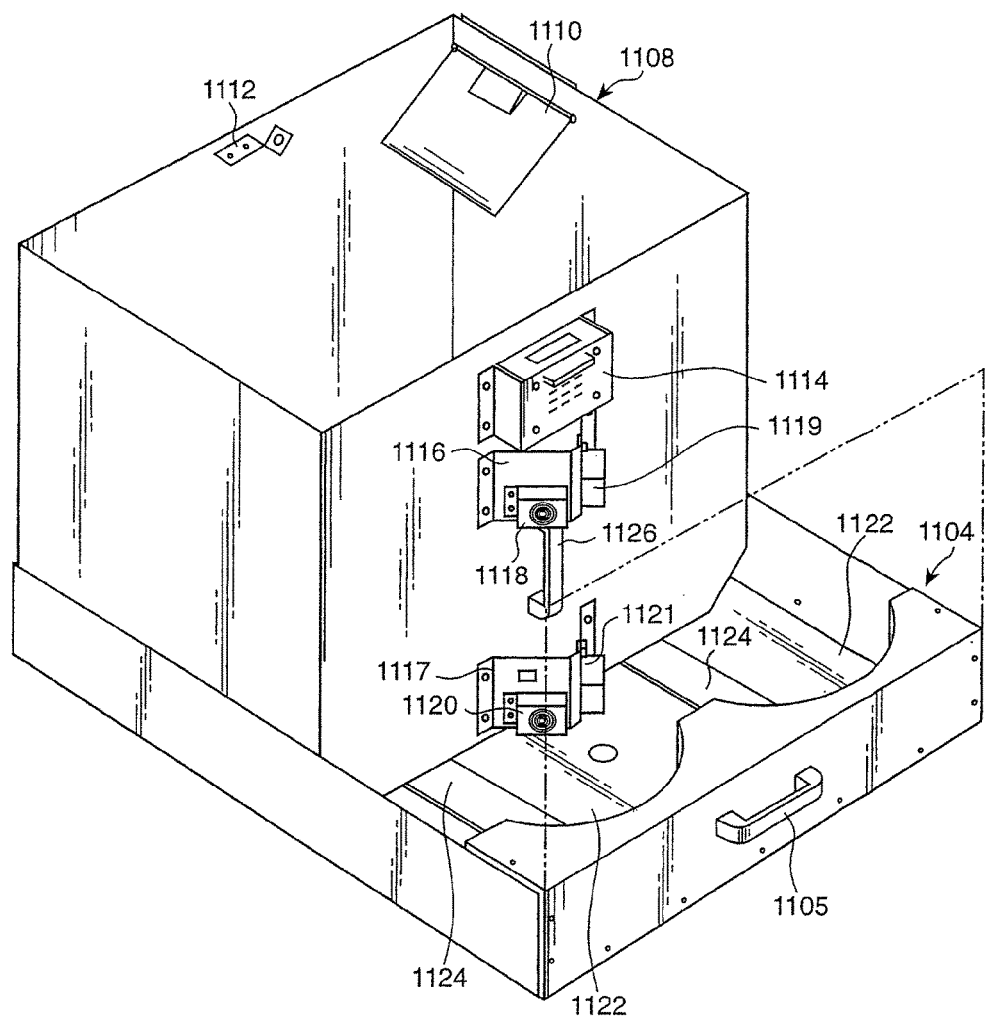
FIG. 53 is a perspective view of a right-side drawer of the lower chassis.
Figure 54:
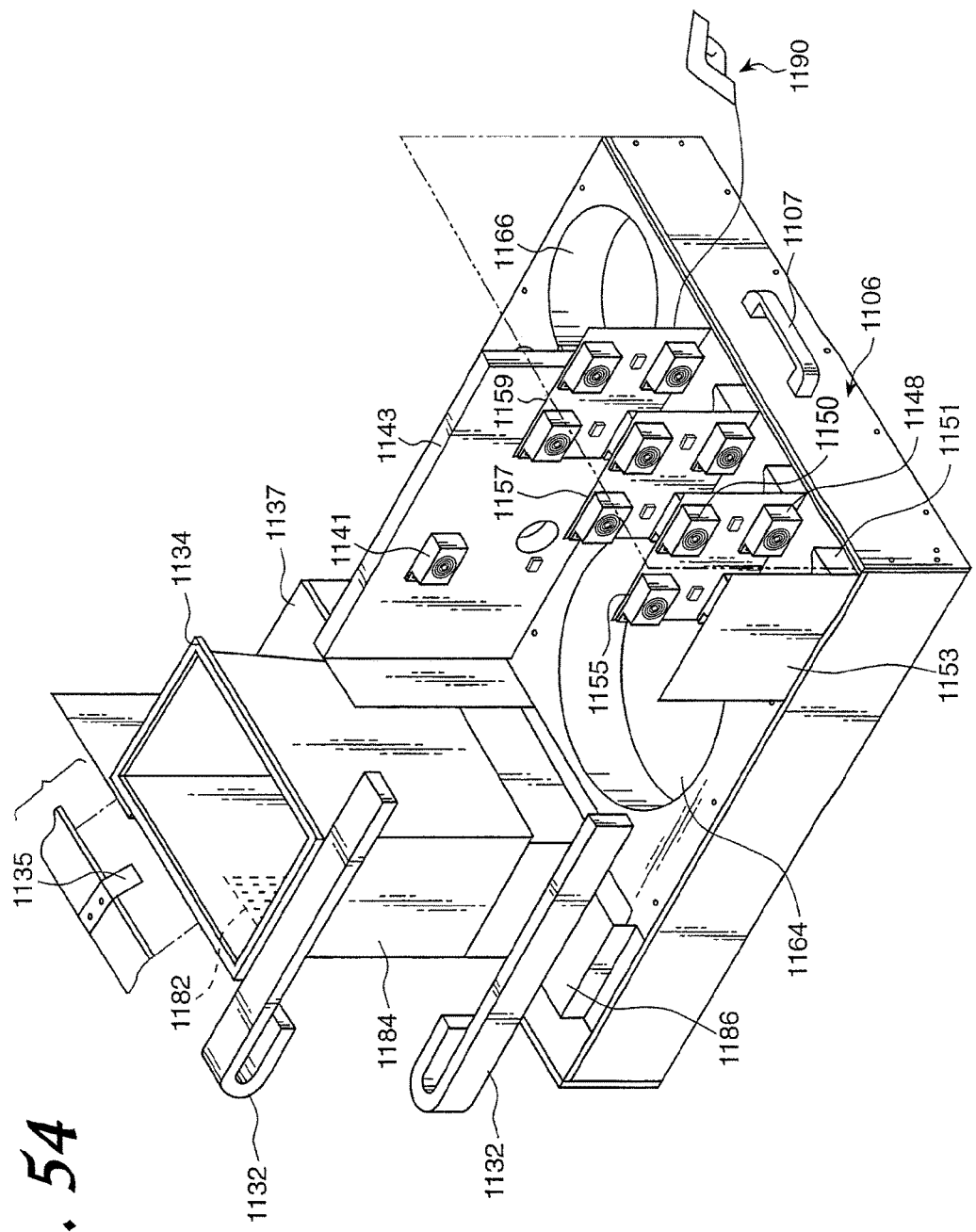
FIG. 54 is a perspective view of a left-side drawer of the lower chassis.

An embodiment of the lower chassis of the present invention is shown in FIGS. 52-54. The lower chassis 1100 includes a steel frame 1101 with a black polyurethane powder coat, a pull-out drip tray 1102 disposed below the chassis, a right-side drawer 1104, and a left-side drawer 1106. The left-side drawer 1106 is actually centrally disposed within the lower chassis 1100. The far left-side of the lower chassis 1100 houses various power supply system components and other analyzer mechanisms such as, for example, seven syringe pumps 1152 mounted on a mounting platform 1154, a vacuum pump 1162 preferably mounted on the floor of the lower chassis 1100 on vibration isolators (not shown), a power supply unit 1156, a power filter 1158, and fans 1160.

A different syringe pump 1152 is designated for each of the five magnetic separation stations 800, one is designated for the left-side orbital mixer 552, and one is designated for the deactivation queue 750. Although syringe pumps are preferred, peristaltic pumps may be used as an alternative.

The vacuum pump 1162 services each of the magnetic separation stations 800 and the deactivation queue 750. The preferred rating of the vacuum pump is 5.3-6.5 cfm at 0" Hg and 4.2-5.2 cfm at 5" Hg. A preferred vacuum pump is available from Thomas Industries, Inc. of Sheboygan, Wis., as Model No. 2750CGHI60. A capacitor 1172 is sold in conjunction with the pump 1162.

The power supply unit 1156 is preferably an ASTEC, Model No. VS1-B5-B7-03, available from ASTEC America, Inc., of Carlsbad, Calif. Power supply unit 1156 accepts 220 volts ranging from 50-60 Hz, i.e., power from a typical 220 volt wall outlet. Power filter 1158 is preferably a Corcom Model No. 20MV1 filter, available from Corcom, Inc. of Libertyville, Ill. Fans 1160 are preferably Whisper XLDC fans available from Comair Rotron, of San Ysidro, Calif. Each fan is powered by a 24 VDC motor and has a 75 cfm output. As shown in FIG. 52, the fans 1160 are preferably disposed proximate a left-side outer wall of the lower chassis 1100. The fans 1160 are preferably directed outwardly to draw air through the lower chassis from the right-side thereof to the left-side thereof, and thus, to draw excess heat out of the lower chassis.

Other power supply system components are housed in the back left-hand side of the lower chassis 1100, including a power switch 1174, preferably an Eaton circuit breaker switch 2-pole, series JA/S, available from the Cutler-Hammer Division of Eaton Corporation of Cleveland, Ohio, and a power inlet module 1176 at which a power cord (not shown) for connecting the analyzer 50 to an external power source is connected. The power supply system of the analyzer 50 also includes a terminal block (not shown), for attaching thereto a plurality of electrical terminals, a solid state switch (not shown), which is preferably a Crydom Series 1, Model No. D2425, available from Cal Switch, Carson City, Calif., for switching between different circuits, and an RS232 9-pin connector port for connecting the analyzer 50 to the external computer controller 1000.

The right-side drawer and left-side drawer bays are preferably closed behind one or two doors (not shown) in front of the analyzer, which is/are preferably locked by the assay manager program during operation of the analyzer. Microswitches are preferably provided to verify door-closed status. The far left bay is covered by a front panel. End panels are provided on opposite ends of the lower chassis to enclose the chassis.

Four leveler feet 1180 extend down from the four corners of the chassis 1100. The leveler feet 1180 include threaded shafts with pads at the lower ends thereof. When the analyzer is in a desired location, the feet 1180 can be lowered until the pads engage the floor to level and stabilize the analyzer. The feet can also be raised to permit the analyzer to be moved on its casters.

Bulk fluids typically contained in the containers of the lower chassis 1100 may include wash solution (for washing immobilized target), distilled water (for washing fixed pipette tips), diagnostic testing reagents, silicone oil (used as a floating fluid for layering over test reagents and sample), and a bleach-based reagent (used for sample deactivation).

The right-side drawer 1104 is shown in detail in FIG. 53. The right-side drawer 1104 includes a box-like drawer structure with a front drawer handle 1105. Although drawer handle 1105 is shown as a conventional pull-type drawer handle, in the preferred embodiment of the analyzer 50, handle 1105 is a T-handle latch, such as those available from Southco, Inc. of Concordville, Pa. The drawer 1104 is mounted in the lower chassis on slide brackets (not shown) so that the drawer 1104 can be pulled into and out of the lower chassis. A sensor (not shown) is preferably provided for verifying that the drawer 1104 is closed. The front portion of the drawer includes bottle receptacles 1122 for holding bottle 1128 (shown in FIG. 52), which is a dedicated pipette wash waste-containing bottle, and bottle 1130 (also shown in FIG. 52), which is a dedicated waste bottle for containing waste from a magnetic wash, target-capture procedure. Bottle 1130 is preferably evacuated.

The analyzer 50 will not begin processing assays if any of the bottles required in the lower chassis 1100 are missing. Bottle receptacles 1122 preferably include bottle-present sensors (not shown) to verify the presence of a bottle in each receptacle 1122. The bottle-present sensors are preferably diffuse reflective type optical sensors available from SUNX/Ramco Electric, Inc., of West Des Moines, Iowa, Model No. EX-14A.

Right-side drawer 1104 further includes a waste bin 1108 for holding therein spent MTUs and sample tips. Waste bin 1108 is an open box structure with a sensor mount 1112 at a top portion thereof for mounting thereon a sensor, preferably a 24 VDC Opto-diffuse reflector switch (not shown), for detecting whether the waste bin 1108 is full. Another diffuse reflector type optical sensor (not shown) is positioned within right-side drawer 1104 to verify that the waste bin 1108 is in place. Again, diffuse reflective type optical sensors available from SUNX/Ramco Electric, Inc., of West Des Moines, Iowa, Model No. EX-14A, are preferred.

A deflector 1110 extends obliquely from a side of the waste bin 1108. Deflector 1110 is disposed directly below a chute through which spent MTUs are dropped into the waste bin 1108 and deflects the dropped MTUs toward the middle of the waste bin 1108 to avoid MTU pile-ups in a corner of the waste bin 1108. Deflector 1110 is preferably pivotally mounted so that it can pivot upwardly to a substantially vertical position so that when a waste bag, which lines the waste bin 1108 and covers the deflector 1110, is removed from the waste bin 1108, the deflector 1110 will pivot upwardly with the bag as it is pulled out and therefore will not rip the bag.

A printed circuit board (not shown) and cover 1114 can be mounted to the front of the waste bin 1108. Sensor mounts 1116 and 1117 are also mounted to the front of waste bin 1108. Sensors 1118 and 1119 are mounted on sensor mount 1116, and sensors 1120 and 1121 mounted on sensor mount 1117. Sensors 1118, 1119, 1120, and 1121 are preferably DC capacitive proximity sensors. The upper sensors 1118, 1119 indicate when the bottles 1128 and 1130 are full, and the bottom sensors 1120, 1121 indicate when the bottles are empty. Sensors 1118-1121 are preferably those available from Stedham Electronics Corporation of Reno, Nev., Model No. C2D45AN1-P, which were chosen because their relatively flat physical profile requires less space within the tight confines of the lower chassis 1100 and because the Stedham sensors provide the desired sensing distance range of 3-20 mm.

The analyzer 50 will preferably not begin performing any assays if the assay manager program detects that any of the waste fluid containers in the right-side drawer 1104 are not initially empty.

The capacitive proximity sensors 1118-1121 and the bottle-present, waste-bin-present, and waste-bin-full optical sensors of the right-side drawer 1104 are connected to the printed circuit board (not shown) behind cover 1114, and the printed circuit board is connected to the embedded controller of the analyzer 50.

Because the right-side drawer 1104 cannot be pulled completely out of the lower chassis 1100, it is necessary to be able to pull the waste bin 1108 forward so as to permit access to the waste bin for installing and removing a waste bag liner. For this purpose, a handle 1126 is mounted to the front of the waste bin 1108 and teflon strips 1124 are disposed on the bottom floor of the right-side drawer 1104 to facilitate forward and backward sliding of the waste bin 1108 in the drawer 1104 when bottles 1128 and 1130 are removed.

Details of the left-side drawer 1106 are shown in FIG. 54. Left-side drawer 1106 includes a box-like structure with a front mounted handle 1107 and is mounted within the lower chassis 1100 on slide brackets (not shown). Although handle 1107 is shown as a conventional pull-type drawer handle, in the preferred embodiment of the analyzer 50, handle 1107 is a T-handle latch, such as those available from Southco, Inc. of Concordville, Pa. A sensor is provided for verifying that the left-side drawer 1106 is closed.

Left-side drawer 1106 includes a tiplet waste bin 1134 with a mounting structure 1135 for mounting thereon a tiplet-waste-bin-full sensor (not shown). A tiplet-waste-bin-present sensor is preferably provided in the left-side drawer 1106 to verify that the tiplet waste bin 1134 is properly installed. Diffuse reflective type optical sensors available from SUNX/Ramco Electric, Inc., of West Des Moines, Iowa, Model No. EX-14A, are preferred for both the tiplet-waste-bin-full sensor and the tiplet-waste-bin-present sensor.

Bundling structures 1132 are provided for securing and bundling various tubing and/or wires (not shown) within the lower chassis 1100. The bundling structures preferably used are Energy Chain Systems manufactured and sold by Igus, Inc. of East Providence, R.I.

A printed circuit board 1182 is mounted behind a panel 1184 which is located behind the tiplet waste bin 1134. A solenoid valve mounting panel 1186 is located below the tiplet waste bin 1134.

Left-side drawer 1106 includes a forward container-holding structure for holding therein six similarly sized bottles. The container structure includes divider walls 1153, 1155, 1157, and 1159 and container blocks 1151 having a curved bottle-conforming front edge, which together define six container-holding areas. Lower sensors 1148 and upper sensors 1150 (six of each) are mounted on the divider walls 1155, 1157, and 1159. The upper and lower sensors 1148, 1150 are preferably DC capacitive proximity sensors (preferably sensors available from Stedham Electronics Corporation of Reno, Nev., Model No. C2D45AN1-P, chosen for their flat profile and sensing range). The upper sensors 1150 indicate when the bottles held in the container structure are full, and the lower sensors 1148 indicate when the bottles are empty. In the preferred arrangement, the left two bottles 1146 contain a detecting agent ("Detect I"), the middle two bottles 1168 contain silicon oil, and the right two bottles 1170 contain another detecting agent ("Detect II").

Bottle-present sensors (not shown) are preferably provided in each of the container-holding areas defined by the container blocks 1151 and the dividing walls 1153, 1155, 1157, and 1159 to verify the presence of bottles in each container-holding area. The bottle-present sensors are preferably diffuse reflective type optical sensors available from SUNX/Ramco Electric, Inc., of West Des Moines, Iowa, Model No. EX-14A.

A large centrally located container receptacle 1164 holds a bottle 1140 (shown in FIG. 52), preferably containing deionized water. Container receptacles 1166 (only one is visible in FIG. 54) hold bottles 1142 and 1144 (also shown in FIG. 52) preferably containing a wash solution. A dividing wall 1143 between the receptacle 1164 and 1166 has mounted thereon sensors, such as sensor 1141, for monitoring the fluid level in the bottles 1140, 1142, and 1144. The sensors, such as sensor 1141, are preferably DC capacitive proximity sensors (preferably sensors available from Stedham Electronics Corporation of Reno, Nev., Model No. C2D45AN1-P).

Container receptacles 1164 and 1166 preferably include bottle-present sensors (not shown) for verifying that bottles are properly positioned in their respective receptacles. The bottle-present sensors are preferably diffuse reflective type optical sensors available from SUNX/Ramco Electric, Inc., of West Des Moines, Iowa, Model No. EX-14A.

The analyzer 50 will not begin performing any assays if the assay manager program determines that any of the bulk-fluid containers in the left-side drawer 1106 are initially empty.

The capacitive proximity fluid level sensors, the various bottle-present sensors, the tiplet-waste-bin-full sensor, and the tiplet-waste-bin-present sensors are all connected to the printed circuit board 1182, and the printed circuit board 1182 is connected to the embedded controller of the analyzer 50.

Four solenoid valves (not shown) are mounted below the solenoid valve mounting panel 1186. The solenoid valves connect bulk fluid bottles where fluids are stored in pairs of bottles, i.e., the bottles 1140, 1142 containing wash solution, the two bottles 1146 containing the "Detect I" agent, the two bottles 1168 containing oil, and the two bottles 1170 containing the "Detect II" agent. The solenoid valves, in response to signals from the respective capacitive proximity sensors, switch bottles from which fluid is being drawing when one of the two bottles containing the same fluid is empty. In addition, the solenoid valves may switch bottles after a prescribed number of tests are performed. The preferred solenoid valves are teflon solenoid valves available from Beco Manufacturing Co., Inc. of Laguna Hills, Calif., Model Nos. S313W2DFRT and M223W2DFRLT. The two different model numbers correspond to solenoid valves adapted for use with two different tube sizes. Teflon solenoid valves are preferred because they are less likely to contaminate fluids flowing through the valves and the valves are not damaged by corrosive fluids flowing through them.

Bottle 1136 (see FIG. 52) is a vacuum trap held in a vacuum trap bracket 1137, and bottle 1138 contains a deactivating agent, such as bleach-containing reagent. Again, bottle-present sensors are preferably provided to verify the presence of bottles 1136 and 1138.

A hand-held bar code scanner 1190 may be provided in the lower chassis 1100 for scanning information provided on scannable container labels into the assay manager program. Scanner 1190 is connected by a cord to printed circuit board 1182 of the left-side drawer 1106 and is preferably stowed on a bracket (not show) mounted on dividing wall 1143. Scanners available from Symbol Technologies, Inc., of Holtsville, N.Y., series LS2100, are preferred.

Sample RING AND Sample TUBE TRAYS

Samples are contained in the sample tubes 320, and the tubes 320 are loaded into the tube trays 300 outside the analyzer 50. The trays 300 carrying the sample tubes 320 are placed onto the sample ring 250 through the access opening provided by opening the flip-up carousel door 80.

Figure 5:
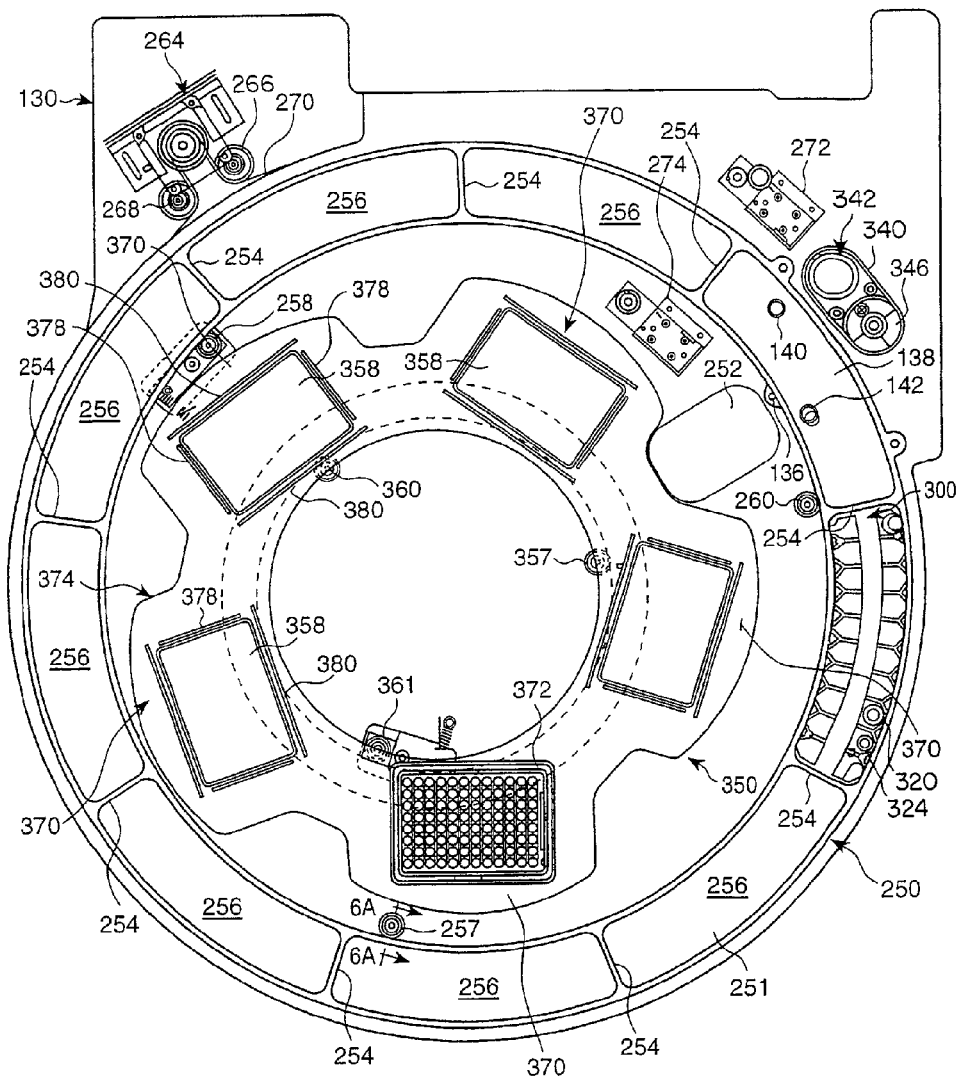
FIG. 5 is a plan view of a sample ring and a pipette tip wheel of the assay processing deck of the analyzer of the present invention.
Figure 6:
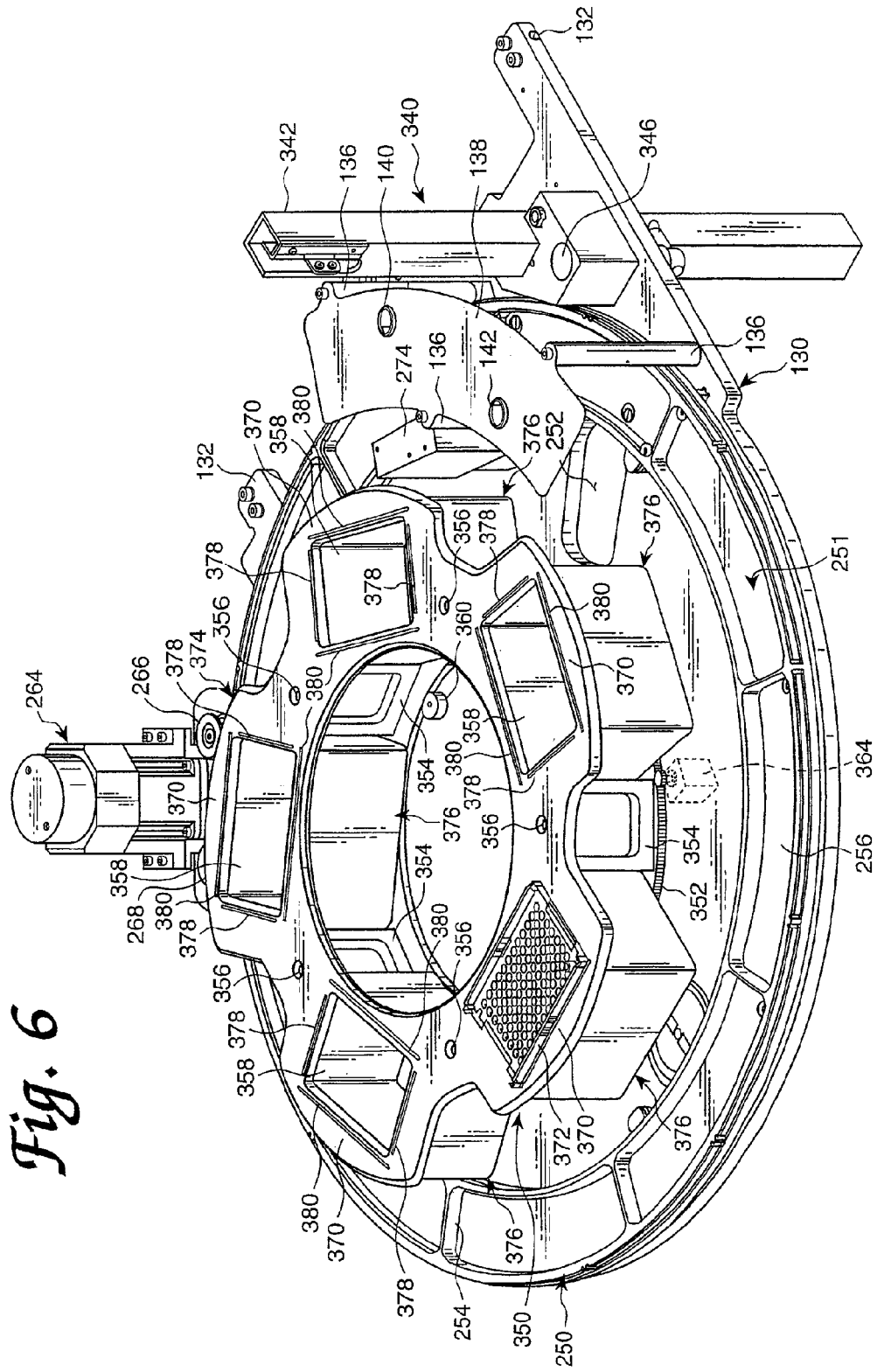
FIG. 6 is a perspective view showing the sample ring and the pipette tip wheel.
Figure 9:
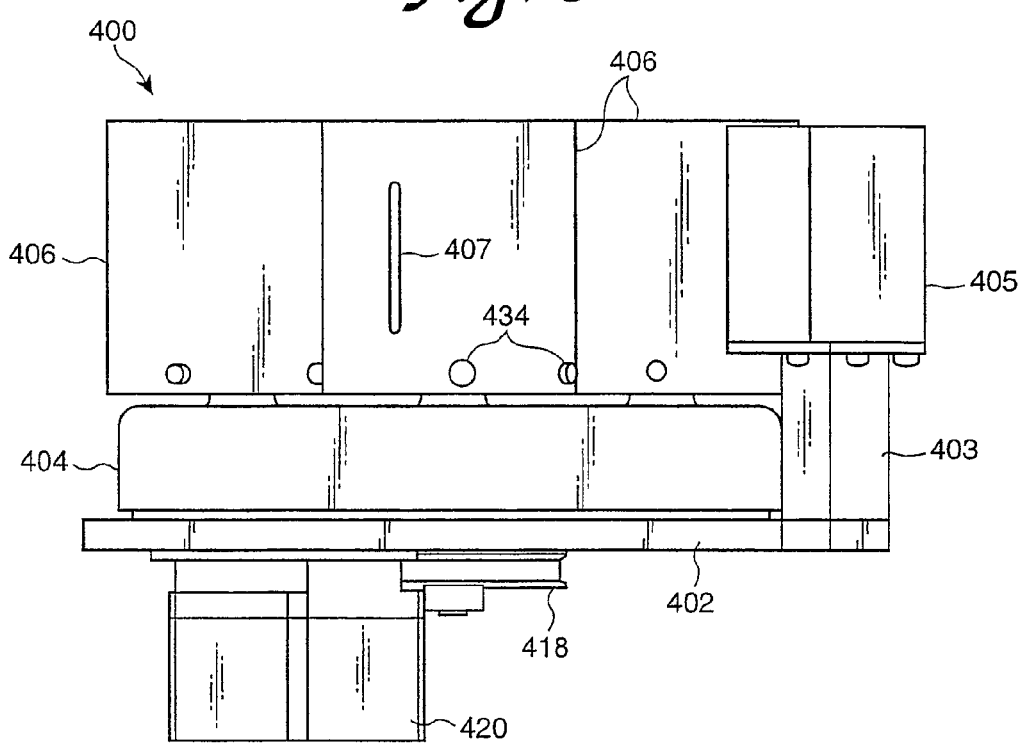
FIG. 9 is a side elevation of the multi-axis mixer.

Referring to FIGS. 5 and 6, the first ring assembly, or sample ring, 250 is formed of milled, unhardened aluminum and includes a raised ring structure defining an annular trough 251 about the outer periphery of ring 250 with a plurality of raised, radially extending dividers 254 extending through trough 251. Preferably, nine dividers 254 divide the trough 251 into nine arcuate sample tube tray-receiving wells 256. The trough 251 and wells 256 define an annular fluid container carrier portion constructed and arranged to carry a plurality of containers as will be described below.

Sample ring 250 is preferably rotationally supported by three 120-spaced V-groove rollers 257, 258, 260 which engage a continuous V-ridge 262 formed on the inner periphery of ring 250, as shown in FIGS. 5, 6, and 6A so that the ring 250 is rotatable about a first central axis of rotation. The rollers are preferably made by Bishop-Wisecarver Corp. of Pittsburgh, Calif., Model No. W1SSX. Rollers 257 and 260 are rotationally mounted on fixed shafts, and roller 258 is mounted on a bracket which pivots about a vertical axis and is spring biased so as to urge roller 258 radially outward against the inner periphery of ring 250. Having two fixed rollers and one radially movable roller allows the three rollers to accommodate an out-of-round inner periphery of the ring 250.

Sample ring 250 is driven by stepper motor 264 (VEXTA stepper motors available from Oriental Motor Co., Ltd. of Tokyo, Japan as Model No. PK266-01A are preferred) via continuous belt 270 (preferably available from SDP/SI of New Hyde Park, N.Y., as Model No. A6R3M444080) which extends over guide rollers 266, 268 and around the outer periphery of ring 250. A home sensor and a sector sensor (not shown), preferably slotted optical sensors, are provided adjacent the ring 250 at a rotational home position and at a position corresponding to one of the sample tube tray receiving wells 256. The ring 250 includes a home flag (not shown) located at a home position on the wheel and nine equally-spaced sector flags (not shown) corresponding to the positions of each of the nine sample tube tray receiving wells 256. The home flag and sector flags cooperate with the home sensor and sector sensors to provide ring position information to the assay manager program and to control the ring 250 to stop at nine discrete positions corresponding to established coordinates for user re-load and access by pipette unit 450. Preferred sensors for the home sensor and sector sensor are Optek slotted optical sensors, Model No. OPB857, available from Optek of Carrollton, Tex.

A sample cover is disposed over a portion of the annular fluid container carrier portion, or trough 251, and comprises an arcuate cover plate 138 fixed in an elevated position with respect to the wheel 250 on three mounting posts 136. Plate 138 has an arcuate shape generally conforming to the curve of the trough 251. A first opening 142 is formed in the plate 138, and a second opening 140 is formed in the plate 138 at a greater radial distance from the axis of rotation of ring 250 than opening 142 and at a circumferentially-spaced position from opening 142.

Referring to FIGS. 55-57, each sample tube tray 300 comprises a test tube rack structure that is curved to conform to the curvature of the ring 250. Each tray 300 comprises a central wall structure 304 with lateral end walls 303 and 305 disposed on either end of wall 304. A floor 312 extends across the bottom of the tray 300. The principle purposes of sample tube tray 300 are to hold sample tubes on the sample ring 250 for access by the sample pipette assembly 450 and to facilitate loading and unloading of multiple sample tubes into and from the analyzer.

A plurality of Y-shaped dividers 302 are equidistantly spaced along opposite edges of the tray 300. Each two adjacent dividers 302 define a test-tube receiving area 330. End wall 303 includes inwardly bent flanges 316 and 318, and end wall 305 includes inwardly bent flanges 326 and 328. The respective inwardly bent flanges of end walls 303 and 305 along with the end-most of the dividers 302 define the end-most tube receiving areas 332. The receiving areas 330, 332 are arcuately aligned along two arcuate rows on opposite sides of central wall structure 304.

Referring to FIG. 57, within each tube receiving area 330, 332, a leaf spring element 310 is attached to central wall 304. Leaf spring element 310, preferably formed of stainless spring steel, elastically deflects when a test tube 320 is inserted into the tube-receiving area 330 or 332 and urges the tube 320 outwardly against the dividers 302. Thus, the tube 320 is secured in an upright orientation. The shape of the dividers 302 and the elasticity of the leaf spring elements 310 allow the tray 300 to accommodate sample tubes of various shapes and sizes, such as tubes 320 and 324. Each tray 300 preferably includes nine dividers 302 along each edge to form, along with end walls 303 and 305, ten tube-receiving areas 330, 332 on each side of central wall structure 304 for a total of twenty tube-receiving areas per tray. Indicia for designating tube-receiving areas 330 and 332, such as raised numerals 306, may be provided on the tray, such as on central wall 304.

Each tray 300 may also include boss structures 308, shown in the illustrated embodiment to be integrally formed with the end-most dividers 302. An upright inverted U-shaped handle (not shown) may be attached to the tray at boss structures 308 or some other suitable location. Upright handles can facilitate handling of the tray 300 when loading and unloading the tray 300 through the arcuate carousel door 80, but are not necessarily preferred.

A gap is provided between adjacent dividers 302 so that bar-code labels 334, or other readable or scannable information, on the tubes 320 is accessible when the tube is placed in the tray 300. When a tray 300 carried on wheel 250 passes beneath the plate 138 of the sample cover, one tube 320 in a curved row at a radially-inward position with respect to wall structure 304 will be aligned with first opening 142 and another tube 320 in a curved row at a radially-outward position with respect to wall 304 will be aligned with second opening 140. The ring 250 is indexed to sequentially move each tube 320 beneath the openings 140, 142 to permit access to the tubes.

Referring again to FIG. 5, bar code scanners 272 and 274 are disposed adjacent the ring 250. Opticon, Inc. scanners, Model No. LHA2126RR1S-032, available from Opticon, Inc. of Orangeburg, N.Y., are preferred. Scanner 272 is located outside ring 250, and scanner 274 is disposed inside ring 250. Scanners 272 and 274 are positioned to scan bar code data labels on each sample tube 320 carried in the sample tube tray 300 as the ring 250 rotates a tray 300 of sample tubes 320 past the scanners 272, 274. In addition, the scanners 272, 274 scan the bar code label 337 (see FIG. 55) on the outer portion of bent flanges 316 and 318 of end wall 303 of each tray 300 as the tray 300 is brought into the sample preparation area. Various information, such as sample and assay identification, can be placed on the tubes and/or each tray 300, and this information can be scanned by the scanners 272, 274 and stored in the central processing computer. If no sample tube is present, the tray 300 presents a special code 335 (see FIG. 55) to be read by the scanners 272, 274.

A preferred sample tube holder is disclosed by Knight et al., "Sample Tube Holder," U.S. Provisional Application No. 60/672,609, which enjoys common ownership herewith. Knight discloses sample tube holders having a plurality of sample tube compartments with aligned sets of finger springs for holding sample tubes in fixed, vertical orientations. For applications in which the sample tubes are capped with penetrable closures, the sample tube holders include a retainer for maintaining sample tubes within the sample tube compartments during sampling procedures. See, e.g., Kacian et al., "Penetrable Cap," U.S. Pat. No. 6,893,612 (discloses a sample tube closed with a cap having a frangible seal and a filter for limiting the dissemination of a contaminating aerosol or bubbles).

Pipette Tip Wheel

As shown primarily in FIGS. 5 and 6, a second ring assembly of the preferred embodiment is a pipette tip wheel 350 and comprises a circular ring 352 at a bottom portion thereof, a top panel 374 defining a circular inner periphery and five circumferentially-spaced, radially-protruding sections 370, and a plurality of generally rectangular risers 354 separating the top panel 374 from the ring 352 and preferably held in place by mechanical fasteners 356 extending through the top panel 374 and ring 352 into the risers 354. Five rectangular openings 358 are formed in the top panel 374 proximate each of the sections 370, and a rectangular box 376 is disposed beneath panel 374, one at each opening 358. Top panel 374, ring 352, and risers 354 are preferably made from machined aluminum, and boxes 376 are preferably formed from stainless steel sheet stock.

The openings 358 and associated boxes 376 are constructed and arranged to receive trays 372 holding a plurality of disposable pipette tips. The pipette tip trays 372 are preferably those manufactured and sold by TECAN (TECAN U.S. Inc., Research Triangle Park, N.C.) under the trade name "Disposable Tips for GENESIS Series". Each tip has a 1000 µL capacity and is conductive. Each tray holds ninety-six elongated disposable tips.

Lateral slots 378 and longitudinal slots 380 are formed in the top panel 374 along the lateral and longitudinal edges, respectively, of each opening 358. The slots 378, 380 receive downwardly-extending flanges (not shown) disposed along the lateral and longitudinal edges of the trays 372. The slots 378, 380 and associated flanges of the trays 372 serve to properly register the trays 372 with respect to openings 358 and to hold the trays 372 in place on the panel 374.

Pipette tip wheel 350 is preferably rotationally supported by three 120-spaced V-groove rollers 357, 360, 361 which engage a continuous V-ridge 362 formed on the inner periphery of ring 352, as shown in FIGS. 5, 6, and 6A, so that the pipette tip wheel 350 is rotatable about a second central axis of rotation that is generally parallel to the first axis of rotation of the sample ring 250. The rollers are preferably made by Bishop-Wisecarver Corp. of Pittsburgh, Calif., Model No. W1SSX. Rollers 357 and 360 are rotationally mounted on fixed shafts, and roller 361 is mounted on a bracket which pivots about a vertical axis and is spring biased so as to urge roller 361 radially outwardly against the inner periphery of ring 352. Having two fixed rollers and one radially movable roller allows the three rollers to accommodate an out-of-round inner periphery of ring 352. In addition, the wheel 350 can be easily installed and removed by merely pushing pivoting roller 361 radially inwardly to allow the ring 352 to move laterally to disengage continuous V-ridge 362 from the fixed V-groove rollers 357, 360.

Pipette tip wheel 350 is driven by a motor 364 having a shaft-mounted spur gear which meshes with mating gear teeth formed on an outer perimeter of ring 352. Motor 364 is preferably a VEXTA gear head stepper motor, Model No. PK243-A1-SG7.2, having a 7.2:1 gear reduction and available from Oriental Motor Co., Ltd. of Tokyo, Japan. A gear head stepper motor with a 7.2:1 gear reduction is preferred because it provides smooth motion of the pipette tip wheel 350, where the spur gear of the motor 364 is directly engaged with the ring 352.

A home sensor and a sector sensor (not shown), preferably slotted optical sensors, are provided adjacent the pipette tip wheel 350 at a rotational home position and at a position of one of the boxes 376. The pipette tip wheel 350 includes a home flag (not shown) located at a home position on the wheel and five equally-spaced sector flags (not shown) corresponding to the positions of each of the five boxes 376. The home flag and sector flags cooperate with the home sensor and sector sensors to provide wheel position information to the assay manager program and to control the pipette tip wheel 350 to stop at five discrete positions corresponding to established coordinates for user re-load and access by pipette unit 450. Preferred sensors for the home sensor and sector sensor are Optek Technology, Inc. slotted optical sensors, Model No. OPB980, available from Optek Technology, Inc. of Carrollton, Tex.

Multi-Axis Mixer

Referring to FIGS. 7-12, the multi-axis mixer 400 includes a rotating turntable structure 414 (see FIG. 10) rotatably mounted on a center shaft 428 supported in center bearings 430 to a fixed base 402 mounted to the jig plate 130 by means of mechanical fasteners (not shown) extending through apertures 419 formed about the outer periphery of the fixed base 402. A cover member 404 is attached to and rotates with turntable 414.

Figure 10:
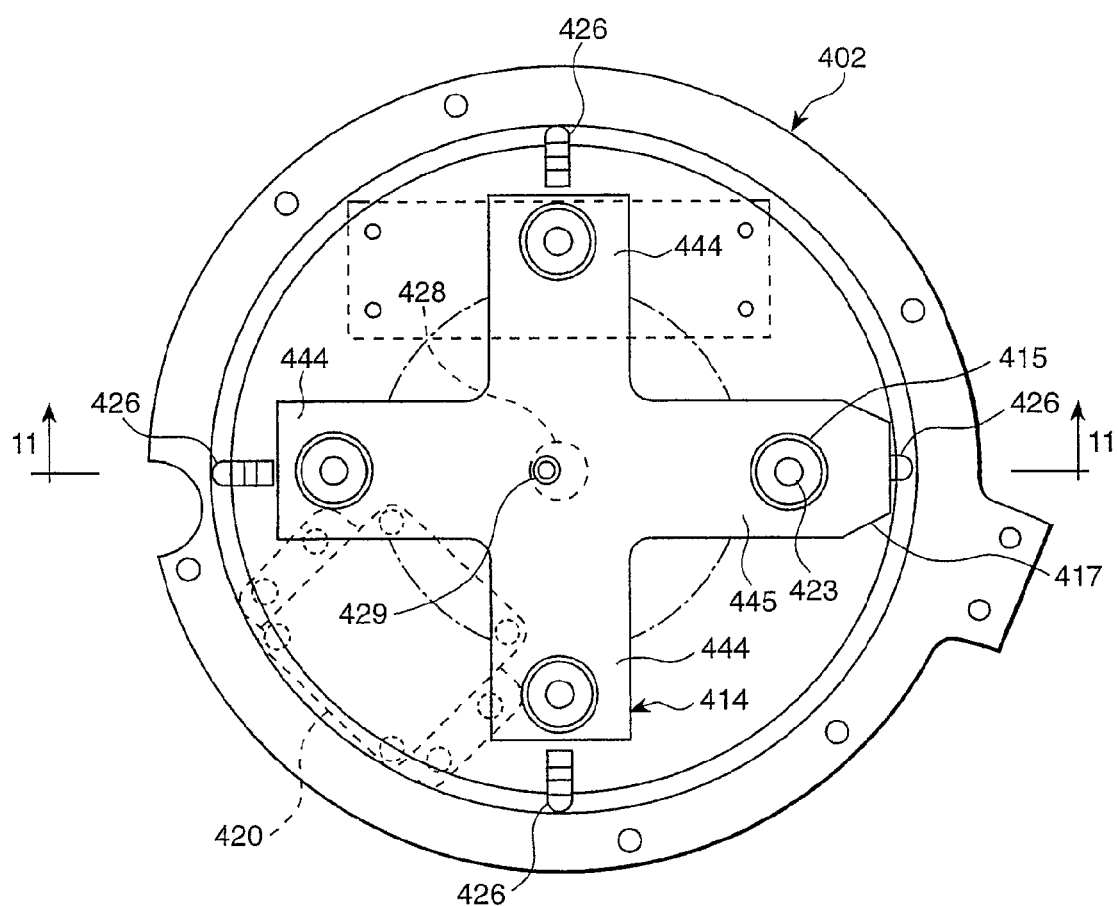
FIG. 10 is a plan view of the multi-axis mixer with container holders and a turntable cover removed therefrom.
Figure 11:
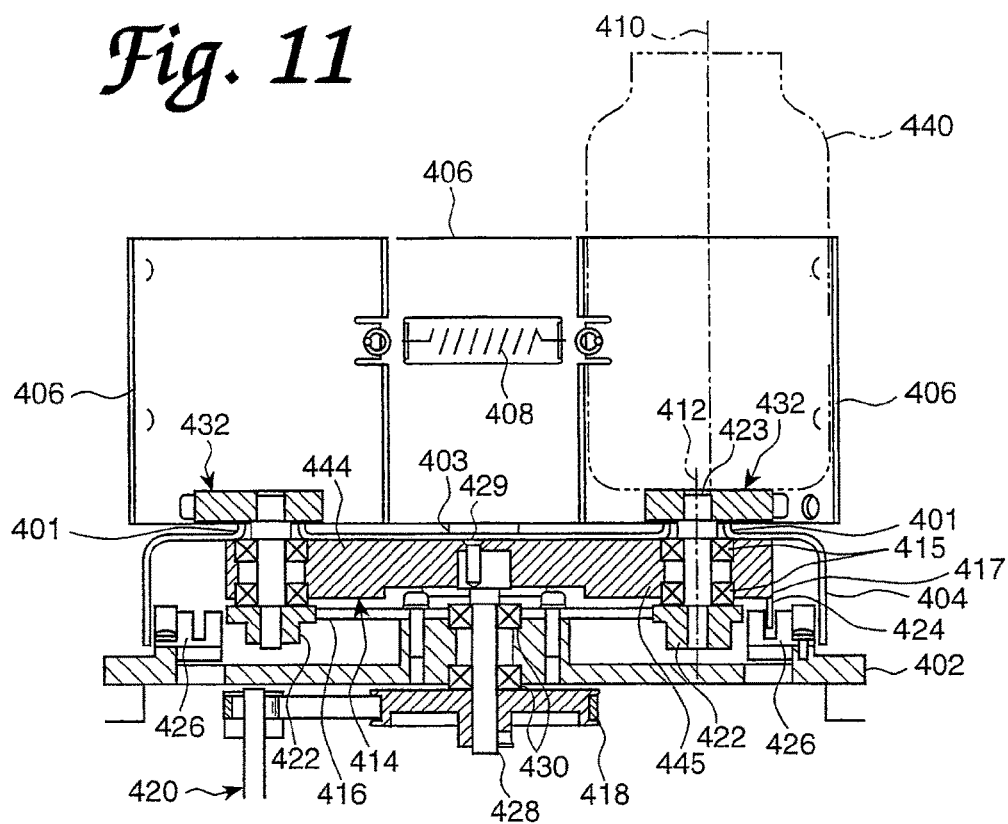
FIG. 11 is a cross-sectional view of the multi-axis mixer taken in the direction 11-11 in FIG. 10.
Figure 12:
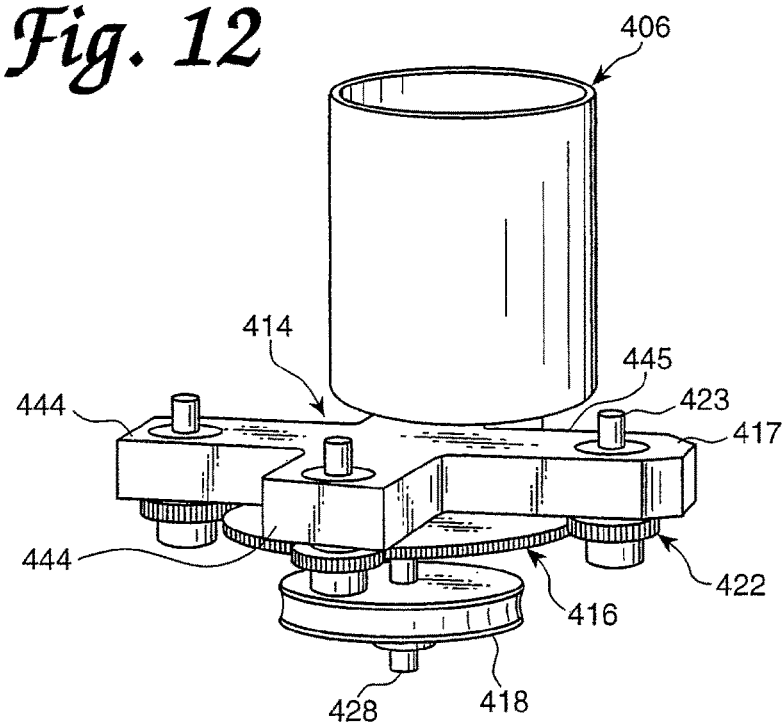
FIG. 12 is a perspective view of a drive assembly of the multi-axis mixer.
Figure 15:
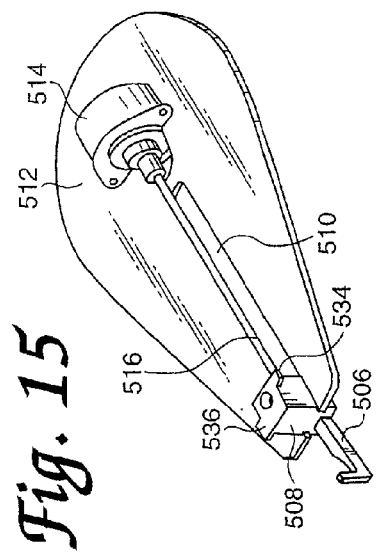
FIG. 15 is the same as FIG. 14, except with the manipulating hook member in the extended position.
Figure 14:
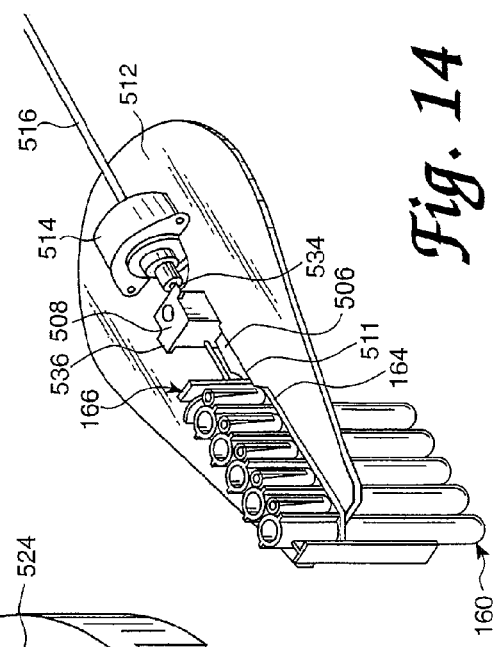
FIG. 14 is a perspective view of a manipulating hook mounting plate and a manipulating hook actuating mechanism of the transport mechanism, with the manipulating hook member engaged with a reaction receptacle and in a retracted position.
Figure 13:
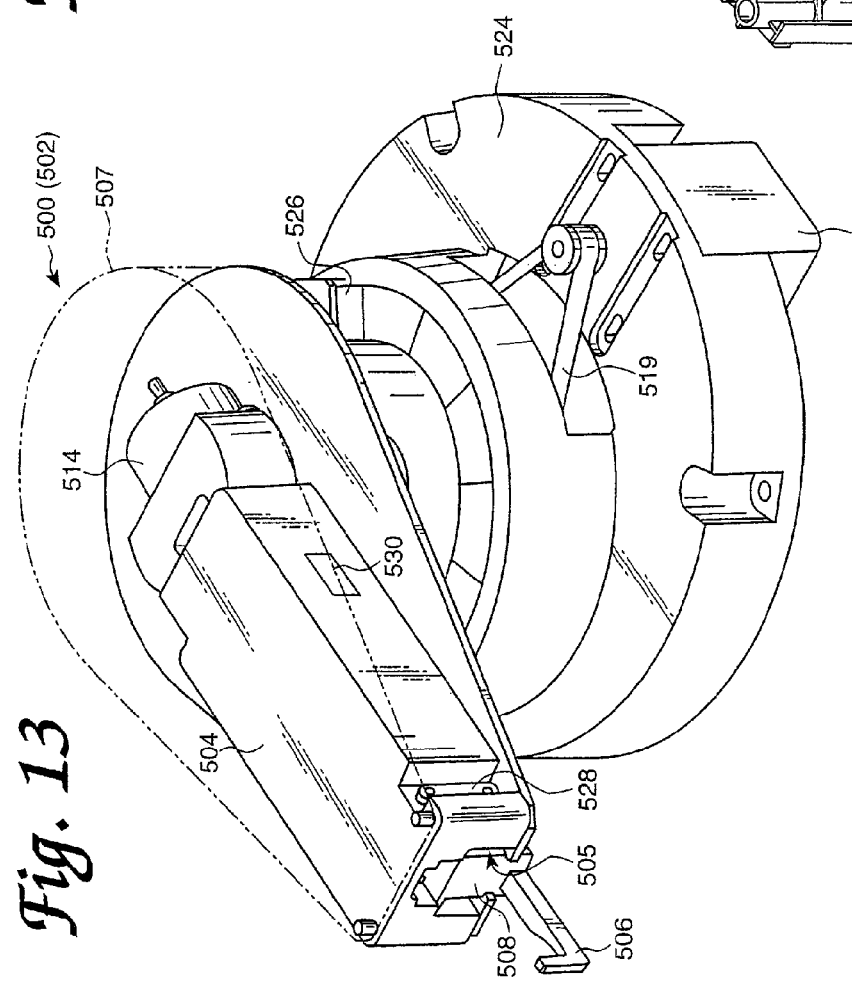
FIG. 13 is a perspective view of a transport mechanism of the processing deck of the analyzer of the present invention.

Turntable 414 is preferably in the form of a right angle cross comprising three 90-spaced rectangular arms 444 of equal length extending radially outwardly from the center of the turntable 414 and a fourth arm 445 having an extension 417 making arm 445 slightly longer than arms 444. As shown in FIGS. 10-12, the center portion of turntable 414 is connected to center shaft 428 by a screw 429.

Four container holders 406 are disposed on the ends of the arms 444 and 445 of turntable frame 414. Each container holder 406 is attached to one of four vertical shafts 423, which are rotatably supported in container holder bearings 415. Container holder bearings 415 are pressed into the arms 444, 445 of the turntable 414 and are disposed at equal radial distances from shaft 428.

The cover member 404 includes four circular openings with upwardly-turned peripheral flanges 401 through which shafts 423 extend. Upward flanges 401 can advantageously prevent spilled liquids from flowing into the openings.

The container holders 406 comprise generally cylindrical members having an open bottom and an open top for receiving and holding a container 440, preferably a plastic bottle, of target capture reagent.

The target capture reagent used with the preferred assay includes magnetically responsive particles with immobilized polynucleotides, polynucleotide capture probes, and reagents sufficient to lyse cells containing the targeted nucleic acids. After cell lysis, targeted nucleic acids are available for hybridization under a first set of predetermined hybridization conditions with one or more capture probes, with each capture probe having a nucleotide base sequence region which is capable of hybridizing to a nucleotide base sequence region contained in at least one of the targeted nucleic acids. Under a second set of predetermined hybridization conditions, a homopolymer tail (e.g., oligo(dT)) of the immobilized polynucleotides is capable of hybridizing with a complementary homopolymer tail (e.g., oligo(dA)) contained in the capture probe, thereby immobilizing targeted nucleic acids. Various target-capture methods and lysing procedures are well known in the art and are readily adapted for use with the analyzer 50 of the present invention. This preferred two-step capture method of capturing and immobilizing a target nucleic acid on a magnetically responsive particle is disclosed by Weisburg et al. in U.S. Pat. No. 6,534,273.

A container retainer spring 408 spans a lateral slot formed in the wall of each container holder 406 and helps to hold the container 440 within the container holder 406 by urging the container 440 toward a portion of the inner peripheral wall of the holder 406 opposite the spring 408.

Each container holder 406 is secured to an associated vertical shaft 423 by a shaft block structure 432. Shaft block structure 432 includes curved end portions which conform to the inside of the cylindrical container holder 406, and the container holder 406 is secured to the block 432 by fasteners 434. A generally circular aperture 449 receives the shaft 423. A slot 438 extends from aperture 449 to an end of the block 432 which does not extend all the way to the inside of the container holder 406, and a second slot 436 extends from an edge of the block 432 generally perpendicularly to slot 438 so as to define a cantilevered arm 435. A machine screw 437 extends through a through-hole 441 formed laterally through block 432 and into a threaded hole 447 formed laterally through arm 435. As screw 437 is tightened, arm 435 deflects, thus tightening aperture 449 around shaft 423.

The shaft block structure 432, the shaft 423, and the container holder bearings 415 associated with each container holder 406 define a preferred container holder mounting structure associated with each container holder 406 that is constructed and arranged to mount the container holder 406 to the turntable 414 and permit the container holder 406 to rotate about an axis of rotation 412 of the shaft 423.

Container holder planetary gears 422 are attached to the opposite ends of shafts 423. The planetary gears 422 operatively engage a stationary sun gear 416. A drive pulley 418 is attached to center shaft 428 and is coupled to a drive motor 420 by a drive belt (not shown). Drive motor 420 is preferably mounted so as to extend through an opening (not shown) in the jig plate 130 below the base 402. Drive motor 420 is preferably a stepper motor, and most preferably a VEXTA stepper motor, Model No. PK264-01A, available from Oriental Motor Co., Ltd. of Tokyo, Japan. The drive motor 420, via the drive belt and drive pulley 418, rotates the center shaft 428 and the turntable 414 attached thereto. As the turntable frame 414 rotates about the center line of center shaft 428, the planetary gears 422 engaged with sun gear 416 cause the shafts 423 and container holders 406 attached thereto to rotate at the ends of the arms 444 of the turntable frame 414. Each container holder 406 is preferably mounted such that the axis of rotation 410 thereof is offset from the axis of rotation 412 of the associated shaft 423. Thus, each container holder 406 rotates eccentrically about axis 412 of the associated shaft 423. Accordingly, the planetary gears 422 and the sun gear 416 constitute rotational motion coupling elements constructed and arranged to cause the container holders 406 to rotate about the respective axes of rotation of the shafts 423 as the turntable 414 rotates about the axis of rotation of the shaft 428.

A bar code scanner device 405 is preferably mounted on a bracket 403 and reads bar code information of the containers 440 through a scanner slot 407 formed in each container holder 406. The preferred scanner is a Model No. NFT1125/002RL scanner, available from Opticon, Inc. of Orangeburg, N.Y.

The multi-axis mixer 400 usually rotates during operation of the analyzer 50 to agitate the fluid contents of the containers 440 to thereby keep the target capture reagent in suspension, stopping only briefly to permit pipette unit 456 to withdraw an amount of mixture from one of the containers. Pipette unit 456 draws mixture from a bottle at the same location each time. Therefore, it is desirable to monitor the positions of the bottles so that the bottle from which mixture is withdrawn each time can be specified.

Four optical slotted sensors 426, each comprising an optical emitter and detector, are stationed around the periphery of fixed base 402, spaced at 90 intervals. Optical sensors available from Optek Technology, Inc. of Carrollton, Tex., Model No. OPB490P11, are preferred. A sensor tab 424 extends down from extension 417 at the end of arm 445 of the turntable 414. When sensor tab 424 passes through a sensor 426, the communication between the emitter and detector is broken thus giving a "container present" signal. The tab 424 is only provided at one location, e.g., the first container location. By knowing the position of the first container, the positions of the remaining containers, which are fixed relative to the first container, are also known.

Power and control signals are provided to the multi-axis mixer 400 via a power and data connector. While the multi-axis mixer 400 provides mixing by rotation and eccentric revolution, other mixing techniques, such as vibration, inversion, etc. may be used.

Sample Preparation Procedure

To begin sample preparation, the pipette unit 456 moves to transfer target capture reagent, preferably mag-oligo reagent, from a container 440 carried on the multi-axis mixer 400 into each of the reaction tubes 162 of the MTU 160. The target capture reagent includes a support material able to bind to and immobilize a target analyte. The support material preferably comprises magnetically responsive particles. At the beginning of the sample preparation procedure, the pipette unit 456 of the right-side pipette assembly 450 moves laterally and longitudinally to a position in which the probe 457 is operatively positioned over a pipette tip in one of the trays 372.

The tip trays 372 are carried on the pipette tip wheel 350 so as to be precisely positioned to achieve proper registration between the pipette tips and the tubular probe 457 of the pipette unit 456. The pipette unit 456 moves down to insert the free end of the tubular probe 457 into the open end of a pipette tip and frictionally engage the pipette tip. The Cavro processors preferably used for pipette unit 456 includes a collar (not shown), which is unique to Cavro processors. This collar is moved slightly upwardly when a pipette tip is frictionally engaged onto the end of the tubular probe 457, and the displaced collar trips an electrical switch on the pipette unit 456 to verify that a pipette tip is present. If tip pick-up is not successful (e.g., due to missing tips in the trays 372 or a misalignment), a missing tip signal is generated and the pipette unit 456 can move to re-try tip engagement at a different tip location.

The assay manager program causes the multi-axis mixer 400 to briefly stop rotating so that the pipette unit 456 can be moved to a position with the tubular probe 457 and attached pipette tip of the pipette unit 456 aligned over one of the stationary containers 440. The pipette unit 456 lowers the pipette tip attached to the tubular probe 457 into the container 440 and draws a desired amount of target capture reagent into the pipette tip. The pipette unit 456 then moves the probe 457 out of the container 440, the multi-axis mixer 400 resumes rotating, and the pipette unit 456 moves to a position above opening 252 and the sample transfer station 255. Next, the pipette unit 456 descends, moving the pipette tip and the tubular probe 457 through the opening 252, and dispenses a required amount of target capture (typically 100-500 μL) into one or more of the reaction tubes 162 of the MTU 160. It is preferred that the target capture reagent is drawn only into the pipette tip and not into the probe 457 itself. Furthermore, it is preferred that the pipette tip be of sufficient volumetric capacity to hold enough reagent for all five reaction tubes 162 of the MTU 160.

After target capture reagent transfer, the pipette unit 456 then moves to a "tip discard" position above tip disposal tube 342, where the disposable pipette tip is pushed or ejected off of the end of the tubular probe 457 of the pipette unit 456, and falls through tube 342 toward a solid waste container. An optical sensor (not shown) is disposed adjacent to tube 342, and before tip discard, the sample pipette assembly 450 moves the pipette unit 456 into a sensing position of the sensor. The sensor detects whether a tip is engaged with the end of the tubular probe 457 to verify that the tip is still held on the tubular probe 457 of the pipette unit 456, thereby confirming that the tip was on the tubular probe 457 throughout sample preparation. A preferred sensor is a wide-gap slotted optic sensor, Model No. OPB900 W, available from Optek Technology, Inc. of Carrollton, Tex.

Preferably, the pipette tip is ejected by the collar (not shown) on the tubular probe 457 of pipette unit 456. The collar engages a hard stop when the tubular probe 457 is raised, so that as the probe 457 continues to ascend, the collar remains fixed and engages an upper end of the pipette tip, thereby forcing it off the tubular probe 457.

After pipetting the target capture and discarding the pipette tip, the probe 457 of the pipette unit 456 can be washed by running distilled water through the tubular probe 457 at the tip wash station basin 346. The tip wash water is collected and drains down into a liquid waste container.

Following the reagent dispensing procedure, the pipette unit 456 on the right pipette assembly 450 moves laterally and longitudinally to a position in which the tubular probe 457 of the pipette unit 456 is centered over a new pipette tip on one of the tip trays 372. After successful tip engagement, the pipette unit 456 moves back over the sample ring 250, adjacent to the sample preparation opening 252 and with-draws a test sample (about 25-900 μL) from a sample tube 320 that is aligned with one of the openings 140, 142 of the cover plate 138. Note that both openings 140, 142 include upwardly extending peripheral flanges to prevent any fluids spilled onto the plate 138 from running into the openings 140, 142. The pipette unit 456 then moves over the MTU 160 in the sample transfer station 255, moves down through opening 252, and dispenses test sample into one of the reaction tubes 162 of the MTU 160 containing target capture reagent. Pipette unit 456 then moves to the "tip discard" position above the tip disposal tube 342, and the disposable pipette tip is ejected into the tube 342. Pipette unit 456 then picks up a new disposable pipette tip from the pipette tip wheel 350, the sample ring 250 indexes so that a new sample tube is accessible by the pipette unit 456, unit 456 moves to and draws sample fluid from the sample tube into the disposable pipette tip, the pipette unit 456 then moves to a position above the sample transfer station 255, and dispenses sample fluid into a different reaction tube 162 containing target capture reagent. This process is preferably repeated until all five reaction tubes 162 contain a combination of fluid sample and target capture reagent.

Alternatively, depending on the assay protocol or protocols to be run by the analyzer 50, the pipette unit 456 may dispense the same test sample material into two or more of the reaction tubes 162 and the analyzer can perform the same or different assays on each of those aliquots.

As described above with respect to pipette units 480, 482, pipette unit 456 also includes capacitive level sensing capability. The pipette tips used on the end of the tubular probe 457 are preferably made from a conductive material, so that capacitive level sensing can be performed with the pipette unit 456, even when a tip is carried on the end of the tubular probe 457. After the pipette unit has completed a test sample dispensing procedure, the pipette unit 456 moves the tubular probe 457 back down into the reaction tube 162 until the top of the fluid level is detected by the change in capacitance. The vertical position of the tubular probe 457 is noted to determine whether the proper amount of fluid material is contained in the reaction tube 162. Lack of sufficient material in a reaction tube 162 can be caused by clotting in the test sample, which can clot the tip at the end of the tubular probe 457 and prevent proper aspiration of test sample material into the tip and/or can prevent proper dispensing of test sample from the tip.

After sample transfer, the pipette tip is discarded into the tip disposal tube 342 as described above. Again, the tubular probe 457 of the pipette of unit can be washed with distilled water if desired, but washing of the probe is typically not necessary because, in the preferred method of operation, sample material only comes into contact with the disposable pipette tip.

The assay manager program includes pipette unit control logic which controls movements of the pipette units 456, 480, 482, and preferably causes pipette unit 456 to move in such a manner that it never passes over a sample tube 320 on the sample ring 250, except when the pipette unit 456 positions the tubular probe 457 over a sample tube 320 to withdraw a test sample or when the sample tube 320 is below the plate 138 of the sample cover. In this way, inadvertent fluid drips from the tubular probe 457 of the pipette unit 450 into another sample tube, which might result in cross-contamination, are avoided.

Following sample preparation, the MTU 160 is moved by the right-side transport mechanism 500 from the sample transfer station to the right orbital mixer 550 in which the sample/reagent mixtures are mixed. The structure and operation of the orbital mixers 550, 552 will be described in further detail below.

After the MTU 160 is withdrawn from the sample transfer station by the right-side transport mechanism 500, the reaction receptacle shuttle assembly within the input queue 150 advances the next MTU into a position to be retrieved by the right-side transport mechanism 500 which moves the next MTU to the sample transfer station. Sample preparation procedures are then repeated for this next MTU.

Transport Mechanisms

The right-side and left-side transport mechanisms 500, 502 will now be described in detail. Referring to FIGS. 13-16, the right-side transport mechanism 500 (as well as the left-side transport mechanism 502) has a manipulating hook member that, in the illustrated embodiment, includes an extendible distributor hook 506 extending from a hook mounting structure 508 that is radially and slidably displaceable in a slot 510 on a plate 512. A housing 504 on top of the plate 512 has an opening 505 configured to receive the upper portion of an MTU 160. A stepper motor 514 mounted on the plate 512 turns a threaded shaft 516, which, in cooperation with a lead screw mechanism, moves the distributor hook 506 from the extended position shown in FIGS. 13 and 15, to the retracted position shown in FIG. 14, the motor 514 and threaded shaft 516 constituting elements of a preferred hook member drive assembly. Stepper motor 514 is preferably a modified HIS, series 46000. HIS stepper motors are available from Haydon Switch and Instrument, Inc. of Waterbury, Conn. The HIS motor is modified by machining the threads off one end of the threaded shaft 516, so that the shaft 516 can receive the hook mounting structure 508.

The housing 504, motor 514, and the plate 512 are preferably covered by a conforming shroud 507.

Figure 16:
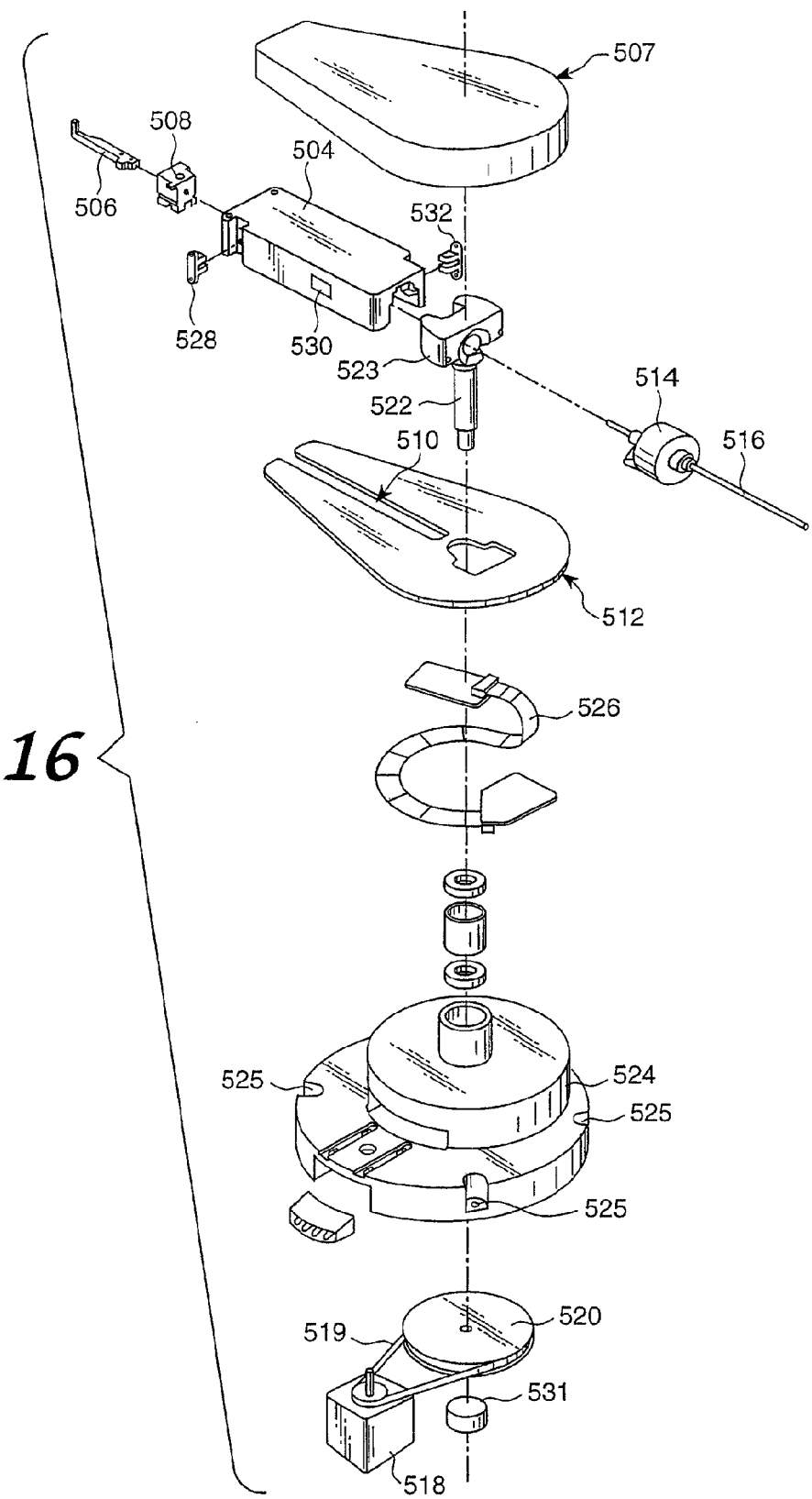
FIG. 16 is an exploded perspective view of the transport mechanism.

As shown in FIG. 16, a stepper motor 518 turns a pulley 520 via a belt 519. (VEXTA stepper motors, Model No. PK264-01A, available from Oriental Motor Co., Ltd. of Tokyo, Japan, and SDP timing belts, Model No. A6R51M200060, available from SDP/SI of New Hyde Park, N.Y., are preferred). Pulley 520 is preferably a custom-made pulley with one hundred sixty-two (162) axial grooves disposed around its perimeter. A main shaft 522 fixedly attached to the plate 512, by means of a uniquely-shaped mounting block 523, extends down through a base 524 and is fixed to the pulley 520. Base 524 is mounted to the datum plate 82 by means of mechanical fasteners extending through apertures 525 formed about the outer periphery of the base 524. A flex circuit 526 provides power and control signals to the hook mounting structure 508 and motor 514, while allowing the plate 512 (and the components carried on the plate) to pivot sufficiently so as to rotate as much as 340 with respect to the base 524. The transport mechanism 500, 502, assembly preferably includes hard stops (not shown) at either end of the unit's rotational path of travel.

An arm position encoder 531 is preferably mounted on an end of the main shaft 522. The arm position encoder is preferably an absolute encoder. A2 series encoders from U.S. Digital in Seattle, Wash., Model No. A2-S-K-315-H, are preferred.

The assay manager program provides control signals to the motors 518 and 514, and to the hook mounting structure 508, to command the distributor hook 506 to engage the MTU manipulating structure 166 on MTU 160. With the hook 506 engaged, the motor 514 can be energized to rotate the shaft 516 and thereby withdraw the hook 506, and the MTU 160, back into the housing 504. The MTU 160 is securely held by the transport mechanism 500, 502 via the sliding engagement of the connecting rib structure 164 of the MTU 160 with opposed edges 511 of plate 512 adjacent slot 510. The plate 512 thereby constitutes an element of a preferred receptacle carrier assembly that is constructed and arranged to be rotatable about an axis of rotation (e.g., the axis of shaft 522) and to receive and carry a reaction receptacle (e.g., MTU 160). The motor 518 can rotate the pulley 520 and shaft 522 via the belt 519 to thereby rotate the plate 512 and housing 504 with respect to the base 524. Rotation of the housing 504 thus changes the orientation of the engaged MTU, thereby bringing that MTU into alignment with a different station on the processing deck.

Sensors 528, 532 are provided in opposite sides of the housing 504 to indicate the position of the distributor hook 506 within the housing 504. Sensor 528 is an end-of-travel sensor, and sensor 532 is a home sensor. Sensors 528, 532 are preferably optical slotted sensors available from Optek Technology, Inc. of Carrollton, Tex., Model No. OPB980T11. For the home sensor 532, the sensor beam is broken by a home flag 536 extending from the hook mounting structure 508 when the hook 506 is in its fully retracted position. The beam of the end-of-travel sensor 528 is broken by an end-of-travel flag 534 extending from the opposite side of the hook mounting structure 508 when the hook 506 is fully extended.

An MTU-present sensor 530 mounted in the side of the housing 504 senses the presence of an MTU 160 in the housing 504. Sensor 530 is preferably a SUNX, infra-red sensor, available from SUNX/Ramco Electric, Inc., of West Des Moines, Iowa.

Temperature Ramping Stations

One or more temperature ramping stations 700 are preferably disposed below the jig plate 130 and sample ring 250 (no temperature ramping stations located below the sample ring 250 are shown in the figures). After mixing the contents of the MTU 160 within the orbital mixer 550, the right-side transport mechanism 500 may move the MTU 160 from the right orbital mixer 550 to a temperature ramping station 700, depending on the assay protocol.

The purpose of each ramping station 700 is to adjust the temperature of an MTU 160 and its contents up or down as desired. The temperature of the MTU and its contents may be adjusted to approximate an incubator temperature before inserting the MTU into the incubator to avoid large temperature fluctuations within the incubator.

Figure 17:
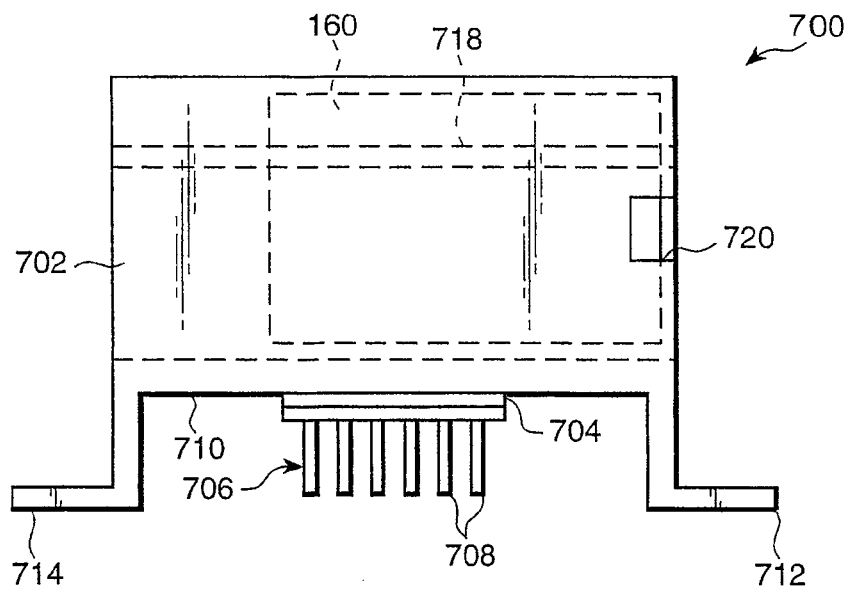
FIG. 17 is a side-elevation of a temperature ramping station of the processing deck of the analyzer of the present invention.
Figure 18:
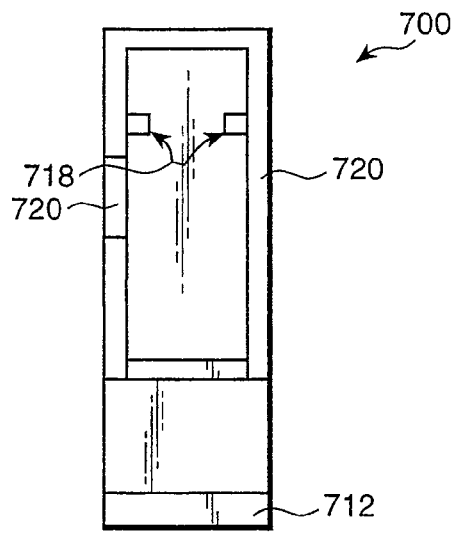
FIG. 18 is a front-elevation of the temperature ramping station.

As shown in FIGS. 17-18, a temperature ramping station 700 includes a housing 702 in which an MTU 160 can be inserted. The housing 702 includes mounting flanges 712, 714 for mounting the ramping station 700 to the datum plate 82. A thermoelectric module 704 (also known as a Peltier device) in thermal contact with a heat sink structure 706 is attached to the housing 702, preferably at the bottom 710. Preferred thermoelectric modules are those available from Melcor, Inc. of Trenton, N.J., Model No. CP1.4-127-06L. Although one thermoelectric module 704 is shown in FIG. 17, the ramping station 700 preferably includes two such thermoelectric modules. Alternatively, the outer surface of the housing 702 could be covered with a mylar film resistive heating foil material (not shown) for heating the ramping station. Suitable mylar film heating foils are etched foils available from Minco Products, Inc. of Minneapolis, Minn. and from Heatron, Inc. of Leavenworth, Kans. For ramp-up stations (i.e., heaters), resistive heating elements are preferably used, and for ramp-down stations (i.e., chillers), thermoelectric modules 704 are preferably used. The housing 702 is preferably covered with a thermal insulating jacket structure (not shown).

The heat sink structure used in conjunction with the thermoelectric module 704 preferably comprises an aluminum block with heat dissipating fins 708 extending therefrom.

Two thermal sensors (not shown) (preferably thermistors rated 10 KOhm at 25° C.) are preferably provided at a location on or within the housing 702 to monitor the temperature. YSI 44036 series thermistors available from YSI, Inc. of Yellow Springs, Ohio are preferred. YSI thermistors are preferred because of their high accuracy and the ±0.1° C. interchangeability provided by YSI thermistors from one thermistor to another. One of the thermal sensors is for primary temperature control, that is, it sends signals to the embedded controller for controlling temperature within the ramping station, and the other thermal sensor is for monitoring ramping station temperature as a back-up check of the primary temperature control thermal sensor. The embedded controller monitors the thermal sensors and controls the heating foils or the thermoelectric module of the ramping station to maintain a generally uniform, desired temperature within the ramping station 700.

An MTU 160 can be inserted into the housing, supported on the MTU support flanges 718 which engage the connecting rib structure 164 of the MTU 160. A cut-out 720 is formed in a front edge of a side panel of the housing 702. The cut-out 720 permits a distributor hook 506 of a transport mechanism 500 or 502 to engage or disengage the MTU manipulating structure 166 of an MTU 160 inserted all the way into a temperature ramping station 700 by lateral movement with respect thereto.

Rotary Incubators

Continuing with the general description of the assay procedure, following sufficient temperature ramp-up in a ramping station 700, the right-side transport mechanism 500 retrieves the MTU from the ramping station 700 and places the MTU 160 into the TC incubator 600. In a preferred mode of operation of the analyzer 50, the TC incubator 600 incubates the contents of the MTU 160 at about 60° C. For certain tests, it is important that the annealing incubation temperature not vary more than ±0.5° C. and that amplification incubation (described below) temperature not vary more than ±0.1° C. Consequently, the incubators are designed to provide a consistent uniform temperature.

The details of the structure and operation of the two embodiments of the rotary incubators 600, 602, 604 and 606 will now be described. Referring to FIGS. 19-23C, each of the incubators has housing with a generally cylindrical portion 610, suitably mounted to the datum plate 82, within an insulating jacket 612 and an insulated cover 611.

The cylindrical portion 610 is preferably constructed of nickel-plated cast aluminum and the metal portion of the cover 611 is preferably machined aluminum. The cylindrical portion 610 is preferably mounted to the datum plate 82 atop three or more resin "feet" 609. The feet 609 are preferably formed of Ultem®-1000 supplied by General Electric Plastics. The material is a poor thermal conductor, and therefore the feet 609 function to thermally isolate the incubator from the datum plate. The insulation 612 and the insulation for the cover 611 are preferably comprised of ½ inch thick polyethylene supplied by the Boyd Corporation of Pleasantown, Calif.

Receptacle access openings 614, 616 are formed in the cylindrical portion 610, and cooperating receptacle access openings 618, 620 are formed in the jacket 612. For incubators 600 and 602, one of the access openings is positioned to be accessible by the right-side transport mechanism 500 and the other access opening is positioned to be accessible by the left-side transport mechanism 502. Incubators 604 and 606 need to be accessible only by the left-side transport mechanism 502 and therefore only have a single receptacle access opening.

Closure mechanisms comprising revolving doors 622, 624 are rotatably positioned within the openings 614 and 616. Each revolving door 622, 624 has a MTU slot 626 extending through a solid cylindrical body. The MTU slot 626 is configured to closely match the profile of the MTU 160, having a wider upper portion compared to the lower portion. A door roller 628, 630 is attached on top of each of the doors 622, 624, respectively. The revolving doors 622, 624 are actuated by solenoids (not shown) which are controlled by commands from the assay manager program to open and close the doors 622, 624 at the proper times. A door 622 or 624 is opened by turning the door 622, 624 so that the MTU slot 626 thereof is aligned with the respective receptacle access opening 614, 616 and is closed by turning the door 622, 624 so that the MTU slot 626 thereof extends transversely to the respective access opening 614, 616. The cylindrical portion 610, cover 611, doors 622, 624, and a floor panel (not shown) constitute an enclosure which defines the incubation chamber.

The doors 622, 624 are opened to permit insertion or retrieval of an MTU into or from an incubator and are closed at all other times to minimize heat loss from the incubator through the access openings 614, 616.

A centrally positioned radial fan 632 is driven by an internal fan motor (not shown). A Papst, Model No. RER 100-25/14 centrifugal fan, available from ebm/Papst of Farmington, Conn., having a 24 VDC motor and rated at 32 cfm is preferred because its shape is well-suited to application within the incubator.

Figure 22:
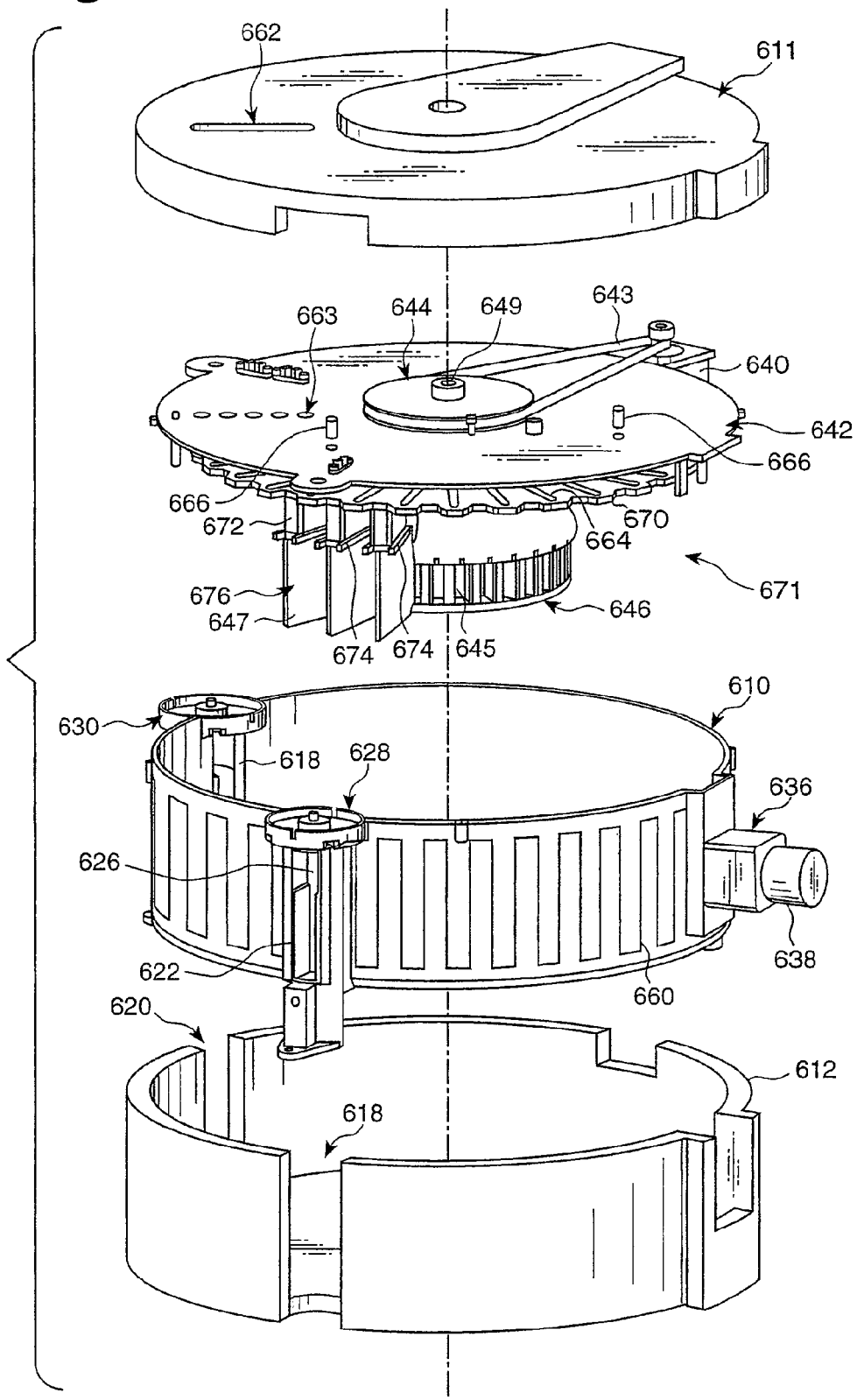
FIG. 22 is an exploded perspective view of the first embodiment of the rotary incubator.

Referring now to FIG. 22, an MTU carousel assembly 671 is a preferred receptacle carrier which carries a plurality of radially oriented, circumferentially-arranged MTUs 160 within the incubator. The MTU carousel assembly 671 is carried by a top plate 642, which is supported by the cylindrical portion 610 of the housing, and is preferably actuated by a rotation motor 640, preferably a stepper motor, supported at a peripheral edge of on the top plate 642. Rotation motor 640 is preferably a VEXTA stepper motor, Model No. PK246-01A, available from Oriental Motor Co., Ltd. of Tokyo, Japan.

The MTU carousel 671 includes a hub 646 disposed below the top plate 642 and coupled, via a shaft 649 extending through the top plate 642, to a pulley 644. Pulley 644 is preferably a custom-made pulley with one hundred sixty-two (162) axial grooves disposed around its perimeter and is coupled to motor 640 through a belt 643, so that motor 640 can rotate the hub 646. Belt 643 is preferably a GT® series timing belt available from SDP/SI of New Hyde Park, N.Y. A 9:1 ratio is preferably provided between the pulley 644 and the motor 640. The hub 646 has a plurality of equally spaced-apart internal air flow slots 645 optionally separated by radially-oriented, circumferentially arranged divider walls 647. In the illustration, only three divider walls 647 are shown, although it will be understood that divider walls may be provided about the entire circumference of the hub 646. In the preferred embodiment, divider walls 647 are omitted. A support disk 670 is attached to hub 646 and disposed below top plate 642 in generally parallel relation therewith. A plurality of radially extending, circumferentially-arranged MTU holding members 672 are attached to the bottom of the support disk 670 (only three MTU holding members 672 are shown for clarity). The MTU holding members 672 have support ridges 674 extending along opposite sides thereof. Radially oriented MTUs are carried on the MTU carousel assembly 671 within stations 676 defined by circumferentially adjacent MTU holding members 672, with the support ridges 674 supporting the connecting rib structures 164 of each MTU 160 carried by the MTU carousel assembly 671.

The MTU carousel assembly rotates on a carousel drive shaft to which the drive pulley (644 in the illustrated embodiment) is attached. A carousel position encoder is preferably mounted on an exterior end of the carousel drive shaft. The carousel position encoder preferably comprises a slotted wheel and an optical slot switch combination (not shown). The slotted wheel can be coupled to the carousel assembly 671 to rotate therewith, and the optical slot switch can be fixed to the cylindrical portion 610 of the housing or top plate 642 so as to be stationary. The slotted wheel/slot switch combination can be employed to indicate a rotational position of the carousel assembly 671 and can indicate a "home" position (e.g., a position in which an MTU station 676 designated the #1 station is in front of the access opening 614). A2 series encoders from U.S. Digital in Seattle, Wash., Model No. A2-S-K-315-H, are preferred.

A heat source is provided in thermal communication with the incubator chamber defined within the incubator housing comprising the cylindrical portion 610 and cover 611. In the preferred embodiment, Mylar film-encased electrically-resistive heating foils 660 surround the housing 610 and may be attached to the cover 611 as well. Preferred mylar film heating foils are etched foils available from Minco Products, Inc. of Minneapolis, Minn. and Heatron, Inc. of Leavenworth, Kans. Alternative heat sources may include internally mounted resistive heating elements, thermal-electric heating chips (Peltiers), or a remote heat-generating mechanism thermally connected to the housing by a conduit or the like.

Figure 19:
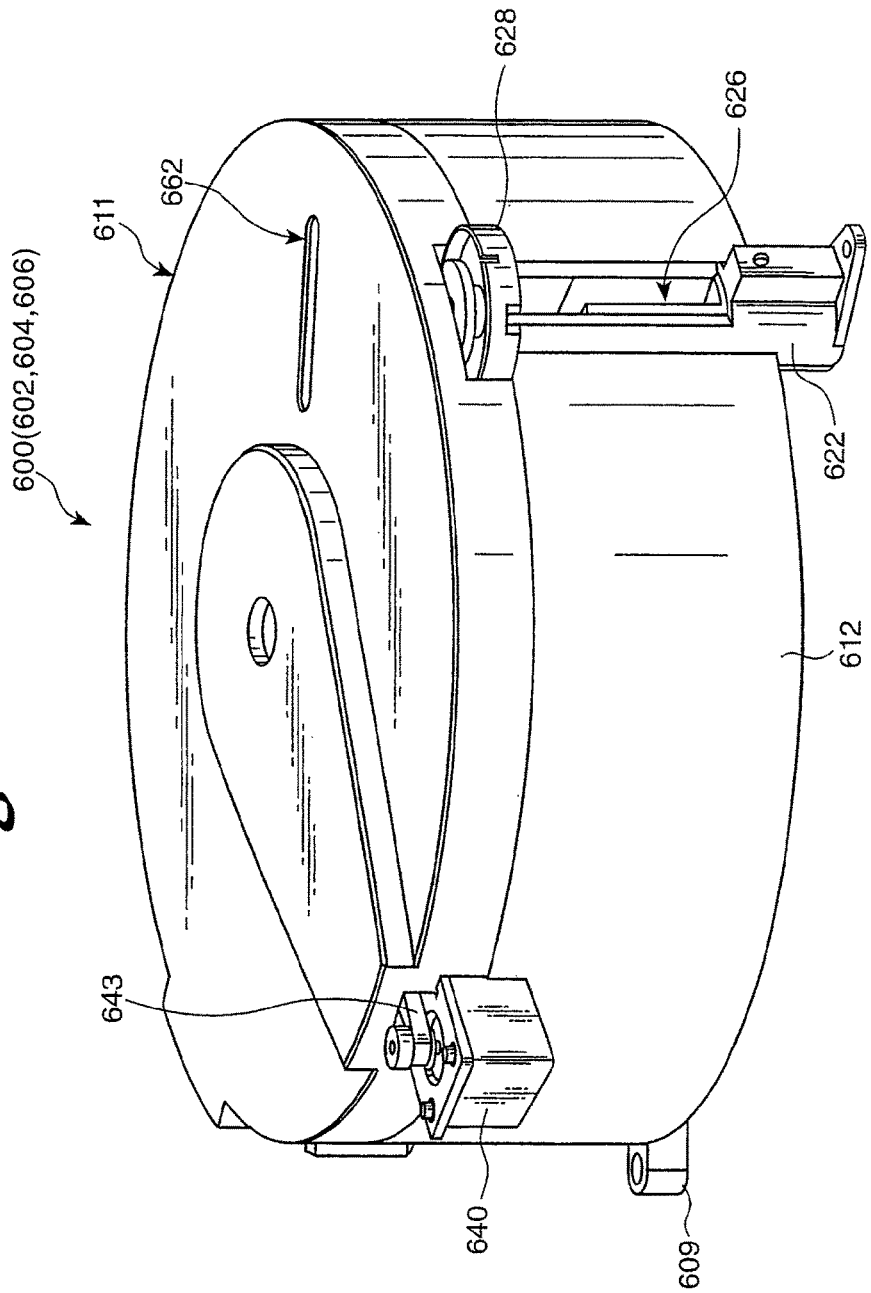
FIG. 19 is a perspective view of a rotary incubator of the processing deck of the analyzer of the present invention.
Figure 20:
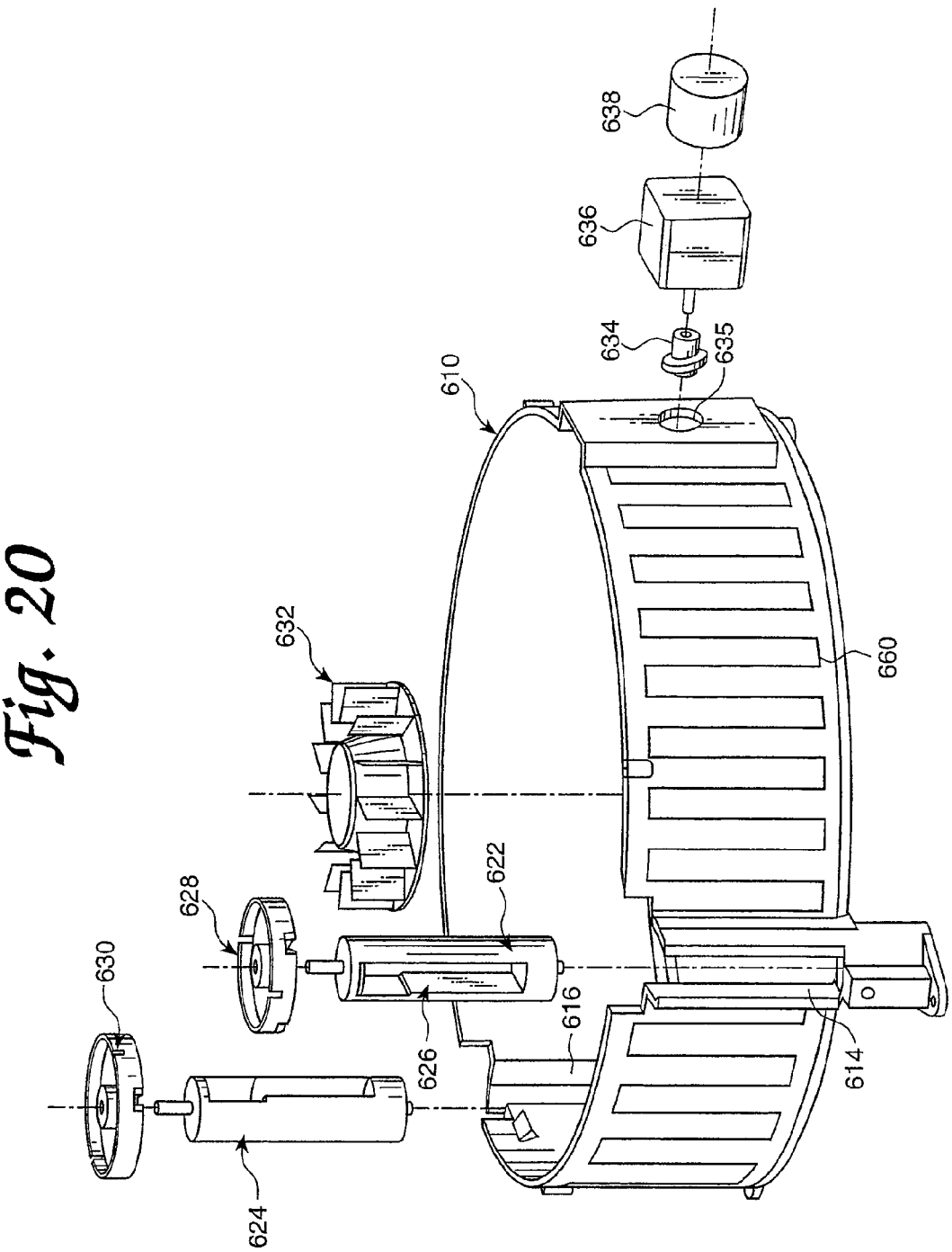
FIG. 20 is an exploded view of a portion of a housing and access opening closure mechanisms according to a first embodiment of the rotary incubator.

As shown in FIGS. 19 and 22, a pipette slot 662 extends through the incubator cover 611, radially-aligned pipette holes 663 extend through the top plate 642, and pipettes slots 664 are formed in the support disk 670 over each MTU station 676, to allow pipetting of reagents into MTUs disposed within the incubators. In the preferred embodiment of the analyzer 50 for the preferred mode of operation, only two of the incubators, the AMP incubator 604 and the hybridization protection assay incubator HYB incubator, include the pipette holes 663 and pipette slots 662 and 664, because, in the preferred mode of operation, it is only in these two incubators where fluids are dispensed into MTUs 160 while they are in the incubator.

Two temperature sensors 666, preferably thermistors (10 KOhm at 25° C.), are positioned in the top plate 642. YSI 44036 series thermistors available from YSI, Inc. of Yellow Springs, Ohio are preferred. YSI thermistors are preferred because of their high accuracy and the ±0.1° C. interchangeability provided by YSI thermistors from one thermistor to another. One of the sensors 666 is for primary temperature control, that is, it sends singles to the embedded controller for controlling temperature within the incubator, and the other sensor is for monitoring temperature of the incubator as a back-up check of the primary temperature control sensor. The embedded controller monitors the sensors 666 and controls the heating foils 660 and fan 632 to maintain a uniform, desired temperature within the incubator housing 610.

As a transport mechanism 500, 502 prepares to load an MTU 160 into an incubator 600, 602, 604, or 606, the motor 640 turns the hub 646 to bring an empty MTU station 676 into alignment with the receptacle access opening 614 (or 616). As this occurs, the door-actuating solenoid correspondingly turns the revolving door 622 (or 624) one-quarter turn to align the MTU slot 626 of the door with the MTU station 676. The access opening 614 is thus exposed to allow placement or removal of an MTU 160. The transport mechanism 500 or 502 then advances the distributor hook 506 from the retracted position to the extended position, pushing the MTU 160 out of the housing 504, through the access opening 614, and into an MTU station 676 in the incubator. After the distributor hook 506 is withdrawn, the motor 640 turns the hub 646, shifting the previously inserted MTU 160 away from the access opening 614, and the revolving door 622 closes once again. This sequence is repeated for subsequent MTUs inserted into the rotary incubator. Incubation of each loaded MTU continues as that MTU advances around the incubator (counter-clockwise) towards the exit slot 618.

An MTU sensor (preferably an infrared optical reflective sensor) in each of the MTU stations 676 detects the presence of an MTU 160 within the station. Optek Technology, Inc. sensors, Model No. OPB770T, available from Optek Technology, Inc. of Carrollton, Tex. are preferred because of the ability of these sensors to withstand the high temperature environment of the incubators and because of the ability of these sensors to read bar code data fixed to the label-receiving surfaces 175 of the label-receiving structures 174 of the MTUs 160. In addition, each door assembly (revolving doors 622, 624) preferably includes slotted optical sensors (not shown) to indicate door open and door closed positions. Sensors available from Optek Technology, Inc. of Carrollton, Tex., Model No. OPB980T11, are preferred because of the relatively fine resolution provided thereby to permit accurate monitoring of door position. A skewed disk linear mixer (also known as a wobbler plate) 634 is provided within housing 610 adjacent MTU carousel assembly 671 and operates as a receptacle mixing mechanism. The mixer 634 comprises a disk mounted in a skewed manner to the shaft of a motor 636 which extends through opening 635 into the housing 610. The motor is preferably a VEXTA stepper motor, Model No. PK264-01A, available from Oriental Motors Ltd. of Tokyo, Japan, which is the same motor preferably used for the MTU carousel assembly 671. A viscous harmonic damper 638 is preferably attached to motor 636 to damp out harmonic frequencies of the motor which can cause the motor to stall. Preferred harmonic dampers are VEXTA harmonic dampers, available from Oriental Motors Ltd. The operation of the skewed disk linear mixer 634 will be described below.

Only two of the incubators, the AMP incubator 604 and the HYB incubator 606, include a skewed disk linear mixer 634, because, in the preferred mode of operation, it is only in these two incubators where fluids are dispensed into the MTUs 160 while they are in the incubator. Thus, it is only necessary to provide linear mixing of the MTU 160 by the skewed disk linear mixer 634 in the AMP incubator 604 and the HYB incubator 606.

To effect linear mixing of an MTU 160 in the incubator by linear mixer 634, the MTU carousel assembly 671 moves the MTU 160 into alignment with the skewed disk linear mixer 634, and the skewed disk of the skewed disk linear mixer 634 engages the MTU manipulating structure 166 of the MTU 160. As the motor 636 spins the skewed disk of the skewed disk linear mixer 634, the portion of the skewed disk structure engaged with the MTU 160 moves radially in and out with respect to the wall of the housing 610, thus alternately engaging the vertical piece 167 of the MTU manipulating structure 166 and the shield structure 169. Accordingly, the MTU 160 engaged with the skewed disk linear mixer 634 is moved radially in and out, preferably at high frequency, providing linear mixing of the contents of the MTU 160. For the amplification incubation step of the preferred mode of operation, which occurs within the AMP incubator 604, a mixing frequency of 10 Hz is preferred. For the probe incubation step of the preferred mode of operation, which occurs within the HYB incubator 606, a mixing frequency of 14 Hz is preferred. Finally, for the select incubation step of the preferred mode of operation, which also occurs within the HYB incubator 606, a mixing frequency of 13 Hz is preferred.

The raised arcuate portions 171, 172 may be provided in the middle of the convex surfaces of the vertical piece 167 and the shield structure 169 of the MTU 160, respectively, (see FIG. 60) to minimize the surface contact between the skewed disk linear mixer 634 and the MTU 160 so as to minimize friction between the MTU 160 and the skewed disk linear mixer 634.

Figure 21:
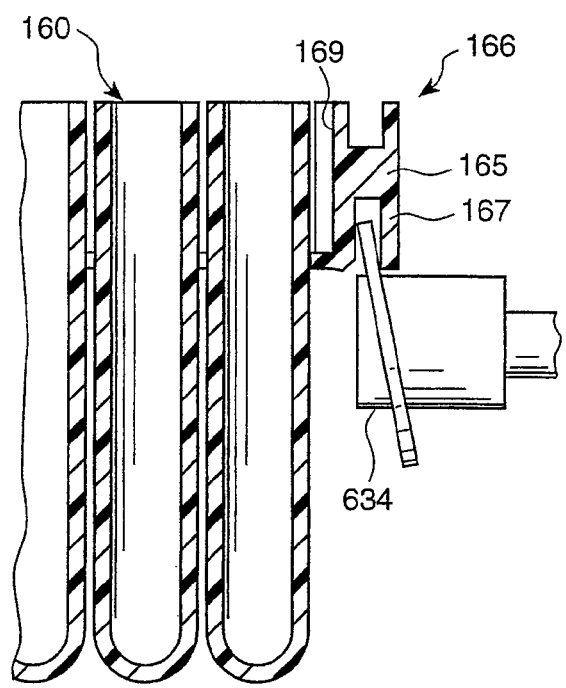
FIG. 21 is a partial view of a skewed disk linear mixer of the rotary incubator, shown engaged with a reaction receptacle employed in a preferred mode of operation of the analyzer of the present invention.

In the preferred embodiment, a sensor is provided at the skewed disk linear mixer 634 to ensure that the skewed disk linear mixer 634 stops rotating in the "home" position shown in FIG. 21, so that MTU manipulating structure 166 can engage and disengage from the skewed disk linear mixer 634 as the MTU carousel assembly 671 rotates. The preferred "home" sensor is a pin extending laterally from the skewed disk linear mixer structure and a slotted optical switch which verifies orientation of the skewed disk linear mixer assembly when the pin interrupts the optical switch beam. Hall effect sensors based on magnetism may also be used.

Figure 23:
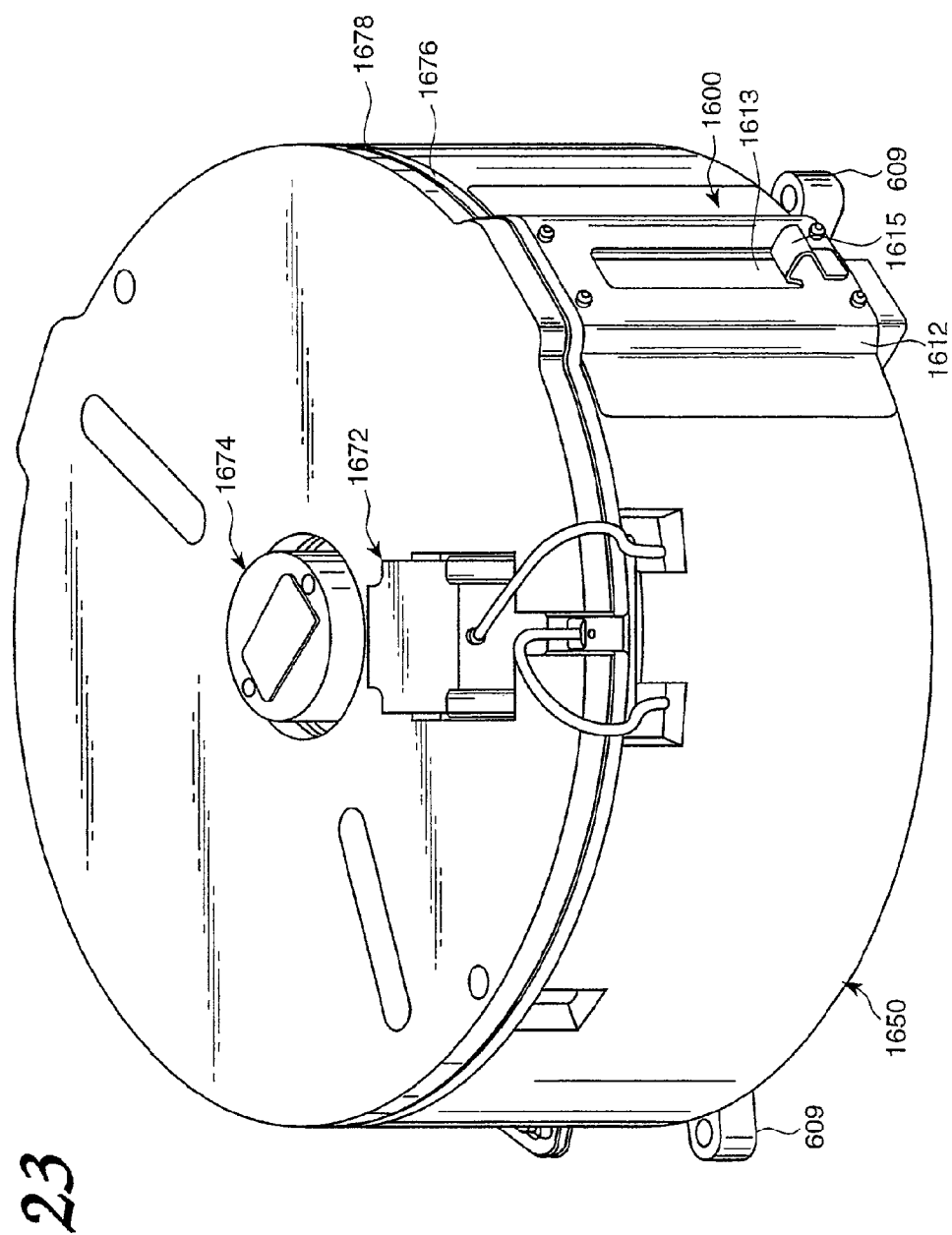
FIG. 23 is a perspective view of the rotary incubator according to a second embodiment thereof.
Figure 23A:
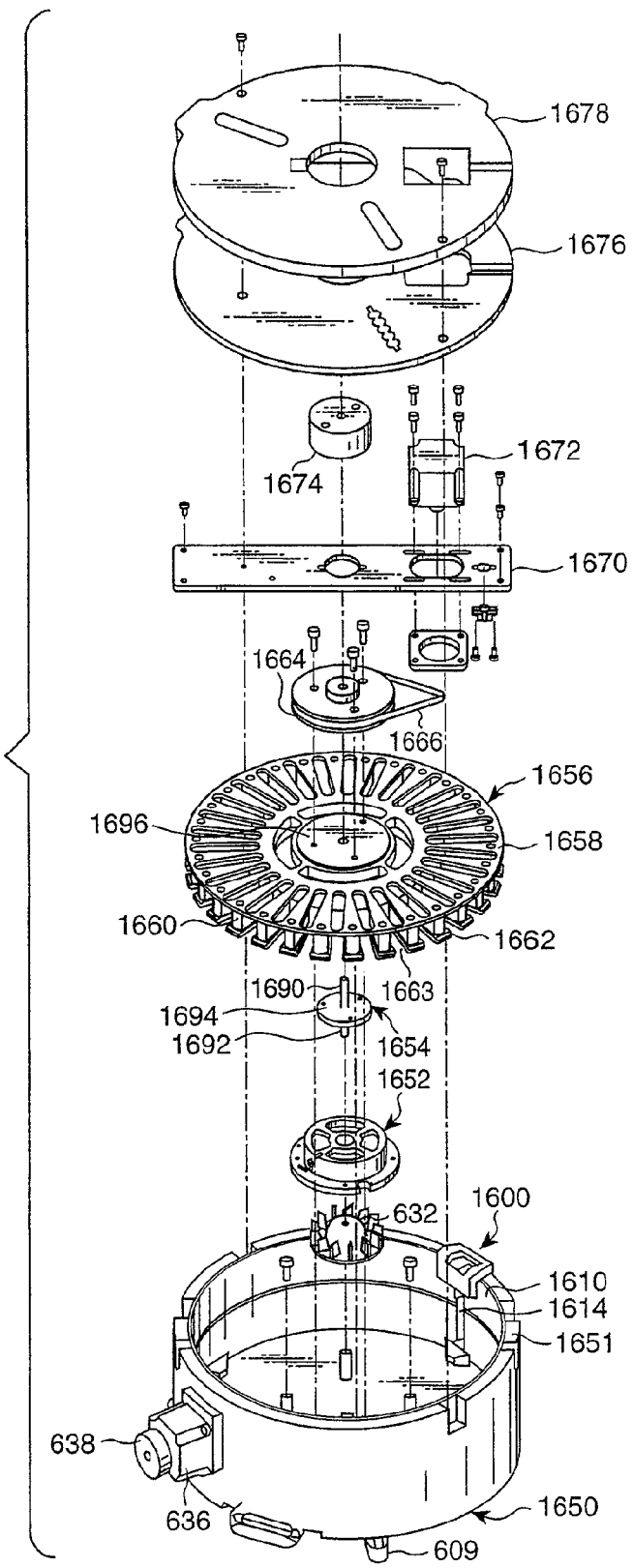
FIG. 23A is an exploded perspective view of the second embodiment of the rotary incubator.
Figure 23B:
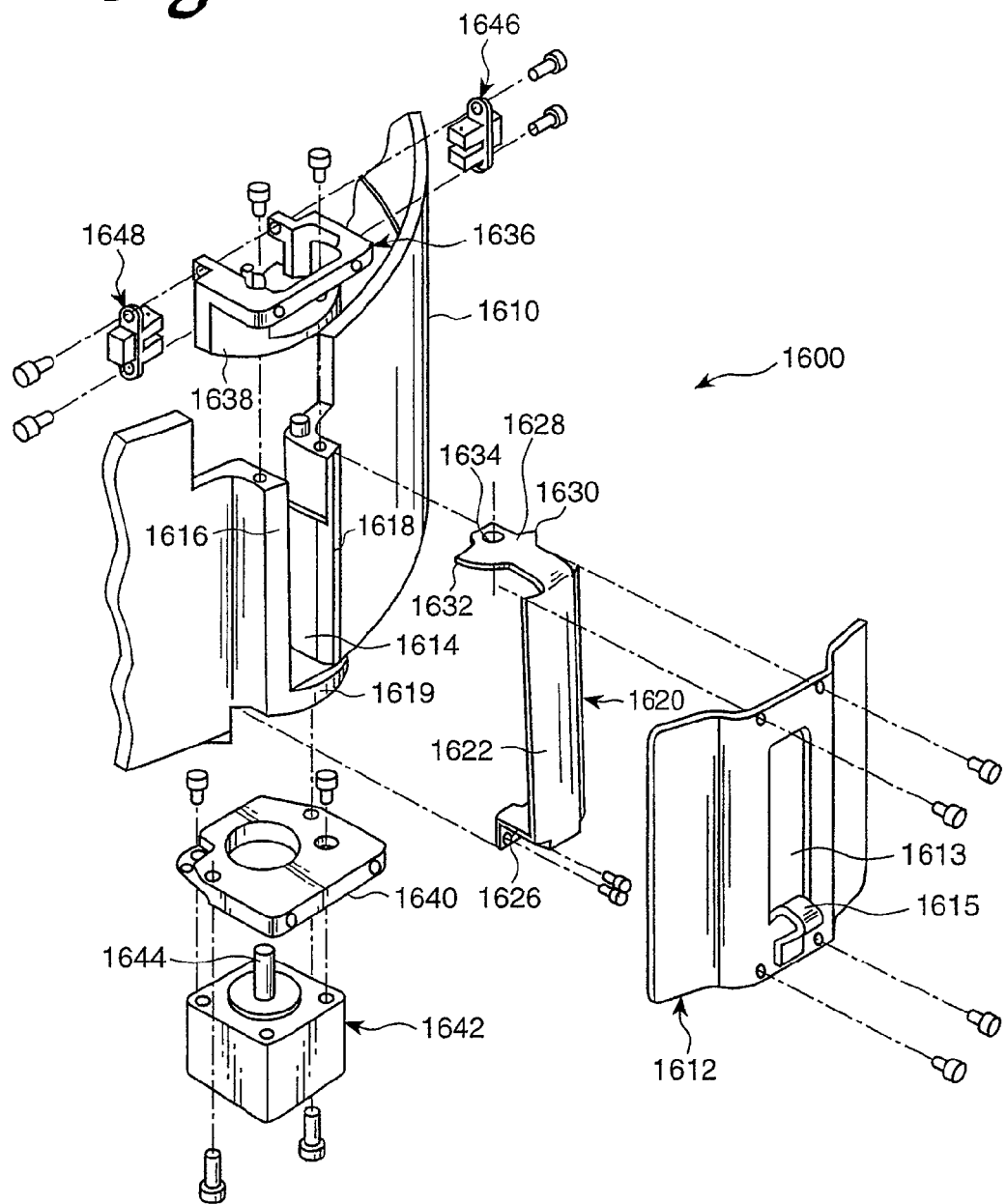
FIG. 23B is a partial exploded perspective view of an access opening closure mechanism of the second embodiment of the rotary incubator.
Figure 23C:
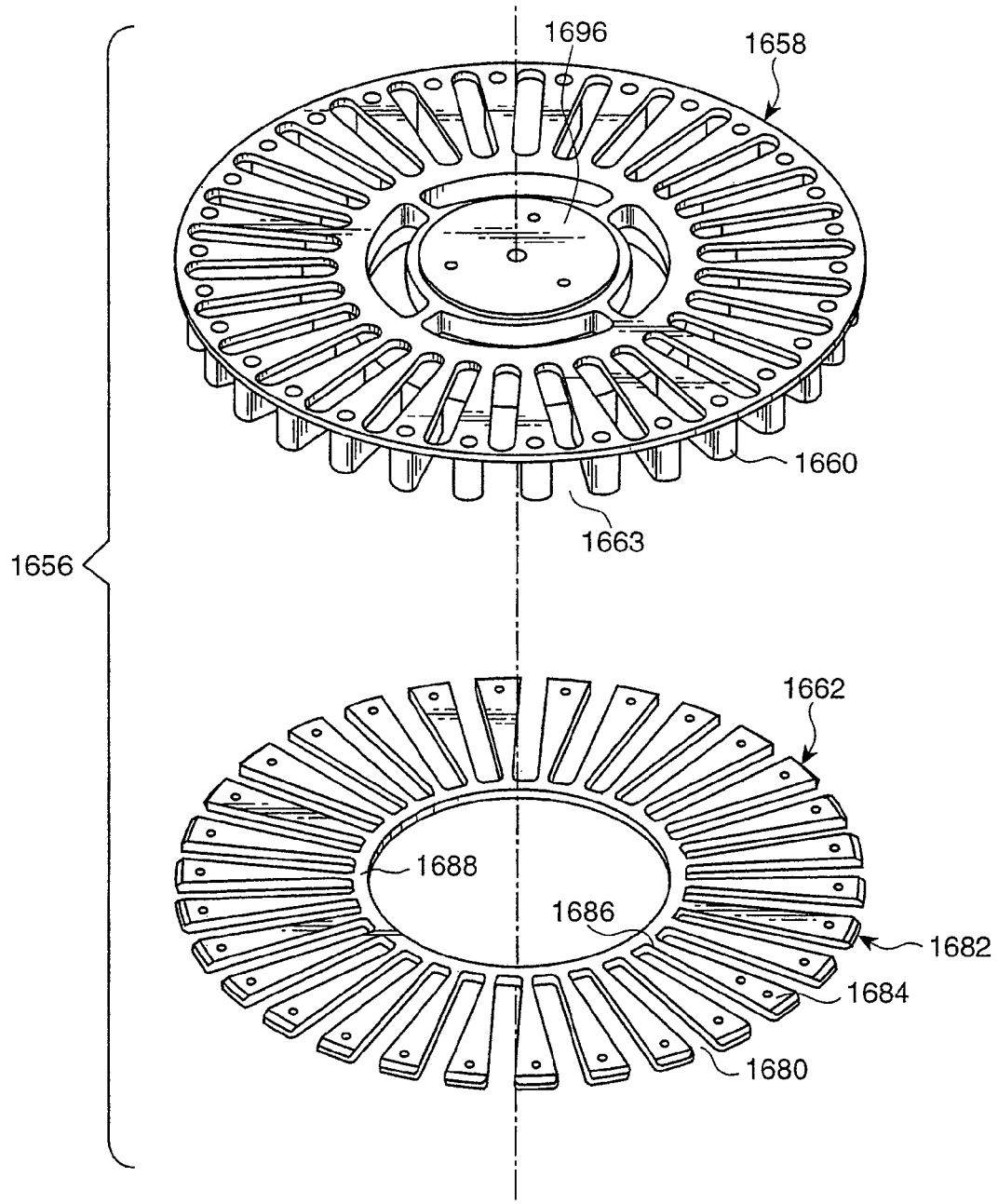
FIG. 23C is an exploded view of a receptacle carrier carousel of the second embodiment of the rotary incubator.

An alternate MTU carousel assembly and carousel drive mechanism are shown in FIGS. 23A and 23C. As shown in FIG. 23A, the alternate incubator includes a housing assembly 1650 generally comprising a cylindrical portion 1610 constructed of nickel-plated cast aluminum, a cover 1676 preferably formed of machined aluminum, insulation 1678 for the cover 1676, and an insulation jacket 1651 surrounding the cylindrical portion 1610. As with the previously described incubator embodiment, the incubator may include a linear mixer mechanism including a linear mixer motor 636 with a harmonic damper 638. A closure mechanism 1600 (described below) operates to close off or permit access through a receptacle access opening 1614. As with the previously described embodiment, the incubator may include one or two access openings 1614 depending on the location of the incubator and its function within the analyzer 50.

A centrifugal fan 632 is mounted at a bottom portion of the housing 1650 and is driven by a motor (not shown). A fan cover 1652 is disposed over the fan and includes sufficient openings to permit air flow generated by the fan 632. A carousel support shaft 1654 includes a lower shaft 1692 and an upper shaft 1690 divided by a support disk 1694. The support shaft 1654 is supported by means of the lower shaft 1692 extending down into the fan cover 1652 where it is rotatably supported and secured by bearings (not shown).

An MTU carousel 1656 includes an upper disk 1658 having a central portion 1696. A top surface of the support disk 1694 engages and is attached to a bottom surface of the central portion 1696 of the upper disk 1658 so that the weight of the carousel 1656 is supported from below. As shown in FIG. 23C, a plurality of radially extending, circumferentially spaced station dividers 1660 are attached beneath the upper disk 1658. A lower disk 1662 includes a plurality of radial flanges 1682 emanating from an annular inner portion 1688. The radial flanges 1682 correspond in number and spacing to the carousel station dividers 1660, and the lower disk 1662 is secured to the bottom surfaces of the carousel station dividers 1660, with each flange 1682 being secured to an associated one of the dividers 1660.

The radial flanges 1682 define a plurality of radial slots 1680 between adjacent pairs of flanges 1682. As can be appreciated from FIG. 23C, the width in the circumferential direction of each flange 1682 at an inner end 1686 thereof is less than the width in the circumferential direction of the flange 1682 at the outer end 1684 thereof. The tapered shape of the flanges 1682 ensures that the opposite sides of the slots 1680 are generally parallel to one another.

When the lower disk 1662 is attached beneath the carousel station dividers 1660, the widths of the flanges along at least a portion of their respective lengths are greater than the widths of the respective dividers 1660, which may also be tapered from an outer end thereof toward an inner end thereof. The flanges 1684 define lateral shelves along the sides of adjacent pairs of dividers 1660 for supporting the connecting rib structure 164 of an MTU 160 inserted into each MTU station 1663 defined between adjacent pairs of dividers 1660.

A pulley 1664 is secured to the top of the central portion 1696 of the upper disk 1658 and a motor 1672 is carried by a mounting bracket 1670 which spans the diameter of the housing 1650 and is secured to the cylindrical portion 1610 of the housing at opposite ends thereof. The motor is preferably a Vexta PK264-01A stepper motor, and it is coupled to the pulley (having a 9:1 ratio with respect to the motor) by a belt 1666, preferably one supplied by the Gates Rubber Company. A position encoder 1674 is secured to a top central portion of the mounting bracket 1672 and is coupled with the upper shaft 1690 of the carousel support shaft 1654. The encoder 1674 (preferably an absolute encoder of the A2 series by U.S. Digital Corporation of Vancouver, Wash.) indicates the rotational position of the carousel 1656.

An incubator cover is defined by an incubator plate 1676, preferably formed of machined aluminum, and a conforming cover insulation element 1678. Cover plate 1676 and insulation element 1678 include appropriate openings to accommodate the encoder 1674 and the motor 1672 and may also include radial slots formed therein for dispensing fluids into MTUs carried within the incubator as described with regard to the above embodiment.

An alternate, and preferred, closure mechanism 1600 is shown in FIG. 23B. The cylindrical portion 1610 of the incubator housing includes at least one receptacle access opening 1614 with outwardly projecting wall portions 1616, 1618 extending integrally from the cylindrical portion 1610 along opposite sides of the access opening 1614.

A rotating door 1620 is operatively mounted with respect to the access opening 1614 by means of a door mounting bracket 1636 attached to the cylindrical portion 1610 of the housing above the access opening 1614. Door 1620 includes an arcuate closure panel 1622 and a transversely extending hinge plate portion 1628 having a hole 1634 for receiving a mounting post (not shown) of the door mounting bracket 1636. The door 1622 is rotatable about the opening 1634 with respect to the access opening 1614 between a first position in which the arcuate closure panel 1622 cooperates with the projecting wall portions 1616, 1618 to close off the access opening 1614 and a second position rotated outwardly with respect to the access opening 1614 to permit movement of a receptacle through the access opening 1614. An inner arcuate surface of the arcuate panel 1622 conforms with an arcuate surface 1638 of the door mounting bracket 1636 and an arcuate surface 1619 disposed below the receptacle access opening 1614 to permit movement of the arcuate panel 1622 with respect to the surfaces 1638 and 1619 while providing a minimum gap between the respective surfaces so as to minimize heat loss there through.

The door 1620 is actuated by a motor 1642 mounted to the incubator housing by means of a motor mounting bracket 1640 secured to the cylindrical portion 1610 of the housing beneath the receptacle access opening 1614. A motor shaft 1644 is coupled to a lower actuating plate 1626 of the rotating door 1620 so that rotation of the shaft 1644 is transmitted into rotation of the rotating door 1620. Motor 1642 is most preferably an HIS 7.5 per step motor available from Haydon Switch and Instrument, Inc. of Waterbury, Conn. The HIS motor is chosen because of its relatively low cost and because the closure assembly 1600 does not require a high torque, robust motor.

Door position sensors 1646 and 1648 (preferably slotted optical sensors) are operatively mounted on opposite sides of the door mounting bracket 1636. The sensor 1646 and 1648 cooperate with sensor tabs 1632 and 1630 on the hinge plate 1628 of the door 1620 for indicating the relative position of the rotating door 1620 and can be configured so as to indicate, for example, a door open and a door closed status.

A door cover element 1612 is secured to the outside of the cylindrical portion 1610 of the housing so as to cover the door mounting bracket 1636 and a portion of the rotating door 1620. The cover element 1612 includes an access opening 1613 aligned with the access opening 1614 of the incubator housing and further includes a receptacle bridge 1615 extending laterally from a bottom edge of the access opening 1613. The receptacle bridge 1615 facilitates the insertion of a receptacle (e.g., an MTU 160) into and withdrawal of the receptacle from the incubator.

While in the TC incubator 600, the MTU 160 and test samples are preferably kept at a temperature of about 60° C.±0.5° C. for a period of time sufficient to permit hybridization between capture probes and target nucleic acids. Under these conditions, the capture probes will preferably not hybridize with those polynucleotides directly immobilized on the magnetic particles.

Following target capture incubation in the TC incubator 600, the MTU 160 is rotated by the incubator carousel to the entrance door 622, also known as the right-side or number one distributor door. The MTU 160 is retrieved from its MTU station 676 within the TC incubator 600 and is then transferred by the right-side transport mechanism 500 to a temperature ramp-down station (not shown) below the sample ring 250. In the ramp-down station, the MTU temperature is brought down to the level of the next incubator. This ramp-down station that precedes the AT incubator 602 is technically a heater, as opposed to a chiller, because the temperature to which the MTU is decreased, about 40° C., is still greater than the ambient analyzer temperature, about 30° C. Accordingly, this ramp-down station preferably uses resistive heating elements, as opposed to a thermoelectric module.

From the ramp-down station, the MTU 160 is transferred by the right-side transfer mechanism 500 into the AT incubator 602. The design and operation of the AT incubator 602 is similar to that of the TC incubator 600, as described above, except that the AT incubator 602 incubates at 40±1.0° C.

In the AT incubator 602, the hybridization conditions are such that the polythymidine ("poly(dT)") tail of the immobilized polynucleotide can hybridize to the polyadenine ("poly(dA)") tail of the capture probe. Provided target nucleic acid has hybridized with the capture probe in the TC incubator 600, a hybridization complex can be formed between the immobilized polynucleotide, the capture probe and the target nucleic acid in the AT incubator 602, thus immobilizing the target nucleic acid.

During active temperature binding incubation, the carousel assembly 1656 (or 671) of the AT incubator 602 rotates the MTU to the exit door 624, also known as the number two, or left-side, distributor door, from which the MTU 160 can be removed by the left-side transport mechanism 502. The left-side transport mechanism 502 removes the MTU 160 from the AT incubator 602 and places it into an available magnetic separation station 800.

Temperature ramping stations 700 can be a bottle neck in the processing of a number of MTUs through the chemistry deck 200. It may be possible to use underutilized MTU stations 676 in one or more of the incubators in which temperature sensitivity is of less concern. For example, the active temperature binding process which occurs within the AT incubator 602 at about 40° C. is not as temperature sensitive as the other incubators, and up to fifteen (15) of the incubator's thirty (30) MTU stations 676 may be unused at any given time. As presently contemplated, the chemistry deck has only about eight ramp-up stations, or heaters. Accordingly, significantly more MTUs can be preheated within the unused slots of the AT incubator 602 than within the ramp-up stations 700. Moreover, using unused incubator slots instead of heaters allows the omission of some or all of the heaters, thus freeing up space on the chemistry deck.

Magnetic Separation Stations

Figure 24:
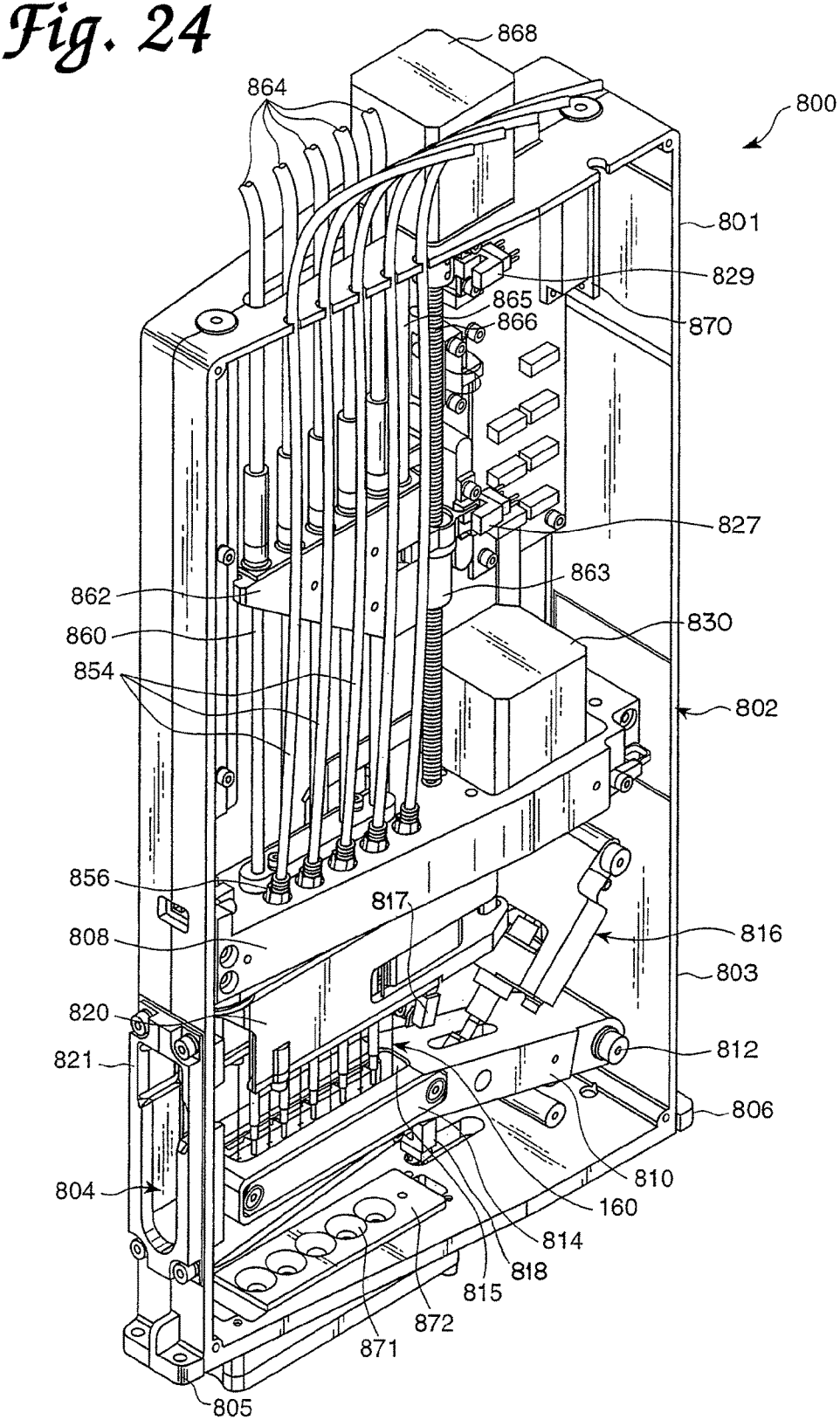
FIG. 24 is a perspective view of a particles of the processing deck of the present invention with a side plate thereof removed.
Figure 25:
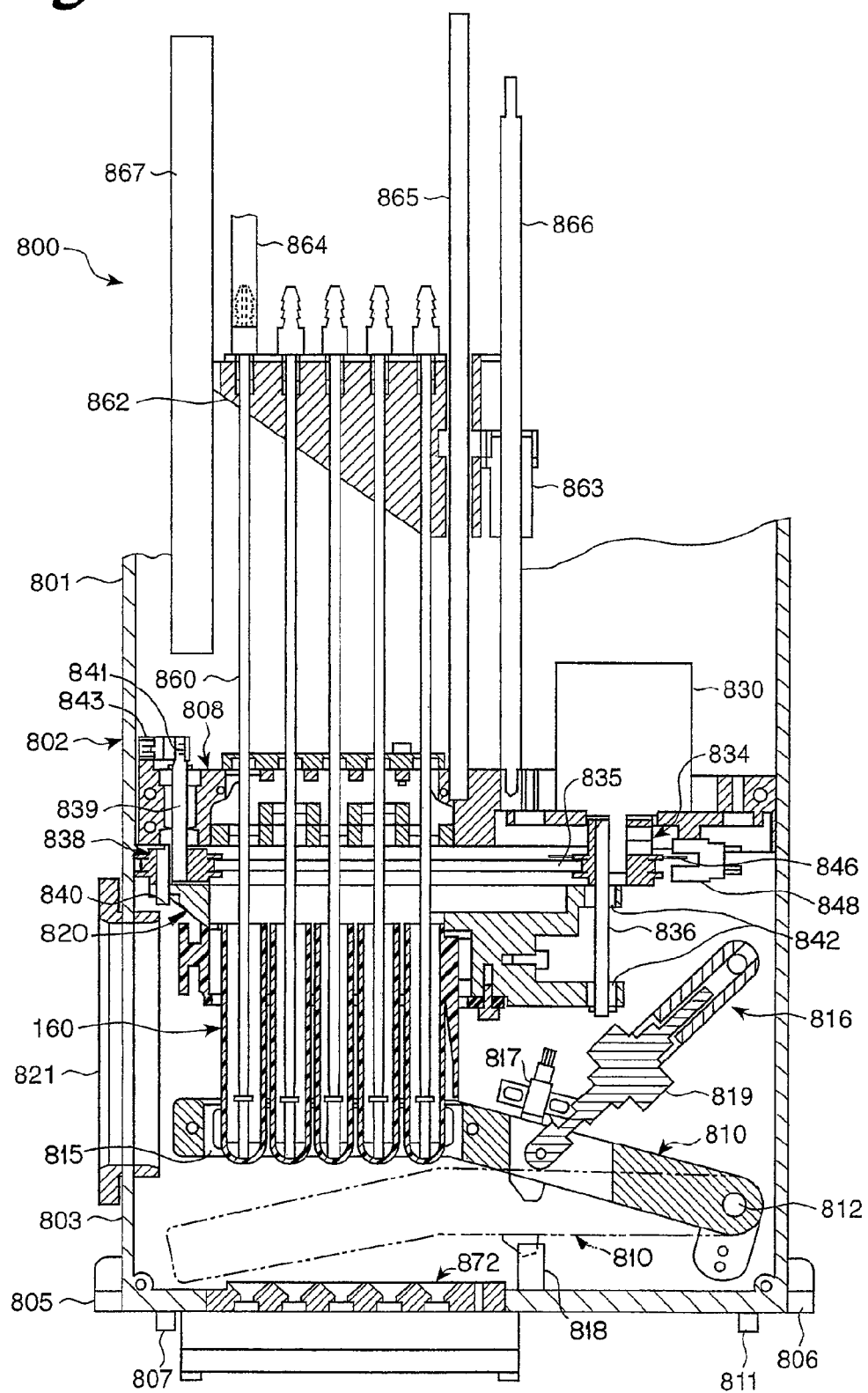
FIG. 25 is a partial transverse cross-section of the particles.

Turning to FIGS. 24-25, each magnetic separation station 800 includes a module housing 802 having an upper section 801 and a lower section 803. Mounting flanges 805, 806 extend from the lower section 803 for mounting the magnetic separation stations 800 to the datum plate 82 by means of suitable mechanical fasteners. Locator pins 807 and 811 extend from the bottom of lower section 803 of housing 802. Pins 807 and 811 register with apertures (not shown) formed in the datum plate 82 to help to locate the magnetic separation stations 800 on the datum plate 82 before the housing 802 is secured by fasteners.

A loading slot 804 extends through the front wall of the lower section 803 to allow a transport mechanism (e.g. 502) to place an MTU 160 into and remove an MTU 160 from the magnetic separation station 800. A tapered slot extension 821 surrounds a portion of the loading slot 804 to facilitate MTU insertion through the slot 804. A divider 808 separates the upper section 801 from the lower section 803.

A pivoting magnet moving structure 810 is attached inside the lower section 803 so as to be pivotable about point 812. The magnet moving structure 810 carries permanent magnets 814, which are positioned on either side of an MTU slot 815 formed in the magnet moving structure 810. Preferably five magnets, one corresponding to each individual reaction tube 162 of the MTU 160, are held in an aligned arrangement on each side of the magnet moving structure 810. The magnets are preferably made of neodymium-iron-boron (NdFeB), minimum grade –35 and have preferred dimensions of 0.5 inch width, 0.3 inch height, and 0.3 inch depth. An electric actuator, generally represented at 816, pivots the magnet moving structure 810 up and down, thereby moving the magnets 814. As shown in FIG. 25, actuator 816 preferably comprises a rotary stepper motor 819 which rotates a drive screw mechanism coupled to the magnet moving structure 810 to selectively raise and lower the magnet moving structure 810. Motor 819 is preferably an HIS linear stepper actuator, Model No. 26841-05, available from Haydon Switch and Instrument, Inc. of Waterbury, Conn.

A sensor 818, preferably an optical slotted sensor, is positioned inside the lower section 803 of the housing for indicating the down, or "home", position of the magnet moving structure 810. Sensor 818 is preferably an Optek Technology, Inc., Model No. OPB980T11, available from Optek Technology, Inc. of Carrollton, Tex. Another sensor 817, also preferably an Optek Technology, Inc., Model No. OPB980T11, optical slotted sensor, is preferably provided to indicate the up, or engaged, position of the magnet moving structure 810.

Figure 26:
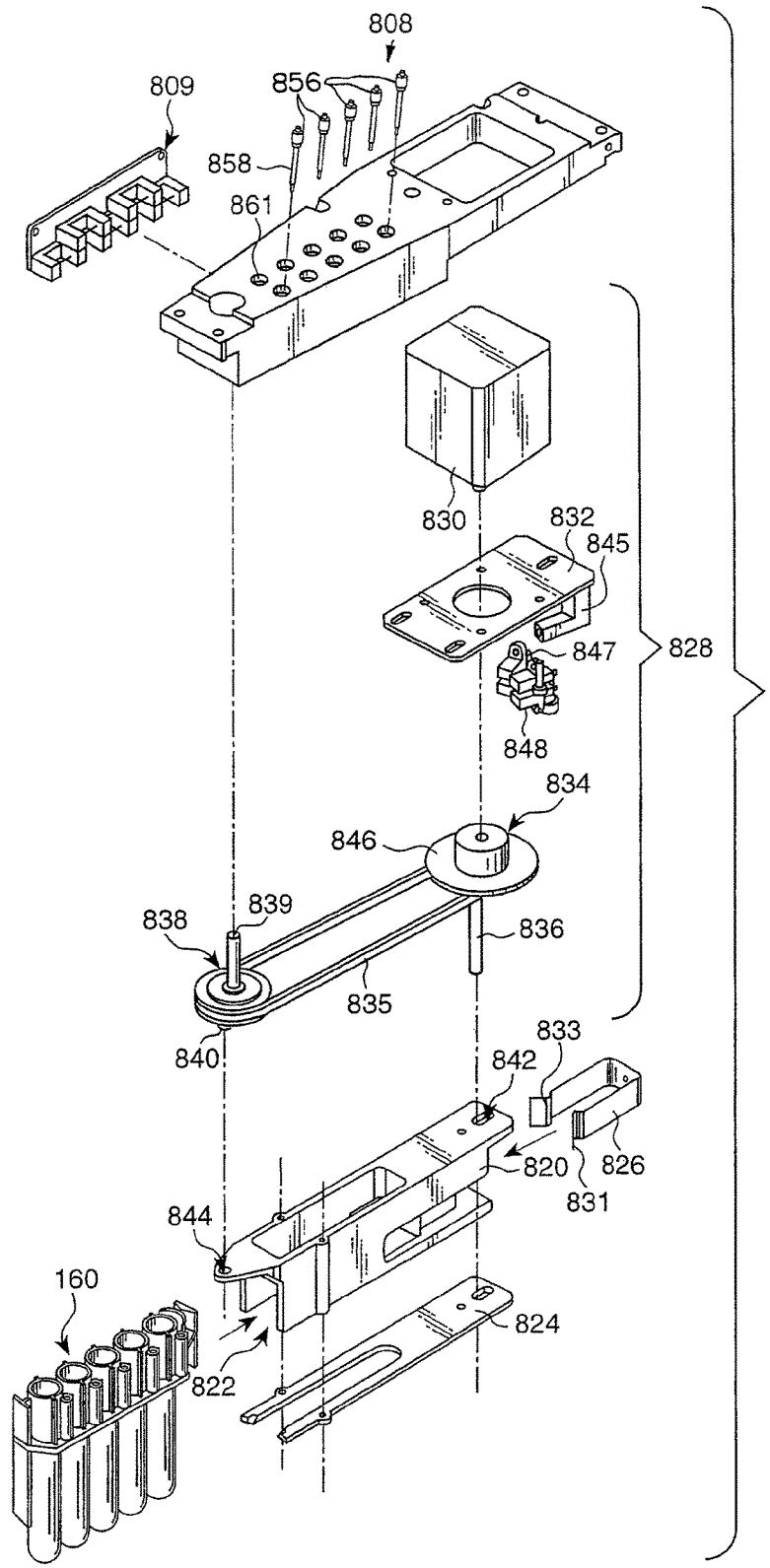
FIG. 26 is an exploded perspective view of a receptacle carrier unit, an orbital mixer assembly, and a divider plate of the particles.

An MTU carrier unit 820 is disposed adjacent the loading slot 804, below the divider 808, for operatively supporting an MTU 160 disposed within the magnetic separation stations 800. Turning to FIG. 26, the MTU carrier unit 820 has a slot 822 for receiving the upper end of an MTU 160. A lower fork plate 824 attaches to the bottom of the carrier unit 820 and supports the underside of the connecting rib structure 164 of the MTU 160 when slid into the carrier unit 820 (see FIGS. 27 and 28). A spring clip 826 is attached to the carrier unit 820 with its opposed prongs 831, 833 extending into the slot 822 to releasably hold the MTU within the carrier unit 820.

An orbital mixer assembly 828 is coupled to the carrier unit 820 for orbitally mixing the contents of an MTU held by the MTU carrier unit 820. The orbital mixer assembly 828 includes a stepper motor 830 mounted on a motor mounting plate 832, a drive pulley 834 having an eccentric pin 836, an idler pulley 838 having an eccentric pin 840, and a belt 835 connecting drive pulley 834 with idler pulley 838. Stepper motor 830 is preferably a VEXTA, Model No. PK245-02A, available from Oriental Motors Ltd. of Tokyo, Japan, and belt 835 is preferably a timing belt, Model No. A 6G16-170012, available from SDP/SI of New Hyde Park, N.Y. As shown in FIGS. 25 and 26, eccentric pin 836 fits within a slot 842 formed longitudinally in the MTU carrier unit 820. Eccentric pin 840 fits within a circular aperture 844 formed in the opposite end of MTU carrier unit 820. As the motor 830 turns the drive pulley 834, idler pulley 838 also rotates via belt 835 and the MTU carrier unit 820 is moved in a horizontal orbital path by the eccentric pins 836, 840 engaged with the apertures 842, 844, respectively, formed in the carrier unit 820. The rotation shaft 839 of the idler pulley 838 preferably extends upwardly and has a transverse slot 841 formed therethrough. An optical slotted sensor 843 is disposed at the same level as the slot 841 and measures the frequency of the idler pulley 838 via the sensor beam intermittently directed through slot 841 as the shaft 839 rotates. Sensor 843 is preferably an Optek Technology, Inc., Model No. OPB980T11, sensor, available from Optek Technology, Inc. of Carrollton, Tex.

Drive pulley 834 also includes a locator plate 846. Locator plate 846 passes through slotted optical sensors 847, 848 mounted to a sensor mounting bracket 845 extending from motor mounting plate 832. Sensors 847, 848 are preferably Optek Technology, Inc., Model No. OPB980T11, sensors, available from Optek Technology, Inc. of Carrollton, Tex. Locator plate 846 has a plurality of circumferentially spaced axial openings formed therein which register with one or both sensors 847, 848 to indicate a position of the orbital mixer assembly 828, and thus a position of the MTU carrier unit 820.

Returning to FIG. 24, wash solution delivery tubes 854 connect to fittings 856 and extend through a top surface of the module housing 802. Wash solution delivery tubes 854 extend through the divider 808 via fittings 856, to form a wash solution delivery network.

As shown in FIGS. 27 and 28, wash solution dispenser nozzles 858 extending from the fittings 856 are disposed within the divider 808. Each nozzle is located above a respective reaction tube 162 of the MTU 160 at a laterally off-center position with respect to the reaction tube 162. Each nozzle includes a laterally-directed lower portion 859 for directing the wash solution into the respective reaction tube from the off-center position. Dispensing fluids into the reaction tubes 162 in a direction having a lateral component can limit splashing as the fluid runs down the sides of the respective reaction tubes 162. In addition, the laterally directed fluid can rinse away materials clinging to the sides of the respective reaction tubes 162.

As shown in FIGS. 24 and 25, aspirator tubes 860 extend through a tube holder 862, to which the tubes 860 are fixedly secured, and extend through openings 861 in the divider 808. A tube guide yoke 809 (see FIG. 26) is attached by mechanical fasteners to the side of divider 808, below openings 861. Aspirator hoses 864 connected to the aspirator tubes 860 extend to the vacuum pump 1162 (see FIG. 52) within the analyzer 50, with aspirated fluid drawn off into a fluid waste container carried in the lower chassis 1100. Each of the aspirator tubes 860 has a preferred length of 12 inches with an inside diameter of 0.041 inches.

The tube holder 862 is attached to a drive screw 866 actuated by a lift motor 868. Lift motor 868 is preferably a VEXTA, Model No. PK245-02A, available from Oriental Motors Ltd. of Tokyo, Japan, and the drive screw 866 is preferably a ZBX series threaded anti-backlash lead screw, available from Kerk Motion Products, Inc. of Hollis, N.H. The tube holder 862 is attached to a threaded sleeve 863 of the drive screw 866. Rod 865 and slide rail 867 function as a guide for the tube holder 862. Z-axis sensors 829, 827 (slotted optical sensors) cooperate with a tab extending from threaded sleeve 863 to indicate top and bottom of stroke positions of the aspirator tubes 860. The Z-axis sensors are preferably Optek Technology, Inc., Model No. OPB980T11, sensors, available from Optek Technology, Inc. of Carrollton, Tex.

Cables bring power and control signals to the magnetic separation stations 800, via a connector 870.

The magnet moving structure 810 is initially in a down position (shown in phantom in FIG. 25), as verified by the sensor 818, when the MTU 160 is inserted into the magnetic separation stations 800 through the insert opening 804 and into the MTU carrier unit 820. When the magnet moving structure 810 is in the down position, the magnetic fields of the magnets 814 will have no substantial effect on the magnetically responsive particles contained in the MTU 160. In the present context, "no substantial effect" means that the magnetically responsive particles are not drawn out of suspension by the attraction of the magnetic fields of the magnets 814. The orbital mixer assembly 828 moves the MTU carrier unit 820 a portion of a complete orbit so as to move the carrier unit 820 and MTU 160 laterally, so that each of the tiplets 170 carried by the tiplet holding structures 176 of the MTU 160 is aligned with each of the aspiration tubes 860, as shown in FIG. 28. The position of the MTU carrier unit 820 can be verified by the locator plate 846 and one of the sensors 847, 848. Alternatively, the stepper motor 830 can be moved a known number of steps to place the MTU carrier unit 820 in the desired position, and one of the sensors 847, 848 can be omitted.

The tube holder 862 and aspirator tubes 860 are lowered by the lift motor 868 and drive screw 866 until each of the aspirator tubes 860 frictionally engages a tiplet 170 held in an associated carrying structure 176 on the MTU 160.

Figure 25A:
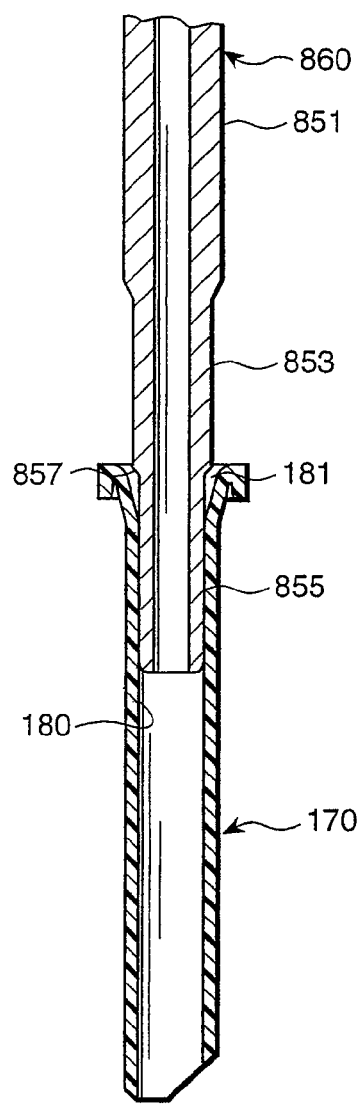
FIG. 25A is a partial transverse cross-section of a tip of an aspirating tube of the particles with a contamination-limiting tiplet carried on the end thereof.

As shown in FIG. 25A, the lower end of each aspirator tube 860 is characterized by a tapering, step construction, whereby the tube 860 has a first portion 851 along most of the extent of the tube, a second portion 853 having a diameter smaller than that of the first portion 851, and a third portion 855 having a diameter smaller than that of the second portion 853. The diameter of the third portion 855 is such as to permit the end of the tube 860 to be inserted into the flared portion 181 of the through hole 180 of the tiplet 170 and to create an interference friction fit between the outer surface of third portion 855 and the two annular ridges 183 (see FIG. 59) that line the inner wall of hole 180 of tiplet 170. An annular shoulder 857 is defined at the transition between second portion 853 and third portion 855. The shoulder 857 limits the extent to which the tube 860 can be inserted into the tiplet 170, so that the tiplet can be stripped off after use, as will be described below.

The tiplets 170 are at least partially electrically conductive, so that the presence of a tiplet 170 on an aspirator tube 860 can be verified by the capacitance of a capacitor comprising the aspirator tubes 860 as one half of the capacitor and the surrounding hardware of the magnetic separation stations 800 as the other half of the capacitor. The capacitance will change when the tiplets 170 are engaged with the ends of the aspirator tubes 860.

In addition, five optical slotted sensors (not shown) can be strategically positioned above the divider 808 to verify the presence of a tiplet 170 on the end of each aspirator tube 860. Preferred "tiplet-present" sensors are Optek Technology, Inc., Model No. OPB930W51, sensors, available from Optek Technology, Inc. of Carrollton, Tex. A tiplet 170 on the end of an aspirator tube 860 will break the beam of an associated sensor to verify presence of the tiplet 170. If, following a tiplet pick-up move, tiplet engagement is not verified by the tiplet present sensors for all five aspirator tubes 860, the MTU 160 must be aborted. The aborted MTU is retrieved from the magnetic separation stations 800 and sent to the deactivation queue 750 and ultimately discarded.

After successful tiplet engagement, the orbital mixer assembly 828 moves the MTU carrier unit 820 back to a fluid transfer position shown in FIG. 27 as verified by the locator plate 846 and one or both of the sensors 847, 848.

The magnet moving structure 810 is then raised to the up position shown in FIG. 24 so that the magnets 814 are disposed adjacent opposite sides of the MTU 160. With the contents of the MTU subjected to the magnetic fields of the magnets 814, the magnetically responsive particles bound indirectly to the target nucleic acids will be drawn to the sides of the individual reaction tubes 162 adjacent the magnets 814. The remaining material within the reaction tubes 162 should be substantially unaffected, thereby isolating the target nucleic acids. The magnet moving structure 810 will remain in the raised position for an appropriate dwell time, as defined by the assay protocol and controlled by the assay manager program, to cause the magnetic particles to adhere to the sides of the respective reaction tubes 162.

The aspirator tubes are then lowered into the reaction tubes 162 of the MTU 160 to aspirate the fluid contents of the individual reaction tubes 162, while the magnetic particles remain in the reaction tubes 162, adhering to the sides thereof, adjacent the magnets 814. The tiplets 170 at the ends of the aspirator tubes 860 ensure that the contents of each reaction tube 162 do not come into contact with the sides of the aspirator tubes 860 during the aspirating procedure. Because the tiplets 170 will be discarded before a subsequent MTU is processed in the magnetic separation stations 800, the chance of cross-contamination by the aspirator tubes 860 is minimized.

The electrically conductive tiplets 170 can be used in a known manner for capacitive fluid level sensing within the reaction tubes 162 of the MTUs. The aspirator tubes 860 and the conductive tiplets 170 comprise one half of a capacitor, the surrounding conductive structure within the particles comprises the second half of the capacitor, and the fluid medium between the two halves of the capacitor constitutes the dielectric. Capacitance changes due to a change in the nature of the dielectric can be detected.

The capacitive circuitry of the aspirator tubes 860 can be arranged so that all five aspirator tubes 860 operate as a single gang level-sensing mechanism. As a gang level-sensing mechanism, the circuitry will only determine if the fluid level in any of the reaction tubes 162 is high, but cannot determine if the fluid level in one of the reaction tubes is low. In other words, when any of the aspirator tubes 860 and its associated tiplet 170 contacts fluid material within a reaction tube, capacitance of the system changes due to the change in the dielectric. If the Z-position of the aspirator tubes 860 at which the capacitance change occurs is too high, then a high fluid level in at least one reaction tube is indicated, thus implying an aspiration failure. On the other hand, if the Z-position of the aspirator tubes at which the capacitance change occurs is correct, the circuitry cannot differentiate between aspirator tubes, and, therefore, if one or more of the other tubes has not yet contacted the top of the fluid, due to a low fluid level, the low fluid level will go undetected.

Alternatively, the aspirator tube capacitive circuitry can be arranged so that each of the five aspirator tubes 860 operates as an individual level sensing mechanism.

With five individual level sensing mechanisms, the capacitive level sensing circuitry can detect failed fluid aspiration in one or more of the reaction tubes 162 if the fluid level in one or more of the reaction tubes is high. Individual capacitive level sensing circuitry can detect failed fluid dispensing into one or more of the reaction tubes 162 if the fluid level in one or more of the reaction tubes is low. Furthermore, the capacitive level sensing circuitry can be used for volume verification to determine if the volume in each reaction tube 162 is within a prescribed range. Volume verification can be performed by stopping the descent of the aspirator tubes 860 at a position above expected fluid levels, e.g. 110% of expected fluid levels, to make sure none of the reaction tubes has a level that high, and then stopping the descent of the aspirator tubes 860 at a position below the expected fluid levels, e.g. 90% of expected fluid levels, to make sure that each of the reaction tubes has a fluid level at least that high.

Following aspiration, the aspirator tubes 860 are raised, the magnet moving structure 810 is lowered, and a prescribed volume of wash solution is dispensed into each reaction tube 162 of the MTU 160 through the wash solution dispenser nozzles 858. To prevent hanging drops of wash solution on the wash solution dispenser nozzles 858, a brief, post-dispensing air aspiration is preferred.

The orbital mixer assembly 828 then moves the MTU carriers 820 in a horizontal orbital path at high frequency to mix the contents of the MTU 160. Mixing by moving, or agitating, the MTU in a horizontal plane is preferred so as to avoid splashing the fluid contents of the MTU and to avoid the creation of aerosols. Following mixing, the orbital mixer assembly 828 stops the MTU carrier unit 820 at the fluid transfer position.

To further purify the targeted nucleic acids, the magnet moving structure 810 is again raised and maintained in the raised position for a prescribed dwell period. After magnetic dwell, the aspirator tubes 860 with the engaged tiplets 170 are lowered to the bottoms of the reaction tubes 162 of the MTU 160 to aspirate the test sample fluid and wash solution in an aspiration procedure essentially the same as that described above.

One or more additional wash cycles, each comprising a dispense, mix, magnetic dwell, and aspirate sequence, may be performed as defined by the assay protocol. Those skilled in the art of nucleic acid-based diagnostic testing will be able to determine the appropriate magnetic dwell times, number of wash cycles, wash solutions, etc. for a desired target capture procedure.

While the number of magnetic separation stations 800 can vary, depending on the desired throughput, analyzer 50 preferably includes five magnetic separation stations 800, so that a magnetic separation wash procedure can be performed on five different MTUs in parallel.

After the final wash step, the magnet moving structure 810 is moved to the down position and the MTU 160 is removed from the magnetic separation stations 800 by the left-side transport mechanism 502 and is then placed into the left orbital mixer 552.

After the MTU 160 is removed from the wash station, the tiplets 170 are stripped from the aspiration tubes 860 by a stripper plate 872 located at the bottom of the lower section 803 of the housing 802.

Figure 29B:
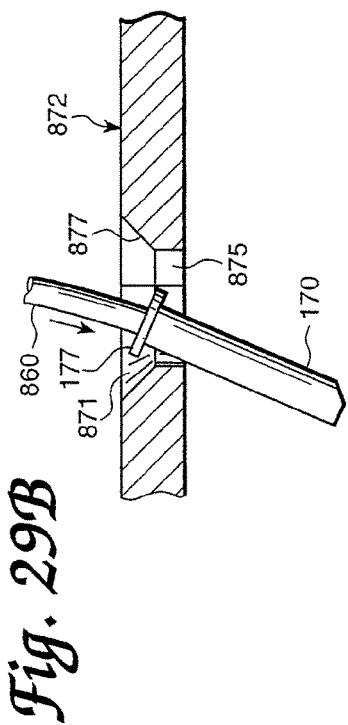
FIGS. 29A-29D show a partial cross-section of a first embodiment of a tiplet stripping hole of a tiplet stripping plate of the particles and a tiplet stripping operation using the tiplet stripping hole.
Figure 29D:
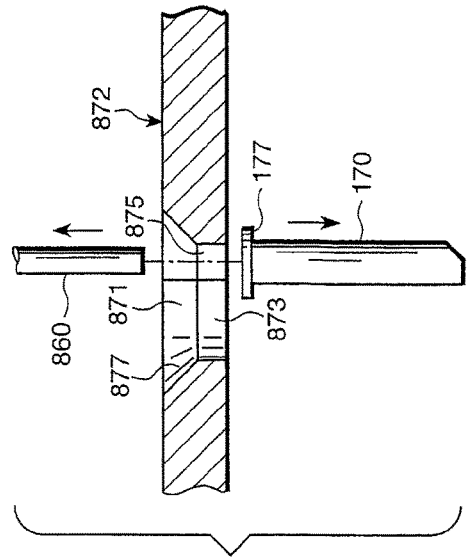
Figure 29A:
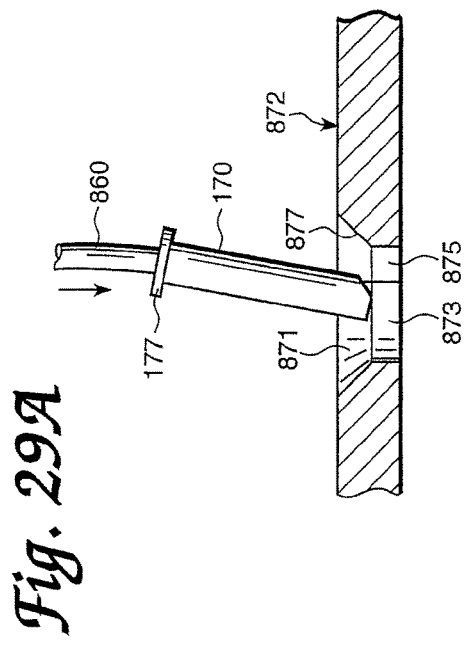
Figure 29C:
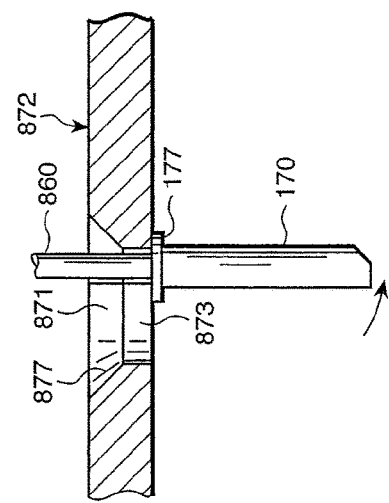

The stripper plate 872 has a number of aligned stripping holes 871 corresponding in number to the number of aspiration tubes 860, which is five in the preferred embodiment. As shown in FIGS. 29A to 29D, each stripping hole 871 includes a first portion 873, a second portion 875 smaller than first portion 873, and a bevel 877 surrounding portions 873 and 875. The stripper plate 872 is oriented in the bottom of the housing 802 so that the small portion 875 of each stripping hole 871 is generally aligned with each associated aspiration tube 860, as shown in FIG. 29A. The aspiration tubes 860 are lowered so that the tiplet 170 at the end of each aspirator tube 860 engages the stripping hole 871. Small portion 875 is too small to accommodate the diameter of a tiplet 170, so the bevel 877 directs the tiplet 170 and the aspirator tube 860 toward the larger portion 873, as shown in FIG. 29B. The aspirator tubes 860 are made of an elastically flexible material, preferably stainless steel, so that, as the aspirator tubes 860 continue to descend, the beveled portion 877 causes each of aspirator tubes 860 to deflect laterally. The small portion 875 of the stripping hole 871 can accommodate the diameter of the aspirator tube 860, so that after the rim 177 of the tiplet 170 clears the bottom of stripping hole 871, each of the aspirator tubes 860 snaps, due to its own resilience, into the small portion 875 of the stripping hole 871 as shown in FIG. 29C. The aspirator tubes 860 are then raised, and the rim 177 of each tiplet 170 engages the bottom peripheral edge of the small portion 875 of stripping hole 871. As the aspirator tubes 860 ascend further, the tiplets 170 are pulled off the aspirator tubes 860 by the stripping holes 871 (see FIG. 29D). The stripped tiplets 170 are directed by a chute into a solid waste container, such as the tiplet waste bin 1134.

The capacitance of the aspiration tubes 860 is sampled to verify that all tiplets 170 have been stripped and discarded. The stripping step can be repeated if necessary.

Figure 31A:
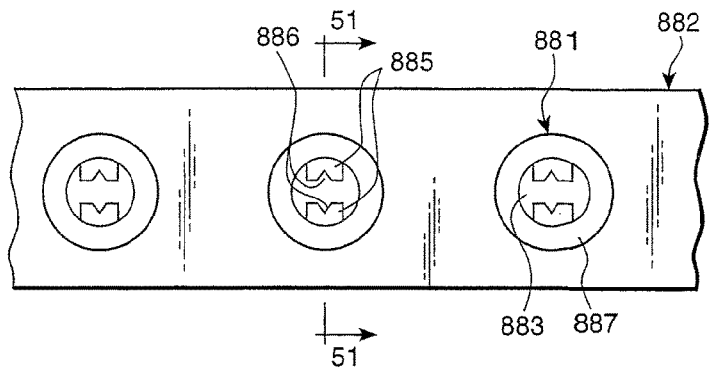
FIG. 31A is a plan view of a third embodiment of a tiplet stripping hole of a tiplet stripping plate of the particles.
Figure 31B:
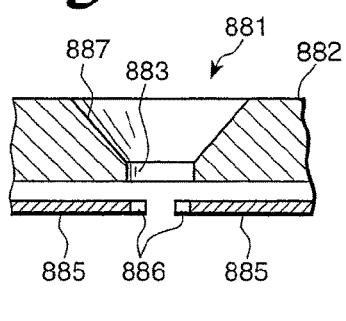
FIGS. 31B-31C show a partial cross-section of the third embodiment of the tiplet stripping hole and a tiplet stripping operation using the tiplet.
Figure 31C:
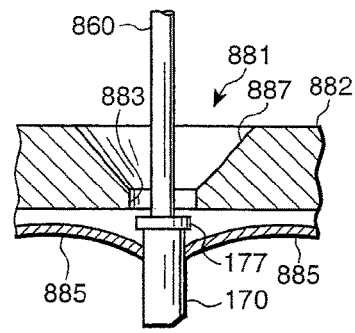

An alternate stripper plate 882 is shown in FIGS. 31A to 31C. Stripper plate 882 includes a number of stripping holes 881 corresponding to the number of aspirator tubes 860, which is five in the preferred embodiment. Each stripping hole 881 includes a through-hole 883 surrounded by a beveled countersink 887. A pair of tangs 885 extend laterally from diametrically opposed positions below the through-hole 883. Tangs 885 are preferably made from a spring steel and include a v-notch 886 at their ends.

As an aspirator tube 860 with a tiplet 170 disposed on its end is lowered toward stripping hole 881, beveled portion 887 ensures that any misaligned tubes are directed into the through-hole 883. The spacing between the ends of the opposed tangs 885 is less than the diameter of the tiplet 170, so as the aspirator tube 860 and tiplet 170 are lowered, the tiplet engages the tangs 885, causing them to deflect downwardly as the tiplet 170 is forced between tangs 885. When the aspirator tubes 860 are raised, the notches 886 of the tangs 885 grip the relatively soft material of the tiplet 170, thus preventing upward relative movement of the tiplet 170 with respect to the tangs 885. As the tubes continue to ascend, the tangs 885 pull the tiplet 170 off the tube 860. When the aspirator tubes 860 are subsequently lowered to strip a subsequent set of tiplets, the tiplet held between the tangs from the previous stripping is pushed through the tangs by the next tiplet and is directed toward waste bin 1134 (see FIG. 52) located in the lower chassis 1100 generally below the five magnetic separation stations 800.

Still another alternate, and the presently preferred, stripper plate 1400 is shown in FIGS. 30A-30D. Stripper plate 1400 includes five stripper cavities 1402, each including an initial frusto-conical portion 1404. The frusto-conical portion 1404 tapers down to a neck portion 1406 which connects to an enlarged straight section 1408. Straight section 1408 is offset with respect to the center of neck portion 1406, so that one side of the straight section 1408 is flush with a side of the neck portion 1406, and an opposite side of the straight section 1408 is offset from and undercuts the side of the neck portion 1406, thereby forming a ledge 1414. Following the straight section 1408, a sloped portion 1410 is provided on a side of the stripper cavity 1402 opposite the ledge 1414. Sloped portion 1410 tapers inwardly toward a bottom opening 1412.

As an aspirator tube 860 with a tiplet 170 on its end is moved toward the stripper cavity 1402, the frusto-conical portion 1404 directs the tiplet 170 and tube 860 toward the neck portion 1406. The aspirator tube 860 continues to descend, and the tiplet 170 enters the straight section 1408 as the rim 177 of the tiplet 170 clears the bottom of the frusto-conical portion 1404 and passes through the neck portion 1406.

If the aspirator tube 860 and the stripper cavity 1402 are in proper, preferred alignment, a portion of the rim 177 of the tiplet 170 will be disposed below the ledge 1414 of the stripper cavity 1402 when the tiplet 170 has moved through the neck portion 1406 and into the straight section 1408. To ensure that a portion of the rim 177 will be disposed beneath the ledge 1414, the tiplet 170 engages the lower sloped portion 1410 as the aspirator tube 860 descends further to urge the aspirator tube laterally to direct the tiplet 170 below the ledge 1414.

The annular shoulder 857 (see FIG. 25A) formed at the bottom of the aspirator tube 860 ensures that the tube 860 is not forced further into the through hole 180 of the tiplet 170 as the tube 860 is lowered into the stripper cavity 1402. The aspirator tube 860 then ascends, and the ledge 1414 catches the rim 177 and strips the tiplet 170 off the tube 860. The stripped tiplet 170 falls through bottom opening 1412 and into the waist bin 1134 in the lower chassis 1100 (see FIG. 52).

With each of the stripper plates described above, the position of the tiplet-stripping elements are not all the same. For example, the ledges 1414 of the stripper cavities 1402 of the stripper plate 1400 are not at the same height throughout all the cavities. Preferably, three tiplet-stripping elements are at one height, and two tiplet-stripping elements are at a slightly different height above or below the other three elements. The result of the offset tiplet-stripping elements is that the static friction of the tiplet 170 on the end of the aspirator tube 860 need not be overcome, or broken, for all five tubes 860 at once. As the aspirator tubes 860 begin to ascend, static friction of the tiplets 170 is broken for one set (two or three) of aspirator tubes 860 first, and then, as the tubes 860 continue to ascend, static friction of the tiplets 170 is broken for the remaining tubes 860. By not breaking static friction of the tiplets 170 for all five aspirator tubes 860 at once, the loads to which the tube holder 862, drive screw 866, threaded sleeve 863, and lift motor 868 are subjected are kept to a lower level.

Orbital Mixers

Figure 32:
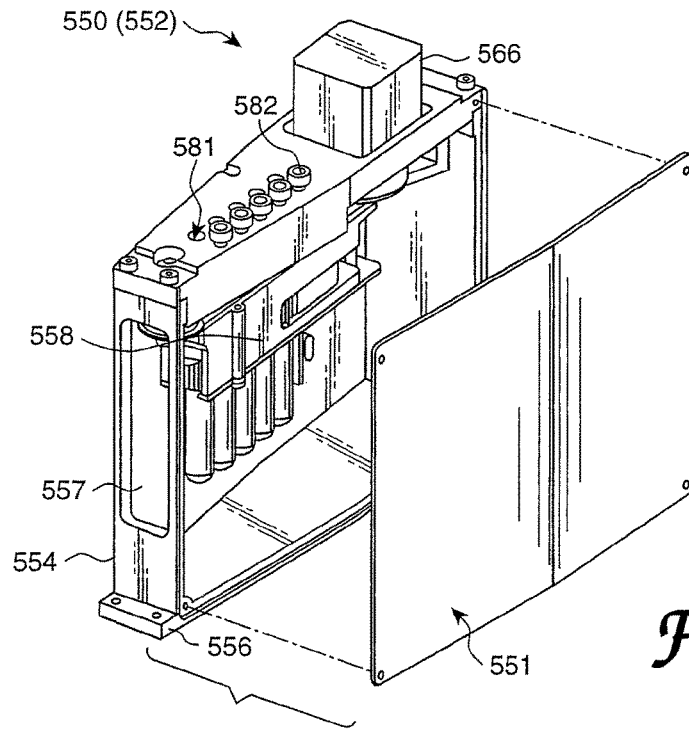
FIG. 32 is a perspective view of an orbital mixer with a front plate thereof removed.
Figure 33:
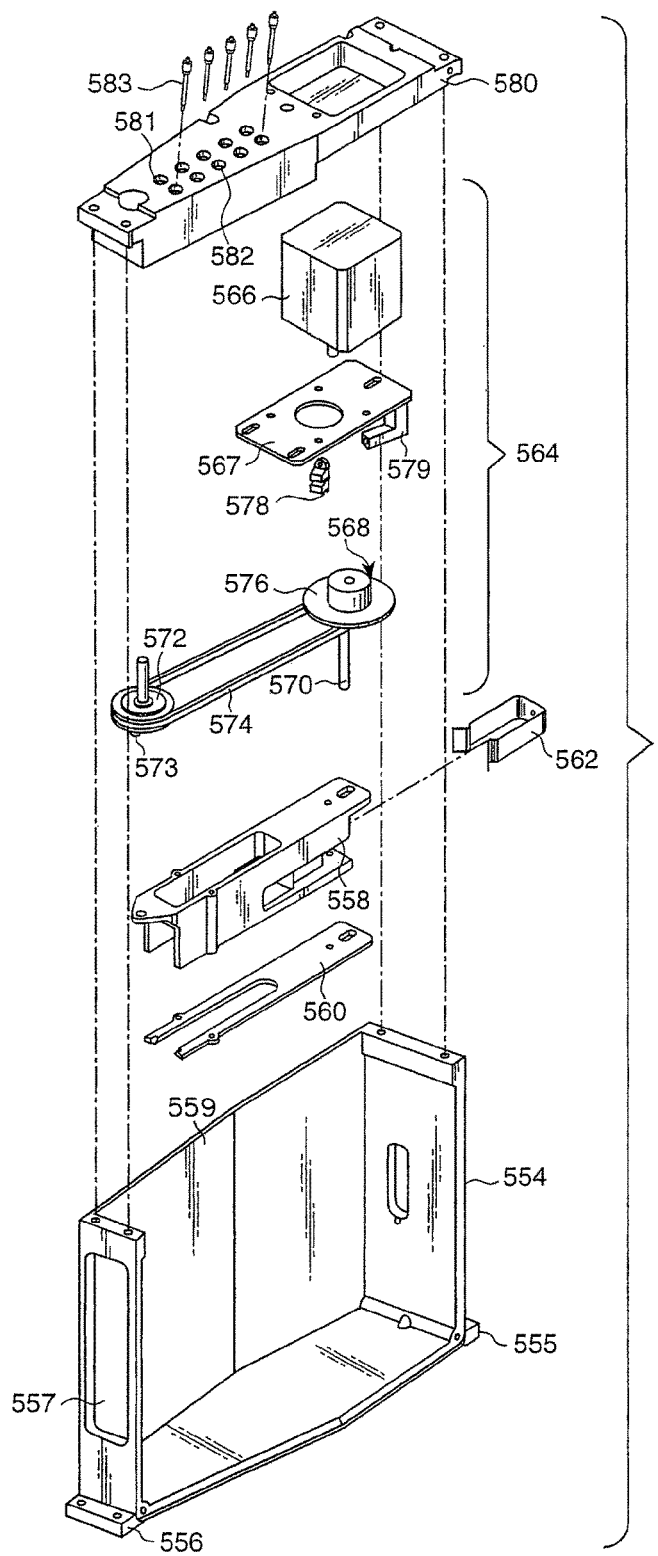
FIG. 33 is an exploded view of the orbital mixer of the processing deck of the analyzer of the present invention.
Figure 34:
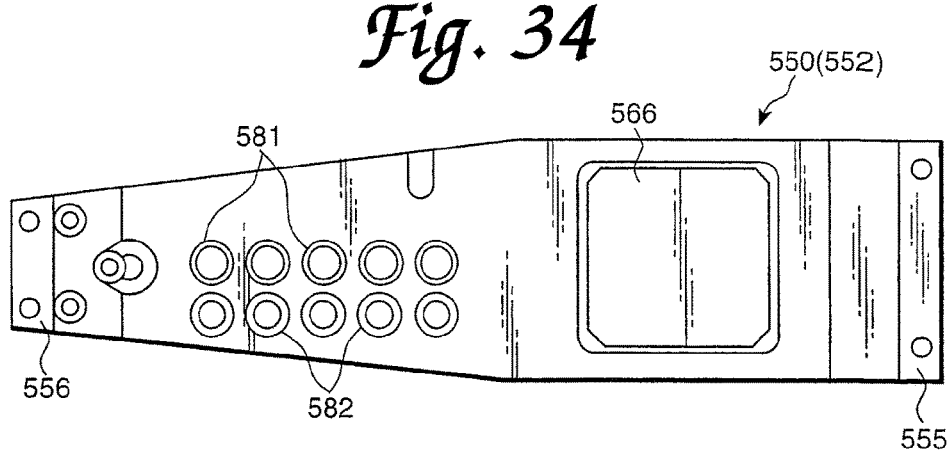
FIG. 34 is a top-plan view of the orbital mixer.

The left orbital mixer 552 (and the right orbital mixer 550), as shown in FIGS. 32-34, are constructed and operate in the same manner as the lower housing section 803 and the orbital mixer assembly 828 of the magnetic separation stations 800 described above. Specifically, the orbital mixer 550 (552) includes a housing 554, including a front plate 551, a back plate 559, and mounting flanges 555, 556, for mounting the orbital mixer 550 (552) to the datum plate 82. An insert opening 557 is formed in a front edge of the housing 554. An MTU carrier 558 has a fork plate 560 attached to the bottom thereof and an MTU-retaining clip 562 attached to a back portion of the carrier 558 with opposed prongs of the clip 562 extending into an inner cavity of the carrier 558 that accommodates the MTU. An orbital mixer assembly 564 includes a drive motor 566 mounted to a motor mounting plate 567, a drive wheel 568 having an eccentric pin 570, an idler wheel 572 having an eccentric pin 573, and a belt 574. Drive motor 566 is preferably a stepper motor, and most preferably a VEXTA, Model No. PK245-02A, available from Oriental Motors Ltd. of Tokyo, Japan. Belt 574 is preferably a timing belt, Model No. A 6G16-170012, available from SDP/SI of New Hyde Park, N.Y. The orbital mixer assembly 564 is coupled to the MTU carrier 558 through the eccentric pins 570, 573 to move the MTU carrier 558 in an orbital path to agitate the contents of the MTU. The drive wheel 568 includes a locator plate 576, which, in conjunction with sensor 578 attached to sensor mounting bracket 579, verifies the proper positioning of the MTU carrier 558 for inserting an MTU 160 into the orbital mixer 552 (550) and retrieving an MTU 160 from the orbital mixer. Sensor 578 is preferably an Optek Technology, Inc., Model No. OPB980T11, sensor, available from Optek Technology, Inc. of Carrollton, Tex.

A top plate 580 is attached atop housing 554. Top plate 580 of the left orbital mixer 552 includes a number of tube fittings 582, preferably five, to which are coupled a like number of flexible delivery tubes (not shown) for delivering a fluid from a bulk fluid container to an MTU 160 located within the mixer via dispenser nozzles 583. Top plate 580 also includes a plurality of pipette openings 581, corresponding in number to the number of individual reaction tubes 162 comprising a single MTU 160, which is preferably five.

With the MTU 160 held stationary in the left orbital mixer 552, pipette unit 480 of the left pipette assembly 470 transfers a prescribed volume of amplification reagent from a container within the reagent cooling bay 900 into each reaction tube 162 of the MTU 160 through the pipette openings 581. The amplification reagent contains at least one amplification oligonucleotide, such as a primer, a promoter-primer, and/or a promoter oligonucleotide, nucleoside triphosphates, and cofactors, such as magnesium ions, in a suitable buffer. The specific components of the amplification reagent will, however, depend on the amplification procedure being practiced. See, e.g., Kacian et al. in U.S. Pat. No. 5,399,491. Other amplification procedures are well known to those skilled in the art of nucleic acid-based testing, some of which are identified supra in the "Background of the Invention" section, and may be adapted for use in the analyzer 50 of the present invention.

Next, the contents of the MTU are mixed by the orbital mixer assembly 564 of the orbital mixer 552 to ensure proper exposure of the target nucleic acid to amplification reagent. For any particular amplification procedure, those skilled in the art will be able to determine the appropriate components and amounts of an amplification reagent, as well as mix frequencies and durations.

After pipetting amplification reagent into the MTU 160, the pipette unit 480 is moved to a rinse basin (described below) on the processing deck 200, and pipette unit 480 is washed by running distilled water through probe 481. The distilled water is pumped from bottle 1140 in the lower chassis 1100, and the purge water is collected in a liquid waste container 1128 in the lower chassis 1100.

After mixing the contents of the MTU 160, a layer of silicone oil is dispensed into each reaction tube 162 through the dispenser nozzles 583. The layer of oil, pumped from bottles 1168 in the lower chassis 1100, helps prevent evaporation and splashing of the fluid contents of the MTU 160 during subsequent manipulation and incubation of the MTU 160 and its contents.

Reagent Cooling Bay

The reagent cooling bay 900 will now be described. Referring to FIGS. 35-39, the reagent cooling bay 900 includes an insulating jacket 902 fitted around a cylindrical housing 904, preferably made from aluminum. A cover 906, preferably made of Delrin, sits atop housing 904 with a registration tab 905 of cover 906 fitting within slot 907 in housing 904 to ensure proper orientation of the cover 906. An optical sensor may be provided proximate to or within slot 907 for verifying that tab 905 is seated within slot 907. Alternatively, an optical sensor assembly 909 can be secured to an edge of an upper rim of the housing 904 for verifying cover placement. The optical sensor assembly 909 cooperates with a sensor-tripping structure (not shown) on the cover 906 to verify that the cover is in place. Optical sensor assembly 909 preferably includes an Optek Technology, Inc. slotted optical sensor, Model No. OPB980T11, available from Optek Technology, Inc. of Carrollton, Tex. The cover 906 also includes pipette openings 908 through which pipette units 480, 482 can access reagent containers within the cooling bay 900.

The housing 904 is attached to a floor plate 910, and the floor plate 910 is attached to the datum plate 82 by means of suitable mechanical fasteners extending through openings formed in mounting flanges 911 spaced about the periphery of the floor plate 910. Cooling units 912, preferably two, are attached to floor plate 910. Each cooling unit 912 comprises a thermoelectric module 914 attached cool-side-up to the bottom surface of floor plate 910. Thermoelectric modules available from Melcor, Inc. of Trenton, N.J., Model No. CP1.4-127-06L, provide the desired cooling capacity. A heat sink 916, including a plurality of heat-dissipating fins 915, is attached to, or may be integral with, the bottom surface of floor plate 910, directly below the thermoelectric module 914. A fan unit 918 is attached in a position to drain heat away from heat sink 916. Fan units 918 are preferably Orix fans, Model No. MD825B-24, available from Oriental Motors Ltd. of Tokyo, Japan. Together, the cooling units 912 cool the interior of the housing 904 to a prescribed temperature for the benefit of temperature-sensitive reagents (e.g., enzymes) stored within the bay 900.

Two temperature sensors (only one temperature sensor 920 is shown) are disposed within the cooling bay 900 housing 904 for monitoring and controlling the interior temperature thereof. The temperature sensors are preferably thermistors (10 KOhm at 25° C.), and YSI 44036 series thermistors available from YSI, Inc. of Yellow Springs, Ohio are most preferred. YSI thermistors are preferred because of their high accuracy and the ±0.1° C. interchangeability provided by YSI thermistors from one thermistor to another. One of the sensors is a primary temperature control sensor, and the other is a temperature monitoring sensor. On the basis of the temperature indications from the primary control sensor, the embedded controller adjusts power to the thermoelectric modules 914 and/or power to the fan units 918 to control cooling bay temperature. The temperature monitoring sensor provides a verification check of the primary temperature control sensor.

Figure 38:
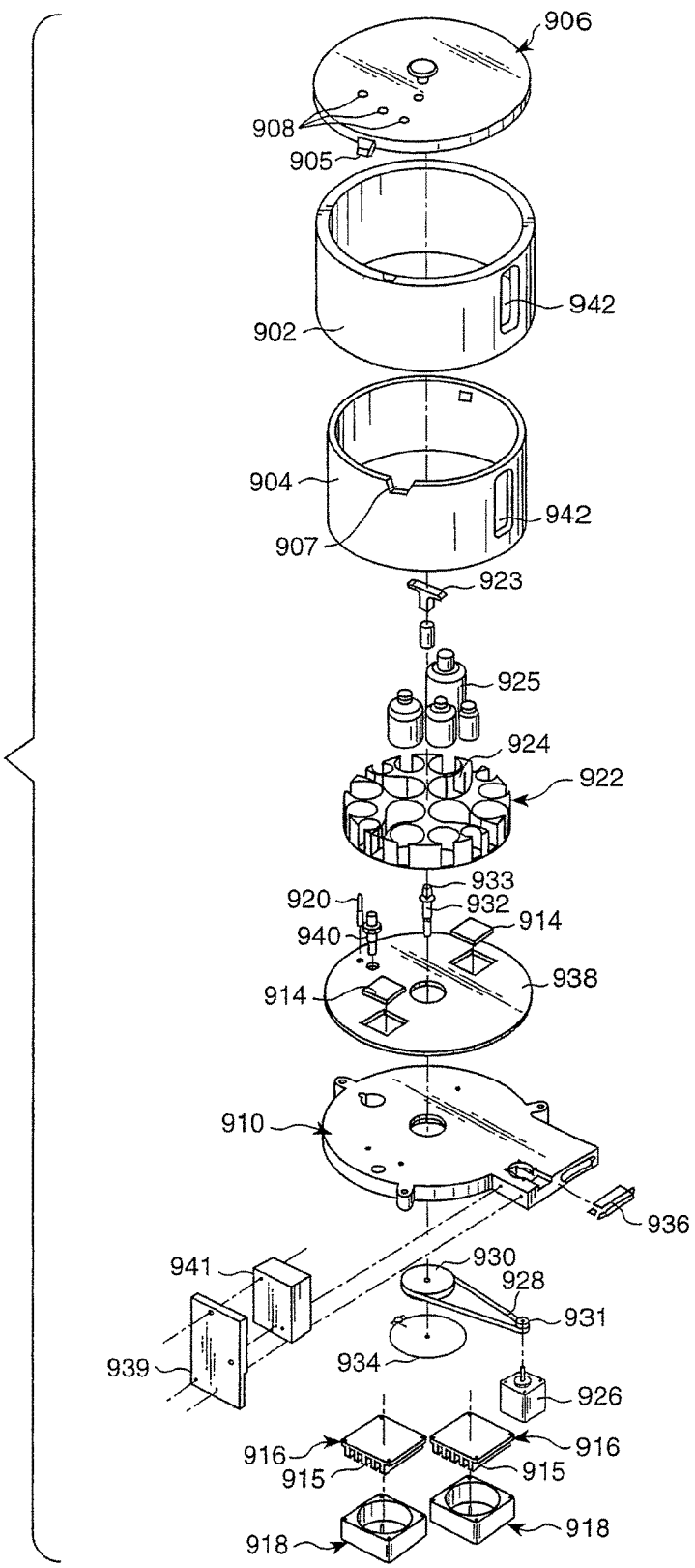
FIG. 38 is an exploded view of the reagent cooling bay.

As shown in FIG. 38, container tray 922 is a one-piece turntable structure with bottle-holding cavities 924 sized and shaped to receive and hold specific reagent bottles 925. A drive system for container tray 922 includes a motor 926, a small pulley 931 on the shaft of motor 926, a belt 928, a pulley 930, and a shaft 932. (a VEXTA stepper motor, Model No. PK265-02A, available from Oriental Motor Co., Ltd. of Tokyo, Japan, and an SDP timing belt, GT® Series, available from SDP/SI of New Hyde Park, N.Y., are preferred). Motor 926 and cooling units 912 extend through openings (not shown) formed in the datum plate 82 and extend below the floor plate 910.

Container tray 922 may include a central, upstanding handle 923 to facilitate installation of the tray 922 into and removal of the tray 922 from the housing 904. A top portion 933 of shaft 932 extends through floor plate 910 and is received by a mating aperture (not shown) formed in the bottom of the tray 922. A sensor 940 extending up through the floor plate 910 and into the housing 904 verifies that tray 922 is in place within the housing 904. Sensor 940 is preferably a capacitive proximity sensor available from Advanced Controls, Inc., of Bradenton, Fla., Model No. FCP2.

A position encoder 934 (preferably a slotted disk) in conjunction with an optical sensor 935 may be used to detect the position of the container tray 922, so that a specific reagent bottle 925 may be aligned under the pipette openings 908 in the cover 906.

Figure 37:
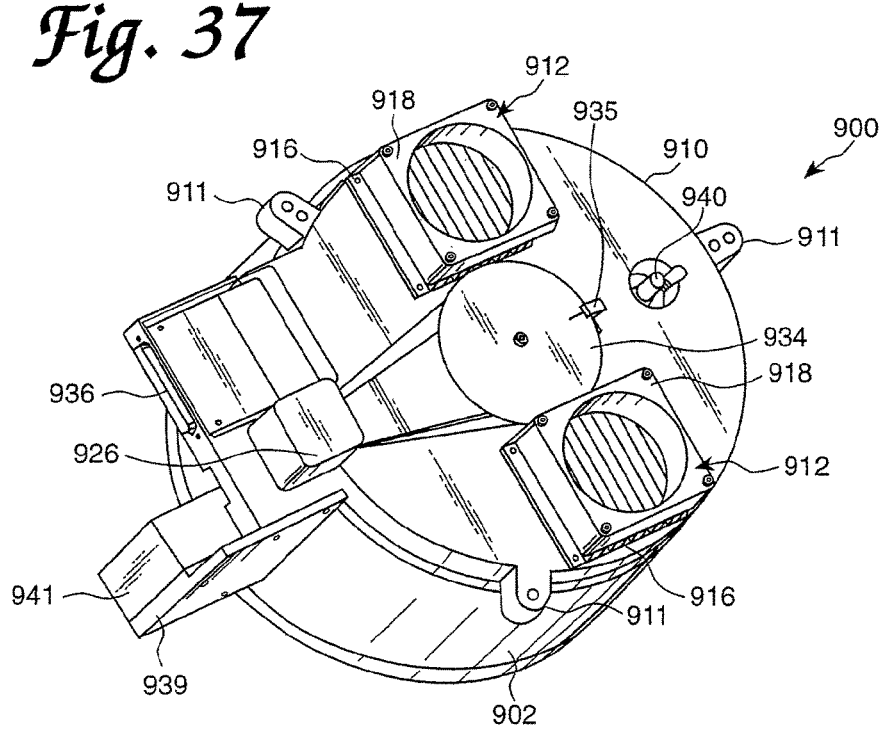
FIG. 37 is a bottom plan view of the reagent cooling bay.

As shown in FIG. 37, a preferred alternative to the position encoder 934 and optical sensor 935 includes four slotted optical sensors 937 (only two sensors are visible in FIG. 36) provided inside the housing 904 along with a flag pin (not shown) extending from the bottom of container tray 922. One sensor is provided for each quadrant of the container tray 922, and the flag trips one of the four sensors to indicate which quadrant of the container tray 922 is aligned with the pipette openings 908. Sensors 937 are preferably Optek Technology, Inc. sensors, Model No. OPB980T11, available from Optek Technology, Inc. of Carrollton, Tex.

Figure 35:
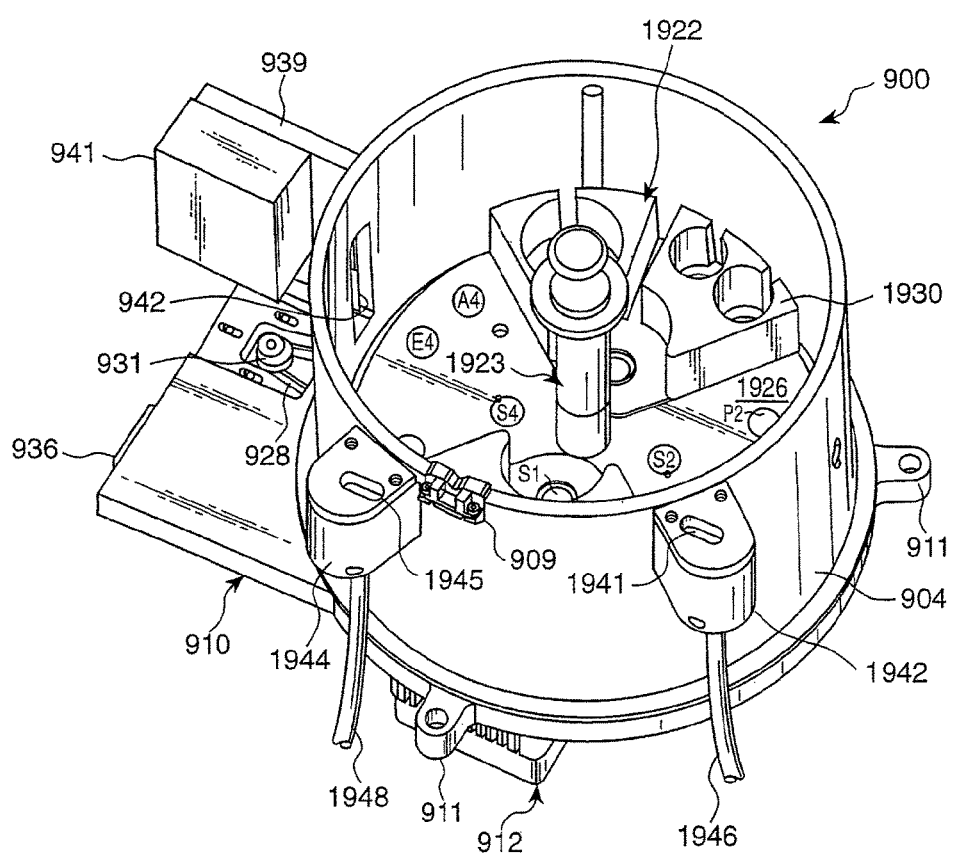
FIG. 35 is a top perspective view of a reagent cooling bay of the processing deck of the analyzer of the present invention.
Figure 36:
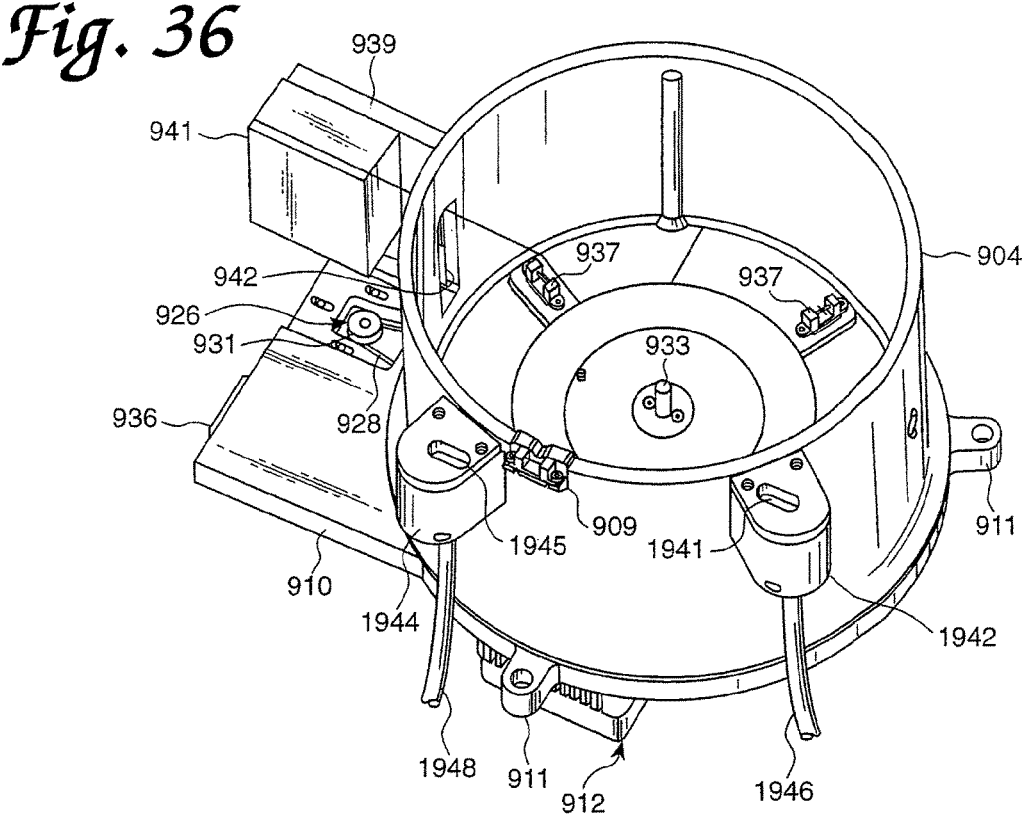
FIG. 36 is a top perspective view of a reagent cooling bay with the container tray removed therefrom.
Figure 39:
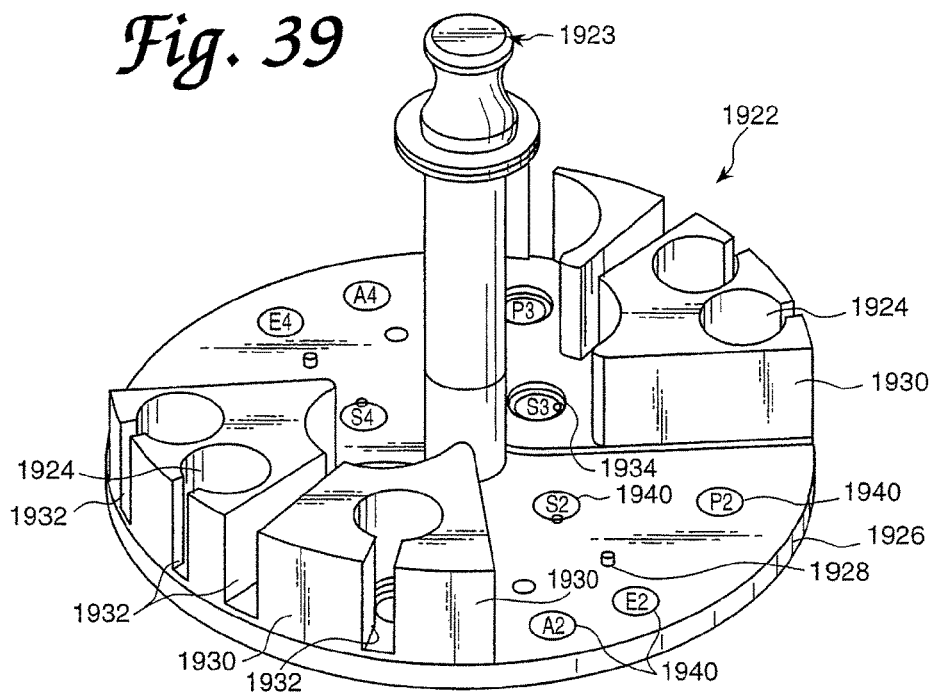
FIG. 39 is a top perspective view of a modular container tray of the reagent cooling bay.
Figure 40:
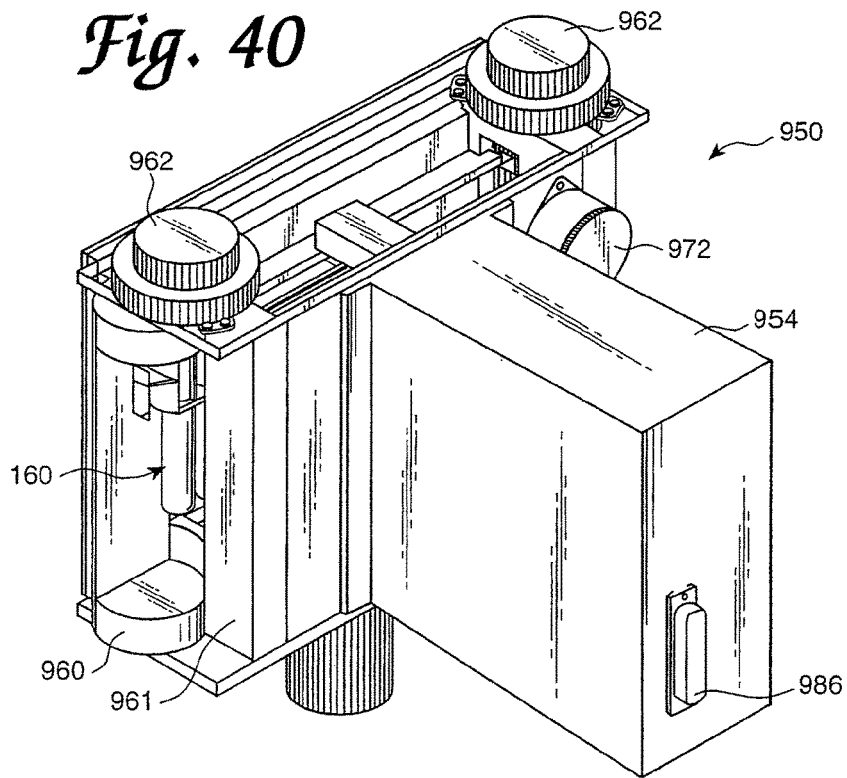
FIG. 40 is a perspective view of a first embodiment of a luminometer of the processing deck of the analyzer of the present invention.

A preferred alternative to the one-piece container tray 922 shown in FIG. 38 is a modular tray 1922 shown in FIGS. 35 and 39. Tray 1922 includes a circular base plate 1926 and an upstanding handle post 1923 attached to a central portion thereof. Modular pieces 1930 having bottle-holding cavities 1924 are preferably connected to one another and to the base plate 1926 by pins 1928 and screws (not shown) to form the circular tray 1922. Other means of securing the modular pieces 1930 may be employed in the alternative to pins 1928 and screws. The modular pieces 1930 shown in the figures are quadrants of a circle, and thus, of course, four such pieces 1930 would be required to complete the tray 1922. Although quadrants are preferred, the modular pieces may however be sectors of various sizes, such as, for example, ½ of a circle or ⅛ of a circle.

Alphanumeric bottle location labels 1940 are preferably provided on the base plate 1926 to identify positions within the tray 1922 for reagent containers. The preferred label scheme includes an encircled letter-number pair comprising a leading letter A, E, P, or S with a trailing number 1, 2, 3, or 4. The letters A, E, P, and S, designate amplification reagent, enzyme reagent, probe reagent, and select reagent, respectively, corresponding to the preferred mode of use of the analyzer 50, and the numbers 1-4 designate a quadrant of the tray 1922. Each modular piece 1930 includes a circular hole 1934 at the bottom of each bottle-holding cavity 1924. The holes 1934 align with the bottle location labels 1940, so that the labels 1940 can be seen when the modular pieces 1930 are in place on the base plate 1926.

The modular pieces 1930 of the container tray 1922 are configured to accommodate reagent containers of different sizes corresponding to reagent quantities sufficient for performing two hundred fifty (250) assays or reagent quantities sufficient for performing five hundred (500) assays. Four 250-assay modular quadrants permit the reagent cooling bay to be stocked for 1000 assays, and four 500-assay modular quadrants permit the reagent cooling bay to be stocked for 2000 assays. Modular quadrants for 250 or 500 assay reagent kits can be mixed and matched to configure the container tray for accommodating various numbers of a single assay type or various numbers of multiple different assay types.

An insulation pad 938 is disposed between the container tray 922 and the floor plate 910. Power, control, temperature, and position signals are provided to and from the reagent cooling bay 900 by a connector 936 and a cable (not shown) linked to the embedded controller of the analyzer 50.

A bar code scanner 941 is mounted to an upstanding scanner mounting plate 939 attached to floor plate 910 in front of an opening 942 formed in a side-wall of the cooling bay 900. The bar code scanner 941 is able to scan bar code information from each of the reagent containers carried on the container tray 922. As shown in FIG. 39, longitudinal slots 1932 are formed along the bottle-holding cavities 1924, and bar code information disposed on the sides of the reagent container held in the bottle-holding cavities 1924 can be align with the slots 1932 to permit the bar code scanner 941 to scan the bar code information. A preferred bar code scanner is available from Microscan of Newbury Park, Calif. under Model No. FTS-0710-0001.

Pipette rinse basins 1942, 1944 are attached to the side of the housing 904. Each rinse basin 1942, 1944 provides an enclosure structure with a probe-receiving opening 1941, 1945, respectively, formed in a top panel thereof and a waste drain tube 1946, 1948, respectively, connected to a bottom portion thereof. A probe of a pipette unit can be inserted into the rinse basin 1942, 1944 through the probe-receiving opening 1941, 1945, and a wash and/or rinse fluid can be passed through the probe and into the basin. Fluid in the rinse basin 1942, 1944 is conducted by the respective waste drain tube 1946, 1948 to the appropriate waste fluid container in the lower chassis 1100. In the preferred arrangement and mode of operation of the analyzer 50, probe 481 of pipette unit 480 is rinsed in rinse basin 1942, and probe 483 of pipette unit 482 is rinsed in rinse basin 1944.

After the amplification reagent and oil are added to the reaction tubes 162 of MTU 160 in the left orbital mixer 552, the left-side transport mechanism 502 retrieves the MTU 160 from the left orbital mixer 552 and moves the MTU 160 to an available temperature ramp-up station 700 that is accessible to the left-side transport mechanism 502, i.e. on the left-side of the chemistry deck 200, to increase the temperature of the MTU 160 and its contents to about 60° C.

After sufficient ramp-up time in the ramp-up station 700, the left-side transport mechanism 502 then moves the MTU 160 to the TC incubator 600. The left-side distributor door 624 of the TC incubator 600 opens, and the MTU carousel assembly 671 within the TC incubator 600 presents an empty MTU station 676 to permit the left-side transport mechanism to insert the MTU into the TC incubator 600. The MTU 160 and its contents are then incubated at about 60° C. for a prescribed incubation period. During incubation, the MTU carousel assembly 671 may continually rotate within the TC incubator 600 as other MTUs 600 are removed from and inserted into the TC incubator 600.

Incubating at 60° C. in the TC incubator 600 permits dissociation of the capture probe/target nucleic acid hybridization complex from the immobilized polynucleotide present in the assay solution. At this temperature, an amplification oligonucleotide (e.g., a primer, promoter-primer or promoter oligonucleotide) introduced from the reagent cooling bay 900 can hybridize to the target nucleic acid and subsequently facilitate amplification of the target nucleotide base sequence.

Following incubation, the MTU carousel assembly 671 within the TC incubator 600 rotates the MTU 160 to the left-side distributor door 624, the left-side distributor door 624 opens, and the left-side transport mechanism 502 retrieves the MTU 160 from the MTU carousel assembly 671 of the TC incubator 600. The left-side transport mechanism 502 then moves the MTU 160 to, and inserts the MTU 160 into, an available temperature ramp-down station 700 that is accessible to the left-side transport mechanism 502. The temperature of the MTU 160 and its contents is decreased to about 40° C. in the ramp-down station. The MTU 160 is then retrieved from the ramp-down station by the left-side transport mechanism 502 and is moved to the AT incubator 602. The left-side distributor door 624 of the AT incubator 602 opens, and the MTU carousel assembly 671 within the AT incubator 602 presents an empty MTU station 676, so that the left-side transport mechanism 502 can insert the MTU into the AT incubator 602. Within the AT incubator 602, the MTU is incubated at about 41° C. for a period of time necessary to stabilize the temperature of the MTU.

From the AT incubator 602, the MTU is moved by transport mechanism 502 to the AMP incubator 604 in which the temperature of the MTU is stabilized at 41.5° C. The MTU carousel assembly 671 within the AMP incubator 604 rotates to place the MTU at the pipetting station below the pipette openings 662 formed in the cover 611 (see, e.g., FIG. 19). The container tray 922 within the reagent cooling bay 900 rotates to place the enzyme reagent container below a pipette opening 908, and pipette unit 482 of pipette assembly 470 transfers an enzyme reagent containing one or more polymerases needed for enzymatic synthesis from the reagent cooling bay 900 to each of the reaction tubes 162 of the MTU 160.

As explained above, pipette units 480, 482 use capacitive level sensing to ascertain fluid level within a container and submerge only a small portion of the end of the probe 481, 483 of the pipette unit 480, 482 to pipette fluid from the container. Pipette units 480, 482 preferably descend as fluid is drawn into the respective probe 481, 483 to keep the end of the probe submerged to a constant depth. After pipetting reagent into the pipette unit 480 or 482, the pipette unit creates a minimum travel air gap of 10 µl in the end of the respective probe 481 or 483 to ensure no drips fall from the end of the probe.

After enzyme reagent is added to each reaction tube 162, the MTU carousel assembly 671 of AMP incubator 604 rotates MTU 160 to the skewed disk linear mixer 634 within AMP incubator 604 and the MTU 160 and its contents are mixed as described above at about 10 Hz to facilitate exposure of the target nucleic acid to the added enzyme reagent. The pipette unit 482 is moved to rinse basin 1942, and the probe 483 is rinsed by passing distilled water through it.

The MTU 160 is then incubated within AMP incubator 604 at about 41.5° C. for a prescribed incubation period. The incubation period should be sufficiently long to permit adequate amplification of at least one target nucleotide base sequence contained in one or more target nucleic acids which may be present in the reaction tubes 162. Although the preferred embodiment is designed to facilitate amplification following a TMA procedure, practitioners will easily appreciate those modifications necessary to perform other amplification procedures using the analyzer 50. In addition, an internal control sequence is preferably added at the beginning of the assay to provide confirmation that the amplification conditions and reagents were appropriate for amplification. Internal controls are well known in the art and require no further discussion here. See, e.g., Wang et al., "Quantitation of Nucleic Acids Using the Polymerase Chain Reaction," U.S. Pat. No. 5,476,774.

Following amplification incubation, the MTU 160 is moved by the left-side transport mechanism 502 from the AMP incubator 604 to an available ramp-up station 700 that is accessible to the left-side transport mechanism 502 to bring the temperature of the MTU 160 and its contents to about 60° C. The MTU 160 is then moved by the left-side transport mechanism 502 into the HYB incubator 606. The MTU 160 is rotated to a pipetting station in the HYB incubator 606, and a probe reagent from the reagent cooling bay 900 is pipetted into each reaction tube 162, through openings 662 in the cover 611 of the HYB incubator 606, by the pipette unit 480. In a preferred embodiment, the probe reagent includes a chemiluminescent detection probe, and preferably acridinium ester (AE)-labeled probe which can be detected in a Hybridization Protection Assay (HPA). Acridinium ester-labeled probes and HPA methods are well known in the art. See, e.g., Arnold et al., U.S. Pat. Nos. 5,639,604, 4,950,613, 5,185,439, and 5,585,481; and Campbell et al., U.S. Pat. No. 4,946,958. While AE-labeled probes and HPA are preferred, the analyzer 50 can be conveniently adapted to accommodate a variety of detection methods and associated probes, both labeled and unlabeled. Confirmation that detection probe has been added to the reaction tubes 162 can be accomplished using an internal control that is able to hybridize (or a complement of the internal control that is able to hybridize) to a probe in the probe reagent, other than the detection probe which binds to the target sequence or its complement, under HPA conditions extant in the reaction tubes 162 in the HYB incubator 606. The label of this probe must be distinguishable from the label of the detection probe. See, e.g., Nelson et al., "Compositions and Methods for the Simultaneous Detection and Quantitation of Multiple Specific Nucleic Acid Sequences," U.S. Pat. No. 5,827,656.

After dispensing probe reagent into each of the reaction tubes 162 of the MTU 160, the pipette unit 480 moves to the pipette rinse basin 1944, and the probe 481 of the pipette unit is rinsed with distilled water.

The MTU carousel assembly 671 rotates the MTU 160 to the skewed disk linear mixer 634 where the MTU 160 and its contents are mixed, as described above, at about 14 Hz to facilitate exposure of amplification product containing the target sequence or its complement to the added detection probe. The MTU 160 is then incubated for a period of time sufficient to permit hybridization of the detection probes to the target sequence or its complement.

After hybridization incubation, the MTU 160 is again rotated within the HYB incubator 606 by the MTU carousel assembly 671 to the pipetting position below the pipette openings 662. A selection reagent stored in a container in the reagent cooling bay 900 is pipetted into each reaction tube 162 by the pipette unit 480. A selection reagent is used with the HPA assay and includes an alkaline reagent that specifically hydrolyzes acridinium ester label which is associated with unhybridized probe, destroying or inhibiting its ability to chemiluminesce, while acridinium ester label associated with probe hybridized to an amplification product containing the target sequence or its complement is not hydrolyzed and can chemiluminesce in a detectable manner under appropriate detection conditions.

Following addition of the selection reagent to each of the reaction tubes 162 of the MTU 160, the pipette probe 481 of the pipette unit 480 is rinsed with distilled water at the pipette rinse basin 1944. The MTU 160 is rotated by the MTU carousel assembly 671 within the HYB incubator 606 to the skewed disk linear mixer 634 and mixed, as described above, at about 13 Hz to facilitate exposure of the amplification product to the added selection reagent. The MTU is then incubated in the HYB incubator 606 for a period of time sufficient to complete the selection process.

After selection incubation is complete, the left-side transport mechanism 502 transfers the MTU 160 into an available ramp-down station 700 that is accessible to the left-side transport mechanism 502 to cool the MTU 160. After the MTU 160 is cooled, it is retrieved from the ramp-down station by the left-side transport mechanism 502 and is moved by the transport mechanism 502 into the AT incubator 602 to stabilize the temperature of the MTU 160 at about 40° C.

When a period sufficient to stabilize the temperature of the MTU 160 has passed, the MTU carousel assembly 671 within AT incubator 602 rotates to present the MTU 160 at the right-side distributor door of the AT incubator 602. The right-side distributor door 622 is opened and the MTU 160 is removed from AT incubator 602 by right-side transport mechanism 500.

The right-side transport mechanism 500 moves the MTU to a bar code scanner (not shown) which scans MTU bar code information posted on the label-receiving surface 175 of the label-receiving structure 174 of the MTU 160. The bar code scanner is preferably attached to an outer wall of the housing of the luminometer 950. A preferred bar code scanner is available from Opticon, Inc., of Orangeburg, N.Y., as part number LHA1127RR1S-032. The scanner verifies the total time of assay prior to entering the luminometer 950 by confirming the correct MTU at the correct assay time. From the bar code reader, the right-side transport mechanism 500 moves the MTU 160 to the luminometer 950.

In a preferred mode of operation, before the right-side transport mechanism 500 moves the MTU 160 into the luminometer 950, the MTU 160 is placed by the right-side transport mechanism 500 into an available MTU ramp-down station, or chiller, to decrease the temperature of the MTU 160 to 24±3° C. It has been determined that the MTU contents exhibit a more consistent chemiluminescent "light-off" at this cooler temperature.

Luminometer

Referring to FIGS. 40-42C, a first embodiment of the luminometer 950 includes an electronics unit (not shown) within a housing 954. A photomultiplier tube (PMT) 956 linked to the electronics unit extends from within the housing 954 through a PMT plate 955, with the front end of the PMT 956 aligned with an aperture 953. A preferred PMT is available from Hamamatsu Corp. of Bridgewater, N.J. as Model No. HC 135. Signal measurements using the preferred PMT are based on the well-known photon counter system.

The aperture 953 is centered in an aperture box 958 in front of the PMT plate 955. The aperture 953 and aperture box 958 are entirely enclosed by a housing, defined by a floor plate 964, a top plate 966, the PMT plate 955, and a back frame 965 and back plate 967, which prevents stray light from entering the aperture 953 and which is attached to the datum plate 82. An MTU transport path extends through the housing in front of the aperture 953, generally transversely to an optical axis of the aperture. MTUs 160 pass through the luminometer 950 via the MTU transport path. A back rail 991 and a front rail 995 are disposed on opposite sides of the MTU transport path and provide parallel horizontal flanges which support the connecting rib structure 164 of an MTU 160 disposed within the luminometer 950. Revolving doors 960 are supported for rotation within associated door housings 961 disposed on opposite ends of the MTU transport path and are turned by door motors 962, which may comprise stepper motors or DC gear motors.

The door housings 961 provide openings through which MTUs 160 can enter and exit the luminometer 950. An MTU 160 enters the luminometer 950 by means of the right-side transport mechanism 500 inserting the MTU 160 through one of the door housings 961. The MTU 160 exits the luminometer under the influence of an MTU transport assembly, various embodiments of which are described below, which moves MTUs through the MTU transport path and eventually out of the luminometer through the other door housing 961.

Revolving doors 960 are generally cylindrical and include a cut-out portion 963. Each revolving door 960 can be rotated between an open position, in which the cut-out portion 963 is generally aligned with the opening of the associated door housing 961, so that an MTU 160 can pass through the opening, and a closed position, in which a side of the revolving door opposite the cut-out portion 963 extends across the opening of the associated door housing 961 so that neither an MTU 160 nor light can pass through the opening. Except when an MTU 160 is entering or exiting the luminometer 950, the revolving doors 960 are preferably in their respective closed positions to prevent stray light from entering the luminometer. Because test results are ascertained by the amount of light detected by the PMT 956, stray light from sources other than the receptacle 160 being sampled can cause erroneous results.

As shown in FIGS. 40-42C, the MTU transport assembly may include an MTU advance motor 972 which drives a lead screw 974 through a timing belt (not shown) or bevel gears (not shown). A screw follower 976 engaged to the lead screw 974 is coupled to an MTU bracket 977 extending away from lead screw 974 to engage the MTU 160. The MTU bracket 977 has a guide flange 978 with an elongated, slightly arcuate guide hole 979 formed therein. A guide rod 980 extends through the luminometer 950 adjacent and parallel to the lead screw 974. Guide rod 980 extends through guide hole 979.

Figure 42A:
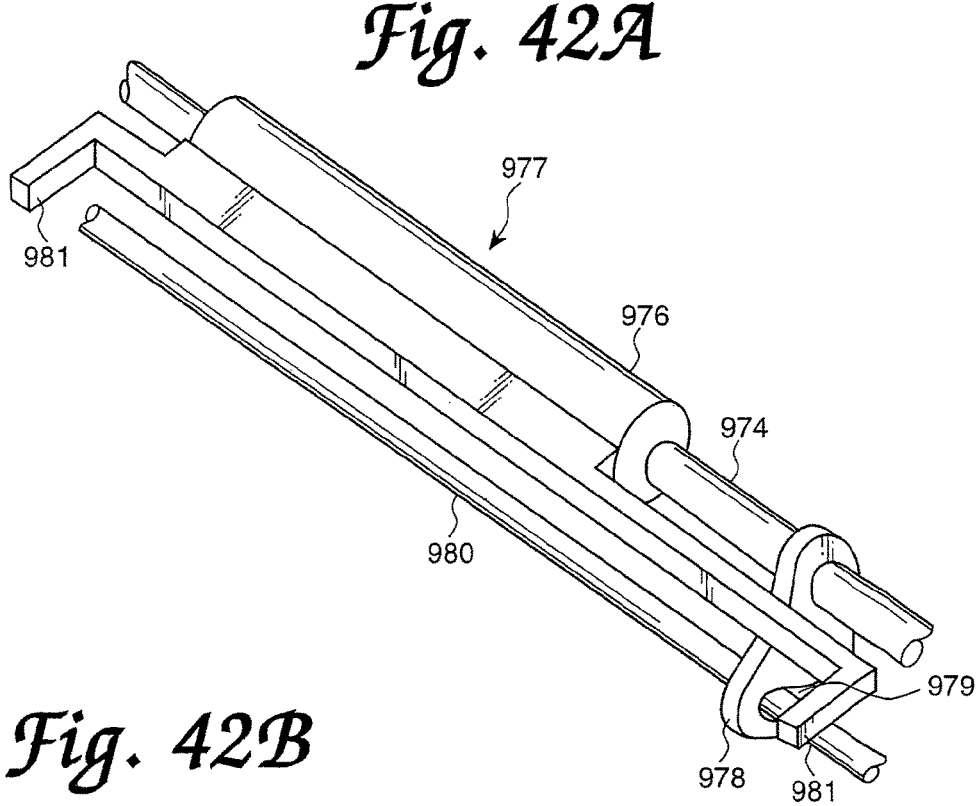
FIG. 42A is a partial perspective view of a receptacle transport mechanism of the first embodiment of the luminometer.
Figure 42B:
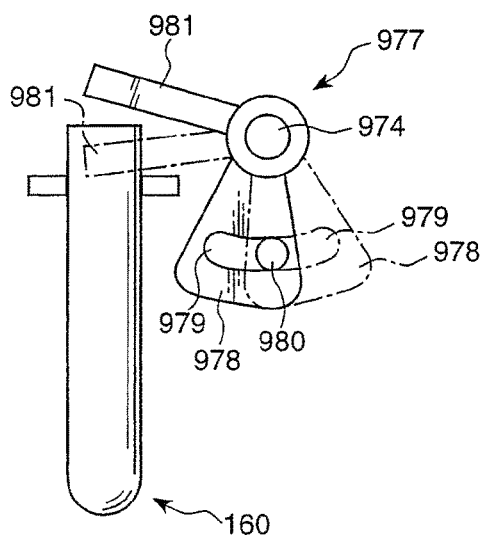
FIG. 42B is an end view of the receptacle transport mechanism of the first embodiment of the luminometer.
Figure 42C:
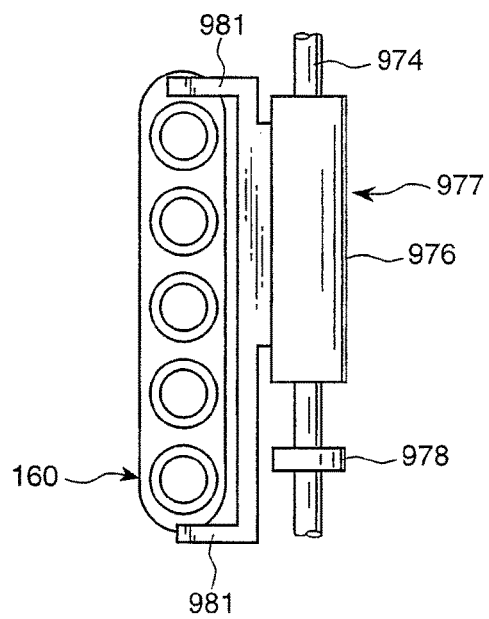
FIG. 42C is a top view of the receptacle transport mechanism of the first embodiment of the luminometer.

To advance the MTU bracket 977 (from bottom to top in FIG. 42C), the lead screw 974 turns counter-clockwise, as viewed in FIG. 42B. Due to system friction, the screw follower 976 and the MTU bracket 977 will also turn counter-clockwise with the lead screw 974 until the guide rod 980 contacts the left-side of the guide hole 979. When guide rod 980 contacts the side of guide hole 979, MTU bracket 977 and screw follower 976 can no longer rotate with lead screw 974, and further rotation of the lead screw 974 will cause the MTU bracket 977 and screw follower 976 to advance along the lead screw 974. Arms 981 extending from the MTU bracket 977 will also rotate counter-clockwise over a limited arc to engage the MTU 160 and advance it through the luminometer 950, as the lead screw 974 rotates.

Figure 41:
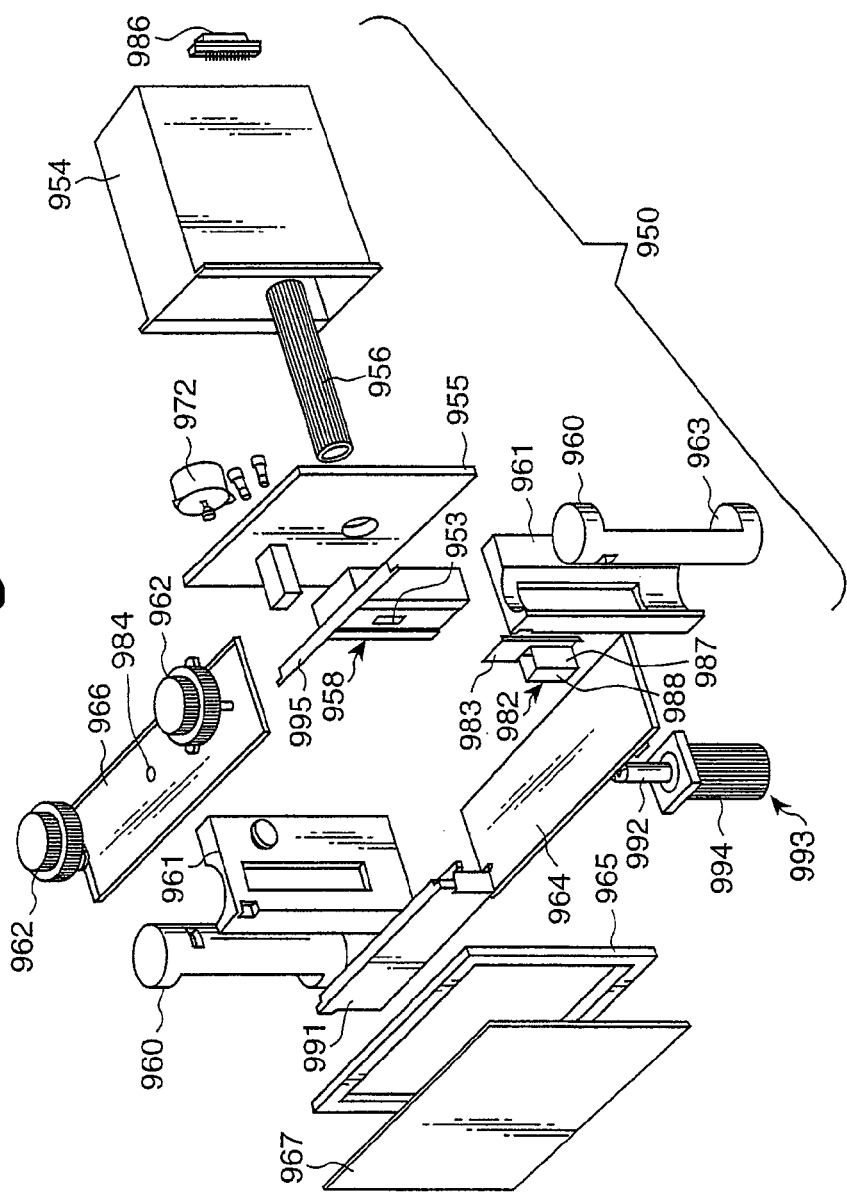
FIG. 41 is a partial exploded perspective view of the luminometer of the first embodiment.

After the MTU 160 has passed the PMT 956, that MTU is ejected from the luminometer 950 and the next MTU can be pulled through the luminometer 950. The MTU bracket 977 moves toward the MTU entrance end of the MTU transport path by clockwise rotation of the lead screw 974. System friction will cause the screw follower 976 and MTU bracket 977 to rotate clockwise until the guide rod 980 contacts the right-side of guide opening 979, after which, continued rotation of the lead screw 974 will cause the screw follower 976 and the MTU bracket 977 to retreat along the lead screw 974. This clockwise movement of the MTU bracket 977 will cause the arms 981 to rotate clockwise over a limited arc to disengage from the MTU, so the MTU bracket 977 can retreat without contacting the MTU. That is, the arms 981 will pass over the top of the MTU as the MTU bracket 977 retreats As shown in FIG. 41, a blinder 982, driven by a blinder actuator 993, moves vertically up and down, in alignment with the aperture 953. Blinder 982 includes a front panel 983 which is mounted for sliding movement with respect to the aperture box 958 and which includes a generally rectangular opening (not shown) formed therein which can be aligned with the aperture 953. A top portion of the front panel 983 blocks the aperture 953 when the opening formed in panel 983 is not aligned with the aperture 953 and thus operates as a shutter for the aperture 953. The blinder 982 includes two side-walls 987, arranged in parallel on opposite sides of the opening and generally perpendicular to the front panel 983, and a back wall 988 spanning the back edges of the sidewalls 987 opposite the front wall 983 and generally parallel to the front wall 983. The side-walls 987 and the back wall 988 define a partial rectangular enclosure sized to accommodate one reaction tube 162 of the MTU 160 when the blinder 982 is moved up beneath one of the reaction tubes 162 of an MTU 160 by the blinder actuator 993. Blinder actuator 993 may be a linear stepper actuator including a stepper motor 992 and a lead screw 994. HIS linear stepper actuators, available from Haydon Switch and Instrument, Inc. of Waterbury, Conn. have been used.

After the MTU 160 is placed into the luminometer 950 by the right-side transport mechanism 500, the motor 972 is energized to pull the first reaction tube of the MTU into alignment with the aperture 953. The blinder 982, which is normally stowed out of the MTU transport path, is raised by the blinder actuator 993 until the side walls 987 and back wall 988 of the blinder 982 surround the reaction tube 162 and the opening formed in the front panel 983 of the blinder 982 is aligned with the aperture 953. The blinder 982 substantially prevents light from sources other than the reaction tube 162 in front of the aperture 953 from reaching the aperture 953, so that the PMT 956 detects only light emissions from the reaction tube directly in front of the aperture 953.

With the PMT shutter open, different detection reagents (Detect I and Detect II), drawn from containers 1146, 1170 of the lower chassis 1100, are sequentially delivered into the aligned reaction tube 162 through dedicated delivery lines (not shown) extending to a reagent port 984 at the top of the luminometer 950. The Detect I and Detect II reagents are hydrogen peroxide-containing and sodium hydroxide-containing reagents, respectively, and combine to form a basic hydrogen peroxide solution which enhances the chemiluminescence of acridinium ester label which has not been hydrolyzed. Because basic hydrogen peroxide is unstable, the Detect I and Detect II reagents are preferably combined in the reaction tube 162 just prior to detection in the luminometer 950.

After the addition of Detect II, the light emitted from the contents of the reaction tube 162 is detected using the PMT 956 and the PMT shutter is then closed. The PMT 956 converts light emitted by chemiluminescent labels into electrical signals processed by the electronics unit and thereafter sent to the controller 1000 or other peripheral unit via cables (not shown) linked to a connector 986.

In cases where less sensitivity is required, it may be possible to use an optical sensor in place of a photomultiplier tube. A diode is an example of an acceptable optical sensor which can be used with the luminometer 950. An optical sensor may also be appropriate when the material of the MTU 160 is relatively transparent, rather than the translucent appearance of the preferred polypropylene material. When selecting a material for the MTU 160, care should be taken to avoid materials that naturally luminesce or are predisposed to electrostatic build-up, either of which can increase the chances of a false positive or interfering with quantification measurements.

The above-described process is repeated for each reaction tube 162 of the MTU 160. After the chemiluminescent signal from each reaction tube 162 of the MTU 160 has been measured, the motor 972 advances to move the MTU 160 through the exit door 961 and out of the luminometer 950 and into the amplicon deactivation station 750.

An alternate, and presently preferred, luminometer is generally designated by reference number 1360 in FIG. 43. Luminometer 1360 includes a housing 1372 having a bottom wall 1370, door assemblies 1200 on opposite sides of the bottom wall 1370 which define end portions of the housing 1372, an optical sensor shutter assembly 1250 which defines a front wall of the housing 1370, a top wall (not shown), and a back wall (not shown), which complete the housing 1370 and define an enclosure therein. The right-side door assembly 1200 defines a receptacle entrance opening 1374, and the left-side door assembly 1200 defines a receptacle exit opening 1376 through which a MTU 160 can be passed into and out of the housing 1370. Each door assembly 1200 controls access through the respective opening 1374 or 1376 and comprises an end wall 1202, a cover plate 1232, and a rotating door 1220 rotatably disposed between the end wall 1202 and the cover plate 1232. The optical sensor aperture shutter assembly 1250 controls light entering an optical sensor (not shown in FIG. 43), for example a photomultiplier tube. Luminometer 1360 includes a light receiver mounting wall 1250 and a cover plate 1290 having an aperture 1292 formed therein.

A bar code scanner 1368 is attached to a front portion of the housing 1372 for scanning MTUs prior to their entry to the luminometer 1360.

A receptacle transport assembly 1332 moves a receptacle (e.g., a MTU 160) through the luminometer 1360 from the entrance opening 1374 to the exit opening 1376. The assembly 1332 includes a transport 1342 movably carried on a threaded lead screw 1340 that is rotated by a motor 1336 coupled to the lead screw 1340 by a belt (not shown).

A dispensing nozzle 1362 is attached in the top wall (not shown) and is connected by conduit tubes 1364 and 1366 to a pump and ultimately to bottles 1146 and 1170 in the lower chassis 1100. Nozzle 1362 dispenses the "Detect I" and the "Detect II" reagents into the receptacles 162 of the MTU 160 within the housing 1372.

A reaction tube positioner assembly 1300 is disposed within the housing 1372 and is constructed and arranged to position each reaction tube 162 of the MTU 160 in front of the aperture 1292 and to optically isolate each reaction tube being positioned from adjacent reaction tubes, so that only light from one reaction tube at a time enters the aperture 1292. The positioner assembly 1300 comprises a receptacle positioner 1304 rotatably mounted within a positioner frame 1302 that is secured to the floor 1370 of the housing 1372.

Figure 44:
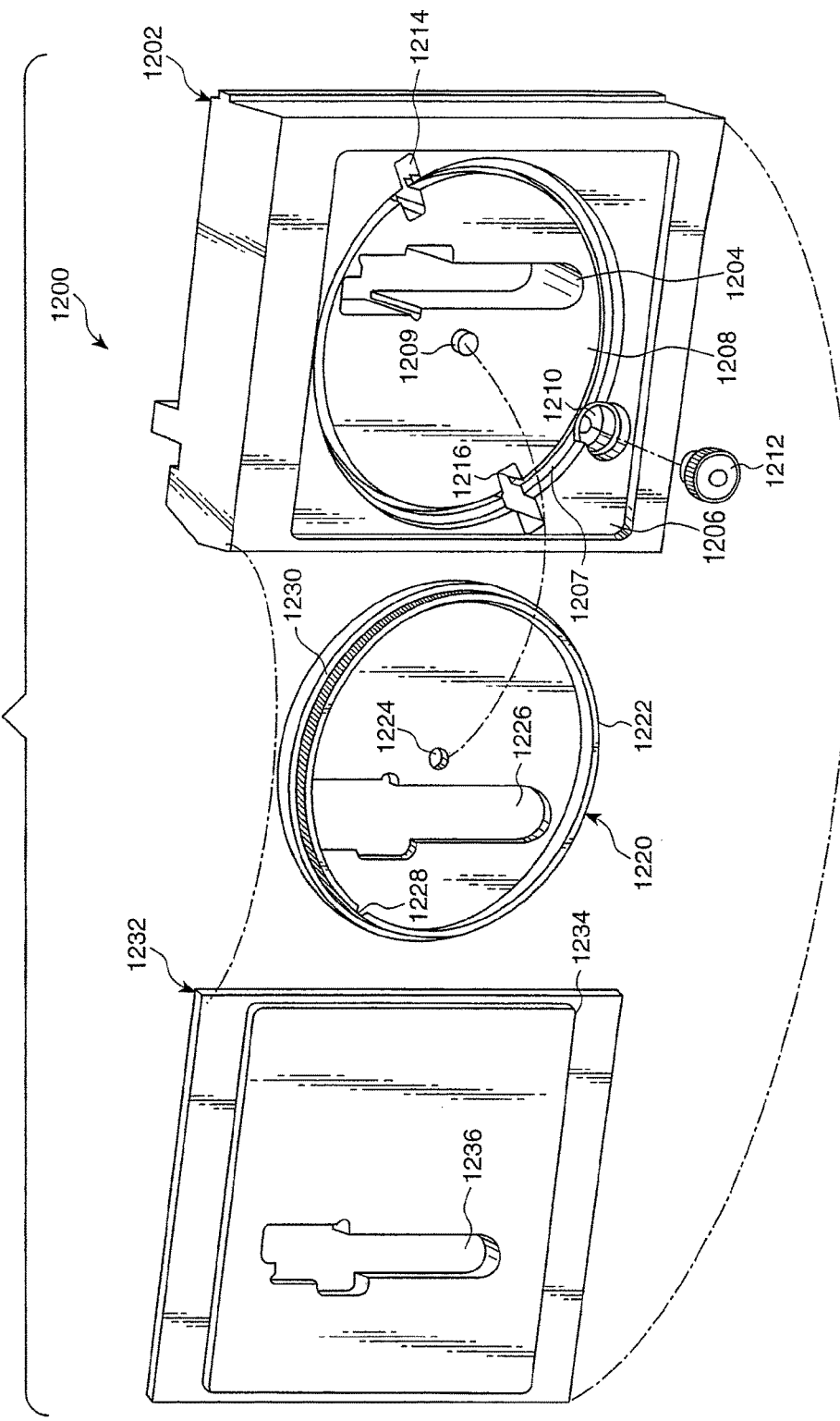
FIG. 44 is an exploded perspective view of a multi-tube unit door assembly for the luminometer of the second embodiment.

The door assembly 1200 for the MTU entrance opening 1374 and exit opening 1376 of the luminometer 1360 is shown in FIG. 44. Door assembly 1200 includes a luminometer end-wall 1202 which forms an end wall of the luminometer housing 1372. End-wall 1202 includes a first recessed area 1206 with a second, circular recessed area 1208 superimposed on the first recessed area 1206. A circular groove 1207 extends about the periphery of the circular recessed area 1208. A slot 1204, having a shape generally conforming to a longitudinal profile of an MTU 160, is formed in the circular recessed area 1208 to one side of the center thereof. A short center post 1209 extends from the center of the circular recessed area 1208.

The rotating door 1220 is circular in shape and includes an axial wall 1222 extending about the periphery of the rotating door 1220. The axial wall 1222 is disposed a short radial distance from the outer peripheral edge of the rotating door 1220, thus defining an annular shoulder 1230 about the outermost peripheral edge outside the axial wall 1222. A slot 1226, having a shape generally conforming to the longitudinal profile of an MTU is formed in the rotating door 1220 at an off-center position.

The rotating door 1220 is installed into the circular recessed area 1208 of the end-wall 1202. A central aperture 1224 receives the center post 1209 of the end-wall 1202, and circular groove 1207 receives axial wall 1222. The annular shoulder 1230 rests on the flat surface of the recessed area 1206 surrounding the circular recessed area 1208.

End-wall 1202 includes a drive gear recess 1210 which receives therein a drive gear 1212 attached to the drive shaft of a motor 1213 (See FIG. 43 in which only the motor 1213 for the right-side door assembly 1200 is shown). Motor 1213 is preferably a DC gear motor. A preferred DC gear motor is available from Micro Mo Electronics, Inc. of Clearwater, Fla., under Model No. 1524TO24SR 16/7 66:1. The outer circumference of the axial wall 1222 of the rotating door 1220 has gear teeth formed thereon which mesh with the drive gear 1212 when the shutter is installed into the circular recess 1208.

The cover plate 1232 is generally rectangular in shape and includes a raised area 1234 having a size and shape generally conforming to the recessed area 1206 of the end-wall 1202. Cover plate 1232 has formed therein an opening 1236 having a shape generally conforming to the longitudinal profile of an MTU, and, when the cover plate 1232 is installed onto the end-wall 1202, the raised rectangular area 1234 is received within the rectangular recessed area 1206 and opening 1236 is in general alignment with opening 1204. Thus, the rotating door 1220 is sandwiched between the cover plate 1232 and the end-wall 1202, and the openings 1236 and 1204 together define the entrance opening 1374 and exit opening 1376.

When the drive gear 1212 is rotated by the motor 1213, the rotating door 1220, enmeshed with the drive gear 1212, is caused to rotate about the center post 1209. When the opening 1226 is aligned with openings 1204 and 1236, MTUs 160 can be passed through the opening 1374 (1376) of the door assembly 1200. With the rotating door 1220 disposed within the circular recessed area 1208 and the raised area 1234 of the cover plate 1232 disposed within the recessed area 1206 of the end-wall 1202, a substantially light-tight structure is achieved, whereby little or no light enters through the door, when the opening 1226 is not aligned with openings 1204 and 1236.

Optical slotted sensors are disposed within slots 1214 and 1216 disposed on the outer edge of the circular recessed area 1208 at diametrically opposed positions. Preferred sensors are available from Optek Technology, Inc. of Carrollton, Tex., Model No. OPB857. The slotted sensors disposed within slots 1214 and 1216 detect the presence of a notch 1228 formed in the axial wall 1222 to signal door open and door closed status.

Figure 45:
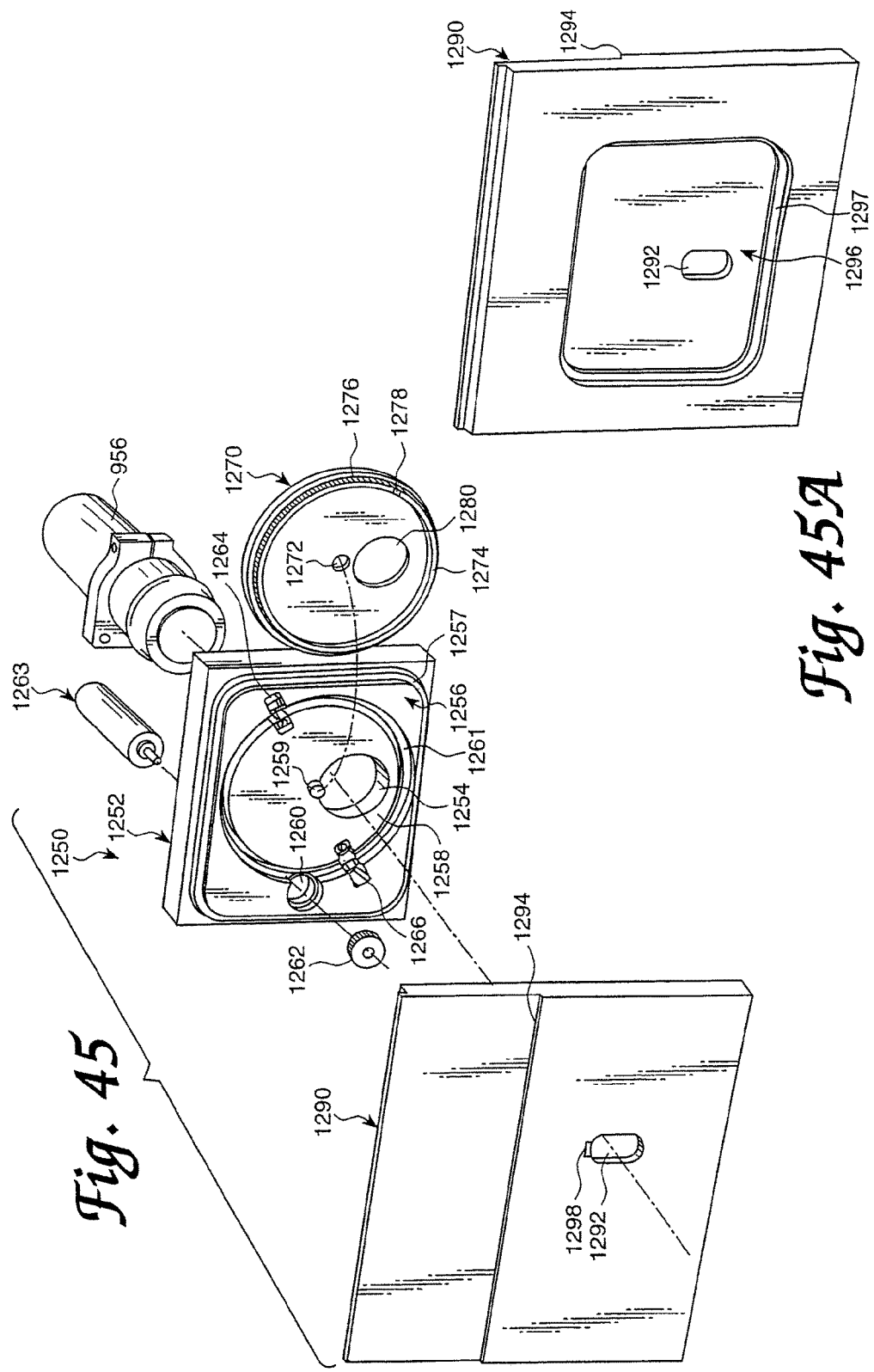
FIG. 45 is an exploded perspective view of a shutter assembly for a photosensor aperture for the luminometer of the second embodiment.

The optical sensor aperture shutter assembly 1250 is shown in FIG. 45. A light receiver, such as a photomultiplier tube 956, is coupled with a light receiver opening 1254 formed in a light receiver mounting wall 1252. The light receiver mounting wall 1252 includes a generally rectangular, two-tiered raised area 1256, which defines a generally rectangular shoulder 1257 and a circular recessed area 1258 superimposed on the rectangular raised area 1256. A circular groove 1261 extends about the periphery of circular recessed area 1258. A center post 1259 is positioned at the center of the circular recessed area 1258. Light receiver opening 1254 is formed in the circular recessed area 1258. In the illustrated embodiment, the light receiver opening 1254 is disposed below the center post 1259, but the light receiver opening 1254 could be placed at any position within the circular recessed area 1258.

The aperture shutter assembly 1250 includes a rotating shutter 1270 having an axial wall 1274 with gear teeth formed on the outer periphery thereof. Axial wall 1274 is formed near, but not at, the outer periphery of the shutter 1270, thereby defining annular shoulder 1276. Rotating shutter 1270 is installed in the circular recessed area 1258 with center post 1259 received within a central aperture 1272 formed in the rotating shutter 1270 and with axial wall 1274 received within circular groove 1261. A drive gear 1262 disposed within a gear recess 1260 and coupled to a drive motor 1263 meshes with the outer gear teeth formed on the axial wall 1274 of the rotating shutter 1270 to rotate the rotating shutter 1270 about the center post 1259. A preferred drive motor 1263 is a DC gear motor available from Micro Mo Electronics, Inc. of Clearwater, Fla., as Model No. 1524TO24SR 16/7 66:1. Micro Mo gear motors are preferred because they provide a high quality, low backlash motor. An opening 1280 is formed in the rotating shutter 1270 which can be moved into and out of alignment with light receiver opening 1254 as the rotating shutter 1270 is rotated.

With the shutter 1270 installed in the circular recessed area 1258, a cover plate, or sensor aperture wall, 1290 is installed onto the sensor mount 1252. As shown in FIG. 45A, sensor aperture wall 1290 includes a generally rectangular, two-tiered recessed area 1296 which defines a generally rectangular shoulder 1297 and which is sized and shaped to receive therein the rectangular raised area 1256 of the sensor mount 1252. A sensor aperture 1292 is formed through the aperture wall 1290 and is generally aligned with the light receiver opening 1254 formed in the sensor mount 1252. The sensor aperture 1292 is generally in the shape of an elongated oval having a width generally corresponding to the width of an individual reaction tube 162 of an MTU 160 and a height corresponding to the height of the intended viewing area. Although opening 1280 of shutter 1270 is shown in the illustrated embodiment to be circular, opening 1280 can have other shapes, such as rectangular, with a width corresponding to the width of a reaction tube 162 or an elongated oval similar to sensor aperture 1292. Rotation of the rotating shutter 1270 to a position in which the opening 1280 is aligned with the light receiver opening 1254 and the sensor aperture 1292 permits light to reach the PMT 956, and rotation of the rotating shutter 1270 to a position in which the opening 1280 is not aligned with light receiver opening 1254 and sensor aperture 1292 prevents light from reaching the PMT 956.

Slotted optical sensors are disposed in slots 1264 and 1266 and detect a notch 1278 formed in the axial wall 1274 of the shutter 1270 to detect opened and closed positions of the shutter 1270. Preferred slotted optical sensors are available from Optek Technology, Inc., of Carrollton, Tex., as Model No. OPB857.

The aperture wall 1290 includes an upwardly facing shoulder 1294 extending across the width thereof. A downwardly facing shoulder of the MTU 160, defined by the connecting rib structure 164 of the MTU 160 (see FIG. 58), is supported by the shoulder 1294 as the MTU 160 slides through the luminometer.

Figure 46:
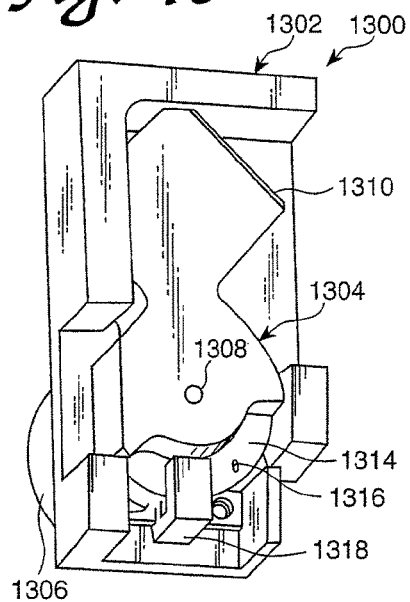
FIG. 46 is a perspective view of a reaction tube positioner assembly of the luminometer of the second embodiment, including a reaction tube positioner disposed within a reaction tube positioner frame.
Figure 48:
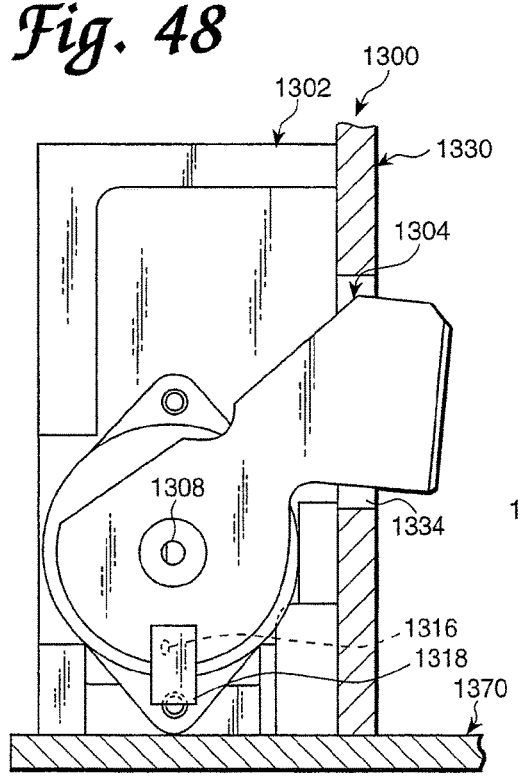
FIG. 48 is a side elevation of the reaction tube positioner assembly.
Figure 49:
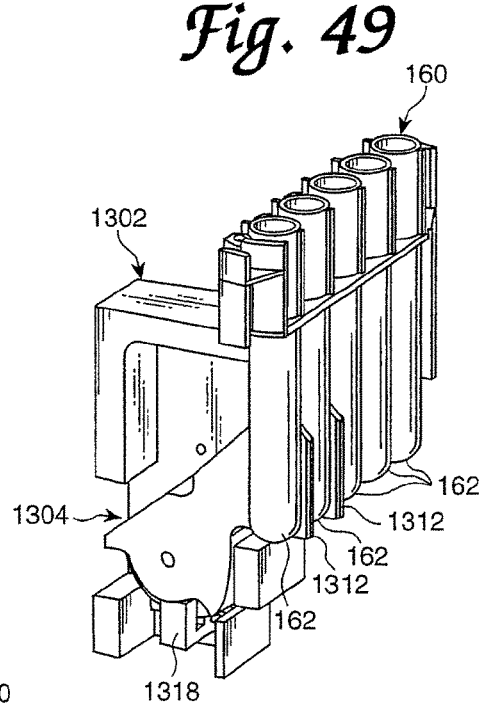
FIG. 49 is a perspective view showing the reaction tube positioner of the reaction tube positioner assembly operatively engaging a multi-tube unit employed in a preferred mode of operation of the analyzer.

The reaction tube positioner assembly 1300 is shown in FIGS. 46 and 48-49. The reaction tube positioner 1304 is operatively disposed within the reaction tube positioner frame 1302. The reaction tube positioner 1304 is mounted in the reaction tube positioner frame 1302 for rotation about a shaft 1308. Shaft 1308 is operatively coupled to a rotary solenoid, or, more preferably, a gear motor 1306, to selectively rotate the reaction tube positioner 1304 between the retracted position shown in FIG. 46 and the fully extended position shown in FIG. 48. A preferred gear motor drive is available from Micro Mo Electronics, Inc. of Clearwater, Fla., as Model No. 1724T0245+16/7 134:1+X0520.

Figure 47:
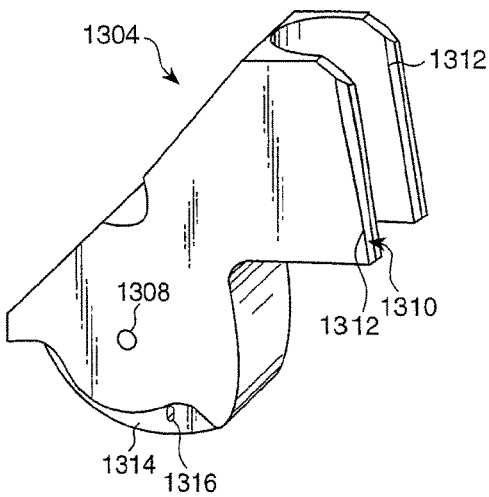
FIG. 47 is a perspective view of the reaction tube positioner.

As shown in FIG. 47, the reaction tube positioner 1304 includes a V-block structure 1310 defining two parallel walls 1312. Reaction tube positioner 1304 further includes an area at the lower end thereof where a portion of the thickness of the reaction tube positioner 1304 is removed, thus defining a relatively thin arcuate flange 1314.

When an MTU 160 is inserted into the luminometer 1360, the reaction tube positioner 1304 is in the retracted position shown in FIG. 46. When an individual reaction tube 162 is disposed in front of the sensor aperture 1292 (see FIG. 45A), so that a sensor reading of the chemiluminescence of the contents of the reaction tube 162 can be taken, the reaction tube positioner 1304 rotates forwardly to the engaged position shown in FIG. 49. In the engaged position shown in FIG. 49, the V-block 1310 engages the reaction tube 162, thus holding the reaction tube in the proper position in alignment with the light receiver aperture 1292 of the luminometer. As shown in FIG. 45, aperture wall 1290 includes a protrusion 1298 extending from the back of wall 1290 into the MTU passage of the luminometer. The protrusion 1298 is aligned with the aperture 1292 so that when the reaction tube positioner 1304 engages a reaction tube 162, the reaction tube is pushed laterally and encounters protrusion 1298 as a hard stop, thus preventing the reaction tube positioner 1304 from significantly tilting the reaction tube 162 within the MTU passage. The parallel sidewalls 1312 of the V-block 1310 prevent stray light from adjacent reaction tubes 162 of the MTU 160 from reaching the light receiver while a reading is being taken of the reaction tube 162 disposed directly in front of the aperture 1292.

A slotted optical sensor 1318 is mounted to a lower portion of the frame 1302, with the arcuate flange 1314 operatively positioned with respect to the sensor 1318. A preferred slotted optical sensor is available from Optek Technology, Inc., of Carrollton, Tex., as Model No. OPB930W51. An opening 1316 is formed in the flange 1314. Opening 1316 is properly aligned with the sensor 1318 when the reaction tube positioner 1304 engages a reaction tube 162 and the reaction tube 162 and protrusion 1298 prevent further rotation of the reaction tube positioner 1304. If a reaction tube 162 is not properly positioned in front of the reaction tube positioner 1304, the reaction tube positioner 1304 will rotate forwardly to the position shown at FIG. 48, in which case opening 1316 will not be aligned with the sensor 1318 and an error signal will be generated.

If a gear motor 1306 is employed for rotating the reaction tube positioner 1304, it is necessary to provide a second sensor (not shown) to generate a positioner-retracted, i.e., "home", signal to shut off the gear motor when the reaction tube positioner 1304 is fully retracted, as shown in FIG. 46. A preferred sensor is available from Optek Technology, Inc. of Carrollton, Tex. as Model No. OPB900 W.

Figure 50:
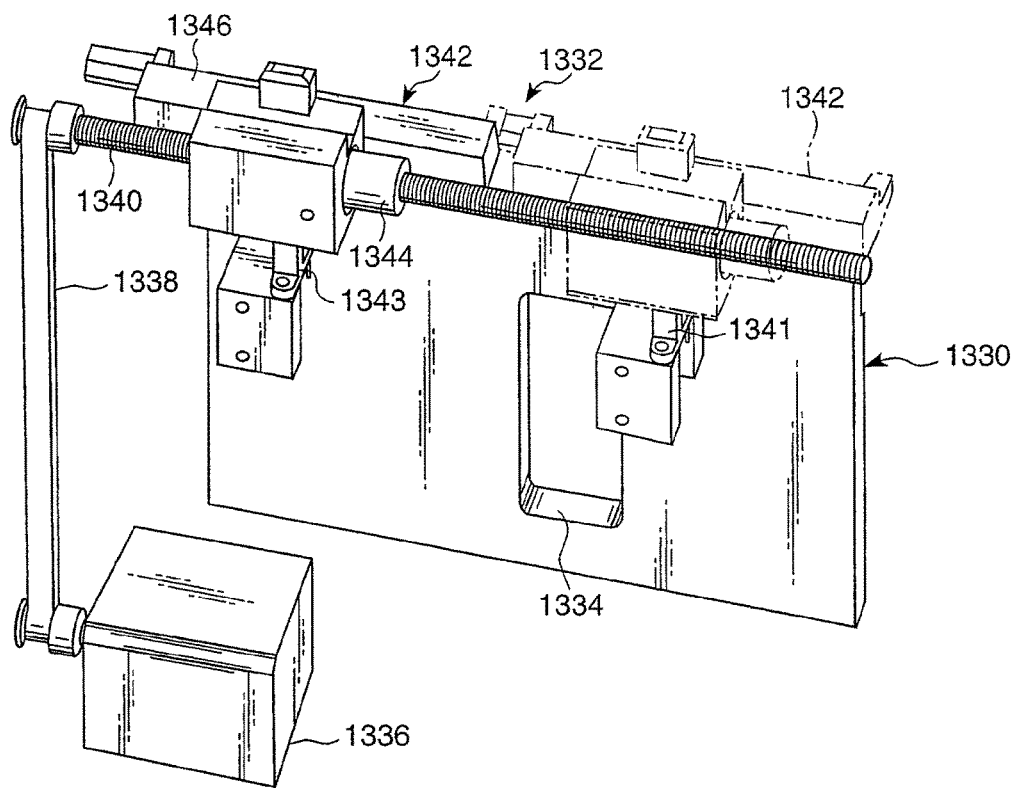
FIG. 50 is a perspective view of a multi-tube unit transport mechanism of the luminometer of the second embodiment.

The MTU transport assembly 1332 is shown in FIG. 50. The MTU transport assembly 1332 is operatively positioned adjacent a top edge of an intermediate wall 1330 (not shown in FIG. 43) of the luminometer 1360. Intermediate wall 1330, which defines one side of the MTU transport path through the luminometer housing 1372, includes a rectangular opening 1334. The reaction tube positioner frame 1302 (see, e.g., FIG. 48) is mounted to the intermediate wall 1330 proximate the opening 1334, and the reaction tube positioner 1304 rotates into engagement with an MTU 160 through the opening 1334.

Figure 51:
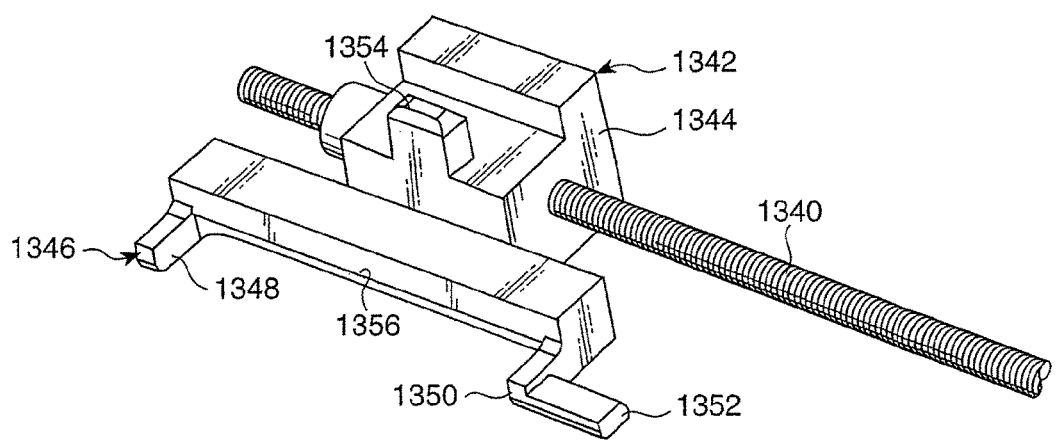
FIG. 51 is a partial perspective view showing a multi-tube unit transport and drive screw of the multi-tube unit transport mechanism of the luminometer.

The MTU transport 1342 is carried on the threaded lead screw 1340 and includes a screw follower 1344 having threads which mesh with the threads of the lead screw 1340 and an MTU yoke 1346 formed integrally with the screw follower 1344. As shown in FIG. 51, the MTU yoke 1346 includes a longitudinally-extending portion 1356 and two laterally-extending arms 1348 and 1350, with a longitudinal extension 1352 extending from the arm 1350. The lead screw 1340 is driven, via a drive belt 1338, by the stepper motor 1336. A preferred stepper motor is a VEXTA motor, available from Oriental Motors Ltd. of Tokyo, Japan, Model No. PK266-01A, and a preferred drive belt is available from SDP/SI of New Hyde Park, N.Y.

When an MTU 160 is inserted into the MTU transport path of the luminometer 950 by the right-side transport mechanism 500, the first reaction tube 162 of the MTU 160 is preferably disposed directly in front of the sensor aperture 1292 and is thus properly positioned for the first reading. The width of the yoke 1346 between the lateral arms 1348 and 1350 corresponds to the length of a single MTU 160. The transport 1342 is moved between a first position shown in phantom in FIG. 50 and a second position by rotation of the lead screw 1340. Slotted optical sensors 1341 and 1343 respectively indicate that the transport 1342 is in the either the first or second position. Due to friction between the lead screw 1340 and the screw follower 1344, the MTU transport 1342 will have a tendency to rotate with the lead screw 1340. Rotation of the MTU transport 1342 with the lead screw 1340 is preferably limited, however, to 12 degrees by engagement of a lower portion of the yoke 1346 with the top of the intermediate wall 1330 and engagement of an upper stop 1354 with the top cover (not shown) of the luminometer housing 1372.

To engage the MTU that has been inserted into the luminometer 1360, the lead screw 1340 rotates in a first direction, and friction within the threads of the screw follower 1344 and the lead screw 1340 causes the transport 1342 to rotate with lead screw 1340 upwardly until the upper stop 1354 encounters the top cover (not shown) of the luminometer 1360. At that point, continued rotation of the lead screw 1340 causes the transport 1342 to move backward to the position shown in phantom in FIG. 50. The lateral arms 1348, 1350 pass over the top of the MTU as the transport 1342 moves backward. Reverse rotation of the lead screw 1340 first causes the transport 1342 to rotate downwardly with the lead screw 1340 until a bottom portion of the yoke 1346 encounters the top edge of the wall 1330, at which point the lateral arms 1348 and 1350 of the yoke 1346 straddle the MTU 160 disposed within the luminometer 1360.

The MTU transport mechanism 1332 is then used to incrementally move the MTU 160 forward to position each of the individual reaction tubes 162 of the MTU 160 in front of the optical sensor aperture 1292. After the last reaction tube 162 has been measured by the light receiver within the luminometer, the transport 1342 moves the MTU 160 to a position adjacent the exit door, at which point the lead screw 1340 reverses direction, thus retracting the transport 1342 back, as described above, to an initial position, now behind the MTU 160. Rotation of the lead screw 1340 is again reversed and the transport 1342 is then advanced, as described above. The exit door assembly 1200 is opened and the longitudinal extension 1352 of the yoke 1346 engages the MTU manipulating structure 166 of the MTU 160 to push the MTU 160 out of the luminometer exit door and into the deactivation queue 750.

Deactivation Station

In the amplicon deactivation station 750, dedicated delivery lines (not shown) add a deactivating solution, such as buffered bleach, into the reaction tubes 162 of the MTU 160 to deactivate nucleic acids in the remaining fluid in the MTU 160. Examples of nucleic acid deactivating solutions are disclosed in, for example, Dattagupta et al., U.S. Pat. No. 5,612,200, and Nelson et al., U.S. Patent Application Publication No. US 2005-0202491 A1. The fluid contents of the reaction tubes are aspirated by tubular elements (not shown) connected to dedicated aspiration lines and collected in a dedicated liquid waste container in the lower chassis 1100. The tubular elements preferably have a length of 4.7 inches and an inside diameter of 0.041 inches.

An MTU shuttle (not shown) moves the MTUs 160 incrementally (to the right in FIG. 3) with the delivery of each subsequent MTU 160 into the deactivation station 750 from the luminometer 950. Before an MTU can be delivered to the deactivation queue 750 by the luminometer 950, the MTU shuttle must be retracted to a home position, as sensed by a strategically positioned optical slot switch. After receiving an MTU 160 from the luminometer, the shuttle moves the MTU 160 to a deactivation station where the dedicated delivery lines connected to dedicated injectors dispense the deactivating solution into each reaction tube 162 of the MTU 160. Previous MTUs in the deactivation queue, if any, will be pushed forward by the distance moved by the MTU shuttle. Sensors at the deactivation station verify the presence of both the MTU and the MTU shuttle, thus preventing the occurrence of a deactivating fluid injection into a non-existent MTU or double injection into the same MTU.

An aspiration station (not shown) includes five, mechanically coupled aspirator tubes mounted for vertical movement on an aspirator tube rack and coupled to an actuator for raising and lowering the aspirator tubes. The aspiration station is at the last position along the deactivation queue before the MTUs are dropped through a hole in the datum plate 82 and into the waste bin 1108. Each time an MTU moves into the deactivation station, the aspirator tubes cycle up and down one time, whether an MTU is present in the aspiration station or not. If an MTU is present, the aspirator tubes aspirate the fluid contents from the MTU. When the next MTU is moved into the deactivation station by the MTU shuttle, the last-aspirated MTU is pushed off the end of the deactivation queue and falls into the waste bin 1108.

Ideally, the analyzer 50 can run about 500 preferred assays in an 8 hour period, or about 1,000 preferred assays in a 12 hour period. Once the analyzer 50 is set-up and initialized, it ordinarily requires little or no operator assistance or intervention. Each sample is handled identically for a given assay, although the analyzer is capable of simultaneously performing multiple assay types in which different MTUs may or may not be handled identically. Consequently, manual pipetting, incubation timing, temperature control, and other limitations associated with manually performing multiple assays are avoided, thereby increasing reliability, efficiency, and throughput. And because an operator's exposure to samples is generally limited to the loading of samples, risks of possible infection are greatly reduced.

Real-Time Amplification Assays

Real-time amplification assays can be used to determine the presence and amount of a target nucleic acid in a sample which, by way of example, is derived from a pathogenic organism or virus. By determining the quantity of a target nucleic acid in a sample, a practitioner can approximate the amount or load of the organism or virus in the sample. In one application, a real-time amplification assay may be used to screen blood or blood products intended for transfusion for blood borne pathogens, such as hepatitis C virus (HCV) and human immunodeficiency virus (HIV), or to monitor the efficacy of a therapeutic regimen in a patient infected with a pathogenic organism or virus. Real-time amplification assays may also be used for diagnostic purposes, as well as in gene expression determinations. In a preferred application of the present invention discussed above, the presence of an organism or virus of interest is determined using a probe which, under the particular conditions of use, exhibits specificity in a sample for a target nucleic acid sequence derived from the organism or virus of interest (i.e., contained within target nucleic acid obtained from the organism or virus or an amplification product thereof). To exhibit specificity, a probe must have a nucleotide base sequence which is substantially complementary to the target or its complement such that, under selective assay conditions, the probe will detectably hybridize to the target sequence or its complement but not to any non-target nucleic acids which may be present in the sample.

In addition to the "end-point" amplification assays described above, where the amount of amplification products containing the target sequence or its complement is determined in a detection station, such as the luminometer 950, at the conclusion of an amplification procedure, the present invention is also able to perform "real-time" amplification assays, where the amount of amplification products containing the target sequence or its complement is determined during an amplification procedure. In the real-time amplification assay, the concentration of a target nucleic acid can be determined by making periodic determinations of the amount of amplification product in the sample which contains the target sequence, or its complement, and calculating the rate at which the target sequence is being amplified. Preferably, the instrument can be selectively used in an end-point or real-time detection mode or simultaneously in both modes.

For real-time amplification assays, the probes are preferably unimolecular, self-hybridizing probes having a pair of interacting labels which interact to emit different signals, depending on whether the probes are in a self-hybridized state or hybridized to the target sequence or its complement. See, e.g., Diamond et al., "Displacement Polynucleotide Assay Method and Polynucleotide Complex Reagent Therefor," U.S. Pat. No. 4,766,062; Tyagi et al., "Detectably Labeled Dual Conformation Oligonucleotide Probes, Assays and Kits," U.S. Pat. No. 5,925,517; Tyagi et al., "Nucleic Acid Detection Probes Having Non-FRET Fluorescence Quenching and Kits and Assays Including Such Probes," U.S. Pat. No. 6,150,097; and Becker et al., "Molecular Torches," U.S. Pat. No. 6,361,945. Other probes are contemplated for use in the present invention, including complementary, bimolecular probes, probes labeled with an intercalating dye and the use of intercalating dyes to distinguish between single-stranded and double-stranded nucleic acids. See, e.g., Morrison, "Competitive Homogenous Assay," U.S. Pat. No. 5,928,862; Higuchi, "Homogenous Methods for Nucleic Acid Amplification and Detection," U.S. Pat. No. 5,994,056; and Yokoyama et al., "Method for Assaying Nucleic Acid," U.S. Pat. No. 6,541,205. Examples of interacting labels include enzyme/substrate, enzyme/cofactor, luminescent/quencher, luminescent/adduct, dye dimers and Forrester energy transfer pairs. Methods and materials for joining interacting labels to probes for optimal signal differentiation are described in the above-cited references.

In a preferred real-time amplification assay, the interacting labels include a fluorescent moiety and a quencher moiety, such as, for example, 4-(4-dimethylaminophenylazo) benzoic acid (DABCYL). The fluorescent moiety emits light energy (i.e., fluoresces) at a specific emission wavelength when excited by light energy at an appropriate excitation wavelength. When the fluorescent moiety and the quencher moiety are held in close proximity, light energy emitted by the fluorescent moiety is absorbed by the quencher moiety. But when a probe hybridizes to nucleic acid present in the sample, the fluorescent and quencher moieties are separated from each other and light energy emitted by the fluorescent moiety can be detected. Fluorescent moieties which are excited and emit at different and distinguishable wavelengths can be combined with different probes. The different probes can be added to a sample, and the presence and amount of target nucleic acids associated with each probe can be determined by alternately exposing the sample to light energy at different excitation wavelengths and measuring the light emission from the sample at the different wavelengths corresponding to the different fluorescent moieties.

In one example of a multiplex, real-time amplification assay, the following may be added to a sample prior to initiating the amplification reaction: a first probe having a quencher moiety and a first fluorescent dye (having an excitation wavelength $ë_{ex1}$ and emission wavelength $ë_{em1}$) joined to its 5' and 3' ends and having specificity for a nucleic acid sequence derived from HCV; a second probe having a quencher moiety and a second fluorescent dye (having an excitation wavelength $ë_{ex2}$ and emission wavelength $ë_{em2}$) joined to its 5' and 3' ends and having specificity for a nucleic acid sequence derived from HIV Type 1 (HIV-1); and a third probe having a quencher moiety and a third fluorescent dye (having an excitation wavelength $ë_{ex3}$ and emission wavelength $ë_{em3}$) joined to its 5' and 3' ends and having specificity for a nucleic acid sequence derived from West Nile virus (WNV). After combining the probes in a sample with amplification reagents, the samples can be periodically and alternately exposed to excitation light at wavelengths $ë_{ex1}$, $ë_{ex2}$, and $ë_{ex3}$, and then measured for emission light at wavelengths $ë_{em1}$, $ë_{em3}$, and $ë_{em3}$, to detect the presence (or absence) and amount of all three viruses in the single sample. The components of an amplification reagent will depend on the assay to be performed, but will generally contain at least one amplification oligonucleotide, such as a primer, a promoter-primer, and/or a promoter oligonucleotide, nucleoside triphosphates, and cofactors, such as magnesium ions, in a suitable buffer.

Where an amplification procedure is used to increase the amount of target sequence, or its complement, present in a sample before detection can occur, it is desirable to include a "control" to ensure that amplification has taken place and, thereby, to avoid false negatives. Such a control can be a known nucleic acid sequence that is unrelated to the sequence(s) of interest. A probe (i.e., a control probe) having specificity for the control sequence and having a unique fluorescent dye (i.e., the control dye) and quencher combination is added to the sample, along with one or more amplification reagents needed to amplify the control sequence, as well as the target sequence(s). After exposing the sample to appropriate amplification conditions, the sample is alternately exposed to light energy at different excitation wavelengths (including the excitation wavelength for the control dye) and emission light is detected. Detection of emission light of a wavelength corresponding to the control dye confirms that the amplification was successful (that is, that the control sequence was indeed amplified), and thus, any failure to detect emission light corresponding to the probe(s) of the target sequence(s) is not likely due to a failed amplification. Conversely, failure to detect emission light from the control dye is likely indicative of a failed amplification, thus rendering any results from that assay suspect.

Figure 61:
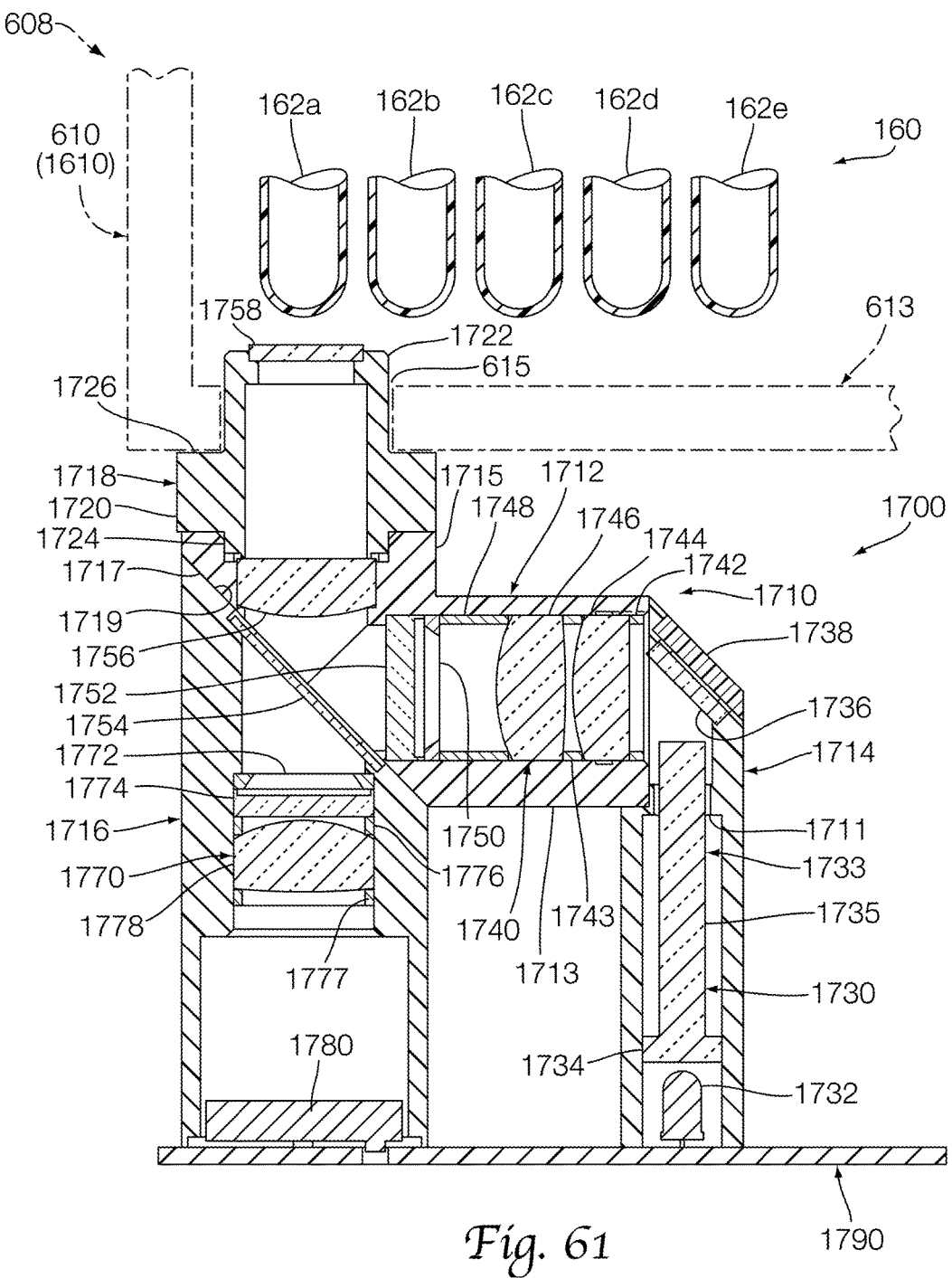
FIG. 61 is a side elevation in cross-section showing an optical detection module and portions of a real-time fluorometer and a multi-tube unit.
Figure 64:
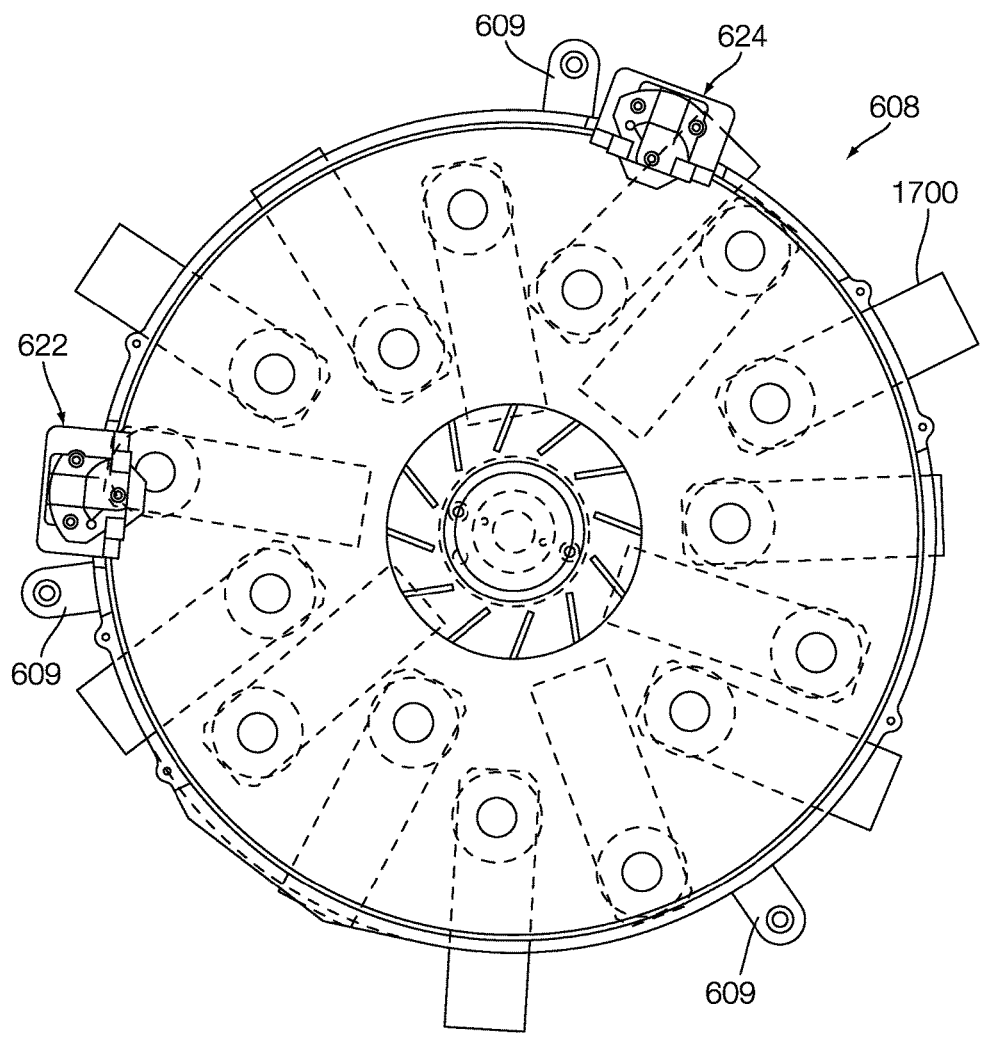
FIG. 64 is a top plan view of a real-time fluorometer showing preferred positions of the optical detection modules.
Figure 65:
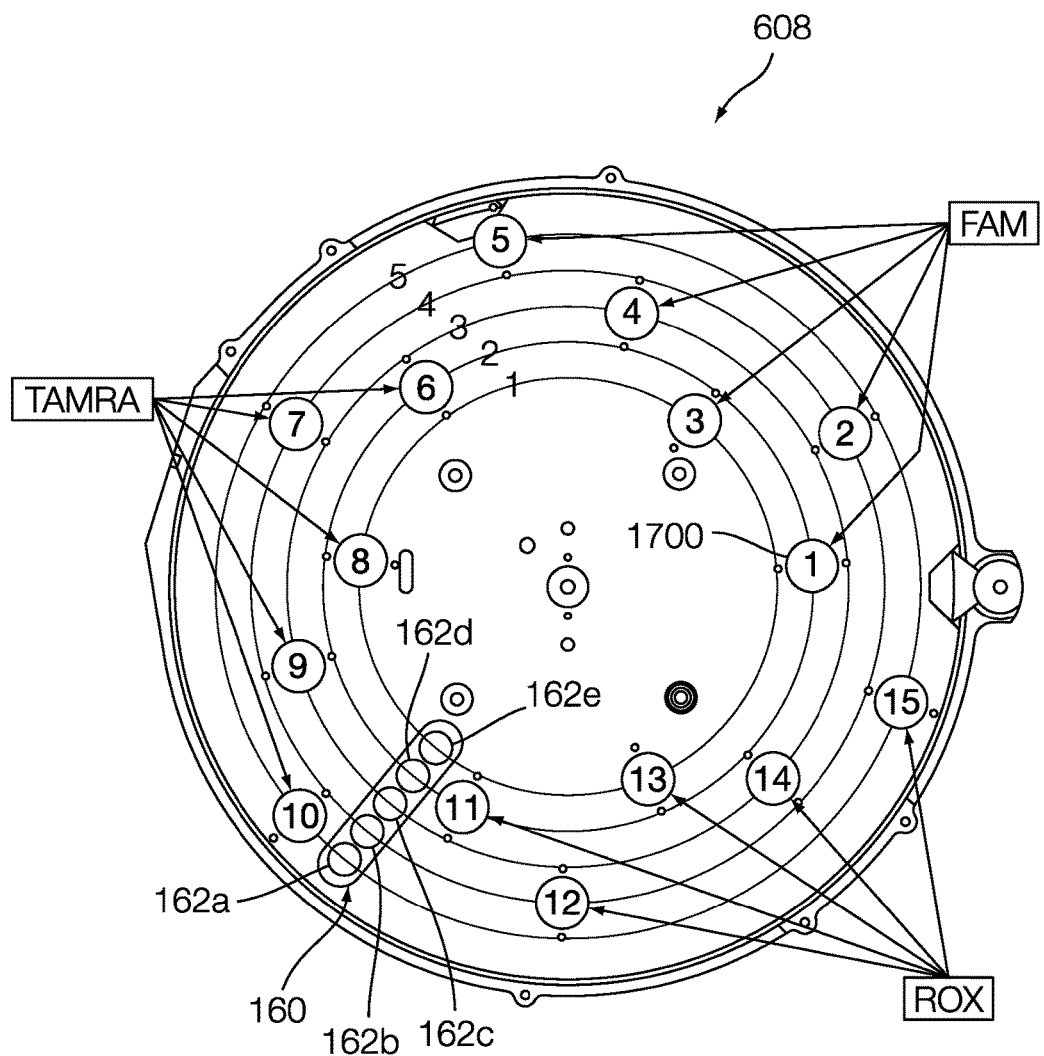
FIG. 65 is a schematic view of a real-time fluorometer showing preferred positions of the optical detection modules.

Real-time amplification assays are performed in a real-time incubator ("RT incubator"), which is a modified version of the AT incubator 602 described above. The RT incubator, designated by reference number 608 in FIGS. 61 and 64-65, is essentially a rotary incubator, such as incubators 600, 602, 604 and 606. The RT incubator includes instruments attached thereto for detecting, in a real-time manner, the amplification occurring within the reaction tubes 162 of an MTU 160 carried in the RT incubator by measuring the fluorescence emitted by a dye or dyes within each reaction tube 162 of the MTU 160 when the MTU 160 is illuminated with an excitation light corresponding to each dye. The RT incubator 608 can be integrated into the automated diagnostic analyzer 50 by modifying the AT incubator 602 so as to enable it to function as either the AT incubator 602 for end-point amplification assays or as the RT incubator 608 for real-time amplification assays. Alternatively, the RT incubator 608 can be secured on a structure (not shown) that is ancillary to the housing 60 if it is desired to keep the AT incubator 602 separate from the RT incubator 608. In this case, it can be appreciated that additional mechanisms, such as transport mechanisms 500, 502 will be necessary to transport the MTU 160 from the processing deck 200 of the analyzer 50 to the RT incubator 608 carried on an ancillary structure adjacent to the processing deck 200.

The instruments attached to the RT incubator 608 for real-time fluorescence detection are known as optical detection modules (a type of a signal measuring device), as will now be described.

An optical detection module generally designated by reference number 1700 is shown in side cross-section in FIG. 61. Also shown in FIG. 61 is a portion of the floor 613 of the RT incubator 608 with the optical detection module 1700 extending through an opening 615 formed in the floor 613. A portion of the cylindrical wall 610 is shown, but, for clarity of illustration, insulating jacket 612 is not shown in FIG. 61. In addition, the datum plate 82, to which the RT incubator 608 is mounted and below which most of the optical detection module 1700 is located, is not shown in FIG. 61. A portion of an MTU 160 is shown positioned above the optical detection module 1700 with the optical detection module 1700 positioned below a first reaction tube 162a of the MTU 160. Substantially identical optical detection modules 1700 are preferably positioned with respect to each of the other reaction tubes 162b, 162c, 162d, and 162e at different locations on the RT incubator 608.

Figure 62:
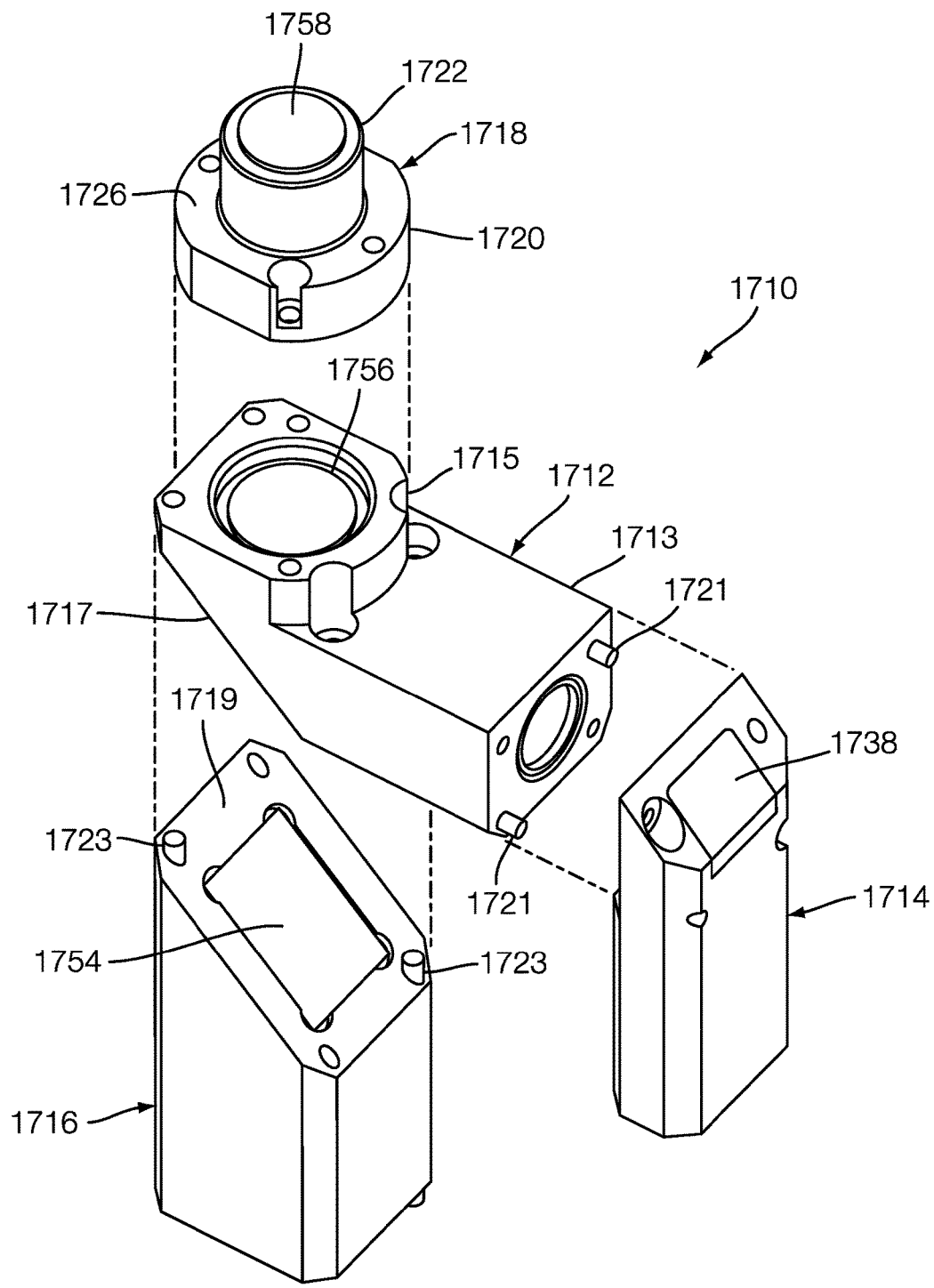
FIG. 62 is an exploded perspective view of the housing of the optical detection module.
Figure 63:
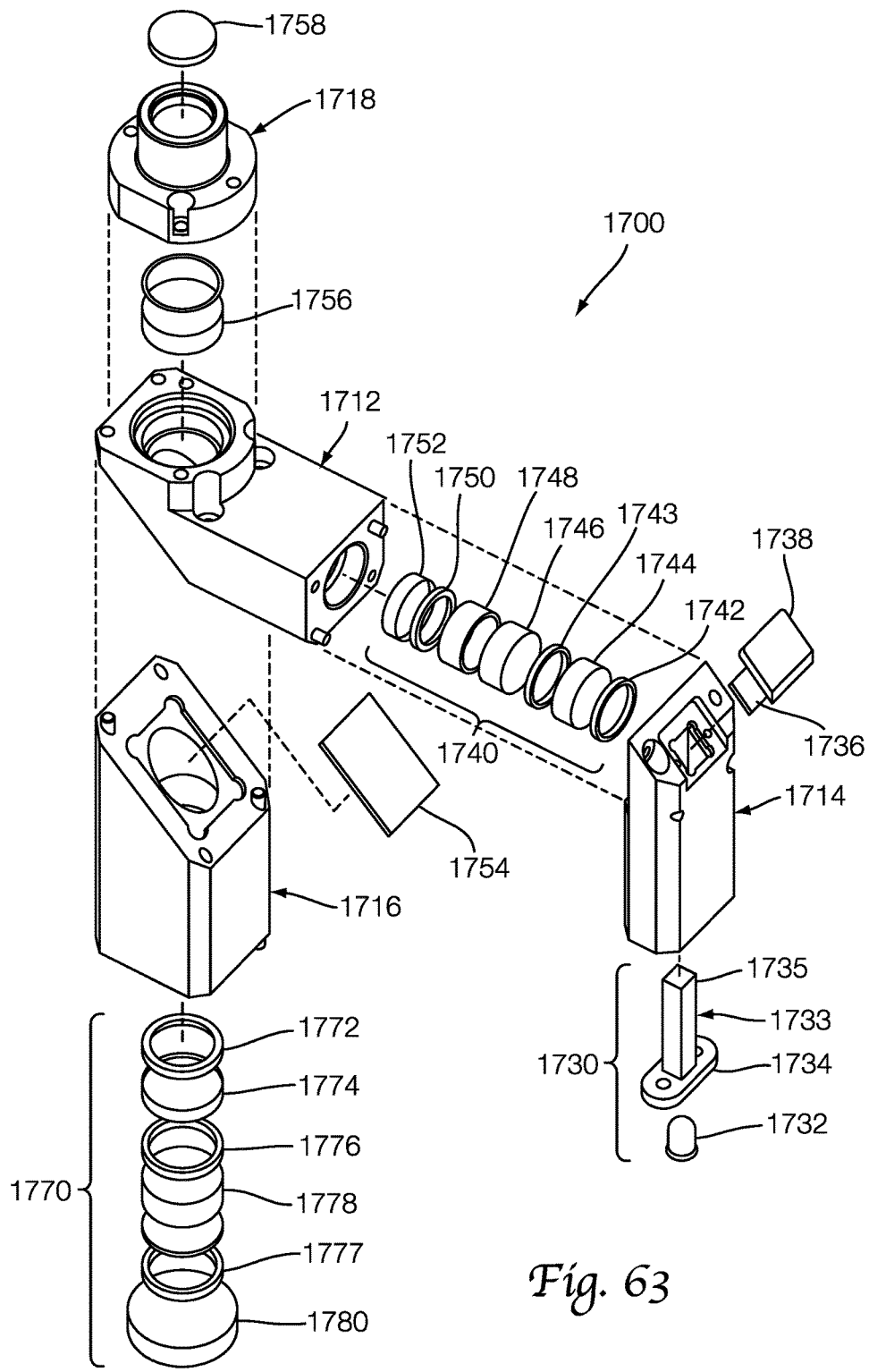
FIG. 63 is an exploded perspective view of the optical detection module.

As shown in FIGS. 61-63, the optical detection module 1700 includes a housing 1710 attached to a printed circuit board 1790. The housing 1710 includes four sections: the excitation light housing 1714, the excitation lens housing 1712, the adaptor pipe 1718, and the emission lens housing 1716. The excitation lens housing 1712, the excitation light housing 1714, and the emission lens housing 1716 are each preferably formed from machined 6061-T6 aluminum with a black anodize finish. The adaptor pipe 1718 is preferably formed from a Delrin® resin. As can be seen in FIG. 61, the adaptor pipe 1718 is in close proximity to the incubator floor 613 of the RT incubator 608. Accordingly, to provide a level of thermal isolation of the optical detection module 1700 from the RT incubator 608, the adaptor pipe 1718 is preferably formed from a material having low thermal conductivity, such as a Delrin® resin. The adapter pipe 1718 also provides additional electrical isolation between the housing 1710 and the circuit board 1790.

The excitation light housing 1714 houses the excitation light assembly 1730 (described in more detail below) and is attached at a lower end thereof to the printed circuit board 1790 and at an upper end thereof to an end of the excitation lens housing 1712. The excitation light housing 1714 is attached to the excitation lens housing 1712 by means of mechanical fasteners, such as screws (not shown). The assembly may also include location pins 1721 (see FIG. 62)

extending between the excitation light housing 1714 and the excitation lens housing 1712 to facilitate precise relative positioning of the respective housings during assembly thereof.

The excitation lens housing 1712 includes a first portion 1713 oriented horizontally in the illustration and a second portion 1715 extending at a right angle from the first portion 1713 and oriented vertically in the figure. An oblique surface 1717 preferably has an angle of 45° with respect to the longitudinal axes of the first portion 1713 and second portion 1715.

The adaptor pipe 1718 includes a base portion 1720 adapted to mate in a light-tight manner with the end of the second portion 1715 of the excitation lens housing 1712. More specifically, the base portion 1720 of the adaptor pipe 1718 includes a projection 1724, preferably circular in shape (see FIG. 61), which extends into a recession of mating size and shape formed in the upper end of the second portion 1715 of the excitation lens housing 1712. An upper portion 1722 of the adaptor pipe 1718 projects above the base portion 1720. Upper portion 1722 is preferably circular in shape and adapted to project through an opening 615 formed in the floor 613. Upper portion 1722 preferably has a smaller cross-wise dimension than that of the base portion 1720, thereby forming a shoulder 1726 between the upper portion 1722 and the base portion 1720, the shoulder 1726 bearing against the bottom of the floor 613 when the optical detection module 1700 is installed on the RT incubator 608.

The adaptor pipe 1718 is preferably secured to the excitation lens housing 1712 by means of mechanical fasteners, such as screws (not shown), and locator pins (not shown) may extend between the adaptor pipe 1718 and the second portion 1715 of the excitation lens housing 1712 to facilitate precise relative positioning of the respective parts during the assembly thereof.

The emission lens housing 1716 is attached at a lower end thereof to the printed circuit board 1790 at a spaced apart position from the excitation light housing 1714. An upper end of the emission lens housing 1716 is in the form of an oblique surface 1719 having a preferred angle of 45° and conforming to the oblique surface 1717 of the excitation lens housing 1712. The excitation lens housing 1712 and the emission lens housing 1716 are preferably connected to one another by mechanical fasteners such as screws (not shown) and may also include locating pins 1723 extending between the housings to facilitate precise positioning of the housings during the assembly thereof.

Gasket material (not shown) may be placed on mating surfaces between any of the respective housings to limit light infiltration into the housing 1710. Such gasket material may, for example, comprise a foam material.

As shown in FIGS. 61 and 63, the internal optics of the optical detection module 1700 include an excitation light assembly 1730, an excitation lens assembly 1740, and an emission lens assembly 1770.

Figure 66:
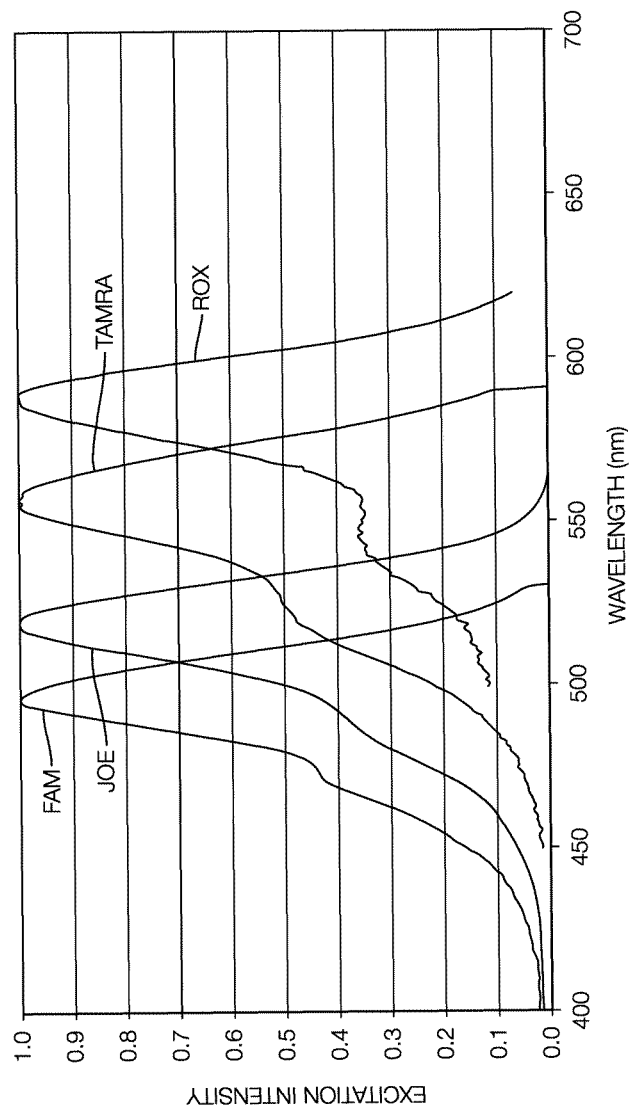
FIG. 66 is a graph showing excitation spectra of preferred amplification detection dyes.

The excitation light assembly 1730 includes a light emitting diode (LED) 1732 connected in the conventional manner to the printed circuit board 1790. Different fluorescent dyes are excited at different wavelengths. In one multiplex application of the present invention, preferred dyes include the rhodamine dyes tetramethyl-6-rhodamine ("TAMRA") and tetrapropano-6-carboxyrhodamine ("ROX") and the fluorescein dyes 6-carboxyfluorescein ("FAM") and 2',7'-dimethoxy-4',5'-dichloro-6-carboxyrhodamin ("JOE"), each in combination with a DABCYL quencher. The excitation spectra of the preferred dyes are shown in FIG. 66. Because the preferred dyes are excited at different wavelengths, the optical detection module 1700 is preferably tailored to emit an excitation light at or near the desired excitation wavelength (i.e., color) for the particular dye for which the optical detection module is intended. Accordingly, component selection for the optical system will in many instances be governed by the particular dye for which the optical detection module is intended. For example, with respect to the LED 1732, the particular LED (manufacturer and model number) selection will depend on the dye for which the optical detection module is intended. For the FAM dye, the preferred LED is available from Kingbright Corporation, City of Industry, Calif., as Model No. L7113PBCH; for the TAMRA dye, the preferred LED is available from Kingbright as Model No. L7113VGC/H; for the ROX dye, the preferred LED is available from Agilent Technologies, Inc., Palo Alto, Calif., as Model No. HLMP-EL16-VY000; and for the JOE dye, the preferred LED is available from Kingbright as Model No. L7113VGC/H.

A light pipe 1733 is positioned above the LED 1732 and includes a base portion 1734 and an elongate portion 1735 projecting from the base portion 1734. The light pipe 1733, also known as a mixing rod, is preferably a molded or extruded transparent acrylic. The light pipe 1733 takes light emitted by the LED 1732, transmits it upwardly away from the LED 1732 and creates a spatially homogenous light distribution at the end of the elongate portion 1735 of the light pipe 1733 opposite the LED 1732. The light pipe acts as a light transmitter and a physical spacer which makes the height of the excitation light assembly 1730 conform to the height of the emission lens assembly 1770. Also, spatially homogeneous excitation light leads to better fluorometer reads and facilitates radiometric repeatability. The light pipe 1733 extends through a restricted opening 1711 formed in the interior of the excitation light housing 1714.

Light from the light pipe 1733 is directed toward a mirror 1736 disposed at an upper end of the light pipe housing 1714. Preferred mirrors include mirrors available from Edmund Optics Inc., Barrington, N.J., as Part No. Y43-790 (enhanced aluminum), and as Part No. Y43-791 (protected gold). The mirror 1736 is preferably oriented at an angle of about 45°. A cover 1738, preferably made from a Delrin® resin or other suitable material, is attached to the upper end of the excitation light housing 1714 above the mirror 1736. The mirror 1736 is installed into a counter bored opening formed in the upper end of the light pipe housing 1714, and thereafter the housing is closed by means of the cover 1738.

The excitation lens assembly 1740 includes a first lens 1744 and a second lens 1746. Preferred lenses for the first lens 1744 include lenses available from Edmund Optics as Part No. Y32-913, and suitable lenses for the second lens 1746 include lenses available from Edmund Optics as Part No. Y45-348. Lenses 1746 and 1744 are separated from one another by a spacer element 1743, preferably formed from 6061-T6 aluminum with a black anodize finish. Light reflected off the mirror 1736 is directed through the lenses 1744 and 1746, which collimate the reflected light to within a preferred tolerance of +/−10°. Light passing through the second lens 1746 passes thereafter through a baffle aperture 1750. The baffle aperture 1750 is a ring with an inner surface that is angled at 35° with respect to the longitudinal axis of the first portion 1713 of housing 1712 (i.e., the optical axis) and is preferably made from machined 6061-T6 aluminum with a black anodize finish. The purpose of the baffle 1750 is to block out stray light that is not within the +/−10° tolerance. The second lens 1746 is separated from the aperture baffle 1750 by means of a spacer element 1748, preferably made from 6061-T6 aluminum with a black anodize finish.

Following the aperture baffle 1750, the light passes through an excitation filter 1752 to remove unwanted spectral components of the excitation light. Again, the specific filter used will depend on the excitation spectra of the dye for which the optical detection module 1700 is intended. The preferred filters are available from Chroma Technology Corp., Rockingham, Vt., as Part No. HQ480/43x for the dye FAM, as Part No. HQ525/50x for the dye TAMRA, as Part No. HQ590/20x for the dye ROX, and as Part No. HQ514/22x for the dye JOE. The elements of the excitation lens assembly 1750 are held in place within the excitation lens housing 1712 by means of a retainer ring 1742. Suitable retainer rings are available from Thorlabs, Inc. of Newton, N.J. as Part No. SM18RR.

Following the excitation filter 1752, the light impinges upon dichroic beam splitter 1754. The dichroic beam splitter 1754 is oriented at 45° and redirects the excitation light passing through excitation filter 1752 by 90° toward lens 1756 disposed in the adaptor pipe 1718 (described below). The specific beam splitter employed depends on the dye for which the optical detection module 1700 is intended. Preferred beam splitters are as follows: for the FAM dye, suitable beam splitters are available from Chroma Technology as Part No. 511LP; for the TAMRA dye, suitable beam splitters are available from Chroma Technology as Part No 560LP; for the ROX dye, suitable beam splitters are available from Chroma Technology as Part No. 615LP; and for the JOE dye, suitable beam splitters are available from Chroma Technology as Part No 535LP. Lens 1756 is a focusing lens that directs light through window 1758, which then impinges upon a reaction tube 162 of the MTU 160. Suitable focusing lenses are available from Edmund Optics as Part No. Y32-913.

When excited by the light of the correct bandwidth, and assuming the presence of a particular dye in question, the contents of the reaction tube 162 will fluoresce, thereby emitting light. Light emitted by the contents of a reaction tube 162 passes through the window 1758 and back through the lens 1756, which collects and focuses as much of the emitted light as possible. The lens 1756 also collimates the emitted light preferably to within a tolerance of +/−10°. The light passing through the lens 1756 thereafter impinges upon the dichroic beam splitter 1754 and, being of a different wavelength than the excitation light, the emitted light passes through and is not redirected by the beam splitter 1754. After light passes through the dichroic beam splitter 1754, it passes into the emission lens assembly 1770, where it first encounters an aperture baffle 1772. Baffle 1772 is preferably formed from 6061-T6 aluminum with a black anodize finish and having an interior opening that is angled at 35° with respect to its longitudinal axis. Aperture baffle 1772 blocks light that is not within the +/−10° tolerance.

Figure 67:
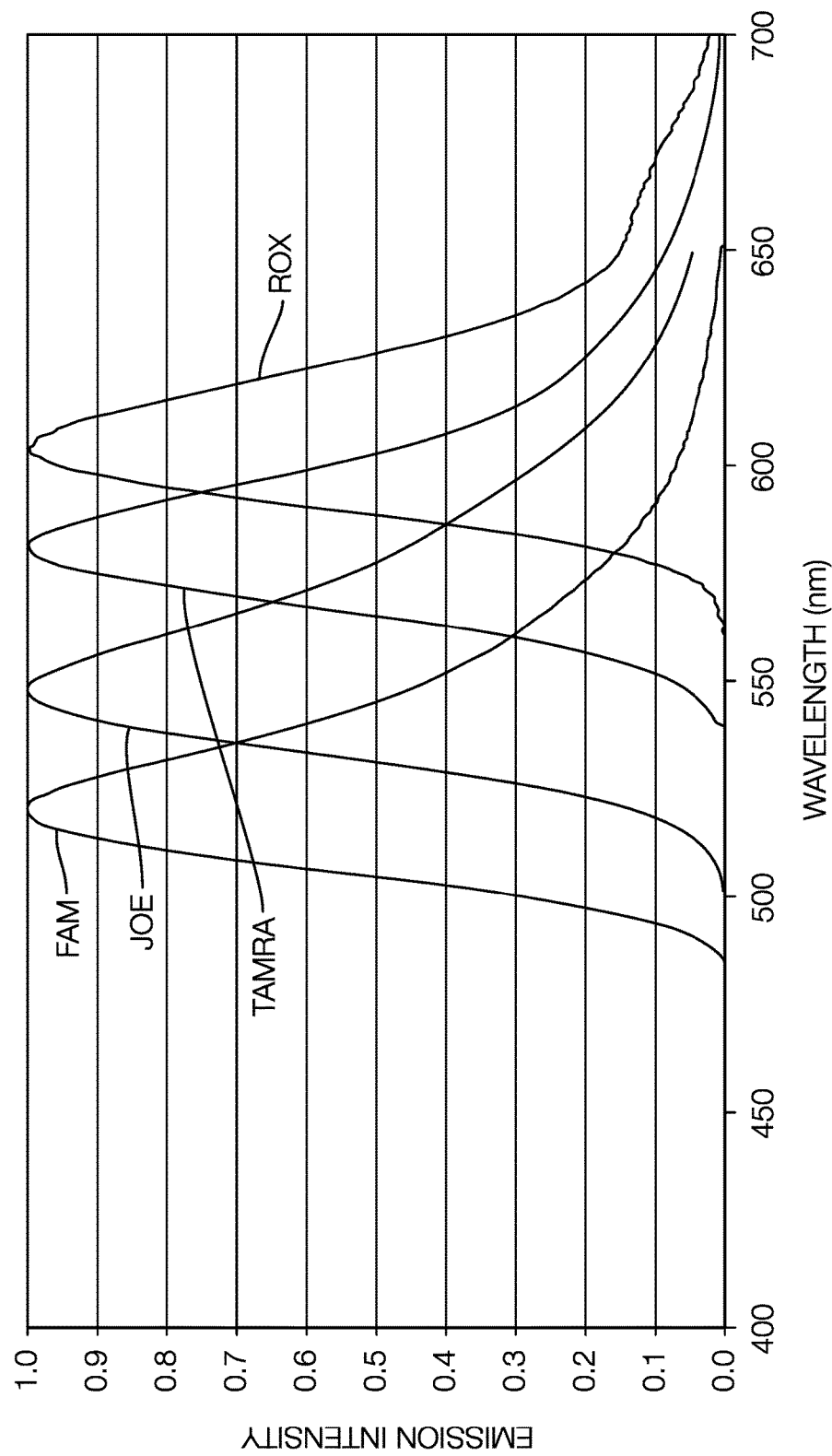
FIG. 67 is a graph showing emission spectra of preferred amplification detection dyes.

After passing through the aperture baffle 1772, the light encounters emission filter 1774, which removes unwanted spectral components present in the emission light. The specific filter preferred depends on the wavelength of the light emitted from the specific dye for which the optical detector module is intended. FIG. 67 shows the emission spectra of the preferred dyes used in association with the present invention. Preferred emission filters are as follows: for the FAM dye, suitable filters are available from Chroma Technology as Part No. HQ533/24m; for the TAMRA dye, suitable filters are available from Chroma Technology as Part No. HQ588/35m; for the ROX dye, suitable filters are available from Chroma Technology as Part No. HQ640/40m; and for the JOE dye, suitable filters are available from Chroma Technology as Part No. HQ560/30m.

Light next passes through a focusing lens 1778. Suitable lenses are available from Edmund Optics as Part No. Y45-348. The emission light is focused by the lens 1778 onto a photodiode 1780 which generates a current signal in proportion to the intensity of the emission light. Suitable photodiodes are available from UDT Sensors, Inc. of Hawthorne, Calif., as Model No. PIN-10DI. Lens 1778 and filter 1774 are separated from one another by a spacer element 1776, preferably formed from 6061-T6 aluminum with a black anodize finish. The elements of the emission lens assembly 1770, other than the photodiode 1780, are held in place within the emission lens housing 1716 by means of a retainer ring 1777. Suitable retainer rings are available from Thorlabs, Inc. of Newton, N.J., as Part No. SM18RR. The photodiode 1780 is connected to the printed circuit board 1790.

FIGS. 68A-68F illustrate a suitable circuit (including an amplifier circuit that produces a voltage that is proportional to the current generated by photodiode 1780) for circuit board 1790 which includes LED 1732 and photodiode 1780.

The electronic circuit 1790 includes the following components: power supply 1800 and power filters formed by capacitors C6, C10, and C17 and resistors R11 and R25 (FIG. 68E), an excitation source (LED) 1732 (FIG. 68F), excitation drive source circuit including U1 and various components (FIG. 68F), receiver (photodiode) 1780 and various components (FIG. 68A), pre-amplifier circuit U6 (pins 5-7), U7, and various components (FIG. 68A), offset compensation circuit U6 (pins 1-3) and various components (FIG. 68A), microprocessor circuit U5 and various components (FIG. 68B), analog switch circuit SW1 and various components (FIG. 68B), and low-pass differential filter circuit U2 and U3 (FIG. 68C), U4 (FIG. 68D) and various components.

In order to reject the effects of varying background ambient light, circuit 1790 incorporates microprocessor U5, which controls LED 1732 (on/off) and creates a clock (set at 250 Hz for FAM/ROX, 350 Hz for TAM) that is used to modulate LED 1732 and control the analog switch SW1. By modulating the LED 1732 (excitation) and changing the state of the analog switch SW1 (changing the gain of the subsequent differential filter U2 from positive to negative gain and back) at the same frequency, a matched transmitter/receiver pair is created. Only those optical signals arriving at the same frequency as this clock will be amplified; all ambient light and light signals modulated at a different frequency are suppressed.

A pre-amplifier (transimpedance) circuit—including U6 (pins 5-7) and U7—receives an electrical current from the photodiode 1780 and converts it to an amplified voltage. In addition, the offset compensation circuit—including U6 (pins 1-3)—provides a bias current that compensates for electrical current out of the photodiode 1780 that is in response to any ambient light (not modulated) incident on the photodiode 1780. This is so that ambient light (which can be many orders of magnitude greater than the modulated light of interest) does not saturate the output of the pre-amplifier which, given the gain in this pre-amplifier (20 mV/nA), is easily and frequently accomplished.

Due to the high gain and the small signal being measured, the pre-amplifier circuit can be highly susceptible to errors in measurement as a result of EMI/RFI interference and changes in temperature and humidity. To minimize these effects, circuit traces and components comprising high impedance circuits, especially the photodiode 1780 and connected points, are located as far as possible from other circuits. Additionally, the printed circuit board 1790 is preferably constructed to facilitate the complete removal of contaminants that may collect adjacent critical high impedance components, especially components R33, R36 and C21. To minimize the amount of contaminants and residual flux remaining on the circuit board 1790 after assembly, the board is first washed with saponifiers appropriate for the solder/flux to be used for soldering and then rinsed with deionized water. Following these preparatory steps, the photodiode 1780 is preferably soldered to the circuit board 1790 with a "no-wash flux" core solder and any residual flux remaining on the circuit board 1790 provides a protective barrier and, therefore, is preferably not removed. These steps should alleviate the effects of long term drift and circuit sensitivity associated with changes in temperature and humidity. In addition, the pre-amplifier portion of the circuit board 1790 is fully contained within a grounded housing (Faraday cage) to suppress any EMI/RFI interference.

Figure 68A:
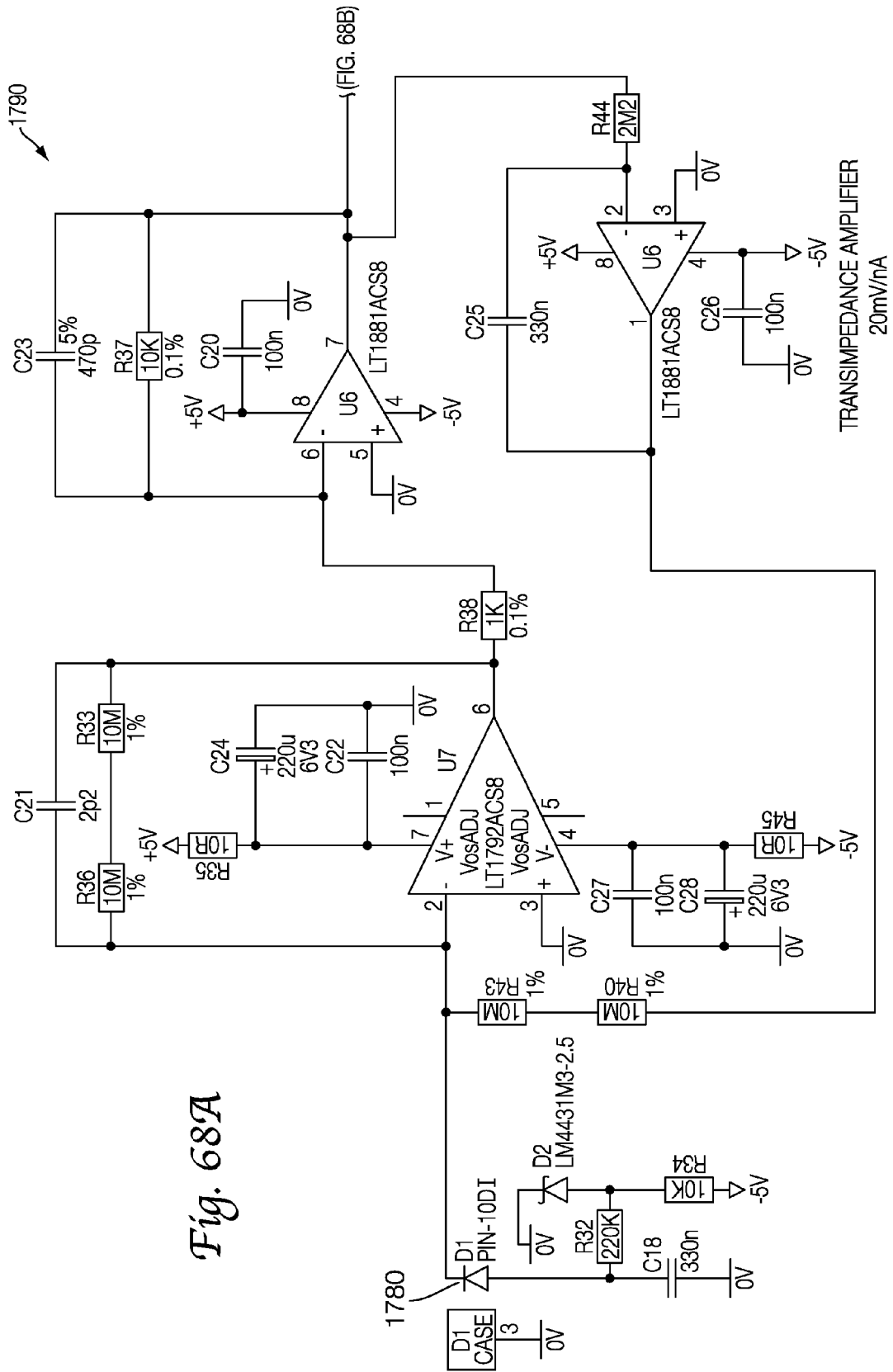

Referring to FIG. 68A, amplifiers U7 and U6 (pins 5-7) form the first two stages of amplification of the optical signal. Components C20, C22, C24, C26, C27, C28, R35, and R45 provide power supply bypassing/filtering to the amplifiers. C18, D2, R32, and R34 form a filtered-2.5V power supply that biases the anode of the photodiode 1780. Feedback resistors R33 and R36 convert electrical current from the photodiode 1780 into a voltage while C21 provides filtering for signals of frequency 3.6 KHz and higher. The voltage divider formed by R37 and R38 provide a voltage gain of 10 in the next pre-amplification stage while capacitor C23 provides additional low pass filtering.

Amplifier U6 (pins 1-3) creates a DC bias current that negates the electrical current from the photodiode 1780 that is attributed to background ambient light and other natural DC offsets in the circuit. The circuit forms an integrating amplifier that generates an electrical current that is fed back into the input of the initial pre-amplifier circuit (formed by U7). This results in an output signal at U7 and at U6, pin 7 that has a zero DC component, i.e., the signal is centered around 0V.

Microprocessor U5 (FIG. 68B) controls LED function (e.g., turns off the LED 1732 or modulates the LED 1732 at its intended operating frequency, 250 Hz for FAM and ROX, 350 Hz for TAM) and differential amplifier gain. Depending on its input signals (pins 6 and 7), microprocessor U5 controls the LED 1732 into an 'off' or 'modulated' state. The gain of the differential filter circuit U2, U3, U4 is adjustable within the range of plus or minus twelve depending on the phase relationship between the control signals to the LED 1732 and the analog switch SW1.

Figure 68B:
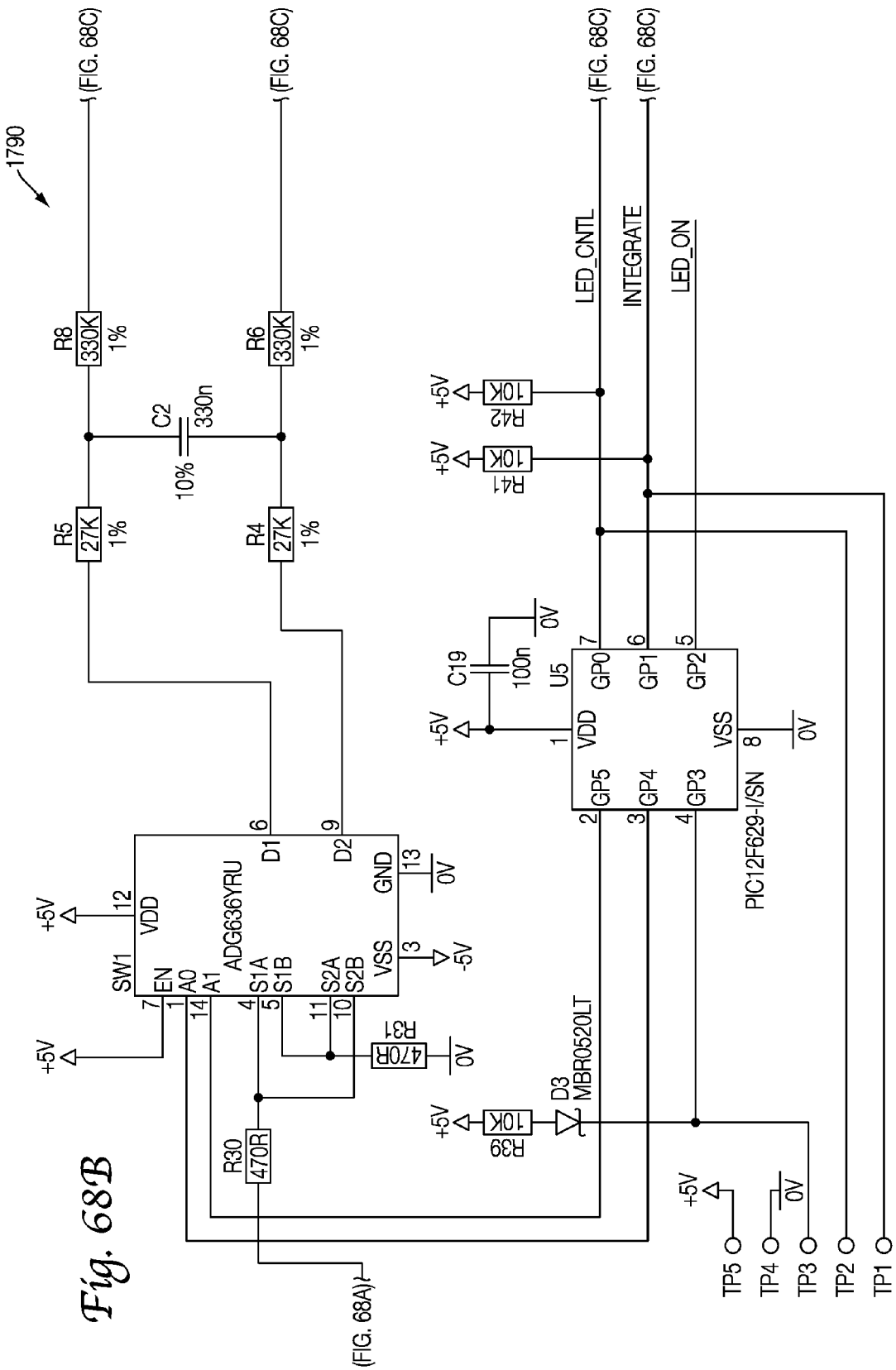
Figure 68D:
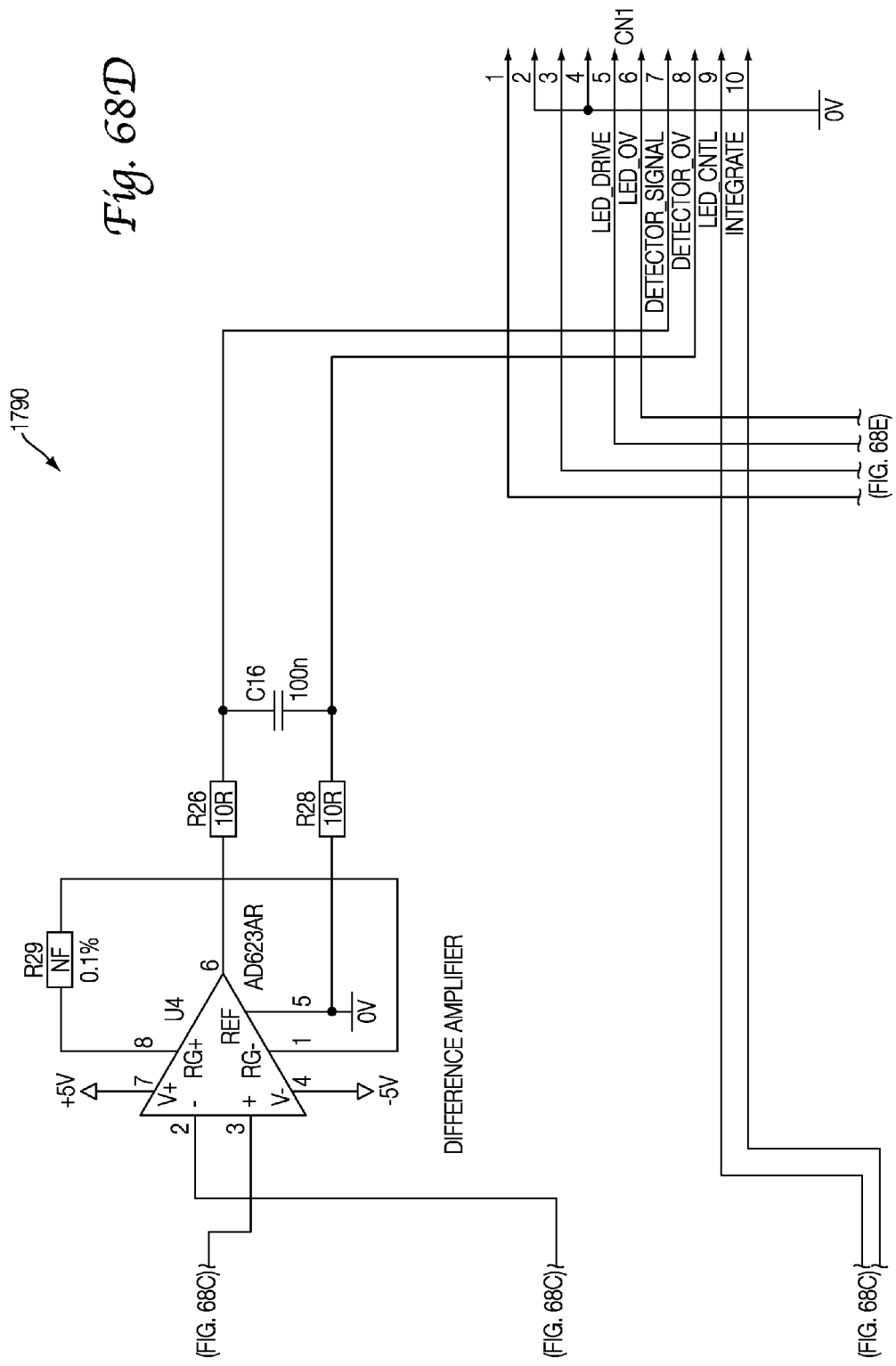
Figure 68E:
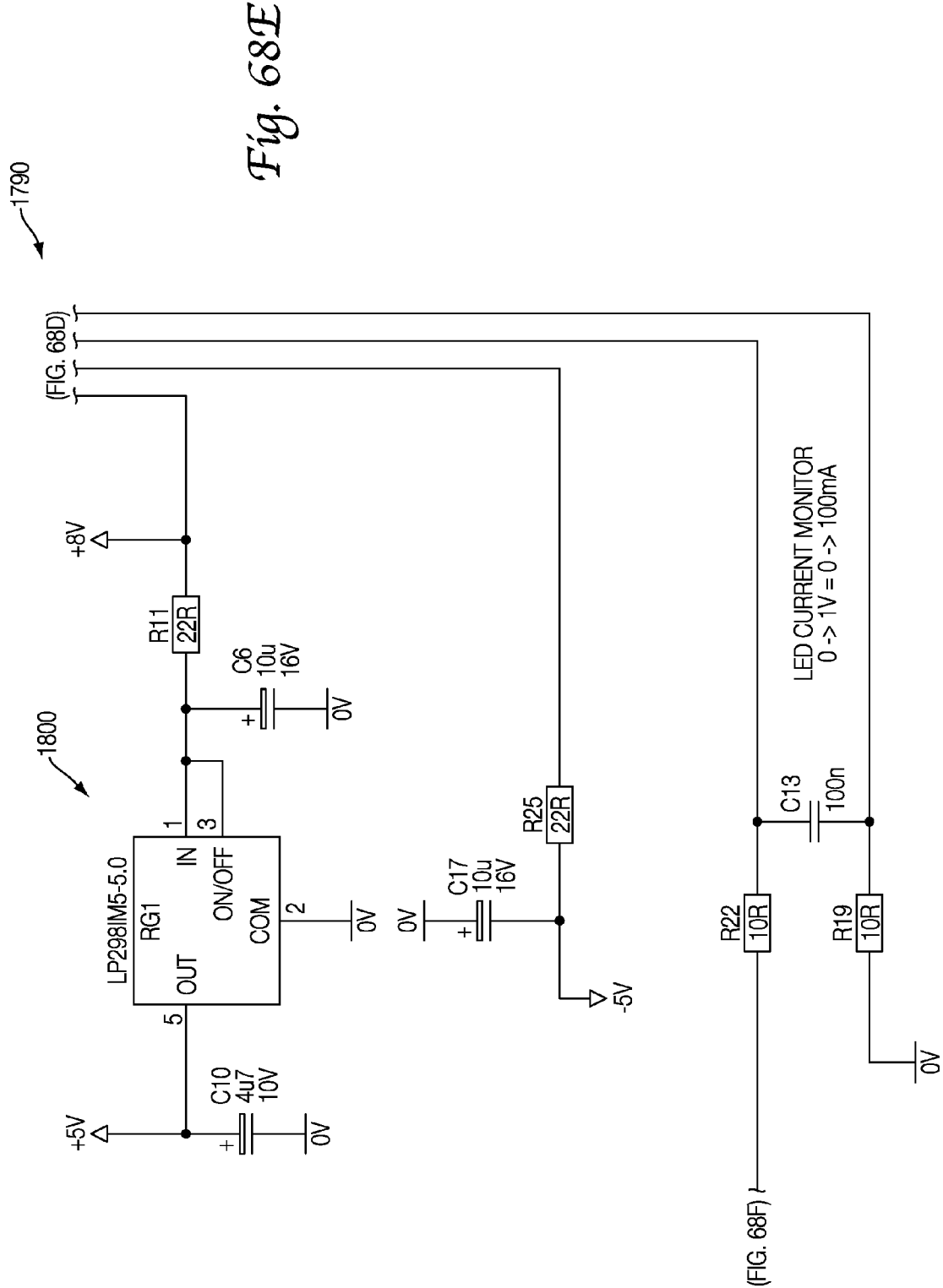
Figure 68F:
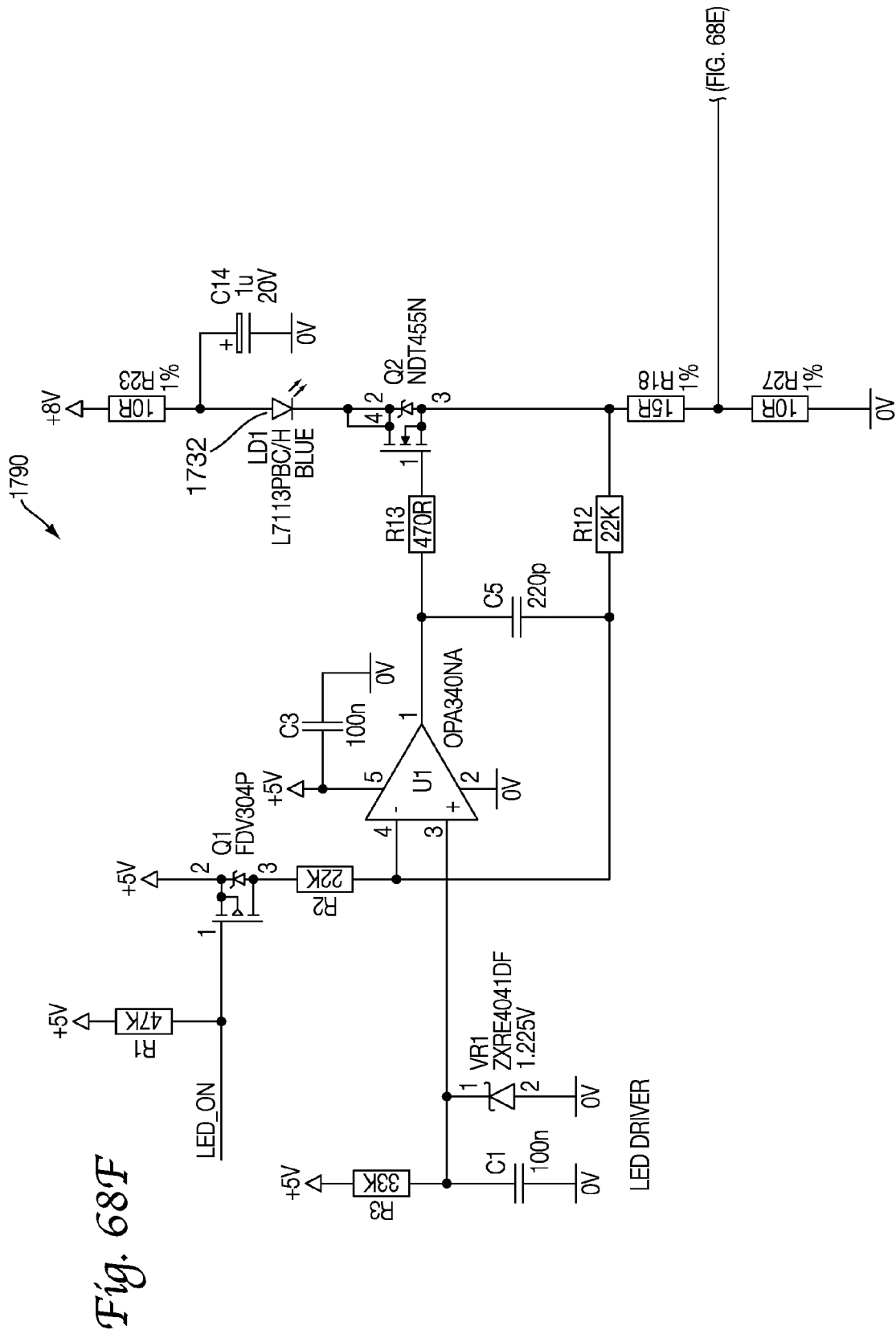
Figure 69:
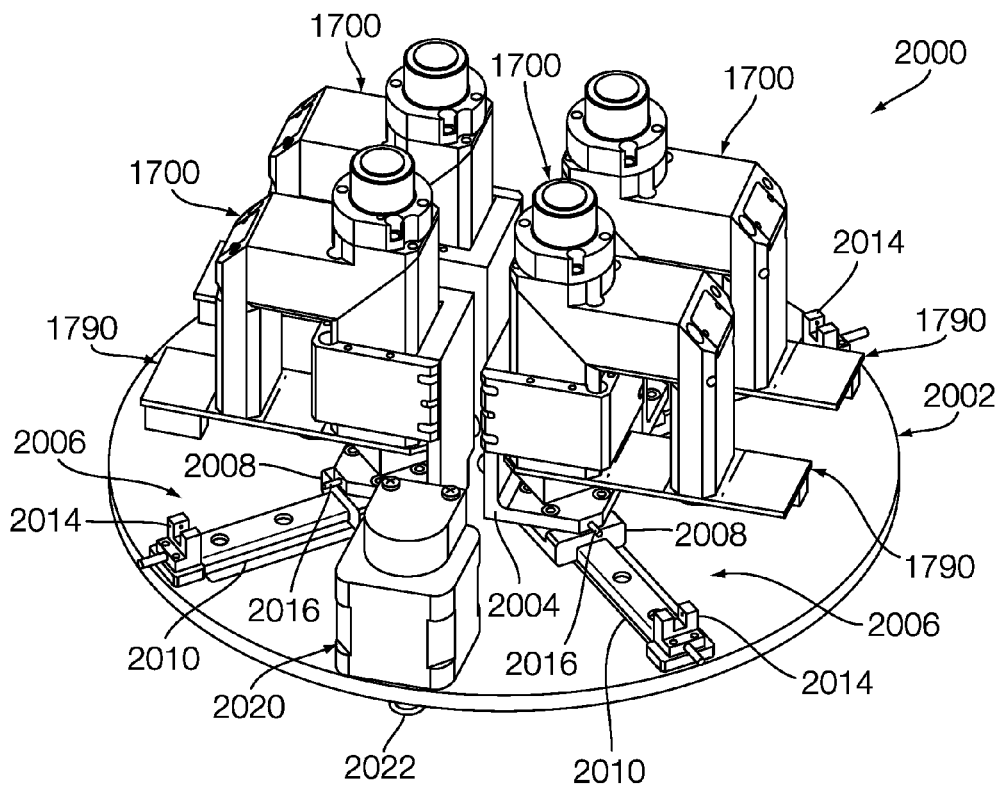
FIG. 69 is a perspective view showing the optical detector scanning assembly of a scanning real-time fluorometer.
Figure 70:
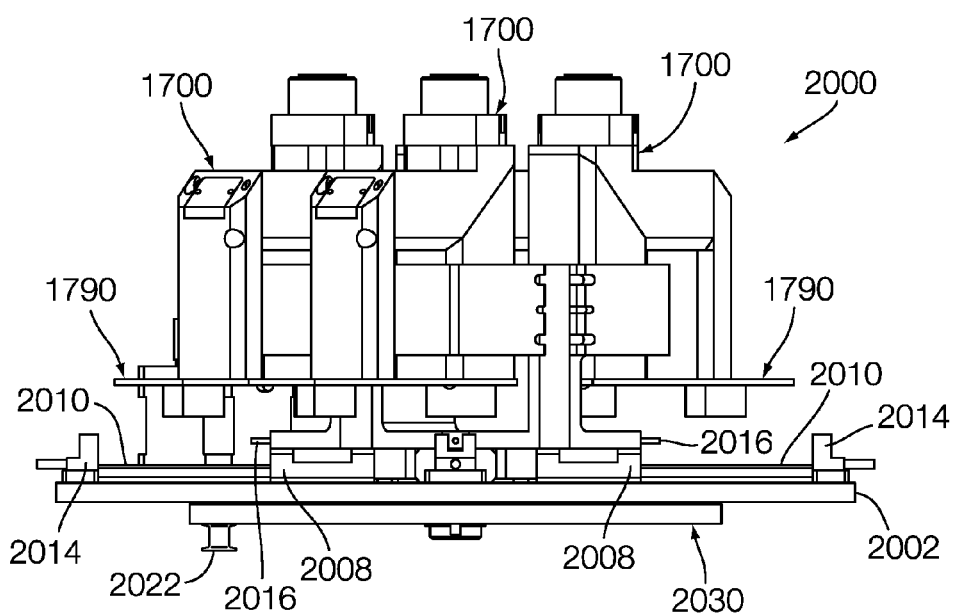
FIG. 70 is a side elevation of the detector scanning assembly.
Figure 71:
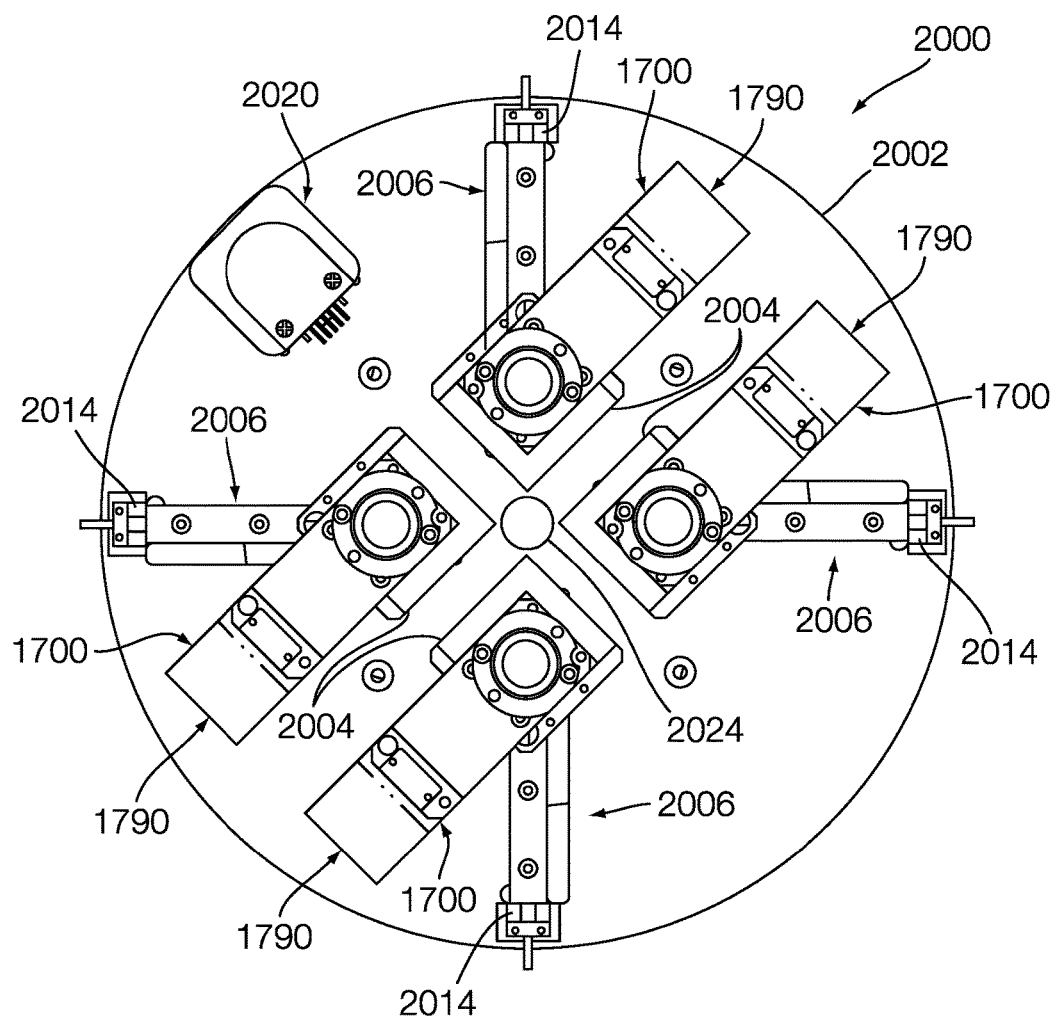
FIG. 71 is a top plan view of the detector scanning assembly.

Referring to FIG. 68F, components C1, R3, and VR1 form a reference voltage circuit, and these components, along with resistors R18 and R27, establish the LED current (when LED 1732 is turned on). Components R1, R2, and Q1 form the LED control circuit which, when the FET switch Q1 is turned on, the voltage at the input pin of the amplifier U1 is raised, forcing the amplifier's output to go to a low voltage, effectively turning off LED current switch Q2. If Q1 is not turned on, then U1 controls the voltage on the gate of the FET switch Q2 such that electrical current through the LED 1732 is controlled at the established set-point. LED modulation frequency and off/on control is controlled by the input 'LED_ON' from the microprocessor U5 described above (FIG. 68B).

Referring to FIG. 68B, the analog switch SW1 is used to 'invert' the input voltage to the differential filter that follows. The frequency at which the signal is inverted is set and controlled by the microprocessor U5. Depending on the setting of the inputs A0 and A1 of analog switch SW1, one set of switches (internal to the analog switch SW1) are turned on, passing the signal as wired through the device (either switches S1A and S2A are "on" or switches S1B and S2B are "on," connected through to outputs D1 and D2, respectively). In this circuit, the inputs to the analog switch SW1 are wired such that when the LED 1732 is turned on, the signal out of the pre-amplifier U6 (pins 5-7) is directed to the positive input of the differential filter U2 (pin 3) while ground is applied to the negative input of the differential filter U2 (pin 5). The output signal (after filtering) of the differential filter (U4) is roughly twelve times that amplitude. When the LED 1732 is turned off (while modulating), the output of the pre-amplifier circuit goes negative and with approximately the same amplitude as when the LED 1732 was turned on. The inputs to the differential filter now are wired the other way around, such that the negative signal out of the pre-amplifier U6 (pin 7) is directed to the negative input of the differential filter U2 (pin 5) while ground is applied to the positive input U2 (pin 3). Output signal (after filtering) is still approximately the same amplitude as with the LED on and the analog switch in the other position.

The differential amplifier/filter U2, U3, U4 provides minimal gain (12×) and provides multi-pole low pass filtering of the signal (cutoff at 10 Hz) while handling the signal differentially. This filter is used to attenuate any and all signals from the pre-amplifier that fall outside of a 10 Hz range around the operating frequency of the LED/analog switch, (240-260 Hz for FAM/ROX, 340-360 Hz for TAM). Attenuation of the electrical signal conducted by the photodiode 1780 increases rapidly as frequency deviates outside this range.

A final amplifier circuit (U4) functions as a difference amplifier with zero gain. Its function is to convert the voltage differential between the two signals out of the differential filter into a positive voltage referenced to circuit ground.

FIGS. 64 and 65 both show a top view of an RT incubator 608 and illustrate the positioning of optical detection modules 1700 mounted to the bottom of the RT incubator 608. In the embodiment illustrated in FIGS. 64 and 65, the RT incubator includes 15 optical detection modules 1700, 5 optical detection modules 1700 (one for each of the reaction tubes 162a-162e of the MTU 160) for each of three different dyes, namely FAM, TAMRA and ROX. Thus, on each of five radii corresponding to each of the five reaction tubes 162a-162e of the MTU 160, there are three optical detection modules 1700, one for each of the dyes. The optical detection modules 1700 are positioned at 24° increments around the RT incubator. During detection at one particular module 1700, it is possible that stray light from an adjacent reaction tube that is being excited at the same time can affect the emission detected at the module 1700. In addition, excitation light can scatter off a reaction tube 162 and excite adjacent reaction tubes 162. This condition is known as cross-talk. The optical detection modules are preferably positioned so as to maximize the distance between the detection windows of adjacent optical detection modules 1700, thereby minimizing cross-talk between adjacent optical detection modules 1700. Cross-talk can also be prevented by providing light isolating baffles (not shown) in the form of concentric circular walls positioned between adjacent reaction tubes 162 of the MTU 160.

Another method for reducing cross-talk between the emissions of adjacent reaction tubes and for subtracting background signals due to, for example, stray light, is by using phase-synchronous detection techniques. The excitation light is frequency modulated by applying a signal of known frequency to LED 1732. For the TAMRA dye, an excitation signal frequency of 350 Hz is used, and for the FAM and ROX dyes, an excitation signal frequency of 250 Hz is used. Accordingly, the resulting emission light will display a frequency that is governed by the frequency of the excitation light, and any emission signal having a frequency that is inconsistent with the frequency of the excitation light can be discarded as not resulting from the excitation light. Known phase-detector circuits can be used to output a voltage that is proportional to the phase difference between the excitation and emission signals.

As shown in FIG. 65, optical detection modules 1700 are preferably grouped according to the dye for which the module is intended. That is, modules 1-5 are intended for the FAM dye, modules 6-10 are intended for the TAMRA dye, and modules 11-15 are intended for the ROX dye. It has been discovered that cross-talk is actually worse between adjacent optical detection modules with excitation signals of different wavelengths than between adjacent optical detection modules with excitation signals of the same wavelength. Thus, grouping like-wavelength detectors together, as shown in FIG. 65, reduces cross-talk.

Also, to minimize the transmissions and reflections of stray light, the interior components of an RT incubator 608 are preferably black in color.

In a preferred embodiment, the optical detection modules 1700 mounted to the bottom floor 613 of the RT incubator 608, and disposed mostly below the datum plate 82 of the processing deck 200, are surrounded by a shield (known as Faraday shield, not shown) which blocks stray electromagnetic interference which can affect the optical detection modules.

FIGS. 64 and 65 show an RT incubator 608 with 15 optical detection modules 1700. Such an arrangement permits real-time scanning for a 5-reaction tube 162 MTU 160 and three dyes. If it becomes desirable to incorporate a fourth dye into the procedure, for example as described above for detecting amplification products associated with three different viruses and an internal control, it would be necessary, in this embodiment, to incorporate 20 optical detection modules into the RT incubator 608, which, as can be appreciated from FIG. 2 62 and 63, would be nearly impossible given space constraints and the size of the illustrated embodiment of the optical detection module 1700.

To avoid the need for 20 optical detection modules, i.e., 5 optical detection modules for each of the four individual dyes, a scanning real-time fluorometer can be used in which four optical detection modules, one for each dye, are mounted so as to be movable with respect to the RT incubator 608, so that each optical detection module can be selectively positioned beneath each of the five reaction tubes 162*a*-162*e* of the MTU 160. (The number of optical detection modules can be adjusted in the scanning real-time fluorometer based on the number of dyes to be detected.) A scanning fluorometer assembly for such a scanning real-time fluorometer is designated generally by reference number 2000 in FIGS. 69-72. In the scanning fluorometer assembly shown, four optical detection modules 1700 are mounted so as to be movable in a radial direction with respect to a fixed scanning disk 2002. Each optical detection module 1700 is mounted into an optical detection module mounting bracket 2004 which is carried on a translating assembly 2006 for effecting radial movement of the optical detection module 1700 with respect to the scanning disk 2002. The translating assembly 2006 comprising a sliding, linear bearing 2008 to which the mounting bracket 2004 is attached and a bearing track 2010 mounted to the scanning disk 2002 and along which the bearing 2008 is slidably translatable. A slotted optical sensor 2014 is secured to the scanning disk 2002 at the radially outward end of the bearing track 2010, and a projection 2016 extending from the bearing 2008 extends into the sensor 2014 when the optical detection module 1700 is at the furthest out radial position, thereby providing a "home" signal. Generally radial slots 2040 are formed in the scanning disk 2002 (see FIG. 72).

Figure 72:
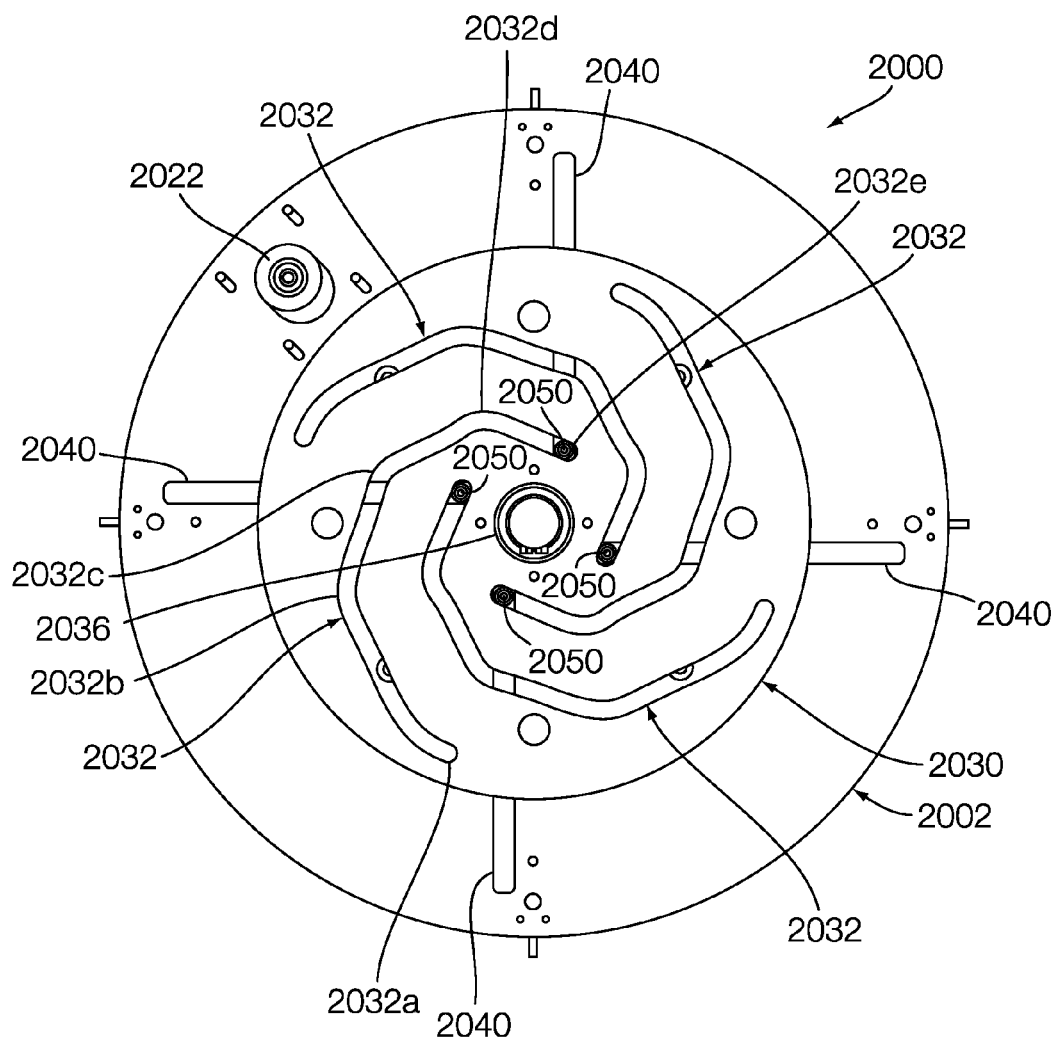
FIG. 72 is a bottom plan view of the detector scanning assembly.
Figure 73:
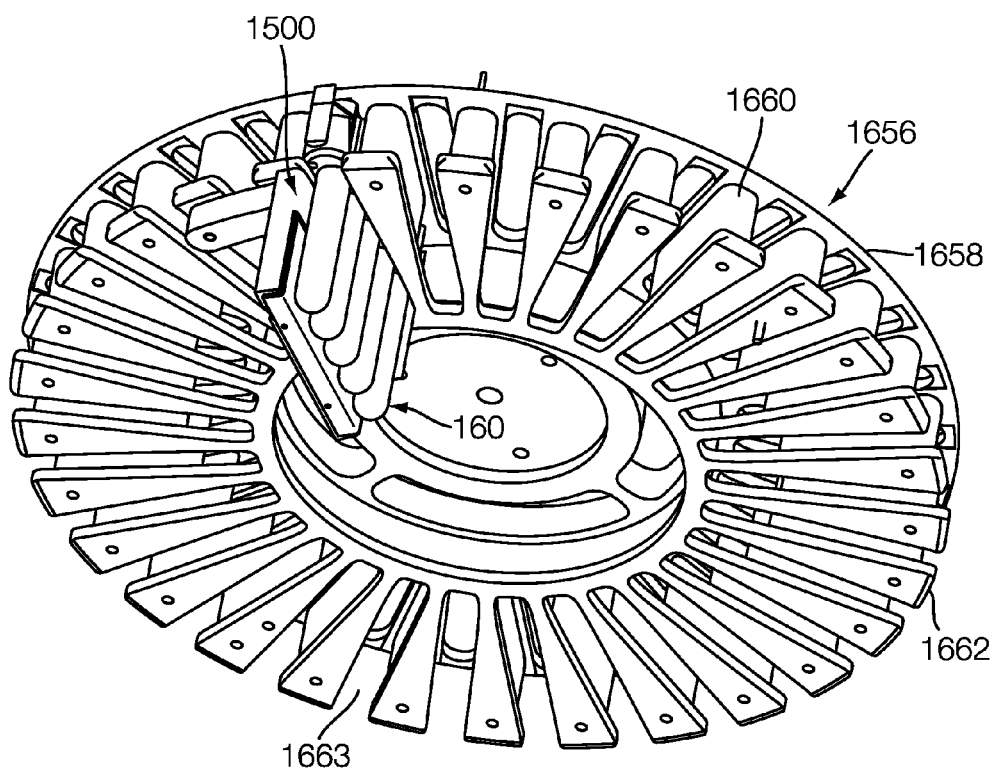
FIG. 73 is a perspective view of a portion of a carousel of the real-time fluorometer.

FIG. 72 shows the bottom plan view of the scanning fluorometer assembly 2000. A cam disk 2030 is arranged coaxially with and parallel to the scanning disk 2002 and is rotatable about shaft 2024 (see FIG. 71). The cam disk 2030 has four arcuate cam slots 2032 formed therein, one for each of the optical detection modules 1700. A pin 2050 extending down from the bearing 2008 of each translating assembly 2006 extends through the radial slot 2040 and into a respective one of the cam slots 2032.

A motor 2020 is mounted on top of the fixed scanning disk 2002. An output shaft 2022 of the motor is coupled to the cam disk 2030 (e.g., by a belt and pulley arrangement (not shown) or a meshing gear arrangement (not shown)). A preferred embodiment employs a pulley arrangement with a 6:1 ratio which achieves a speed of 50 in 0.25 seconds (i.e., 200/sec.). Rotation of the output shaft 2022 coupled to the cam disk 2030 causes rotation of the cam disk 2030. As the cam disk 2030 rotates, the engagement of each pin 2050 with a respective one of the cam slots 2032 formed in the cam disk 2030 causes radial, translating motion of a corresponding one of the bearings 2008 along its respective bearing track 2010, thereby causing radial translation of the corresponding module mounting bracket 2004 and optical detection module 1700. An encoder (not shown) on the motor monitors motor rotations, thereby allowing the position of the cam disc 2030 to be monitored. Alternatively, other position sensing devices, such as optical sensors, can be used to directly monitor the cam disk 2030 position.

Each cam slot 2032 includes positioning points 2032*a*, 2032*b*, 2032*c*, 2032*d*, and 2032*e*. (To minimize clutter, the positioning points 2032*a*, 2032*b*, 2032*c*, 2032*d*, and 2032*e* are labeled for only one of the cam slots 2032.) The positioning points 2032*a-e* position the optical detection modules 1700 during rotation of the cam disk 2030. When the pin 2050 associated with a particular optical detection module 1700 is at position 2032*a* the optical detection module 1700 is at the radial position furthest out from the center of disk 2002 for scanning the furthest out reaction tube 162*a* of the MTU 160. As the cam disk 2030 rotates and the pin 2050 associated with the optical detection module 1700 moves to point 2032*b*, the corresponding optical detection module will move radially inwardly by a distance corresponding to the distance to the next reaction tube 162*b* of the MTU 160. The optical detection module 1700 can then scan the reaction tube 162*b* at that position. Further rotation of the cam disk 2030 causes the pin 2050 associated with the module 1700 to move to position 2032*c*, thereby moving the module 1700 radially inwardly by a distance corresponding to the distance to reaction tube 162*c* of the MTU 160. The module 1700 can then scan reaction tube 162*c* at that position. Further rotation of the cam disk 2030 causes the pin 2050 associated with the module 1700 to translate radially inwardly by a distance corresponding to the distance to reaction tube 162*d*. The module 1700 can then scan reaction tube 162*d* at that position. Further rotation of the cam disk 2030 causes the pin 2050 associated with the module 1700 to translate inwardly by a distance corresponding to the distance to reaction tube 162e. The module 1700 can then scan the reaction tube 162e at that position. Accordingly, a single movable optical detection module 1700 can detect emissions from each of the reaction tubes 162a-e of each MTU 160.

Each optical detection module 1700 of the scanning fluorometer assembly 2000 extends up into the incubator housing of the RT incubator 608. Since the detectors 1700 move radially, elongated, radial openings (not shown) are formed in the floor 613 of the RT incubator 608 through which each optical detection module scans the MTUs 160 within the RT incubator. In one embodiment, a shutter mechanism (not shown) is positioned in each radial opening. The shutter mechanism has a movable opening through which the adapter pipe 1718 of each optical detection module 1700 extends. As the optical detection module 1700 translates radially, the opening of the shutter mechanism translates with it while the rest of the radial opening remains closed, thereby limiting heat loss and stray light through the radial opening.

As an alternative to the optical detection module described above, the optical detection module may be a multiple wavelength fluorometer, for example, a fluorometric microscope with a filter changer or a fluorometric microscope with multiple bandwidth filters and multiple bandwidth beam splitters.

The inventors have determined that the magnetic particles used for target capture in a preferred embodiment of the present invention can affect real-time detection of amplification products. Two particular interfering effects have been identified. First, magnetic particles can inhibit amplification by adsorption of oligonucleotides (e.g., amplification oligonucleotides and probes) and enzyme reagents (e.g., nucleic acid polymerases). In addition, the presence of magnetic particles (settled or in suspension) can result in the dissipation of the fluorescence, thereby blocking or partially blocking the amount of excitation light that reaches the detection dyes and the amount of light emitted from the reaction tubes 162 of the MTUs 160. This is known as the black cloud effect.

To minimize this effect, in one embodiment of the RT incubator 608 a magnetic divider 1500 is provided as shown in FIGS. 73, 74, 75, and 75A. In a preferred embodiment of the invention, the RT incubator 608 holds 15 MTUs 160 at a time, each spaced at 24° increments around the carousel. Assuming a 30-position carousel, such as carousel 1656, is used, this means that only every other MTU station 1663 holds an MTU 160 in the RT incubator 608. Thus, as shown in the figures, the magnetic divider 1500 can be positioned so as to span every other MTU station 1663 on the carousel 1656 (described above), thereby leaving only 15 of 30 stations available to receive an MTU 160. In alternative embodiments, magnet holders could be constructed to fit between each of the 30 stations or to be positioned adjacent every other station, thereby permitting the contents of every other MTU 160 in the RT incubator 608 to be processed in accordance with an alternative assay procedure. Such magnet holders may be formed from a ferrous sheet metal to which the magnets will adhere. A ferrous sheet metal material would also have the advantage of greatly reducing the magnetic field on the opposite side of the magnets.

Figure 74:
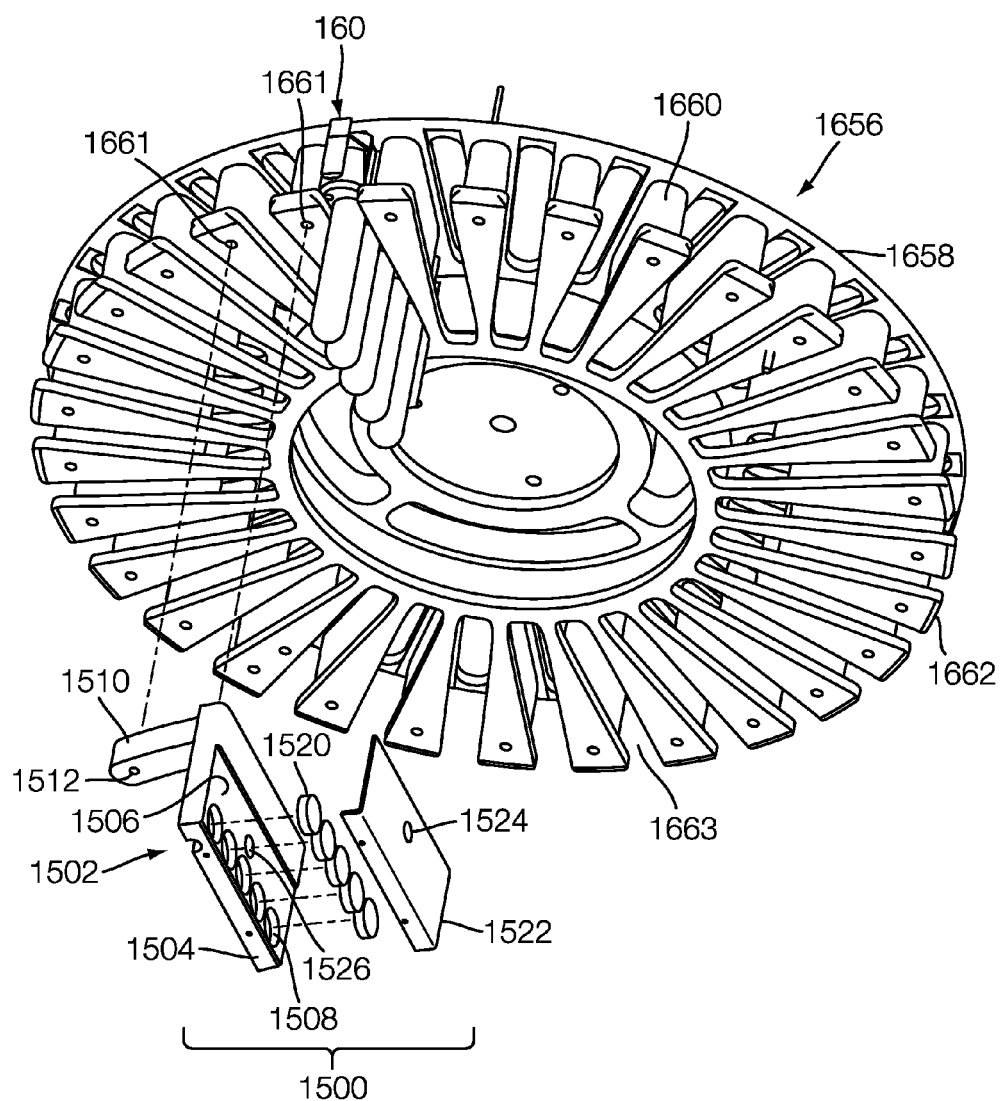
FIG. 74 is an exploded perspective view showing the carousel of the real-time fluorometer and a magnetic divider.
Figure 75:
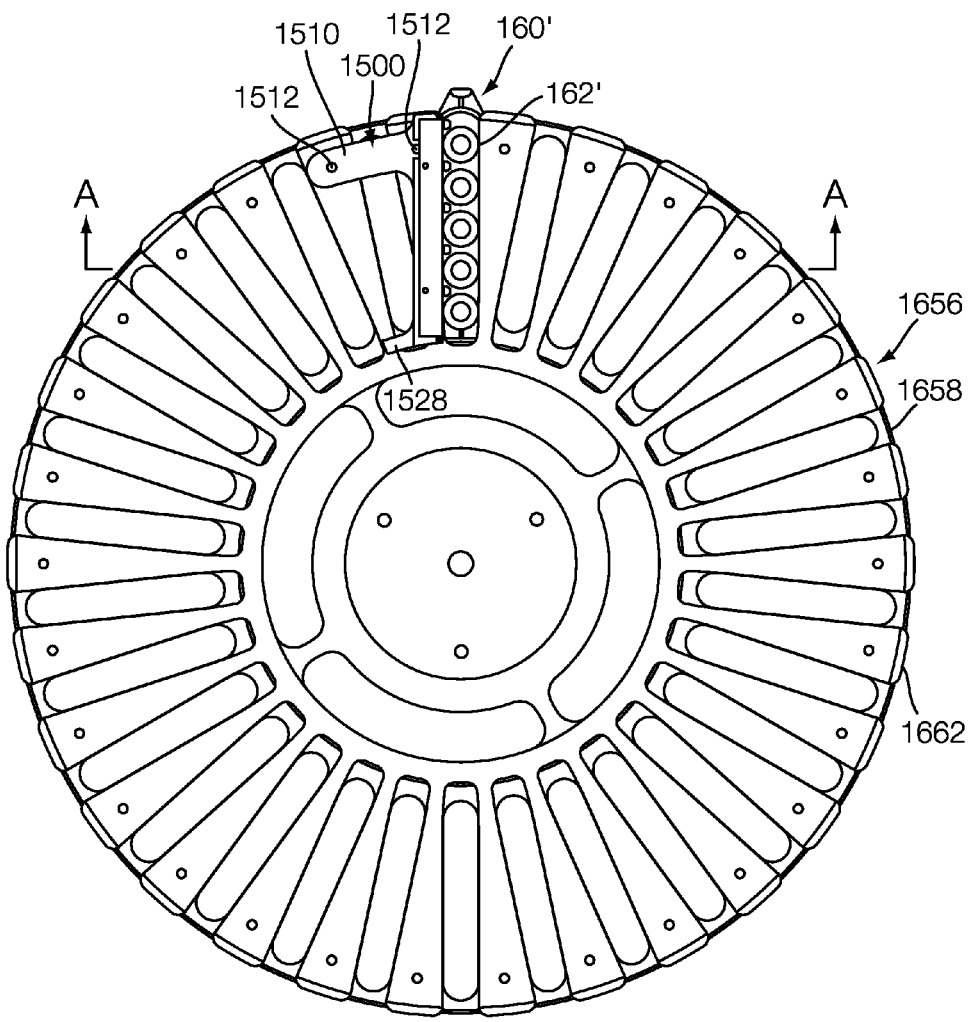
FIG. 75 is a bottom plan view of the carousel of the real-time fluorometer showing a single magnetic divider attached thereto.
Figure 75A:
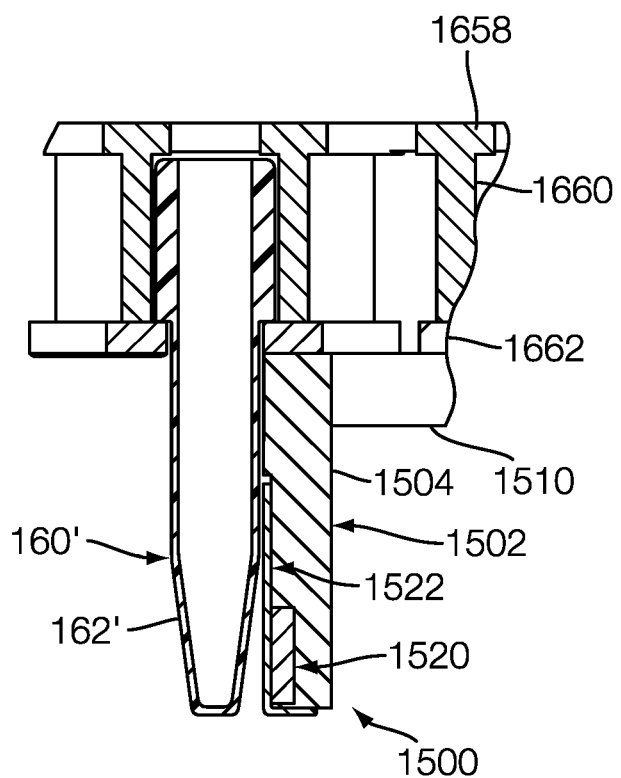
FIG. 75A is a partial cross-sectional view taken along the line A-A in FIG. 75.

As shown primarily in FIGS. 74 and 75A, which, for simplicity, show only a single magnetic divider 1500, the magnetic divider includes a magnet holder 1502 which comprises a magnet block 1504 and an attachment arm 1510. A rectangular recessed area 1506 is formed in the magnet block 1504, and openings 1508 are formed in the magnet block 1504 to receive like sized and shaped magnets 1520. In the illustrated embodiment, the openings 1508 are circular and the magnets 1520 are disc shaped. Currently preferred magnets are nickel plate coated neodymium-iron-boron discs measuring ½ inch (diameter) by inch (thickness) and having a Br max of 12,100 and a Bh max of MGOe (ForceField, Fort Collins, Colo.; Item No. 0022). The magnets 1520 are placed within the associated openings 1508 and are held within the block 1504 by means of a retainer plate 1522, which may be secured to the magnetic holder 1502 by means of a mechanical fastener, such as a screw or a bolt (not shown), passing through openings 1524 and 1526 formed in the retainer plate 1522 and the magnet block 1504, respectively.

The attachment arm 1510 extends from the magnet block 1504 and includes fastener holes 1512 which align with corresponding fastener holes 1661 formed in a lower plate 1662 and dividers 1660 of the carousel 1656. The magnetic dividers 1500 can be secured to the carousel 1656 by means of suitable mechanical fasteners, such as screws or bolts (not shown), extending through the fastener holes 1512 and 1661.

The magnetic dividers 1500 may also include an inboard arm 1528 (see FIG. 75). Inboard arm 1528 stabilizes the magnetic divider 1500 and provides an additional attachment point for attaching the magnetic divider 1500 to the carousel 1656.

As shown in FIGS. 75 and 75A, when an MTU 160' is placed into an MTU slot in the carousel 1656, each reaction tube 162' is positioned adjacent to one of the magnets 1520 carried in the magnetic divider 1500. The magnet 1520 will cause at least portion of the magnetic particles to be drawn toward the wall of the reaction tube 162' adjacent the magnet 1520, thereby leaving a substantially reduced concentration of magnetic particles in suspension within the remainder of the contents of the reaction tube 162' or settled on the bottom of the reaction tube 162'.

As noted above, the preferred material for the MTU 160 is polypropylene. Polypropylene has, however, been determined to autofluoresce under certain conditions. Accordingly, alternative MTU materials, such as acrylics, polystyrene, and cyclic olefins are contemplated. Also, as illustrated in FIGS. 75 and 75A by reaction tubes 162' of MTU 160', to concentrate the sample in the bottom of the individual reaction tubes 162' of the MTU 160—thereby facilitating more consistent excitation of and emission from the sample and to permit use of smaller reagent volumes—it is contemplated to use an MTU having reaction tubes with frustoconically shaped ends, instead of the rounded ends of the reaction tubes 162 of the MTU 160 shown, for example, in FIG. 74.

Figure 76A:
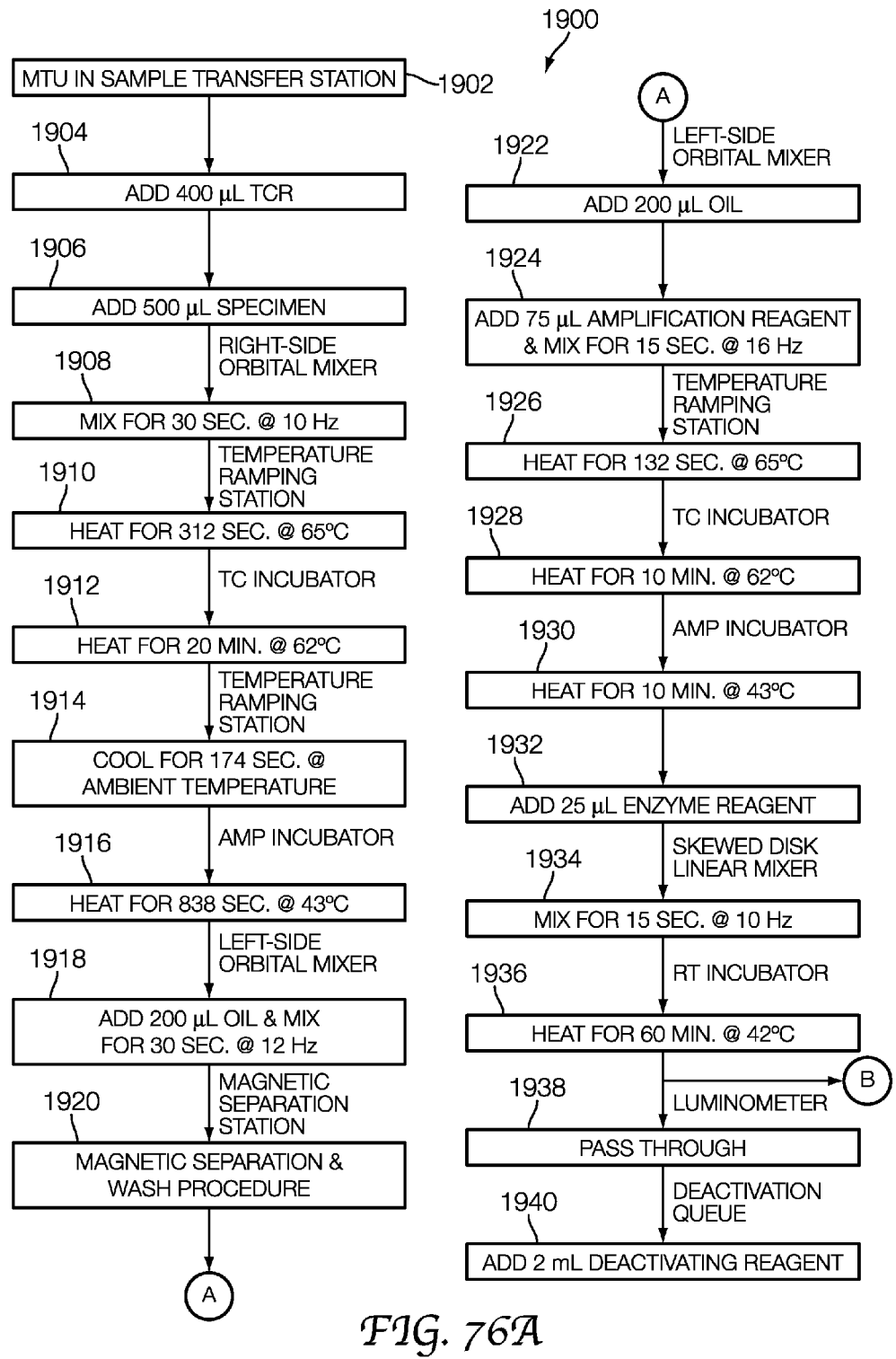
FIG. 76A is a flow chart showing the protocols of a preferred real-time amplification assay and a portion of a preferred end-point amplification assay which stops after exposure to amplification conditions, both assays being in accordance with the present invention.
Figure 76B:
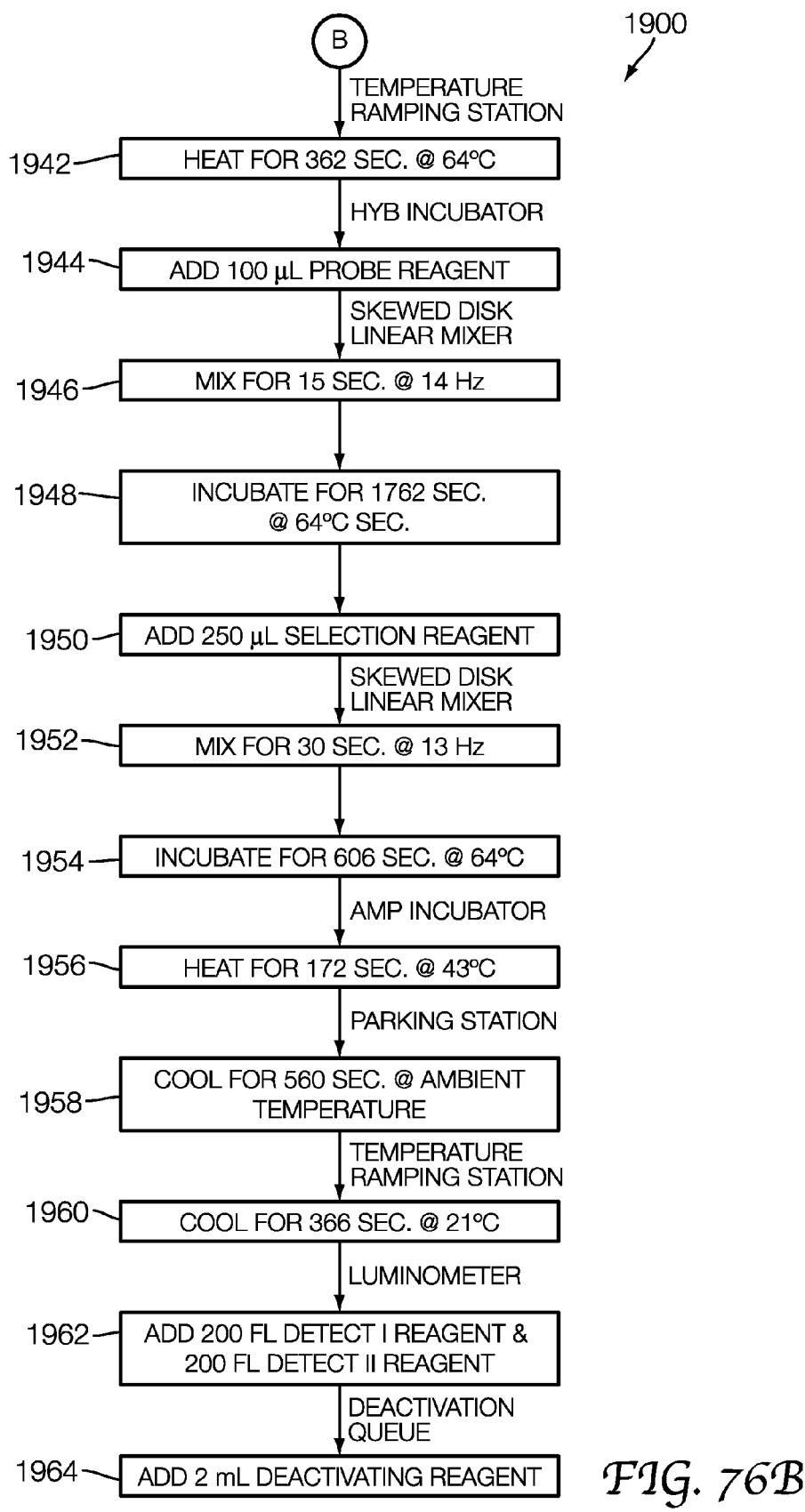
FIG. 76B is a flow chart showing the remainder of the protocol for the preferred end-point amplification assay of FIG. 76A following exposure to amplification conditions.

The process steps of real-time and end-point amplification assays performed in accordance with the present invention are illustrated in the flow chart shown in FIG. 76. (FIG. 76A shows the steps of a complete real-time TMA amplification assay and those of an end-point TMA amplification assay through amplification; FIG. 76B shows the steps of the end-point TMA amplification assay after exposing the contents of the reaction tubes 162 to amplification conditions.) The steps described represent exemplary TMA procedures only. Persons of ordinary skill will recognize that the steps described below may be varied or omitted or that other steps may be added or substituted in accordance with other real-time and end-point amplification assay procedures now known or yet to be developed. Reagent formulations for performing a host of amplification procedures are well known in the art and could be used in or readily adapted for use in the present invention. See, e.g., Kacian et al., U.S. Pat. No. 5,399,491; Becker et al., U.S. Patent Application Publication No. US 2006-0046265 A1; Linnen et al., Compositions and Methods for Detecting West Nile Virus, U.S. Patent Application No. US 2004-0259108 A1; Weisburg et al., "Compositions, Methods and Kits for Determining the Presence of *Trichomonas Vaginalis* in a Test Sample," U.S. Patent Application Publication No. US 2004-0235138 A1; and Linnen et al., "Compositions and Methods for Determining the Presence of SARS Coronavirus in a Sample," U.S. patent application Ser. No. 10/825,757, which enjoys common ownership herewith.

The process steps of the exemplary real-time and end-point TMA amplification assays begin with step 1902, in which an MTU 160 is moved to a pipetting position in the sample transfer station 250 below the sample preparation opening 252 provided in the jig plate 130. In step 1904, the sample pipette assembly 450 dispenses 400 µL of a target capture reagent ("TCR") into each reaction tube 162 of the MTU 160. The target capture reagent includes a capture probe, a detergent-containing lytic agent, such as lithium lauryl sulfate, for lysing cells and inhibiting the activity of RNAses present in the sample material, and about 40 µg Sera-Mag™ MG-CM Carboxylate Modified (Seradyn, Inc., Indianapolis, Ind.; Cat. No. 24152105-050250), 1 micron, super-paramagnetic particles having a covalently bound poly(dT)$_{14}$. The capture probe includes a 5' target binding region and a 3' region having a poly(dA)$_{30}$ tail for binding to the poly(dT)$_{14}$ bound to the magnetic particle. The target binding region of the capture probe is designed to bind to a region of the target nucleic acid distinct from the regions targeted by the primers and the detection probe.

In step 1906, the pipette assembly 450 dispenses 500 µL of sample into each of the reaction tubes. In step 1908, the right-side transport mechanism 500 moves the MTU 160 to the right-side orbital mixer 550 to mix the sample and the TCR, preferably at 10 Hz for 30 seconds. Note that the times given in FIG. 76 and the description thereof are desired times, and the actual times may, in practice, vary from the given desired times.

In step 1910, the right-side transport mechanism 500 moves the MTU 160 from the right-side orbital mixer 550 to one of the temperature ramping stations 700 located under the jig plate 130. The MTU 160 preferably resides in the temperature ramping station 700 at a temperature of 65° C. for 312 seconds. In step 1912, the right-side transport mechanism 500 moves the MTU 160 from the ramping station 700 to the TC incubator 600 where it resides at 62° C. for 20 minutes for hybridization of the capture probe to target nucleic acids which may have been extracted from the sample. (At this temperature, there will be no appreciable hybridization of the capture probe to the immobilized poly (dT)$_{14}$ oligonucleotide.) In step 1914, the left-side transport mechanism 502 moves the MTU 160 from the TC incubator to one of the temperature ramping stations 700 located on the left-side of the processing deck 200, where it is held for 174 seconds at ambient temperature. In step 1916, the left-side transport mechanism 502 moves the MTU 160 from the ramping station 700 to the AMP incubator 604, where the MTU resides at 43° C. for 838 seconds to allow for immobilized oligonucleotides associated with the magnetic particles to bind to the capture probes.

In step 1918, the left-side transport mechanism 502 moves the MTU 160 from the AMP incubator 604 to the left-side orbital mixer 552. The left-side orbital mixer 552 includes dispensers for dispensing, among other substances, oil into the MTU 160. In the left-side orbital mixer 552, 200 µL of silicone oil, a surface treating agent, are added to each reaction tube 162 of the MTU 160, and the MTU is mixed at 12 Hz for 30 seconds. In step 1920, the left-side transport mechanism 502 moves the MTU 160 from the left-side orbital mixer 552 to one of the magnetic separation stations 800 for the magnetic separation wash procedure described above.

An advantage of adding a surface treating agent, such as silicone oil, to the sample solution in step 1918 is that it reduces the amount of material that adheres to the inner surfaces of the reaction tubes 162 during the rinsing and aspiration steps of a magnetic separation wash procedure, thereby facilitating a more effective magnetic separation wash procedure. Although the MTUs 160 are preferably made of a hydrophobic material, such as polypropylene, small droplets of material, such as wash solution, may still form on the inner surfaces of the MTU reaction tubes 162 during the aspiration steps of a magnetic separation wash procedure. If not adequately removed from the reaction tubes 162 during the magnetic separation wash procedure, this residual material, which may contain nucleic acid amplification inhibitors, could affect assay results. In alternative approaches, the surface treating reagent could be added to the reaction tubes 162 and removed prior to adding TCR and sample or the surface treating agent could be added to the reaction tubes after TCR and sample have been aspirated from the reaction tubes, possibly with the wash solution, and then removed prior to adding amplification and enzyme reagents to the reaction tubes. The objective is to provide inner surfaces of the reaction tubes 162 with a coating of the surface treating agent. Inhibitors of amplification reactions are known in the art and depend on the sample source and amplification procedure to being used. Possible amplification inhibitors include the following: hemoglobin from blood samples; hemoglobin, nitrates, crystals and/or beta-human chorionic gonadotropin from urine samples; nucleases; proteases; anionic detergents such as sodium dodecyl sulfate (SDS) and lithium lauryl sulfate (LLS); and EDTA, which is an anticoagulant and fixative of some specimens that binds divalent cations like magnesium, which, as noted above, is a cofactor used in nucleic acid-based amplification reactions. See, e.g., Mahony et al., J. Clin. Microbiol., 36(11):3122-2126 (1998); Al-Soud, J. Clin. Microbiol., 39(2):485-493 (2001); and Kacian et al., "Method for Suppressing Inhibition of Enzyme-Mediated Reactions By Ionic Detergents Using High Concentration of Non-Ionic Detergent," U.S. Pat. No. 5,846,701.

In step 1922, the left-side transport mechanism 502 moves the MTU 160 from the magnetic separation station 800 back to the left-side orbital mixer 552 and 200 µL of silicone oil are added to each reaction tube 162 of the MTU 160 to prevent evaporation and splashing of the fluid contents during subsequent manipulations. In step 1924, the reagent pipette assembly 470 dispenses 75 µL of an amplification reagent into each reaction tube 162 of the MTU 160 disposed within the left-side orbital mixer 552. For the exemplary TMA reactions, the amplification reagents contain an antisense promoter-primer having a 3' target binding region and a 5' promoter sequence recognized by an RNA polymerase, a sense primer that binds to an extension product formed with the promoter-primer, nucleoside triphosphates (i.e., dATP, dCTP, dGTP, dTTP, ATP, CTP, GTP and UTP), and cofactors sufficient to perform a TMA reaction. For the real-time TMA amplification assay, the amplification reagent also contains a strand displacement, molecular torch probes having interacting label pairs (e.g., interacting fluorescent and quencher moieties joined to the 5' and 3' ends thereof by conventional means) and a target specific region capable of detectably hybridizing to amplification products as the amplification is occurring and, preferably, not to any non-target nucleic acids which may be present in the reaction tubes 162. See Kacian et al., U.S. Pat. No. 5,399,491; Becker et al., "Single-Primer Nucleic Acid Amplification," U.S. Patent Application Publication No. US 2006-0046265 A1 (discloses an alternative TMA-based amplification assay in which an antisense primer and a sense promoter oligonucleotide blocked at its 3' end are employed to minimize side-product formation); and Becker et al., U.S. Pat. No. 6,361,945. The MTU 160 is then mixed for 15 seconds at 16 Hz.

In step 1926, the left-side transport mechanism 502 moves the MTU 160 from the left-side orbital mixer 552 to one of the temperature ramping stations 700 located on the left-side of the processing deck 200. The MTU 160 is then incubated at 65° C. for 132 seconds. In step 1928, the left-side transport mechanism 502 moves the MTU 160 from the temperature ramping station 700 to the TC incubator 600, where it is incubated for 10 minutes at 62° C. for binding of the promoter-primer to a target nucleic acid. The preferred promoter-primer in this particular TMA example has a promoter sequence recognized by a T7 RNA polymerase. In step 1930, the left-side transport mechanism 502 moves the MTU 160 from the TC incubator 600 to the AMP incubator 604, where the MTU 160 contents are incubated at 43° C. for 10 minutes to stabilize the MTU contents.

In step 1932, the reagent pipette assembly 470 adds 25 µL of an enzyme reagent held at 20° C. from the reagent cooling bay 900 to each reaction tube 162 of the MTU 160 located in the AMP incubator 604. (By maintaining the temperature of the contents of each reaction tube 162 at a temperature slightly higher than the amplification temperature, the heat-sensitive enzymes can be maintained at a cool temperature prior to initiating amplification.) The enzyme reagent of this example contains a reverse transcriptase and a T7 RNA polymerase for performing TMA, a transcription-based amplification procedure. In step 1934, the linear mixer 634 within the AMP incubator 604 mixes the MTU 160 to which the enzyme reagent has been added for 15 seconds at 10 Hz, and the temperature of the contents of each reaction tube 162 drops to about 42° C. In step 1936 the left-side transport mechanism 502 moves the MTU 160 from the AMP incubator 604 to the RT incubator 608. The MTU 160 is maintained in the RT incubator 608 at 42° C. for 60 minutes to permit amplification of target sequences and, for real-time amplifications, readings are taken at the prescribed frequency to detect hybridization of the probe to amplification product during the amplification process. Since MTUs 160 are being processed in a continual manner through the instrument 50 (typically, a new MTU begins the assay process every 165 seconds), MTUs are continually being added to and removed from (typically every 165 seconds) the RT incubator 608. In step 1938, after the last reading has been taken, the right-side transport mechanism 500 moves the MTU 160 from the RT incubator 608 to the luminometer 1360. In step 1940, the MTU 160 passes from the luminometer 1360 to the deactivation queue 750. Once in the deactivation queue 750, 2 mL of a bleach-based agent are provided to each of the reaction tubes 162 to deactivate nucleic acid (i.e., alter the nucleic acid such that it is non-amplifiable) present in the reaction tubes. See, e.g., Dattagupta et al., U.S. Pat. No. 5,612,200, and Nelson et al., U.S. Patent Application Publication No. US 2005-0202491 A1.

Following step 1936, an MTU 160 having contents being processed in accordance with the exemplary end-point TMA amplification assay proceeds as shown in FIG. 76B. In step 1942 of this process, the left-side transport mechanism 502 transfers the MTU 160 from the RT incubator 608 to a temperature ramping station 700 on the left-side of the processing deck 200, where it is heated at 64° C. for 362 seconds. Alternatively, the MTU 160 is moved from the RT incubator 608 to a designated region of the HYB incubator 606 for temperature ramping. In step 1944, the left-side transport mechanism 502 moves the MTU 160 from the temperature ramping station 700 to the HYB incubator 606, where 100 µL of probe reagent is added to each reaction tube 162. The probe reagent contains a sufficient amount of a probe for detectably binding to an amplification product of the target nucleic acid and, preferably, not to any non-target nucleic acids which may be present in the reaction tubes 162. For the exemplary end-point TMA embodiment, the probe is synthesized to include a non-nucleotide linker which is used for labeling the probe with a chemiluminescent acridinium ester. See Arnold et al., U.S. Pat. Nos. 5,185,439 and 6,031,091. In step 1946, the MTU 160 is positioned within the HYB incubator 606 adjacent the skewed disk linear mixer 634, which is employed to mix the contents of the MTU for 15 seconds at 14 Hz. In step 1948, the contents of the MTU 160 are incubated at 64° C. for 1762 seconds.

For detection, the contents of each reaction tube 162 of the MTU 160 are first provided with 250 µL of a selection reagent in step 1950. As discussed above, the selection reagent in the HPA assay contains an alkaline reagent that specifically hydrolyzes acridinium ester labels associated with unhybridized probe, while acridinium ester labels associated hybridized probe are not hydrolyzed under these conditions and can chemiluminesce in a detectable manner under the conditions described below, thereby permitting the user to distinguish between bound probe and probe free in solution. See Arnold et al., U.S. Pat. No. 5,639,604. After adding the selection reagent to the reaction tubes 162, the MTU 160 is positioned adjacent the skewed disk linear mixer 634 and the contents of the reaction tubes are mixed for 30 seconds at 13 Hz. In step 1954, the contents of the reactions tubes 162 are incubated for 606 seconds at 64° C. to facilitate the selection process.

In step 1956, the left-side transport mechanism 502 transfers the MTU 160 from the HYB incubator 606 to the AMP incubator 604 to cool the contents of the reaction tubes 162 at 43° C. for 172 seconds. Dropping the temperature of the contents of the reaction tubes 162 below 50° C. will generally arrest the activity of the selection reagent, therefore it is important to cool the contents of the reaction tubes of each MTU 160 at substantially the same rate so that the final signal values from the various reaction tubes are comparable. In step 1958, the left-side transport mechanism 502 moves the MTU 160 from the AMP incubator 604 to the RT incubator 608, after which the right-side transport mechanism 500 moves the MTU 160 from the RT incubator 608 to a parking station 210 on the right-side of the processing deck 200, where the contents of the reaction tubes 162 are further cooled at ambient temperature for 560 seconds. In step 1960, the MTU 160 is transferred to a temperature ramping station 700 on the right-side of the processing deck 200 to cool the contents of the reaction tubes 162 at 21° C. for 366 seconds. In an HPA multiplex assay involving multiple chemiluminescent labels, it is preferable to keep the temperature of the contents of the reaction tubes 162 below 29° C. so that the light-off characteristics of the labels are distinguishable. See, e.g., Nelson et al., "Compositions for the Simultaneous Detection and Quantitation of Multiple Specific Nucleic Acid Sequences," U.S. Pat. No. 5,756,709.

In step 1962, the right-side transport mechanism 500 moves the MTU 160 from the ramping station 700 to the luminometer 1360, where each reaction tube 162 receives 2004 of the Detect I reagent followed, by about a 2 second delay, 200 μL of the Detect II reagent. The velocity at which the Detect I and II reagents are injected to the reaction tubes 162 is forceful enough to mix the contents of the reaction tubes without agitation, and the delivery lines (not shown) are primed so that the flow of reagents is uninterrupted by bubbles or air gaps. The preferred top velocity for injecting the Detect I and II reagents into the reaction tubes 162 is 1000 μL/sec. As discussed above, the Detect I and II reagents combine to form a basic hydrogen peroxide solution that enhances the chemiluminescence of those acridinium ester labels which have not been hydrolyzed in the selection process. These reagents are sold as the GEN-PROBE® Detection Reagent Kit (Gen-Probe; Cat. No. 1791).

In step 1964, the MTU 160 passes from the luminometer 1360 to the deactivation queue 750. In the deactivation queue 750, 2 mL of a bleach-based agent are provided to each of the reaction tubes 162 to deactivate nucleic acid present in the reaction tubes. See, e.g., Dattagupta et al., U.S. Pat. No. 5,612,200, and Nelson et al., U.S. Patent Application Publication No. US 2005-0202491 A1.

Fluorescence measurements are preferably made at a rate of one measurement for each of the three or four spectral bands (i.e., for each target dye) per reaction tube 162 every 30 seconds, and thus the carousel 1656 must rotate once every 30 seconds. In a preferred embodiment, there are 15 MTUs 160 carried on the carrousel 1656 of the RT incubator 608, each separated by 24. To permit a read at each of the 15 MTU stations 1663 during the rotation, each read must be completed in 2 second or less. Ideally, the reads are completed in less than two seconds, and each rotation is completed in less than 30 seconds to afford time to place new MTUs 160 into the RT incubator 608 as completed MTUs are being removed from the RT incubator 608, while still maintaining the desired read rate of one measurement for each dye every 30 seconds.

Figure 78:
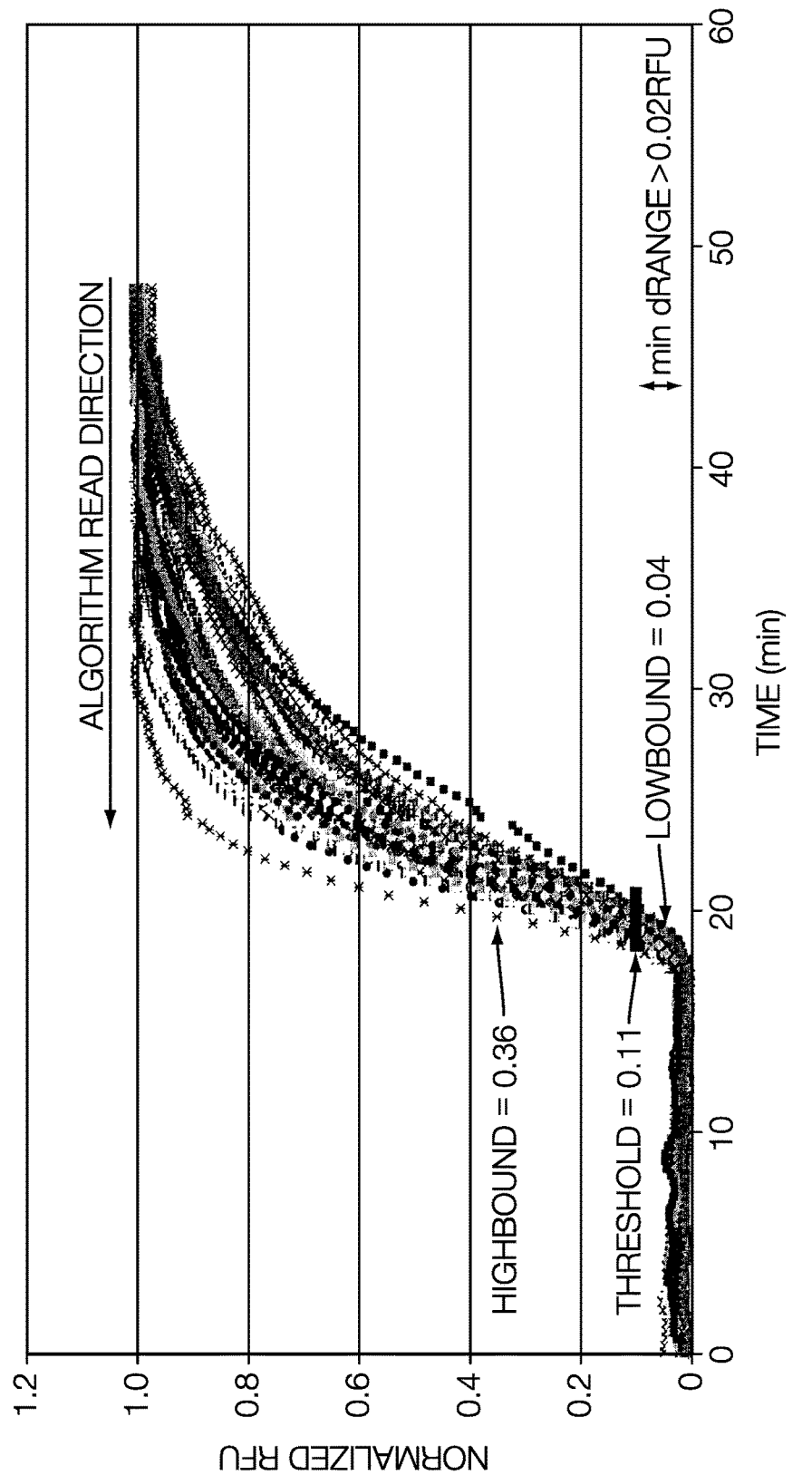
FIG. 78 is a time plot of real-time fluorometer data.

Once the data has been collected by measuring fluorometric emissions from each reaction tube 162 at prescribed intervals for a prescribed period of time, the data is processed to determine the concentration of a particular analyte (e.g., target nucleic acid) in the sample. The measured data, that is, the measure signal, will be referred to in terms of a Relative Fluorescent Unit ("RFU"), which is the signal generated by the printed circuit board 1790 of the optical detection unit 1700 based on the amount of emission fluorescence focused onto the photo diode 1780. Each data point, measured at a given time interval, is RFU(t). Plots of RFU(t) for a variety of data sets, known as "growth curves" are shown in FIG. 78. In general, each RFU(t) plot is generally sigmoidal in shape, characterized by an initial, flat portion (known as the "static level" or "baseline phase") at or near a minimum level, followed by an abrupt and relatively steeply sloped portion (known as the "growth phase"), and ending with a generally flat portion at or near a maximum level (known as the "plateau phase").

As used herein, a "growth curve" refers to the characteristic pattern of appearance of a synthetic product, such as an amplicon, in a reaction as a function of time or cycle number. A growth curve is conveniently represented as a two-dimensional plot of time (x-axis) against some indicator of product amount, such as a fluorescence measurement—RFU (y-axis). Some, but not all, growth curves have a sigmoid-shape. The "baseline phase" of a growth curve refers to the initial phase of the curve wherein the amount of product (such as an amplicon) increases at a substantially constant rate, this rate being less than the rate of increase characteristic of the growth phase (which may have a log-linear profile) of the growth curve. The baseline phase of a growth curve typically has a very shallow slope, frequently approximating zero. The "growth phase" of a growth curve refers to the portion of the curve wherein the measurable product substantially increases with time. Transition from the baseline phase into the growth phase in a typical nucleic acid amplification reaction is characterized by the appearance of amplicon at a rate that increases with time. Transition from the growth phase to the plateau phase of the growth curve begins at an inflection point where the rate of amplicon appearance begins to decrease. The "plateau phase" refers to the final phase of the curve. In the plateau phase, the rate of measurable product formation is substantially lower than the rate of amplicon production in the log-linear growth phase, and may even approach zero.

Figure 77:
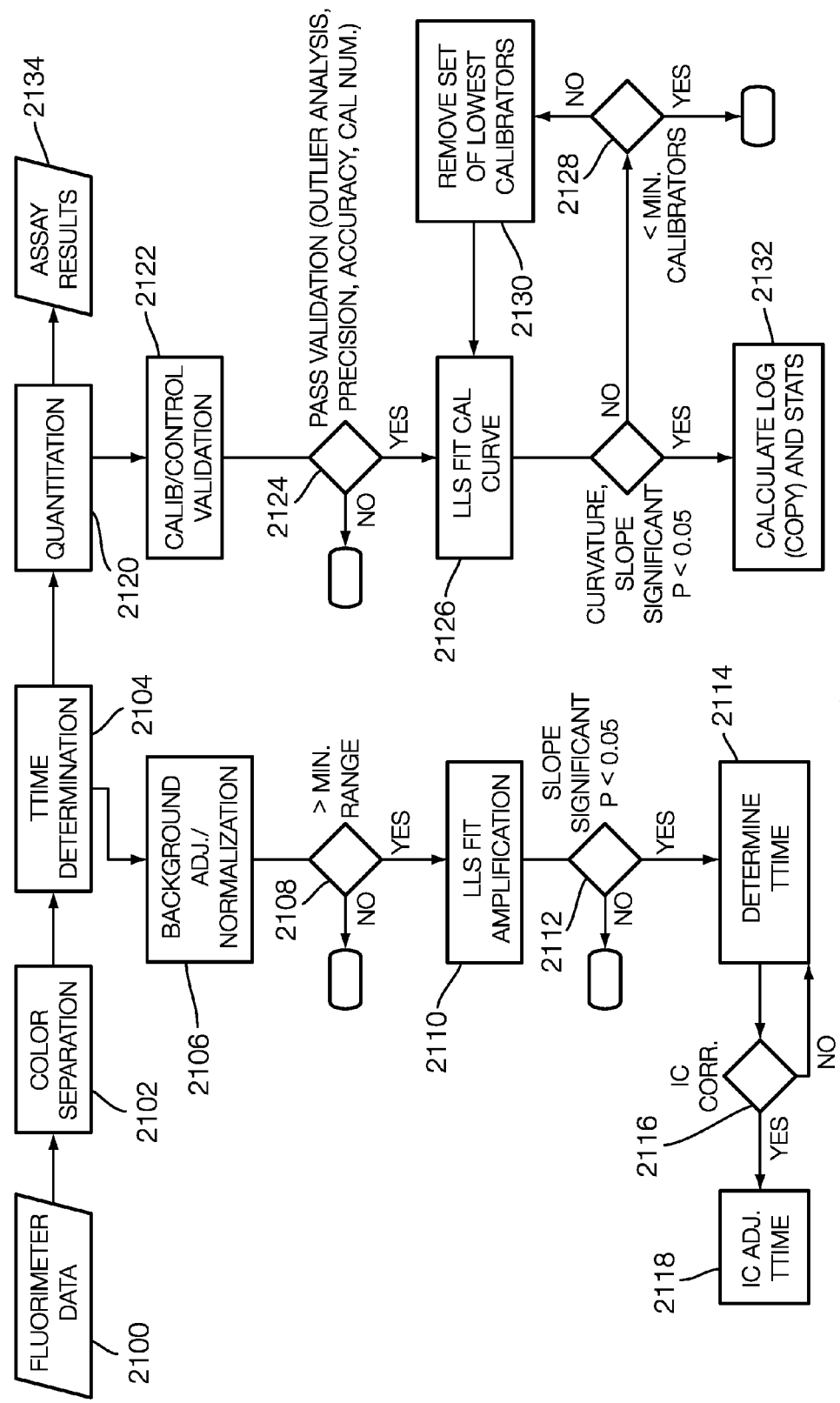
FIG. 77 is a flow chart showing an analyte quantification process.

A process for calculating an analyte concentration is shown by means of a flow chart in FIG. 77. The data RFU(t) from the optical detection module 1700 is input as represented at box 2100. At step 2102, the data RFU(t) goes through a color separation procedure. As can be appreciated from FIG. 67, there can be considerable overlap in the emission spectra of different dyes, especially spectrally adjacent dyes. Accordingly, the RFU(t) data obtained from a particular reaction tube 162 may comprise emission data corresponding to the analyte of interest (i.e., from the dye joined to the probe that binds to the analyte of interest) as well as emission data from one or more different dyes corresponding to different targets. To separate that portion of the RFU(t) signal that is not due to the analyte of interest, standard mathematical techniques, such as deconvolving the different signals obtained by the different, dye-specific optical detection modules 1700, can be employed. Deconvolving is a well known technique in which it is assumed that the signal measured by each optical detection module can be represented as a mathematical function of the emission from each of the dyes present in the sample.

For example, assuming that measurements are made with four optical detection modules:

$$RFU_1(t) = k_1 RFU_A(t) + k_2 RFU_B(t) + k_3 RFU_C(t) + k_4 RFU_D(t)$$

$$RFU_2(t) = k_5 RFU_A(t) + k_6 RFU_B(t) + k_7 RFU_C(t) + k_8 RFU_D(t)$$

$$RFU_3(t) = k_9 RFU_A(t) + k_{10} RFU_B(t) + k_{11} RFU_C(t) + k_{12} RFU_D(t)$$

$$RFU_4(t) = k_{13} RFU_A(t) + k_{14} RFU_B(t) + k_{15} RFU_C(t) + k_{16} RFU_D(t)$$

where:
$RFU_1(t)$=signal measured at optical detection module #1;
$RFU_2(t)$=signal measured at optical detection module #2;
$RFU_3(t)$=signal measured at optical detection module #3;
$RFU_4(t)$=signal measured at optical detection module #4.
$RFU_A(t)$, $RFU_B(t)$, $RFU_C(t)$, $RFU_D(t)$=portion of the emission signal due to each of dyes A, B, C, D; and
$k_1$-$k_{16}$=constants.

The functions corresponding to the signals for all the optical detection modules are placed in a matrix, and a matrix inversion is performed to derive, for each dye, a mathematical representation of the signal due to that dye as a function of the signals from each of the optical detection modules:

$$RFU_A(t)=f_1(RFU_1(t),RFU_2(t),RFU_3(t),RFU_4(t))$$

$$RFU_B(t)=f_2(RFU_1(t),RFU_2(t),RFU_3(t),RFU_4(t))$$

$$RFU_C(t)=f_3(RFU_1(t),RFU_2(t),RFU_3(t),RFU_4(t))$$

$$RFU_D(t)=f_4(RFU_1(t),RFU_2(t),RFU_3(t),RFU_4(t)).$$

From color separation 2102, the data RFU(t) goes to threshold time determination, which begins at 2104. Threshold time, or T-time, (also known as time of emergence) refers to the time at which the data RFU(t), normalized as discussed below, reaches a predefined threshold value. Using calibration curves, as will be described in more detail below, the T-time determined for a particular sample can be correlated with an analyte concentration, thereby indicating the analyte concentration for the sample. In general, the higher the concentration of the analyte of interest, the sooner the T-time.

The first step of the T-time determination procedure is background adjustment and normalization of the data, as represented at box 2106. Background adjustment is performed to subtract that portion of the signal data RFU(t) that is due to background "noise" from, for example, stray electromagnetic signals from other modules of the instrument 50. That is, the background noise includes that part of the RFU(t) signal due to sources other than the analyte of interest. Background adjustment is performed by subtracting a background value "BG" from the data RFU(t) to obtain adjusted data RFU*(t). That is, RFU*(t)=RFU(t)−BG.

The background BG can be determined in a number of ways.

In accordance with one method for determining the background noise, the first step is to determine the time intervals between data points. The time interval is determined by multiplying cycle time (i.e., the time between consecutive data measurements) by the data point (i.e., $0^{th}$ data point, $1^{st}$ data point, $2^{nd}$ data point, . . . , $n^{th}$ data point) and divide by 60 seconds. For example, assuming a cycle time of 30 seconds, the time interval for the $15^{th}$ data point is (15×30 sec.)/60 sec.=7.5.

The next step is to find the midpoint of the signal data by adding the minimum signal data point and the maximum signal data point and dividing by two. That is: ($RFU_{max}$+$RFU_{min}$)/2 Starting at the time corresponding to the midpoint value and working backwards, calculate the slope for each pair of data points: (RFU(t)−RFU(t−1))/Δt(t→t−1).

Next, determine where the slope of RFU(t) flattens out by finding the first slope value that is less than the static slope value (i.e., the value before the RFU(t) curve begins its upward slope). A representative static slope value, also known as the "delta value," includes 0.0001. Once this slope is found, find the next cycle in which the slope that is not negative or is, for example, above the negative delta value (i.e., −0.0001); this value is $H_{index}$. Next, take the mean of the entire range of RFU(t) values starting at the first data point and go to the RFU value that corresponds to the $H_{index}$ value. The mean of this data may be computed using the Excel TRIMMEAN function on this range of data using a static back trim value of 0.15 (that is, the lowest 7.5% of RFU values in the specified range and the highest 7.5% RFU values in the specified range are excluded). This mean value is the background, BG.

Alternatively, the background can be determined in accordance with the procedure described above using a delta value other than 0.0001.

A further alternative method for determining the background eliminates the delta value criterion and instead take a TRIMMEAN mean of the RFU data from cycle 1 to a prescribed end point, such as the first cycle before 5.5 minutes. For this alternative, the static back trim value may be adjusted to, for example, 0.40 (that is, the lowest 20% of RFU values in the specified range and the highest 20% RFU values in the specified range are excluded from the background calculation).

A further alternative method for determining the background is to perform a curve fit on all or a portion of the RFU data to derive an estimate of the baseline value, which is the background to be subtracted. Any curve fit technique suitable for fitting a curve to the RFU data can be used.

An exemplary curve fit technique is to use a portion of the equation derived by Weusten et al. for curve fit of the typically sigmoidal curves associated with nucleic acid amplification. See Weusten et al., *Nucleic Acids Research*, 30(6e26):1-7 (2002). For background subtraction, it is only necessary to ascertain the baseline level. Thus, it is also only necessary to fit a curve to the first portion of the RFU data encompassing the baseline, usually toward the beginning of the curve.

The curve fit may be performed on the RFU(t) data from cycle 1 to the cycle just before 75% of the maximum RFU. The following polynomial equation (3), which, as mentioned above, is a portion of the equation derived by Weusten et al, is used to generate a best fit model of the RFU data:

$$RFU(t)=Y0+a1a2[e^{a2(t-a3)}/(1\pm e^{a2(t-a3)})]\ln(1\pm e^{a2(t-a3)}) \quad (3)$$

Initial estimates for the variables Y0, a1, a2, and a3, as discussed below, are input to the curve-fit equation and an iterative solution fitting the equation to the RFU data is performed, for example, using the SOLVER function of Microsoft EXCEL, to yield the final equation and the final values for Y0, a1, a2, and a3.

Y0=is the baseline; an initial value can be RFU(1).

a1=relates to the steep portion (growth phase) of the RFU(t) data; 0.05 can be a suitable initial estimate for a1.

a2=relates to the steep portion (growth phase) of the RFU(t) data; 1.0 can be a suitable initial estimate for a2.

a3=relates to the transition between the baseline and the slope feature; the time, or cycle, at which RFU(t) reaches a value just before 25% of $RFU_{max}$ is a suitable initial estimate for a3.

When the final values of Y0, a1, a2, and a3 have been derived, Y0 is treated as the back ground, and is subtracted from the RFU(t) data for which the curve fit was performed.

Curve fit equations other than that described above can be used. For example, the commercially available TABLE-CURVE software package (SYSTAT Software Inc.; Richmond, Calif.) can be used to identify and select an equation that described exemplary real-time nucleic acid amplification curves. One such exemplary resulting equation, used for mathematical modeling, is given by equation (4):

$$RFU(t)=Y0+b(1-\exp(-(t-d*\ln(1-2^{-(-1/e)})-c)/d))^{-e} \quad (4)$$

Still another exemplary resulting equation is given by equation (5):

$$RFU(t)=Y0+b/(1+\exp(-(t-d*\ln(2^{-(1/e)}-1)-c)/d))^{-e} \quad (5)$$

In each case, as described above, the equation can be solved, for example, using the SOLVER function of Microsoft EXCEL, to yield the final equation and the final values for Y0 and the other parameters, and the solutions yields a Y0 that is the background to be subtracted from the RFU(t) data.

To normalize the data, each data point, adjusted for the background, is divided by the maximum data point, also adjusted for the background. That is:

Normalized RFU=$RFU_n(t)$=$RFU^*(t)$=RFU(t)−BG $RFU^*_{max}$ $RFU_{max}$−BG

Thus, the $RFU_n(t)$ will be from −1 to 1.

In step 2108, the range of data is calculated by subtracting $RFU_{n(min)}$ from $RFU_{n(max)}$. If the calculated range does not meet or exceed a specified, minimum range (e.g., 0.05), the data is considered suspect and of questionable reliability, and, thus, the T-time will not be calculated. The minimum range is determined empirically and may vary from one fluorescence measuring instrument to the next. Ideally, the specified minimum range is selected to ensure that the variation of data values from minimum to maximum exceeds the noise of the system.

In step 2110, a curve fit procedure is applied to the normalized, background-adjusted data. Although any of the well-known curve fit methodologies may be employed, in a preferred embodiment, a linear least squares ("LLS") curve fit is employed. The curve fit is performed for only a portion of the data between a predetermined low bound and high bound. The ultimate goal, after finding the curve which fits the data, is to find the time corresponding to the point at which the curve intersects a predefined threshold value. In the preferred embodiment, the threshold for normalized data is 0.11. The high and low bounds are determined empirically as that range over which curves fit to a variety of control data sets exhibit the least variability in the time associated with the given threshold value. In the preferred embodiment, the lowbound is 0.04 and the highbound is 0.36. The curve is fit for data extending from the first data point below the low bound through the first data point past the high bound.

At step 2110, determine whether the slope of the fit is statistically significant. For example, if the p value of the first order coefficient is less than 0.05, the fit is considered significant, and processing continues. If not, processing stops. Alternatively, the validity of the data can be determined by the $R^2$ value.

The slope m and intercept b of the linear curve y=mx+b are determined for the fitted curve. With that information, T-time can be determined at step 2104 as follows:

$$T\text{-time} = \frac{\text{Threshold} - b}{m}$$

Figure 79:
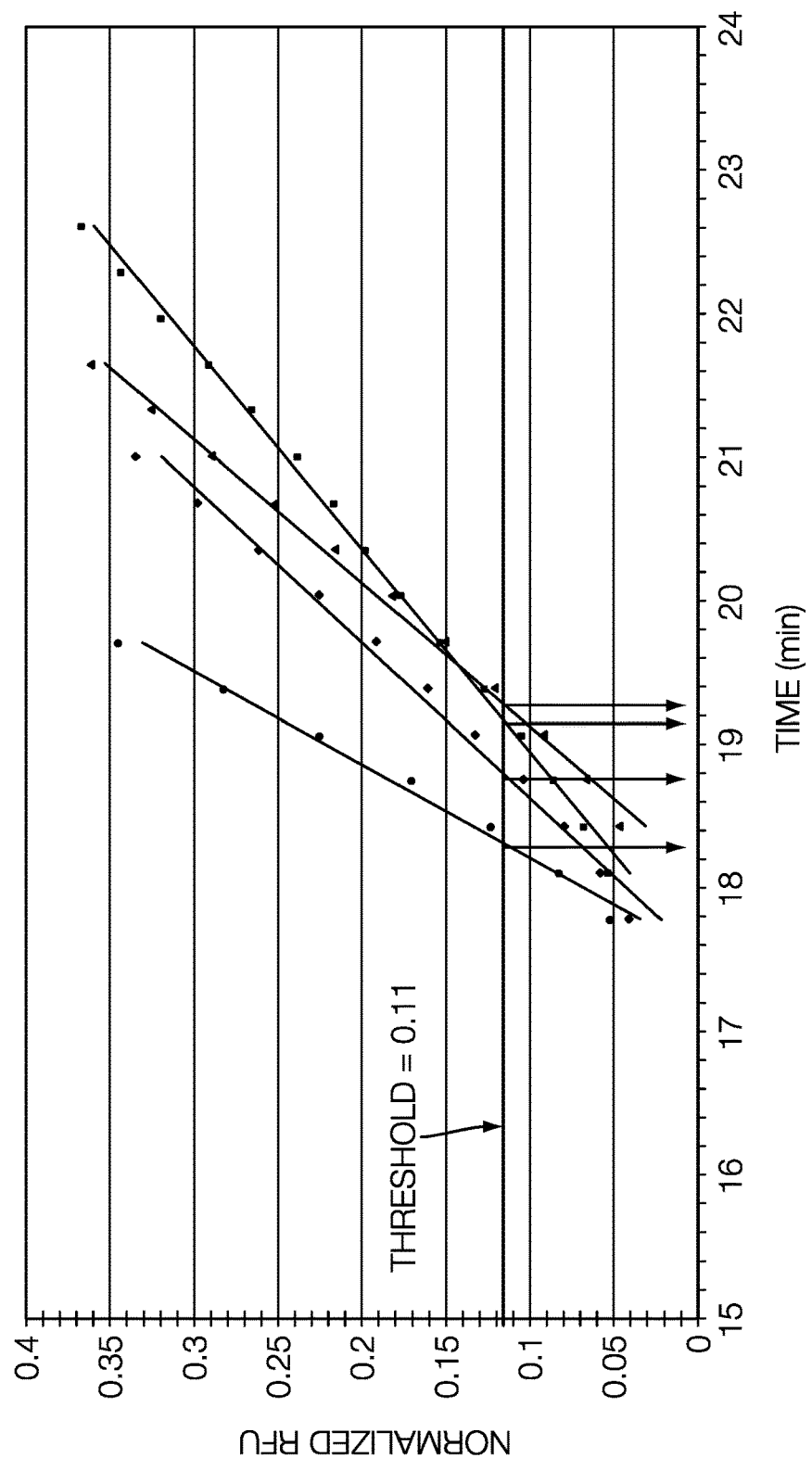
FIG. 79 is a plot showing a method for fitting a curve to real-time fluorometer data and using the fit to determine a threshold time.

The technique of using the fitted curve to determine T-times is illustrated graphically in FIG. 79.

Returning to FIG. 77, at step 2116, it is determined whether or not internal control/calibrator adjustments are desired. Typically, a test procedure would include at least one reaction vessel with a known concentration of a nucleic acid (other than a nucleic acid of interest) as a control, or, alternatively, a control nucleic acid sequence can be added to each sample. The known concentration can be simply used as control to confirm that a reaction did take place in the reaction vessel. That is, if the known concentration is amplified as expected, successful reaction is confirmed and a negative result with respect to the target analyte is concluded to be due to absence of target in the sample. On the other hand, failure to amplify the known concentration as expected indicates a failure of the reaction and any result with respect to the target is ignored.

The known concentration can be used to calibrate the concentration of the target. The T-times corresponding to a series of standards containing internal control and target sequences are determined for a statistically valid number of data sets. Using this data, a calibration plot is constructed from which the test sample's concentration is interpolated as described below.

One method of constructing the calibration plot places the known concentrations of target analyte on the x-axis versus the difference between target and control T-times on the y-axis. Subsequently, the test sample's concentration is interpolated from the calibration curve fit. Another method of construct the calibration plot places the known concentration of target analyte on the x-axis versus the fraction [target T-time/internal control T-time] on the y-axis. Subsequently, the test sample's concentration is interpolated from the calibration curve fit. An example of this is disclosed in Haaland, et al., "Methods, Apparatus and Computer Program Products for Determining Quantities of Nucleic Acid Sequences in Samples Using Standard Curves and Amplification Ratio Estimates," U.S. Pat. No. 6,066,458. A further alternative method of constructing the calibration plot utilizes a parametric calibration method, such as the method described in Carrick et al., "Parametric Calibration Method," U.S. Provisional Application No. 60/737,334, which enjoys common ownership herewith.

Occasionally, data sets exhibit a dip just after the initial static baseline (i.e., the initial, flat part of the RFU(t) curve, see FIG. 78) and just before the data begins its upward slope. To identify and correct such data, and prior to determining the T-time for that data, the following algorithm is employed. Starting at $H_{index}$, check each RFU(t) value to determine if it is less than the background value, BG. If yes, subtract RFU(t) from BG (the result should be a positive number). This will be the CorValue. Add the CorValue to the background subtracted value, this in turn will bring RFU(t) up to the baseline. Perform this analysis working forward on each RFU(t) value until the latest CorValue is less than the preceding CorValue. Add the greatest CorValue to each of the remaining background subtracted RFU(t) values. Now, the corrected data set can be normalized and the T-time determined as described above.

If a curve fit method is used to derive the background level, it may not be necessary to perform the dip correction described above.

It may also be desirable to perform outlier detection on the data set to identify and, if necessary, discard data points that exhibit abnormal values as compared to the remaining data points. Any of the well-known outlier detection methodologies can be used.

The quantitation procedure 2120 is the second part of the analyte concentration determination. T-times are determined for known concentrations of analytes for known conditions. Using this data, relationships between analyte concentrations (typically expressed as log copy) and T-times can be derived. After a T-time is determined for a particular sample, the derived relationship (Log copy=f (T-time)) can be used to determine the analyte concentration for the sample.

More specifically, at steps 2122 and 2124, calibration/control data sets for a control analyte of known concentrations are validated by, for example, outlier analysis and/or any other known data validation methodologies. If the data is found to be valid, calibration continues, otherwise, calibration stops.

T-times for the control data sets are determined, and T-time vs. Log copy is plotted for all samples of a particular condition (e.g., samples processed with reagents from a particular batch lot). In step 2126, a curve fit, such as a linear least squares fit, is performed on a portion of the T-time vs. Log copy plot to find the slope m and intercept b of the line that best fits the data. If the number of available T-time vs. Log copy data points (known as "calibrators") is not less than a predefined minimum number of calibrators (as determined at step 2128), lowest calibrators, if any, are removed at step 2130, as follows:

After finding the best fit line for the calibrator data points, $2^{nd}$ and $3^{rd}$ order curve fits are tested as well. If these fits are significantly better than the $1^{st}$ order, linear fit, the calibrator data point that is furthest from the linear curve fit is discarded, and $1^{st}$, $2^{nd}$, and $3^{rd}$ fits are found and compared again with the remaining calibrators. This process is repeated assuming that the number of calibrators is not less than the minimum acceptable number of calibrators—until the $2^{nd}$ and $3^{rd}$ order fits are not significantly better than the $1^{st}$ order, linear fit.

When the linear T-time vs. Log copy equation has been derived, the concentration (as Log copy) of the analyte of interest for a sample is determined, at step 2132, by plugging the T-time for that sample into the equation. Thus, the assay results are obtained 2134.

Possible enhancements of the RT incubator 608 include self-checking optical detection modules. In such a module, a known, standard excitation signal is emitted by the LED 1732 (or, alternatively, a separate, dedicated LED) and the excitation light is directed to the photo diode 1780 (and/or a separate, dedicated comparator photo diode) to ensure that the excitation signals, emission signals, and the signal output of the printed circuit board 1790 are all correct.

All documents referred to herein are hereby incorporated by reference herein. No document, however, is admitted to be prior art to the claimed subject matter.

While the invention has been described in connection with what are presently considered to be the most practical and preferred embodiments, it is to be understood that the invention is not to be limited to the disclosed embodiments, but, on the contrary, is intended to cover various modifications and equivalent arrangements included within the spirit and scope of the appended claims.

Furthermore, those of the appended claims which do not include language in the "means for performing a specified function" format permitted under 35 U.S.C. §112(¶6), are not intended to be interpreted under 35 U.S.C. § 112(¶6) as being limited to the structure, material, or acts described in the present specification and their equivalents.

The invention claimed is:

1. A method for determining the presence or absence of target nucleic acid sequences in a plurality of samples, the method comprising the steps of:
    a) loading a plurality of samples onto a self-contained, stand-alone analyzer having a view window situated above a generally horizontal work surface, each sample being contained within one of a plurality of receptacles, and each receptacle having an associated label containing machine-readable data;
    b) reading each associated label with a label reading device, wherein the label reading device is in communication with a computer, and wherein the computer associates each sample with one of at least two assays, the at least two assays including a first nucleic acid amplification reaction for amplifying a first target nucleic acid sequence and a second nucleic acid amplification reaction for amplifying a second target nucleic acid sequence, and the first and second target nucleic acid sequences being different from each other;
    c) exposing each sample to a solid support material, the solid support material being capable of immobilizing nucleic acids present in the samples;
    d) isolating the solid support material within each sample and separating a fluid component of the samples from the solid support material;
    e) after step d), washing the solid support material with a wash solution, thereby purifying the nucleic acids immobilized on the solid support material;
    f) forming a plurality of reaction mixtures, each reaction mixture being associated with one of the samples and comprising the nucleic acids from the associated sample that are purified in step e), if any, a first subset of the reaction mixtures comprising a first amplification reagent for performing the first nucleic acid amplification reaction, and a second subset of the reaction mixtures comprising a second amplification reagent for performing the second nucleic acid amplification reaction, wherein the first subset of reaction mixtures does not contain an amplification reagent for amplifying the second target nucleic acid sequence, and wherein the second subset of reaction mixtures does not contain an amplification reagent for amplifying the first target nucleic acid sequence;
    g) transferring the reaction mixtures to a heater disposed on the work surface;
    h) in the heater, simultaneously subjecting a plurality of reaction mixtures from the first and second subsets of reaction mixtures to conditions sufficient to perform the first and second nucleic acid amplification reactions; and
    i) determining the presence or absence of the first target nucleic acid sequence in each of the first subset of reaction mixtures and the presence or absence of the second target nucleic acid sequence in each of the second subset of reaction mixtures,
    wherein a plurality of the reaction mixtures from the second subset of reaction mixtures are provided to the heater while a plurality of the reaction mixtures from the first subset of reaction mixtures are being subjected to conditions sufficient to perform the first nucleic acid amplification reaction,
    wherein the determining step is performed during the subjecting step for the first subset of reaction mixtures, and
    wherein steps b)-i) are automated steps performed on the analyzer.

2. The method of claim 1, wherein each associated label is a bar code.

3. The method of claim 1, wherein the solid support material comprises magnetically-responsive particles or beads.

4. The method of claim 3, wherein the isolating step comprises exposing the samples to a magnetic field.

5. The method of claim 4, wherein the magnetic particles or beads are present in the reaction mixtures during the subjecting step.

6. The method of claim 5, wherein each reaction mixture is exposed to a magnetic field during the subjecting step.

7. The method of claim 1, wherein a plurality of the reaction mixtures from the first subset of reaction mixtures are removed from the heater while a plurality of the reaction mixtures from the second subset of reaction mixtures are being subjected to conditions sufficient to perform the second nucleic acid amplification reaction.

8. The method of claim 7, wherein the plurality of reaction mixtures from the first subset of reaction mixtures are contained in a first set of integrally formed receptacles and the plurality of reaction mixtures from the second subset of reaction mixtures are contained in a second set of integrally formed receptacles.

9. The method of claim 1, wherein the conditions are the same for the plurality of reaction mixtures during the subjecting step.

10. The method of claim 9, wherein the reaction mixtures are maintained at a constant temperature during the subjecting step.

11. The method of claim 9, wherein the first nucleic acid amplification reaction is a real-time nucleic acid amplification reaction.

12. The method of claim 11, wherein the second nucleic acid amplification reaction is an end-point nucleic acid amplification reaction.

13. The method of claim 9, wherein the second nucleic acid amplification reaction is an end-point nucleic acid amplification reaction.

14. The method of claim 1, wherein the determining step is performed outside the heater for the second subset of reaction mixtures.

15. The method of claim 1, wherein the determining step is performed with a luminometer for the second subset of reaction mixtures.

16. The method of claim 1, wherein at least one reaction mixture from the first subset of reaction mixtures and at least one reaction mixture from the second subset of reaction mixtures are contained in an integrally formed set of receptacles.

17. The method of claim 1, wherein the heater comprises an enclosure having one or more closable openings for receiving the receptacles therethrough.

18. The method of claim 17, wherein the one or more closable openings are situated on a side wall of the heater.

19. The method of claim 18, wherein the reaction mixtures are carried on a rotatable carousel within the heater during the subjecting step.

20. The method of claim 1, wherein at least a portion of the second subset of reaction mixtures are transferred to the heater prior to transferring all of the first subset of reaction mixtures to the heater.

21. The method of claim 20, wherein the heater comprises an enclosure having one or more closable openings for receiving the receptacles therethrough.

22. The method of claim 21, wherein the one or more closable openings are situated on a side wall of the heater.

23. The method of claim 22, wherein the reaction mixtures are carried on a rotatable carousel within the heater during the subjecting step.

24. The method of claim 1, wherein the analyzer comprises at least two view windows situated above the work surface.

25. The method of claim 1, wherein the determining step is performed for the first subset of reaction mixtures with one or more fluorometers operatively associated with the heater.

* * * * *